United States Patent
Baccara-Dinet et al.

(10) Patent No.: US 10,544,232 B2
(45) Date of Patent: *Jan. 28, 2020

(54) METHODS FOR TREATING PATIENTS WITH HETEROZYGOUS FAMILIAL HYPERCHOLESTEROLEMIA (HEFH) WITH AN ANTI-PCSK9 ANTIBODY

(71) Applicants: Sanofi Biotechnology, Paris (FR); Regeneron Pharmaceuticals, Inc., Tarrytown, NY (US)

(72) Inventors: Marie Baccara-Dinet, Paris (FR); Corinne Hanotin, Paris (FR); Laurence Bessac, Paris (FR); Umesh Chaudhari, Bridgewater, NJ (US); Robert C. Pordy, Tarrytown, NY (US); William J. Sasiela, Tarrytown, NY (US); Daniel A. Schwemmer Gipe, Tarrytown, NY (US)

(73) Assignees: SANOFI BIOTECHNOLOGY, Paris (FR); REGENERON PHARMACEUTICALS, INC., Tarrytown, NY (US)

( * ) Notice: Subject to any disclaimer, the term of this patent is extended or adjusted under 35 U.S.C. 154(b) by 511 days.

This patent is subject to a terminal disclaimer.

(21) Appl. No.: 14/801,384

(22) Filed: Jul. 16, 2015

(65) Prior Publication Data

US 2016/0137745 A1   May 19, 2016

Related U.S. Application Data

(60) Provisional application No. 62/080,717, filed on Nov. 17, 2014, provisional application No. 62/043,144, filed on Aug. 28, 2014, provisional application No. 62/025,362, filed on Jul. 16, 2014.

(30) Foreign Application Priority Data

Mar. 23, 2015   (EP) .................................... 15305419

(51) Int. Cl.
| | |
|---|---|
| A61K 39/395 | (2006.01) |
| A61P 3/06 | (2006.01) |
| C07K 16/40 | (2006.01) |
| C07K 14/705 | (2006.01) |
| A61K 39/00 | (2006.01) |

(52) U.S. Cl.
CPC .......... *C07K 16/40* (2013.01); *A61K 39/3955* (2013.01); *A61P 3/06* (2018.01); *A61K 2039/505* (2013.01); *C07K 14/705* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 5,260,440 A | 11/1993 | Hira et al. | |
| 5,273,995 A | 12/1993 | Roth | |
| 5,399,670 A | 3/1995 | Bhattacharya et al. | |
| 5,851,999 A | 12/1998 | Ulrich et al. | |
| 5,939,598 A | 8/1999 | Kucherlapati | |
| 6,011,003 A | 1/2000 | Charnock-Jones et al. | |
| 6,171,586 B1 | 1/2001 | Lam et al. | |
| 6,267,958 B1 | 7/2001 | Andya et al. | |
| 6,270,993 B1 | 8/2001 | Shibuya et al. | |
| 6,596,541 B2 | 7/2003 | Murphy | |
| 6,629,949 B1 | 10/2003 | Douglas | |
| 6,659,982 B2 | 12/2003 | Douglas et al. | |
| 6,875,432 B2 | 4/2005 | Liu et al. | |
| 7,001,892 B1 | 2/2006 | Chmielweski et al. | |
| 7,029,895 B2 | 4/2006 | Glucksmann et al. | |
| 7,060,268 B2 | 6/2006 | Andya et al. | |
| 7,129,338 B1 | 10/2006 | Ota et al. | |
| 7,300,754 B2 | 11/2007 | Fadel et al. | |
| 7,482,147 B2 | 1/2009 | Glucksmann et al. | |
| 7,572,618 B2 | 8/2009 | Mintier et al. | |
| 7,608,693 B2 | 10/2009 | Martin et al. | |
| 7,754,208 B2 | 7/2010 | Ledbetter et al. | |
| 8,030,457 B2 | 10/2011 | Jackson et al. | |
| 8,062,640 B2 | 11/2011 | Sleeman et al. | |

(Continued)

FOREIGN PATENT DOCUMENTS

| | | |
|---|---|---|
| CN | 10189565 A | 7/2009 |
| EP | 0521471 B1 | 10/2000 |

(Continued)

OTHER PUBLICATIONS

Robinson et al (Mar. 2013. J Manag Care Pharm. 19(2): 139-149).*
Pordy et al, May-Jun. 2013. Journal of Clinical Lipidology. 7(3): 279.*
clinicaltrials.gov (Oct. 7, 2013) "View of NCT01709513," US National Institutes of Health. [accessible on the internet at: https://clinicaltrials.gov/archive/NCT01709513/2013_10_07].
Daugherty et al. (2006) "Formulation and delivery issues for monoclonal antibody therapeutics," Advanced Drug Delivery Reviews 58:686-706.

(Continued)

*Primary Examiner* — Zachary C Howard
(74) *Attorney, Agent, or Firm* — Lathrop Gage LLP; James V. DeGiulio, Esq.; James H. Velema, Esq.

(57) ABSTRACT

The present invention provides methods for treating hypercholesterolemia. The methods of the present invention comprise administering to patients with heterozygous familial hypercholesterolemia a pharmaceutical composition comprising a PCSK9 inhibitor. In certain embodiments, the PCSK9 inhibitor is an anti-PCSK9 antibody such as the exemplary antibody referred to herein as mAb316P. The methods of the present invention are useful for treating patients with heterozygous familial hypercholesterolemia who are not adequately controlled by maximum tolerated dose statin therapy with or without other lipid lowering therapy.

16 Claims, 16 Drawing Sheets

Specification includes a Sequence Listing.

(56) References Cited

U.S. PATENT DOCUMENTS

| | | |
|---|---|---|
| 8,080,243 B2 | 12/2011 | Liang et al. |
| 8,092,803 B2 | 1/2012 | Furfine et al. |
| 8,168,762 B2 | 5/2012 | Jackson et al. |
| 8,188,233 B2 | 5/2012 | Condra et al. |
| 8,188,234 B2 | 5/2012 | Condra et al. |
| 8,357,371 B2 | 1/2013 | Sleeman et al. |
| 8,501,184 B2 | 8/2013 | Sleeman et al. |
| 8,748,115 B2 | 6/2014 | Ni et al. |
| 8,795,669 B2 | 8/2014 | Walsh et al. |
| 8,829,165 B2 | 9/2014 | Jackson et al. |
| 9,550,837 B2 | 1/2017 | Sleeman et al. |
| 9,561,155 B2 | 2/2017 | Hanotin et al. |
| 2003/0092606 A1 | 5/2003 | L'Italien et al. |
| 2003/0113316 A1 | 6/2003 | Kaisheva et al. |
| 2003/0118592 A1 | 6/2003 | Ledbetter et al. |
| 2003/0133939 A1 | 7/2003 | Ledbetter et al. |
| 2004/0101920 A1 | 5/2004 | Radziejewski et al. |
| 2004/0197324 A1 | 10/2004 | Liu et al. |
| 2005/0281831 A1 | 12/2005 | Davis-Smyth et al. |
| 2006/0147945 A1 | 7/2006 | Edmonds et al. |
| 2007/0082345 A1 | 4/2007 | Ota et al. |
| 2007/0224663 A1 | 9/2007 | Rosen et al. |
| 2008/0008697 A1 | 1/2008 | Mintier et al. |
| 2009/0142352 A1 | 6/2009 | Jackson et al. |
| 2009/0232795 A1 | 9/2009 | Condra et al. |
| 2009/0246192 A1 | 10/2009 | Condra et al. |
| 2009/0269350 A1 | 10/2009 | Glucksmann et al. |
| 2009/0318536 A1 | 12/2009 | Freier et al. |
| 2009/0326202 A1 | 12/2009 | Jackson et al. |
| 2010/0040610 A1 | 2/2010 | Sitlani et al. |
| 2010/0040611 A1 | 2/2010 | Sparrow et al. |
| 2010/0041102 A1 | 2/2010 | Sitlani et al. |
| 2010/0068199 A1 | 3/2010 | Liang et al. |
| 2010/0136028 A1 | 6/2010 | Sparrow et al. |
| 2010/0150937 A1 | 6/2010 | Sparrow et al. |
| 2010/0166768 A1 | 7/2010 | Sleeman et al. |
| 2010/0233177 A1 | 9/2010 | Yowe et al. |
| 2011/0027287 A1 | 2/2011 | Jackson et al. |
| 2011/0033465 A1 | 2/2011 | Hedrick et al. |
| 2011/0065902 A1 | 3/2011 | Sleeman et al. |
| 2011/0098450 A1 | 4/2011 | Igawa et al. |
| 2011/0111406 A1 | 5/2011 | Igawa et al. |
| 2011/0142849 A1 | 6/2011 | Rue et al. |
| 2011/0171241 A1 | 7/2011 | Dix et al. |
| 2011/0229489 A1 | 9/2011 | Pons et al. |
| 2011/0256148 A1 | 10/2011 | Sleeman et al. |
| 2012/0014951 A1 | 1/2012 | Liang et al. |
| 2012/0015435 A1 | 1/2012 | Liang et al. |
| 2012/0020975 A1 | 1/2012 | Jackson et al. |
| 2012/0027765 A1 | 2/2012 | Jackson et al. |
| 2012/0076799 A1 | 3/2012 | Sparrow et al. |
| 2012/0077964 A1 | 3/2012 | Sparrow et al. |
| 2012/0082679 A1 | 4/2012 | Sparrow et al. |
| 2012/0082680 A1 | 4/2012 | Sitlani et al. |
| 2012/0093818 A1 | 4/2012 | Jackson et al. |
| 2012/0097565 A1 | 4/2012 | Dix et al. |
| 2012/0195910 A1 | 8/2012 | Wu et al. |
| 2012/0213794 A1 | 8/2012 | Luo et al. |
| 2012/0213797 A1 | 8/2012 | Jackson et al. |
| 2012/0219558 A1 | 8/2012 | Ni et al. |
| 2012/0231005 A1 | 9/2012 | Luo et al. |
| 2012/0251544 A1 | 10/2012 | Jackson et al. |
| 2013/0011866 A1 | 1/2013 | Igawa et al. |
| 2013/0064825 A1 | 3/2013 | Chan et al. |
| 2013/0064834 A1 | 3/2013 | Sleeman et al. |
| 2013/0085266 A1 | 4/2013 | Sleeman et al. |
| 2013/0243784 A1 | 9/2013 | Swergold |
| 2013/0245235 A1 | 9/2013 | Jackson et al. |
| 2014/0004122 A1 | 1/2014 | Chan et al. |
| 2014/0030270 A1 | 1/2014 | Clogston et al. |
| 2014/0065649 A1 | 3/2014 | Schafer et al. |
| 2014/0099312 A1 | 4/2014 | Sleeman et al. |
| 2014/0154262 A1 | 6/2014 | Hanotin et al. |
| 2014/0161821 A1 | 6/2014 | Udata |
| 2014/0178402 A1 | 6/2014 | Hanotin et al. |
| 2014/0356370 A1 | 12/2014 | Swergold et al. |
| 2014/0356371 A1 | 12/2014 | Swergold et al. |
| 2015/0140002 A1 | 5/2015 | Baccara-Dinet et al. |
| 2015/0152191 A1 | 6/2015 | Baccara-Dinet et al. |
| 2015/0231236 A1 | 8/2015 | Pordy et al. |
| 2015/0283236 A1 | 10/2015 | Baccara-Dinet et al. |
| 2015/0284473 A1 | 10/2015 | Bessac et al. |
| 2015/0284474 A1 | 10/2015 | Sleeman et al. |
| 2016/0115246 A1 | 4/2016 | Sasiela et al. |
| 2016/0137746 A1 | 5/2016 | Hanotin et al. |
| 2016/0152734 A1 | 6/2016 | Udata |
| 2017/0049886 A1 | 2/2017 | Pordy et al. |
| 2017/0096496 A1 | 4/2017 | Sleeman et al. |

FOREIGN PATENT DOCUMENTS

| | | |
|---|---|---|
| EP | 1067182 A2 | 1/2001 |
| EP | 0409281 B1 | 10/2001 |
| EP | 1514933 A1 | 3/2005 |
| EP | 1317537 B1 | 12/2006 |
| EP | 1618212 B1 | 11/2007 |
| EP | 2 703 008 A1 | 3/2014 |
| EP | 2 703 009 A1 | 3/2014 |
| EP | 2 706 070 A1 | 3/2014 |
| WO | 1993/000807 A1 | 1/1993 |
| WO | 1997/035620 A1 | 10/1997 |
| WO | 1998/022136 A2 | 5/1998 |
| WO | 1999/038495 A2 | 8/1999 |
| WO | 2001057081 A2 | 8/2001 |
| WO | 2004/055164 A2 | 7/2004 |
| WO | 2004/097047 A1 | 11/2004 |
| WO | 2005103081 A2 | 11/2005 |
| WO | 2007/143315 A2 | 12/2007 |
| WO | 2007/149334 A2 | 12/2007 |
| WO | 2008057457 A2 | 5/2008 |
| WO | 2008057458 A2 | 5/2008 |
| WO | 2008057459 A2 | 5/2008 |
| WO | 2008063382 A2 | 5/2008 |
| WO | 2008125623 A2 | 10/2008 |
| WO | 2008133647 A2 | 11/2008 |
| WO | 2009026558 A1 | 2/2009 |
| WO | 2009/042765 A1 | 4/2009 |
| WO | 2009055783 A2 | 4/2009 |
| WO | 2009100297 A1 | 8/2009 |
| WO | 2009100318 A1 | 8/2009 |
| WO | 2010/032220 A1 | 3/2010 |
| WO | 2010029513 A2 | 3/2010 |
| WO | 2010077854 A1 | 7/2010 |
| WO | 2010/102241 A1 | 9/2010 |
| WO | 2010/148337 A1 | 12/2010 |
| WO | 2011028938 A1 | 3/2011 |
| WO | 2011039578 A1 | 4/2011 |
| WO | 2011/053759 A1 | 5/2011 |
| WO | 2011/061712 A1 | 5/2011 |
| WO | 2011/072263 A1 | 6/2011 |
| WO | 2011/111007 A2 | 9/2011 |
| WO | 2011/117401 A1 | 9/2011 |
| WO | 2012054438 A1 | 4/2012 |
| WO | 2012064792 A2 | 5/2012 |
| WO | 2012101251 A1 | 8/2012 |
| WO | 2012101252 A1 | 8/2012 |
| WO | 2012101253 A1 | 8/2012 |
| WO | 2012109530 A1 | 8/2012 |
| WO | 2012146776 A1 | 11/2012 |
| WO | 2012154999 A1 | 11/2012 |
| WO | 2013/039958 A1 | 3/2013 |
| WO | 2013039969 A1 | 3/2013 |
| WO | WO2013158984 A1 | 10/2013 |
| WO | 2013/166448 A1 | 11/2013 |
| WO | 2014194111 A1 | 12/2014 |
| WO | WO2014197752 A1 | 12/2014 |
| WO | 2015/054619 A2 | 4/2015 |
| WO | 2015/073494 A1 | 5/2015 |
| WO | WO2015123423 A2 | 8/2015 |
| WO | 2015/140079 A1 | 9/2015 |
| WO | 2015/142668 A1 | 9/2015 |

(56) References Cited

FOREIGN PATENT DOCUMENTS

| WO | 2016/011256 A1 | 1/2016 |
|---|---|---|
| WO | 2016/011260 A1 | 1/2016 |

OTHER PUBLICATIONS

Davidson et al. (2011) "Clinical utility of inflammatory markers and advanced lipoprotein testing: Advice from an expert panel of lipid specialists," Journal of Clinical Lipidology. 5:338-367.

Defesche et al. (Jun. 2-5, 2013) "Natural history of autosomal dominant hypercholesterolemia caused by gain-of-function mutations in proprotein convertase subtilisin/kexin type 9 (PCSK9) (funded by Regeneron/Sanofi)," Abstract of a presentation presented at the 81st European Atherosclerosis Society (EAS) Congress, Jun. 2-5, 2013, Lyon, France.

Defesche et al. (Jun. 2-5, 2013) "Natural history of autosomal dominant hypercholesterolemia caused by gain-of-function mutations in proprotein convertase subtilisin/kexin type 9 (PCSK9) (funded by Regeneron/Sanofi)," Presentation presented at the 81st European Atherosclerosis Society (EAS) Congress, Jun. 2-5, 2013, Lyon, France.

Katayama et al. (2004) "Retrospective statistical analysis of lyophilized Protein Formulations of Progenipoietin Using PLS: Determination of the Critical Parameters for Long-Term Storage Stability," J. Pharm. Sci. 93(10):2609-2623.

Kostner et al. (Jun. 4, 2013) "When should we measure lipoprotein (a)?" European Heart Journal. 34:3268-3276.

Lefranc et al. (2009) "IMGT®, the international ImMunoGeneTics information system®," Nucl. Acids Res. 37:D1006-D1012.

Li et al. (2009) "Recent Patents on PCSK9: A New Target for Treating Hypercholesterolemia," Recent Patents on DNA and Gene Sequences. 3(3):201-212.

Majumdar et al. (2011) "Evaluation of the effect of syringe surfaces on protein formulations," Journal of Pharmaceutical Sciences. 100(7):2563-2573.

McKenney et al. (Jun. 2-5, 2013) "Dynamics between the monoclonal antibody SAR236553/REGN727, proprotein convertase subtilisin/kexin type 9 (PCSK9) and low-density lipoprotein cholesterol (LDL-C) levels (funding: Regeneron/Sanofi)," Abstract of an oral presentation at the 81st European Atherosclerosis Society (EAS) Congress, Jun. 2-5, 2013, Lyon, France.

McKenney et al. (Jun. 2-5, 2013) "Dynamics between the monoclonal antibody SAR236553/REGN727, proprotein convertase subtilisin/kexin type 9 (PCSK9) and low-density lipoprotein cholesterol (LDL-C) levels (funding: Regeneron/Sanofi)," Presented as a poster presentation at the 81st European Atherosclerosis Society (EAS) Congress, Jun. 2-5, 2013, Lyon, France.

Rader et al. (1995) "The Low Density Lipoprotein Receptor Is Not Required for Normal Catabolism of Lp(a) in Humans," The Journal of Clinical Investigation. 95:1403-1408.

Regeneron Pharmaceuticals (Nov. 5, 2012) "Sanofi and Regeneron Announce Patient Enrollment in Cardiovascular Outcome Trial with Antibody to PCSK9 for Hypercholesterolemia," Press Release. Acquire Media.

Robinson (2002) "Protein Deamidation," Proc. Natl. Acad. Sci. USA. 99(8):5283-5288.

Romagnuolo et al. (Mar. 16, 2015) "Lipoprotein(a) Catabolism is Regulated by Proprotein Convertase Subtilisin/Kexin Type 9 through the Low Density Lipoprotein Receptor," The Journal of Biological Chemistry. 290(18)11649-11662.

Scaviner et al. (1999) "Protein Displays of the Human Immunoglobulin Heavy, Kappa and Lambda Variable and Joining Regions," Exp. Clin. Immunogenet. 16:234-240.

Schafer et al. (Mar. 14-16, 2011) "Cholesterol lowering effect of SAR236553/REGN727, a fully human PCSK9 blocking monoclonal antibody in male Syrian hamster," Presented as a poster at the Drugs Affecting Lipid Metabolism (DALM)—XVII International Symposium, Mar. 14-16, 2011, Doha, Qatar.

Varrett et al. (1999) "A third major locus for autosomal dominant hypercholesterolemia Maps to 1p34.1-p32," Am. J. Hum. Genet. 64:1378-1387.

Wang (1999) "Instability, stabilization, and formulation of liquid protein pharmaceuticals," International J. Pharmaceutics 185(2):129-188.

Wang (2009) "Fixed dosing versus body size-based dosing of monoclonal antibodies in adult clinical trials," J Clin Pharmacol. 49(9):1012-1024.

Webb et al. (2002) "A new mechanism for decreasing aggregation of recombinant human interferon-gamma by a surfactant: slowed dissolution of lyophilized formulations in a solution containing 0.03% polysorbate 20," J. Pharm. Sci. 91(2):543-558.

Weterterp, M. et al., Cholesteryl Ester Transfer Protein Decreases High-Density Lipoprotein and Severely Aggravates Atherosclerosis in APOE*3-Leiden Mice; Arterioscler Thromb. Vasc. Biol. Nov. 2006; 26(11):2552-2559; Epub Aug. 3, 2006.

Stahl, N. Early Clinical Development #1 REGN727: anti-PCSK9, Jul. 15, 2010, 21 pages.

Bays E, et al., Alirocumab treatment effect on non-HDL-C: pooled analyses of ten Phase 3 trials in the ODYSSEY program. J Clin Lipidol. 2015;9(3):471-472.(Abstract 183).

Blom, Dirk J. et al.: "A 52-Week Placebo-Controlled Trial of Evolocumab in Hyperlipidemia" The New England Journal of Medicine, vol. 370, No. 19, May 8, 2014 pp. 1809-1819.

Cariou, B. et al., Patient and physician perspectives on administration of the PCSK9 monoclonal antibody alirocumab, an injectable medication to lower LDL-C levels, Int'l Symposium on Atherosclerosis, May 23-26, 2015, Abstract No. 1039, 1 page.

Dufour, R. et al., One year open-label treatment with alirocumab 150 mg every two weeks in heterozygous familial iypercholesterolemic patients. Can J Cardiol. 2014;30(10 suppl):S338.

Gorcyca, K. et al., Prevalence of atherosclerotic cardiovascular disease and diabetes in the United States. J Clin Lipidol. 2015;9(3):424.

Hopkins, PN, et al., Characterization of Autosomal Dominant Hypercholesterolemia Caused by PCSK9 Gain of Function Mutations and its Specific Treatment with Alirocumab, a PCSK9 Monoclonal Antibody. Circ Cardiovasc Genet. 2015. (Epub ahead of print). 43 pages.

Huang, Q, et al. Clinical characteristics and unmet need among real-world atherosclerotic cardiovascular disease (ASCVD) patients stratified by statin use. J Clin Lipidol. 2015;9(3):437-438. (Abstract).

International Preliminary Report on Patentability dated Jul. 30, 2013 for International application No. PCT/EP12/051321, 7 pages.

International Search Report and Written Opinion dated Aug. 19, 2015 for International application No. PCT/US2015/015633, 22 pages.

International Search Report and Written Opinion for PCT/US2014/041204 dated Oct. 17, 2014, 16 pages.

International Search Report and Written Opinion dated May 21, 2015 for International application No. PCT/EP15/55369, 11 pages.

International Search Report dated Apr. 19, 2012 for International application No. PCT/EP12/051321, 4 pages.

Kastelein JJP, et al. Odyssey FH I and FH II: 78-week results with alirocumab treatment in 735 patients with heterozygous familial hypercholesterolemia. Eur Heart J. Epub ahead of print, Sep. 1, 2015,8 pages.

Kuiper, J.G. et al., Statin use and low density lipoprotein cholesterol goal attainment among a high cardiovascular risk population in the Netherlands, Pharmo ISA Poster, May 2015, 1 page.

Moriarty, P.M. et al. Efficacy and safety of alirocumab versus ezetimibe in statin-intolerant patients, with a statin-re-challenge arm: The Odyssey Alternative randomized trial. J Clin Lipidol (2015) Epub ahead of print, 12 pages.

Ray KK. Alirocumab: an investigational treatment for hypercholesterolemia. Clin Lipidol 2015;10(1):9-12.

Reyes-Soffer, G. et al., Abstract 129: Effects of a proprotein convertase subtilisin/kexin type 9 inhibitor, alirocumab, on lipid and lipoprotein metabolism in normal subjects. Arterioscler, Thromb Vasc Biol. 2015;35:A129.

Roth, E.M. et al, Patient and physician perspectives on administration of the PCSK9 monoclonal antibody alirocumab, an injectable medication to lower LDL-C levels. 2015;37(9):1945-1954.e6.

(56) References Cited

OTHER PUBLICATIONS

Roth, E.M. et al., Phase 3 Randomized Trial Evaluating Alirocumab Every Four Weeks Dosing as Add-on to Statin or as Monotherapy: ODYSSEY Choice I, Int'l Symposium on Atherosclerosis, May 23-26, 2015, Abstract No. 254, 1 page.
Barbie et al. (1998) "The Human Immunoglobulin Kappa Variable (IGKV) Genes and Joining (IGKJ) Segments," Exp. Clin. Immunogenet. 15:171-183.
Breen et al. (2001) "Effect of moisture on the stability of a lyophilized humanized monoclonal antibody formulation," Pharmaceutical Research. 18(9):1345-1353.
Cannon et al. (Aug. 31, 2014) "Efficacy and safety of alirocumab in high cardiovascular risk patients with inadequately controlled hypercholesterolaemia on maximally tolerated daily statin: results from the ODYSSEY Combo II study," presentation presented at the ESC Congress 2014.
Carpenter (1997) "Rational Design of Stable Lyophilized Protein Formulations: Some Practical Advice," Pharm. Res. 14(8):969-975.
clinicaltrials.gov (Aug. 10, 2012) "View of NCT01663402," US National Institutes of Health. [accessible on the internet at: https://clinicaltrials.gov/archive/NCT01663402/2012_08_10].
clinicaltrials.gov (Aug. 12, 2013) "View of NCT01617655," US National Institutes of Health. [accessible on be internet at: https://clinicaltrials.gov/archive/NCT01617655/2013_08_12].
clinicaltrials.gov (Dec. 23, 2010) "View of NCT01266876," US National Institutes of Health. [accessible on the internet at: https://clinicaltrials.gov/archive/NCT01266876/2010_12_23].
clinicaltrials.gov (Dec. 27, 2013) "View of NCT02023879," US National Institutes of Health. [accessible on the internet at: https://clinicaltrials.gov/archive/NCT02023879/2013_12_27].
clinicaltrials.gov (Feb. 1, 2011) "View of NCT01288443," US National Institutes of Health. [accessible on the internet at: https://clinicaltrials.gov/archive/NCT01288443/2011_02_01].
clinicaltrials.gov (Feb. 1, 2011) "View of NCT01288469," US National Institutes of Health. [accessible on the internet at: https://clinicaltrials.gov/archive/NCT01288469/2011_02_01].
clinicaltrials.gov (Feb. 1, 2015) "View of NCT01709500," US National Institutes of Health. [accessible on the internet at: https://clinicaltrials.gov/archive/NCT01709500/2015_02_01].
clinicaltrials.gov (Feb. 1, 2015) "View of NCT01709513," US National Institutes of Health. [accessible on the internet at: https://clinicaltrials.gov/archive/NCT01709513/2015_02_01].
clinicaltrials.gov (Feb. 18, 2014) "View of NCT01604824," US National Institutes of Health. [accessible on the internet at: https://clinicaltrials.gov/archive/NCT01604824/2014_02_18].
clinicaltrials.gov (Feb. 24, 2015) "View of NCT01644175," US National Institutes of Health. [accessible on the internet at: https://clinicaltrials.gov/archive/NCT01644175/2015_02_24].
clinicaltrials.gov (Jan. 10, 2012) "View of NCT01507831," US National Institutes of Health. [accessible on the internet at: https://clinicaltrials.gov/archive/NCT01507831/2012_01_10].
clinicaltrials.gov (Jan. 22, 2015) "View of NCT01507831," US National Institutes of Health. [accessible on the internet at: https://clinicaltrials.gov/archive/NCT01507831/2015_01_22].
clinicaltrials.gov (Jan. 26, 2015) "View of NCT01161082," US National Institutes of Health. [accessible on the internet at: https://clinicaltrials.gov/archive/NCT01161082/2015_01_26].
clinicaltrials.gov (Jan. 29, 2015) "View of NCT01288443," US National Institutes of Health. [accessible on the internet at: https://clinicaltrials.gov/archive/NCT01288443/2015_01_29].
clinicaltrials.gov (Jan. 29, 2015) "View of NCT01288469," US National Institutes of Health. [accessible on the internet at: https://clinicaltrials.gov/archive/NCT01288469/2015_01_29].
clinicaltrials.gov (Jan. 29, 2015) "View of NCT01604824," US National Institutes of Health. [accessible on the internet at: https://clinicaltrials.gov/archive/NCT01604824/2015_01_29].
clinicaltrials.gov (Jan. 29, 2015) "View of NCT01812707," US National Institutes of Health. [accessible on the internet at: https://clinicaltrials.gov/archive/NCT01812707/2015_01_29].
clinicaltrials.gov (Jan. 30, 2014) "View of NCT01812707," US National Institutes of Health. [accessible on the internet at: https://clinicaltrials.gov/archive/NCT01812707/2014_01_30].
clinicaltrials.gov (Jul. 10, 2015) "View of NCT01663402," US National Institutes of Health. [accessible on the Internet at: https://clinicaltrials.gov/archive/NCT01663402/2015_07_10].
clinicaltrials.gov (Jul. 12, 2010) "View of NCT01161082," US National Institutes of Health. [accessible on the internet at: https://clinicaltrials.gov/archive/NCT01161082/2010_07_12].
clinicaltrials.gov (Jul. 17, 2012) "View of NCT01644175," US National Institutes of Health. [accessible on the internet at: https://clinicaltrials.gov/archive/NCT01644175/2012_07_17].
clinicaltrials.gov (Jul. 17, 2012) "View of NCT01644188," US National Institutes of Health. [accessible on the internet at: https://clinicaltrials.gov/archive/NCT01644188/2012_07_17].
clinicaltrials.gov (Jul. 18, 2012) "View of NCT01644474," US National Institutes of Health. [accessible on the internet at: https://clinicaltrials.gov/archive/NCT01644474/2012_07_18].
clinicaltrials.gov (Jul. 2, 2013) "View of NCT01288443," US National Institutes of Health. [accessible on the internet at: https://clinicaltrials.gov/archive/NCT01288443/2013_07_02].
clinicaltrials.gov (Jul. 2, 2013) "View of NCT01288469," US National Institutes of Health. [accessible on the internet at: https://clinicaltrials.gov/archive/NCT01288469/2013_07_02].
clinicaltrials.gov (Jul. 8, 2014) "View of NCT01644474," US National Institutes of Health. [accessible on the internet at: https://clinicaltrials.gov/archive/NCT01644474/2014_07_08].
clinicaltrials.gov (Jun. 10, 2014) "View of NCT01663402," US National Institutes of Health. [accessible on the internet at: https://clinicaltrials.gov/archive/NCT01663402/2014_06_10].
clinicaltrials.gov (Jun. 11, 2012) "View of NCT01617655," US National Institutes of Health. [accessible on the internet at: https://clinicaltrials.gov/archive/NCT01617655/2012_06_11].
clinicaltrials.gov (Jun. 18, 2012) "View of NCT01623115," US National Institutes of Health. [accessible on the internet at: https://clinicaltrials.gov/archive/NCT01623115/2012_06_18].
clinicaltrials.gov (Jun. 18, 2015) "View of NCT01266876," US National Institutes of Health. [accessible on the internet at: https://clinicaltrials.gov/archive/NCT01266876/2015_06_18].
clinicaltrials.gov (Jun. 18, 2015) "View of NCT01644188," US National Institutes of Health. [accessible on the internet at: https://clinicaltrials.gov/archive/NCT01644188/2015_06_18].
clinicaltrials.gov (Jun. 19, 2014) "View of NCT01644188," US National Institutes of Health. [accessible on the internet at: https://clinicaltrials.gov/archive/NCT01644188/2014_06_19].
clinicaltrials.gov (Jun. 19, 2014) "View of NCT02023879," US National Institutes of Health. [accessible on the internet at: https://clinicaltrials.gov/archive/NCT02023879/2014_06_19].
clinicaltrials.gov (Jun. 27, 2013) "View of NCT01507831," US National Institutes of Health. [accessible on the internet at: https://clinicaltrials.gov/archive/NCT01507831/2013_06_27].
clinicaltrials.gov (Jun. 27, 2013) "View of NCT01623115," US National Institutes of Health. [accessible on the internet at: https://clinicaltrials.gov/archive/NCT01623115/2013_06_27].
clinicaltrials.gov (Mar. 15, 2013) "View of NCT01812707," US National Institutes of Health. [accessible on the internet at: https://clinicaltrials.gov/archive/NCT01812707/2013_03_15].
clinicaltrials.gov (Mar. 16, 2012) "View of NCT01266876," US National Institutes of Health. [accessible on the internet at: https://clinicaltrials.gov/archive/NCT01266876/2012_03_16].
clinicaltrials.gov (Mar. 26, 2015) "View of NCT01617655," US National Institutes of Health. [accessible on the internet at: https://clinicaltrials.gov/archive/NCT01617655/2015_03_26].
clinicaltrials.gov (Mar. 26, 2015) "View of NCT01623115," US National Institutes of Health. [accessible on the internet at: https://clinicaltrials.gov/archive/NCT01623115/2015_03_26].
clinicaltrials.gov (May 20, 2015) "View of NCT02023879," US National Institutes of Health. [accessible on the internet at: https://clinicaltrials.gov/archive/NCT02023879/2015_05_20].
clinicaltrials.gov (May 23, 2012) "View of NCT01604824," US National Institutes of Health. [accessible on the internet at: https://clinicaltrials.gov/archive/NCT01604824/2012_05_23].

(56) References Cited

OTHER PUBLICATIONS clinicaltrials.gov (May 28, 2014) "View of NCT01644175," US National Institutes of Health. [accessible on the internet at: https://clinicaltrials.gov/archive/NCT01644175/2014_05_28].

clinicaltrials.gov (Nov. 7, 2011) "View of NCT01161082," US National Institutes of Health. [accessible on the internet at: https://clinicaltrials.gov/archive/NCT01161082/2011_11_07].

clinicaltrials.gov (Oct. 17, 2012) "View of NCT01709500," US National Institutes of Health. [accessible on the internet at: https://clinicaltrials.gov/archive/NCT01709500/2012_10_17].

clinicaltrials.gov (Oct. 17, 2012) "View of NCT01709513," US National Institutes of Health. [accessible on the internet at: https://clinicaltrials.gov/archive/NCT01709513/2012_10_17].

clinicaltrials.gov (Oct. 25, 2013) "View of NCT01709500," US National Institutes of Health. [accessible on the internet at: https://clinicaltrials.gov/archive/NCT01709500/2013_10_25].

Timms et al., 'A mutation in PCSK9 causing autosomal-dominant hypercholesterolemia in a Utah pedigree.' Human Genetics. 2004, 114(4):349-353.

Tiwari et al., 'Statins therapy: a review on conventional and novel formulation approaches.' Journal of Pharmacy and Pharmacology. 2011, vol. 63, No. 8, pp. 983-998.

Toth et al., 'Alirocumab, a Proprotein Convertase Substilisin/Kexin Type 9 Monoclonal Antibody, Reduces Cholesterol Concentrations of Serum Remnant Lipoprotein Fractions, Very Low-Density Lipoproteins and Triglycerides.' Circulation. 2013, 128(22):A17492.

Toth PP, et al. Alirocumab, a proprotein convertase subtilisin/kexin type 9 monoclonal antibody, reduces cholesterol concentrations of all serum low-density lipoprotein cholesterol fractions. Circulation. 2013;128:A17313.

Toth PP, et al. Proprotein convertase subtilisin/kexin 9 monoclonal antibody therapy significantly reduces apoprotein CII and CIII levels in serum. Atherosclerosis. 2014;235(2):e107-e108; Abstract 593.

Tutt et al., 'Trispecific F (ab') 3 derivatives that use cooperative signaling via the TCR/CD3 complex and CD2 to activate and redirect resting cytotoxic T cells.' The Journal of Immunology. 1991, vol. 147, No. 1, pp. 60-69.

Vajdos et al., 'Comprehensive functional maps of the antigen-binding site of an anti-ErbB2 antibody obtained with shotgun scanning mutagenesis.' Journal of Molecular Biology. 2002, vol. 320, No. 2, pp. 415-428.

Van Der Hoorn JWA, et al. Alirocumab, a monoclonal antibody to PCSK-9, dose-dependently decreases atherosclerosis, improves plaque stability and shows additive effects with atorvastatin in APOE*3 Leiden.CETP mice. Atherosclerosis. 2014;235(2):e19; Abstract WS16.

Varbo et al., 'Remnant Cholesterol as a Casual Risk Factor for Ischemic Heart Disease.' Journal of the American College of Cardiology. 2013, 61(4):427-436.

Ward et al., 'Binding activities of a repertoire of single immunoglobulin variable domains secreted from *Escherichia coli*.' Nature. 1989, vol. 341, No. 6242, pp. 544-546.

Watanabe et al., 'Optimizing pH response of affinity between protein G and IgG Fc.' J. Biological Chemistry. 2009, 284(18):12373-12383.

Winter et al., 'Humanized Antibodies.' Immunology Today. 1993, 14(6):243-246.

Wong ND, et al. Residual Dyslipidemia According to LDL-C, non-HDL-C and Apolipoprotein B by Cardiovascular Risk Category in Statin Treated US Adults. J Clin Lipidol. 2014;8:323-324. Presented as a poster presentation at the National Lipid Association Scientific Sessions, May 1-4, 2014, Orlando, Florida, USA.

Wu et al., 'Receptor-mediated in vitro gene transformation by a soluble DNA carrier system.' Journal of Biological Chemistry. 1987, vol. 262, No. 10, pp. 4429-4432.

Abifadel, M. et al., 'Identification and characterization of new gain-of-function mutations in the PCSK9 gene responsible for autosomal dominant hypercholesterolemia'; Atherosclerosis 223 (2012) 394-400.

Hopkins et al., 'Familial Hypercholesterolemias: Prevalence, genetics, diagnosis and screening recommendations from the National Lipid Association Expert Panel on Familial Hypercholesterolemia.' Journal of Clinical Lipidology. 2011, 5(3):S9-S17.

Hopkins PN, et al. A randomized placebo-phase clinical trial with the monoclonal antibody alirocumab demonstrates reductions in low-density lipoprotein cholesterol in patients with proprotein convertase subtilisin/kexin type 9 gain-of-function mutations. Circulation. 2013;128:A17156.

Horton et al., 'Molecular biology of PCSK9: its role in LDL metabolism.' Trends Biochem Sci., 2007, 32(2): 71-77.

Hovingh GK, et al. Diagnosis and treatment of familial hypercholesterolaemia. Eur Heart J 2013;34(13):962-971.

Huston et al. 'Protein engineering of antibody binding sites: recovery of specific activity in an anti-digoxin single-chain Fv analogue produced in *Escherichia coli*.' Proceedings of the National Academy of Sciences. 1988, vol. 85, No. 16, pp. 5879.

Igawa et al., 'Antibody recycling by engineered pH-dependent antigen binding improves the duration of antigen neutralization.' Nature Biotechnology. 2010, 28(11):1203-1208.

International Preliminary Report on Patentability and Written Opinion of the International Searching Authority for International Application No. PCT/EP2012/051320, dated Jul. 30, 2013 (16 pages).

International Search Report and Written Opinion dated Apr. 16, 2015 for International Application No. PCT/US2014/060109 (19 pages).

International Search Report and Written Opinion dated Feb. 3, 2015 for International Application No. PCT/US2014/065149 (17 pages).

International Search Report and Written Opinion dated Jun. 12, 2015 for International Application No. PCT/US2015/020564 (20 pages).

International Search Report for International Application No. PCT/EP2012/051320, dated Sep. 21, 2012 (9 pages).

Ito et al., 'The His-probe method: effects of histidine residues introduced into the complementarity-determining regions of antibodies on antigen-antibody interactions at different pH values.' Federation of European Biochemical Societies. 1992, 309(1):85-88.

Jones P, et al. Pooled safety and adverse events in nine randomized, placebo-controlled, phase 2 and 3 clinical trials of alirocumab. J Am Coll Cardiol 2015;65(10_S):A1363.

Jorgensen et al., 'Genetically elevated non-fasting triglycerides and calculated remnant cholesterol as casual risk factors for myocardial infarction.' European Heart Journal. 2013, 34:1826-1833.

Kastelein JJ, et al. Efficacy and Safety of Alirocumab in Patients with Heterozygous Familial Hypercholesterolemia not Adequately Controlled with Current Lipid-Lowering Therapy: Design and Rationale of the ODYSSEY FH Studies. Cardiovasc Drugs Ther 2014; 28(3):281-289.

Kastelein JJP, et al. Efficacy and safety of alirocumab in patients with heterozygous familial hypercholesterolaemia not adequately controlled with current lipid-lowering therapy: results of ODYSSEY FH I and FH II studies; presented at ESC Congress; Aug. 31, 2014, abstract not published.

Kawashiri et al., 'Statin Therapy Improves Fractional Catabolic Rate of LDL without Affecting Impaired VLDL and VLDL Remnant Catabolism in Homozygous FH Patient Due to PCSK9 Gene Mutation: Evidence from Kinetic Study with Stable Isotope.' Circulation. 2012, 126(21):13869.

Kereiakes DJ, et al. Efficacy and safety of alirocumab in high cardiovascular risk patients with suboptimally controlled hypercholesterolemia on maximally tolerated doses of statins: the ODYSSEY Combo I study. Circulation. 2014;130:2119.

Kereiakes DJ, et al. Efficacy and safety of the PCSK9 inhibitor alirocumab among high cardiovascular risk patients on maximally tolerated statin therapy: the ODYSSEY Combo I study. Am Heart J. 2015. 169(6), 906-915.

Koren M, et al. Efficacy, safety and tolerability of 150 mg Q2W dose of the anti-PCSK9 mAb, REGN727/SAR236553: data from 3 phase 2 studies. Eur Heart J 2012;33(Abstract Supplement);37. Abstract 429.

(56) References Cited

OTHER PUBLICATIONS

Koren MJ, et al. Efficacy, safety and tolerability of alirocumab 150 mg Q2W, a fully human PCSK9 monoclonal antibody: a pooled analysis of 352 patients from phase 2. J Clin Lipidol 2013:7(3); 279-280.

Koren MJ, et al. Safety and efficacy of alirocumab 150 mg every 2 weeks, a fully human proprotein convertase subtilisin/kexin type 9 monoclonal antibody: a Phase II pooled analysis. Postgrad Med 2015;22:1-8.

Koren MJ, Kereiakes D, Pourfarzib R, Winegar D, Banerjee P, Hamon S, Hanotin C, McKenney JM. Effects of alirocumab, a fully human monoclonal antibody to proprotein convertase subtilisin/kexin type 9, on lipoprotein particle concentrations determined by nuclear magnetic resonance: substudy of a randomized double-blind phase II clinical trial. J Am Coll Cardiol 2014;63(12 Suppl 1): A1373.

Krauss RM, Banerjee P, Haman S, Hanotin C, Sasiela B, Koren MJ, McKenney JM. Alirocumab, a fully human monoclonal antibody to proprotein convertase subtilisin/kexin type 9, and its effects on lipoprotein subfractions determined by ion mobility. Circulation. 2014;130:A15525.

Kühnast S, et al. Alirocumab inhibits atherosclerosis, improves the plaque morphology, and enhances the effects of a statin. J Lipid Res. 2014;55(10):2103-2112.

Kühnast S, et al. PCSK-9 monoclonal antibody alirocumab dose-dependently decreases atherosclerosis development and enhances the effects of atorvastatin in APOE*3Leiden.CETP mice. Circulation. 2013;128:A15823.

Lagace et al., 'Secreted PCSK9 decreases the number of LDL receptors in hepatocytes and in liver of parabiotic mice.' J Clin Invest Am Soc Clin Invest, 2006, 116(11):2995-3005.

Lambert G, et al. Normalization of Low-Density Lipoprotein Receptor Expression in Receptor Defective Homozygous Familial Hypercholesterolemia by Inhibition of PCSK9 With Alirocumab. J Am Coll Cardiol. 2014;64(21):2299-2300.

Lambert G, et al. The PCSK9 decade. J Lipid Res 2012; 53(12):2515-2524.

Langer et al., 'Medical Applications of Controlled Release.' CRC Press, Boca Raton, Florida. 1974, pp. 115-138.

Langer et al., 'New methods of drug delivery.' Science. 1990, vol. 249, No. 4976, pp. 1527-1533.

Leuenberger et al., 'A Multilingual Glossary of Biotechnological Terms.' Recueil des Travaux Chimiques des Pays Bas. 1996, vol. 115, No. 7, pp. 382.

Lippi et al., 'Lipoprotein(a): from ancestral benefit to modern pathogen?' QJ Med., 2000, 93:75-84.

Lopez, Dayami, 'Inhibition of PCSK9 as a Novel Strategy for the Treatment of Hypercholesterolemia.' Drug News & Perspectives Abstract. 2008, 21(6): 323.

Lose et al., 'Evaluation of Proprotein Convertase Subtilisin/Kexin Type 9: Focus on Potential Clinical and Therapeutic Implications for Low-Density Lipoprotein Cholesterol Lowering.' Journal of Human Pharmacology and Drug Therapy. 2013, 33(4):447-460.

Lunven C, et al. A randomized study of the relative bioavailability, pharmacodynamics, and safety of alirocumab, a fully human monoclonal antibody to proprotein convertase subtilison/ kexin type 9, after single subcutaneous administration at three different injection sites in healthy subjects. J Am Coll Cardiol 2014;63(12 Suppl 1): A1377.

Lunven C, et al. A randomized study of the relative pharmacokinetics, pharmacodynamics and safety of alirocumab, a fully human monoclonal antibody to PCSK9, after single subcutaneous administration at three different injection sites in healthy subjects. Cardiovasc Ther. Dec. 2014.;32(6):297-301.

Maeda et al., 'pH-dependent receptor/ligand dissociation as a determining factor for intracellular sorting of ligands for epidermal growth factor receptors in rat hepatocytes.' J. Controlled Release. 2002, 82:71-82.

Marcovina et al., 'Lipoprotein(a) as a Risk Factor for Coronary Artery Disease.' The American Journal of Cardiology. 1998, 82(12A):57U-66U.

Maxwell et al., 'Adenoviral-mediated expression of Pcsk9 in mice results in a low-density lipoprotein receptor knockout phenotype.' PNAS. 2004, 101(18):7100-7105.

McKenney et al., 'Safety and Efficacy of a Monoclonal Antibody to Proprotein Convertase Subtilisin/Kexin Type 9 Serine Protease, SAR236553/REGN727, in Patients With Primary Hyperchoesterolemia Receiving Ongoing Stable Atorvastatin Therapy.' Journal of American College of Cardiology. 2012, 59(25):2344-2353.

McKenney J, et al. A randomized, double-blind, placebo-controlled trial of the safety and efficacy of a monoclonal antibody to proprotein convertase subtilisin/kexin type 9 serine protease, REGN727/SAR236553, in patients with primary hypercholesterolemia (NCT: 01288443). Presented as a late-breaking oral presentation at the American College of Cardiology (ACC) Annual Scientific Session, Mar. 24-27, 2012, Chicago, Illinois, USA.

Missouri DU Report, Drug Use Review Newsletter, vol. 8, No. 6, Oct./Nov. 2003 "Statin Therapy" pp. 1-9.

Moriarty PM, et al. Efficacy and safety of alirocumab, a monoclonal antibody to PCSK9, in statin-intolerant patients: Design and rationale of ODYSSEY Alternative, a randomized Phase 3 trial. J Clin Lipidol. 2014; 8(6):554-561.

Moriarty PM, et al. Homogeneity of treatment effect of REGN727/SAR236553, a fully human monoclonal antibody against PCSK9, in lowering LDL-C: data from three phase 2 studies. Eur Heart J. 2013;34(Suppl 1):doi:10.1093/eurheartj/eht307.142.

Moriarty PM, Thompson PD, Cannon CP, Guyton JR, Bergeron J, Zieve FJ, Bruckert E, Jacobson TA, Baccara• Dinet MT, Zhao J, Pordy R, Gipe R. ODYSSEY Alternative: Efficacy and safety of the proprotein convertase subtilisin/kexin type 9 monoclonal antibody, alirocurnab, versus ezetimibe, in patients with statin intolerance as defined by a placebo run-in and statin rechallenge arm. Circulation. 2014;130:2108.

Nakasako et al., 'The pH-dependent structural variation of complementarity-determining region H3 in the crystal structures of the Fv fragment from an anti-dansyl monoclonal antibody.' Journal of Molecular Biology. 1999, 291:117-134.

Naureckiene et al., 'Functional characterization of Narc 1, a novel proteinase related to proteinase K.' Archives of Biochemistry and Biophysics. 2003, 420:55-67.

Noguchi et al., 'The E32K variant of PCSK9 exacerbates the phenotype of familial hypercholesterolemia by increasing PCSK9 function and concentration in the circulation.' Atherosclerosis. 2010, 210(1):166-172.

Nordestgaard et al., 'Lipoprotein(s) as cardiovascular risk factor: current status.' European Heart Journal. 2010, 31:2844-2853.

Miettinen et al. (1971) "Cholesterol production in obesity," Circulation. 44(5):842-850.

Padlan et al., 'Identification of specificity-determining residues in antibodies.' The FASEB Journal. 1995, vol. 9, No. 1, pp. 133-139.

Parhofer, 'Lipoprotein(a): Medical Treatment Options for an Elusive Molecule.' Current Pharmaceutical Design. 2011, 17:871-876.

Park et al., 'Lipids and Lipoproteins: Post-transcriptional Regulation of Low Density Lipoprotein Receptor Protein by Proprotein Convertase Subtilisin/Kexin Type 9a in Mouse Liver.' J. Biol. Chem. 2004, 279: 50630-50638.

Partial International Search Report dated Nov. 6, 2014 for International Application No. PCT/US2014/040163.

Pearson, William R., 'Using the FASTA program to search protein and DNA sequence databases.' Computer Analysis of Sequence Data. 1994, pp. 307-331.

Pfizer: 'Safety and Tolerability of Multiple Doses of PF-04950615 (RN316) in Subjects With Hypercholesterolemia.' Nov. 3, 2012, XP002682100. Retrieved from the Internet: URL:http://clinicaltrials.gov/ct2/show?term=rn316&rank=2.

Pordy R, et al. Alirocumab, a fully human monoclonal antibody to proprotein convertase subtilisin/kexin type 9: therapeutic dosing in phase 3 studies. J Clin Lipidol 2013:7(3): 279.

Powell et al., 'Compendium of Excipients for Parenteral Formulations PDA.' Journal of Pharmaceutical Science and Technology. 1998, vol. 52, No. 5, pp. 238-311.

(56) References Cited

OTHER PUBLICATIONS

Qiu et al., 'Small antibody mimetics comprising two complementarity-determining regions and a framework region for tumor targeting.' Nature Biotechnology. 2007, vol. 25, No. 8, pp. 921-929.
Ramanathan A, et al. Role of alirocumab (proprotein convertase subtilisin/kexin type 9 antibody) on CD81 levels and hepatitis C virus entry into hepatocytes. Circulation. 2013;128: A12052.
Rashid et al., 'Decreased plasma cholesterol and hypersensitivity to statins in mice lacking Pcsk9.' PNAS. 2005, 102(15):5374-5379.
Ray KK, et al. Attainment of low-density lipoprotein cholesterol goals in patients at very high cardiovascular risk in the United Kingdom: results from a general practice population study. Value Health 2013;16(7): A513.
Reddy et al., 'Elimination of Fc receptor-dependent effector functions of a modified IgG4 monoclonal antibody to human CD4.' The Journal of Immunology. 2000, vol. 164, No. 4, pp. 1925-1933.
Reineke, Ulrich, 'Antibody epitope mapping using arrays of synthetic peptides.' Antibody Engineering. Humana Press. 2004, pp. 443-463.
Rey J, et al. Randomized, partial blind study of the pharmacodynamics, pharmacokinetics and safety of multiple subcutaneous doses of alirocumab, a fully human monoclonal antibody to proprotein convertase subtilisin/kexin type 9, administered every 4 weeks alone or in combination with ezetimibe or fenofibrate in healthy subjects. J Am Coll Cardiol 2014;63(12 Suppl 1):A1375.
Rhainds et al., 'PCSK9 inhibition and LDL cholesterol lowering: The biology of an attractive therapeutic target and critical review of the latest clinical trials.' Clinical Lipidology. 2012, 7(6):621-640.
Robinson JG, et al. Adverse events in patients with low-density lipoprotein cholesterol levels <25 or <15 mg/dL on at least two consecutive visits in fourteen randomized, controlled, clinical trials of alirocumab. J Am Coll Cardiol 2015;65(10_S): A1350.
Robinson JG, et al. Efficacy and safety of alirocumab as add-on therapy in high—cardiovascular-risk patients with hypercholesterolemia not adequately controlled with atorvastatin (20 or 40 mg) or rosuvastatin (10 or 20mg): design and rationale of the ODYSSEY Options studies. Clin Cardiol. 2014; 37(10): 597-604.
Robinson JG, et al. Efficacy and Safety of Alirocumab in Reducing Lipids and Cardiovascular Events. N Eng J Med. 2015; vol. 372 No. 16; 1489-1499.
Robinson JG, et al. Long-term safety, tolerability and efficacy of alirocumab versus placebo in high cardiovascular risk patients: first results from the ODYSSEY Long Term study in 2,341 patients; presented at ESC Congress Aug. 31, 2014, abstract not published.
Robinson JG, et al. Long-term safety, tolerability and efficacy of alirocumab versus placebo in high cardiovascular risk patients: first results from the ODYSSEY Long Term study in 2,341 patients. Circulation. 2014;130:2120.
Roth EM, et al. A 24-week study of alirocumab monotherapy versus ezetimibe: The first phase 3 data of a proprotein convertase subtilisin/kexin type 9 inhibitor. J Am Coll Cardiol 2014;63(12 Suppl 1).
Roth EM, et al. Atorvastatin with or without an antibody to PCSK9 in primary hypercholesterolemia. N Engl J Med. 2012;367(20):1891-1900.
Roth EM, et al. Monotherapy with the PCSK9 inhibitor alirocumab versus ezetimibe in patients with hypercholesterolemia: Results of a 24 week, double-blind, randomized Phase 3 trial. Int J Cardiol. 2014;176(1):55-61.
Roth EM, et al. ODYSSEY Mono: effect of alirocumab 75 mg subcutaneously every 2 weeks as monotherapy versus ezetimibe over 24 weeks. Future Cardiol 2015;11(1):27-37.
Roth EM, et al. The effects of co-administering a monoclonal antibody to proprotein convertase subtilisin/kexin type 9 serine protease, REGN727/SAR236553, with 10 and 80 mg atorvastatin compared to 80 mg atorvastatin alone in patients with primary hypercholesterolemia (NCT: 01288469). J Am Coll Cardiol 2012;59:E1620.
Roth et al. Alirocumab for hyperlipidemia: physiology of PCSK9 inhibition, pharmacodynamics and Phase I and II clinical trial results of a PCSK9 monoclonal antibody. Future Cardiology. Mar. 2014; vol. 10, No. 2. pp. 183-199.
Sarkar et al., 'Rational cytokine design for increased lifetime and enhanced potency using pH-activated "histidine switching".' Nature Biotechnology. 2002, 20:908-913.
Schwartz GG, et al. Effect of alirocumab, a monoclonal antibody to pcsk9, on long-term cardiovascular outcomes following acute coronary syndromes: Rationale and design of the odyssey outcomes trial. Am Heart J. 2014;168(5):682-689.
Sefton, Michael V., 'Implantable Pumps.' Critical Reviews in Biomedical Engineering. 1986, vol. 14, No. 3, pp. 201-240.
Seidah et al., 'The secretory proprotein convertase neural apoptosis-regulated convertase 1 (NARC-1): liver regeneration and neuronal differentiation.' PNAS. 2003,100(3):928-933.
Shao W. New Therapies for Lowering LDL-C: Targeting PCSK9. Abstract of oral presentation at the Sino-American Pharmaceutical Professionals Association—2014 Scientific Symposium, Apr. 26, 2014, New Jersey, USA.
Shields et al., 'Lack of fucose on human IgG1 N-linked oligosaccharide improves binding to human FcγRIII and antibody-dependent cellular toxicity.' Journal of Biological Chemistry. 2002, vol. 277, No. 30, pp. 26733-26740.
Soutar, Anne, 'Unexpected Roles for PCSK9 in Lipid Metabolism.' Current Opinion in Lipodology. 2011, vol. 22, pp. 192-196.
Steen D, et al. Attainment of Lipid Levels in Patients at High Cardiovascular Risk: Results from a U.S. Managed Care Population Study. Circulation. 2014;130:A19949.
Steen D, et al. Cardiovascular Event Rates in a High-Risk Managed Care Population in the United States. J Am Coll Cardiol 2015;65(10_S):A1647.
Stein E, et al. Safety and efficacy of a monoclonal antibody to PCSK9, REGN727/SAR236553, in statin-treated heterozygous familial hypercholesterolemia patients. Presented as an oral presentation at the 80th European Atherosclerosis Society (EAS) Congress, May 25-28, 2012, Milan, Italy. Abstract 1398.
Stein EA, et al. One year open-label treatment with alirocumab 150 mg every two weeks in heterozygous familial hypercholesterolemic patients. J Am Coll Cardiol 2014;63(12 Suppl 1): A1371.
Stein et al., 'Effect of a monoclonal antibody to PCSK9 on LDL cholesterol.' Obstetrical and Gynecological Survey. 2012, 67(7):413-414.
Stein et al., 'Effect of a Monoclonal Antibody to PCSK9 on LDL Cholesterol.' New England Journal of Medicine. 2012, 366:1108-1118.
Stein et al., 'Effect of a monoclonal antibody to PCSK9, REGN727/SAR236553, to reduce low-density lipoprotein cholesterol in patients with heterozygofamilial hypercholesterolemia on stable statin dose with or without ezetimibe therapy: a phase 2 randomized controlled trial.' The Lancet. 2012, 380:29-36.
Stein et al., 'Potential of proprotein Convertase Subtilisin/Kexin Type 9 Based Therapeutics.' Current Atherosclerosis Reports. 2013, 15(310):1-14.
Stroes E, et al. Efficacy and safety of different dosing regimens of alirocumab (starting doses of 75 mg every two weeks and 150 mg every four weeks) versus placebo in patients with hypercholesterolemia not treated using statins: the ODYSSEY Choice II study. J Am Coll Cardiol 2015;65(10_S):A1370.
Sullivan, et al. Effect of a Monoclonal Antibody to PCSK9 on Low-Density Lipoprotein Cholesterol Levels in Statin-Intolerant Patients. JAMA. Dec. 19, 2012. vol. 308, No. 23. pp. 2497-2506.
Swergold G, et al. Inhibition of proprotein convertase subtilisin/kexin type 9 with a monoclonal antibody REGN727/SAR236553, effectively reduces low-density-lipoprotein cholesterol, as mono or add-on therapy in heterozygous familial and non-familial hypercholesterolemia. Circulation 2011;124:Abstract A16265.
Swergold G, et al. REGN727/SAR236553, a fully human proprotein convertase subtilisin kexin 9 (PCSK9) monoclonal antibody: effects on safety and lipid and lipoprotein profiles when administered subcutaneously. J Am Coll Cardiol 2011;57(1451):E2023.
Swergold G, et al. REGN727/SAR236553, a fully-human monoclonal antibody to proprotein convertase subtilisin kexin 9 (PCSK9), decreases ApoB and non-HDL-C when administered intravenously to healthy volunteers. J Clin Lipidol 2011;5(3):219.

(56) References Cited

OTHER PUBLICATIONS

Swergold G, et al. Safety, lipid, and lipoprotein effects of REGN727/SAR236553, a fully human proprotein convertase subtilisin kexin 9 (PCSK9) neutralizing monoclonal antibody administered intravenously to healthy volunteers. Circulation 2010;122:Abstract A23251.

Swergold GD, et al. Identification and characterization of patients with autosomal dominant hypercholesterolemia caused by gain-of-function mutations in proprotein convertase subtilisin/kexin type 9 and comparison with patients with Familial Hypercholesterolemia (FH) and Familial Defective apolipoprotein B (FDB). Abstract of a poster presentation at the American Society of Human Genetics (ASHG), Oct. 22-26, 2013, Boston, USA.

Teramoto T, et al. Efficacy and safety of alirocumab in Japanese patients with hypercholesterolemia on stable statin therapy: first data with the 75 mg every two weeks dose. Circulation. 2014;130:A13651.

Anthem (Sep. 21, 2015) "Proprotein Convertase Subtilisin Kexin 9 (PCSK9) Inhibitors," Policy No. DRUG.00078. American Medical Association. Accessible on the Internet at URL: https://www.anthem.com/ca/medicalpolicies/policies/mp_pw_c182635.htm. [Last Accessed Apr. 27, 2016] 8 pages.

Dube et al. (Apr. 2012) "Lipoprotein(a): more interesting than ever after 50 years," Curr. Opin. Lipidol. 23:133-140.

Hiriyama et al. (Jan. 1, 2014) "Effects of evolocumab (AMG 145), a monoclonal antibody to PCSK9, in hypercholesterolemic, statin-treated Japanese patients at high cardiovascular risk—primary results from the phase 2 YUKAWA study," Circulation Journal. 78(5):1073-1082.

Junghans et al. (1990) "Anti-Tac-H, a Humanized Antibody to the Interleukin 2 Receptor with New Features for Immunotherapy in Malignant and Immune Disorders," Cancer Research. 50:1495-1502.

Konrad et al. (2011) "Effects of currently prescribed LDL-C-lowering drugs on PCSK9 and implications for the next generation of LDL-C-lowering agents," Lipids in Health and Disease. 10(1):38.

Koschinsky et al. (Dec. 2014) "Lipoprotein(a): an important cardiovascular risk factor and a clinical conundrum," Endocrinol. Metab. Clin. North Am. 43:949-962.

Lamon-Fava et al. (Apr. 7, 2011) "Lipoprotein(a) levels, apo(a) isoform size, and coronary heart disease risk in the Framingham Offspring Study," J. Lipid Res. 52:1181-1187.

Steinberg et al. (2009) "Inhibition of PCSK9: A powerful weapon for achieving ideal LDL cholesterol levels," Proceedings of the National Academy of Sciences USA. 106(24):9546-9547.

Stroes et al. (Jun. 17, 2014) "Anti-PCSK9 Antibody Effectively Lowers Cholesterol in Patients With Statin Intolerance," J. Am. Coll. Cardiol. 63(23):2541-2548.

Tsimikas et al. (Jul. 22, 2015) "Antisense therapy targeting apolipoprotein(a): A randomised double-blind, placebo-controlled phase 1 study," Lancet. 386:1472-1483.

International Search Report with Written Opinion corresponding to International Patent Application No. PCT/EP2012/057890, dated Aug. 28, 2012, 14 pages.

International Search Report with Written Opinion corresponding to International Patent Application No. PCT/US2015/040754, dated Oct. 14, 2015, 15 pages.

International Search Report with Written Opinion corresponding to International Patent Application No. PCT/US2015/040765, dated Nov. 26, 2015, 15 pages.

Third Party Observations corresponding to European Patent Application No. 12761864.3, dated Feb. 24, 2016, 9 pages.

Abifadel et al., 'Mutations and polymorphisms in the proprotein convertase subtilisin kexin 9 (PCSK9) gene in cholesterol metabolism and disease.' Human Mutation. 2009, 30(4):520-529.

Abifadel et al., 'Mutations in PCSK9 cause autosomal dominant hypercholesterolemia.' Nature Genetics. 2003, 34(2):154-156.

Alborn et al., 'Serum proprotein convertase subtilisin Kexin type 9 is correlated directly with serum LDL cholesterol.' Clinical Chemistry. 2007, 53(10):1814-1819.

Almagro et al., 'Humanization of antibodies.' Frontiers in Bioscience. 2008, vol. 13, pp. 1619-1633.

Al-Mashhadi et al., 'Atherosclerosis: Familial hypercholesterolemia and atherosclerosis in clones minipigs created by DNA transposition of a human PCSK9 gain-of-function mutant.' Science Translation Medicine, American Association for the Advancement of Science. 2013, 5(166):44-53.

Altschul et al., 'Basic local alignment search tool.' Journal of Molecular Biology. 1990, vol. 215, No. 3, pp. 403-410.

Amgen: 'Ascending Multiple Dose Study to Evaluate the Safety, Tolerability, Pharmacokinetics and Pharmacodynamics of AMG 145 in Subjects With Hyperlipidemia on Stable Doses of a Statin'. May 27, 2010, XP002682099. Retrieved from the Internet: URL:http://clinicaltrials.gov/ct2/show/nct01133522?term=amg+145&rank=2 Accessed on Aug. 6, 2014.

Angal et al., 'A single amino acid substitution abolishes the heterogeneity of chimeric mouse/human (IgG4) antibody.' Molecular Immunology. 1993, vol. 30, No. 1, pp. 105-108.

Annex to Form PCT/ISA/206—PCT/US2009/068013,Communication Relating to the Results of the Partial International Search, dated Mar. 10, 2010.

Anonymous: A Randomized, Double-Blind, Placebo-Controlled, Parallel Group Study to Evaluate the Effect of Alirocumab (SAR236553/REGN727) on the Occurrence of Cardiovascular Events in Patients Who Have Recently Experienced an Acute Coronary Syndrome. Archive from ClinicalTrials.gov for NCT01663402 on Mar. 11, 2014 (3 pages).

Anonymous: Long-term Safety and Tolerability of Alirocumab SAR236553 (REGN727) in High Cardiovascular Risk Patients With Hypercholesterolemia Not Adequately Controlled With Their Lipid Modifying Therapy: A Randomized, Double-Blind, Placebo-Controlled Study. Archive from ClinicalTrials.gov for NCT01507831 on Jun. 27, 2013 (3 pages).

Attie et al., 'Dual regulation of the LDL receptor—Some clarity and new questions.' Cell Metabolism. 2005, 5:290-292.

Bays H., et al. Efficacy and safety of combining alirocumab with atorvastatin or rosuvastatin versus statin intensification or adding ezetimibe in high cardiovascular risk patients: Odyssey Options I and II. Circulation. 2014;130:2105-2126.

Bays H., et al. PCSK9 Inhibitor Alirocumab as Add-on to Atorvastatin versus Other Lipid Treatment Strategies in Patients at High CVD Risk: ODYSSEY Options I. Circulation. 2014;130:A16194.

Benjannet et al., 'The Proprotein Convertase (PC) PCSK9 Is Inactivated by Furin and/or PC5/6A.' J. Biological Chemistry. 2006, 281(41): 30561-30572.

Bird et al., 'Single-chain antigen-binding proteins.' Science. 1988, vol. 242, No. 4877, pp. 423-426.

Altschul, S.F. et al., Gapped Blast and PSI-Blast: a new generation of protein databse search programs; Nucleic Acids Research 1997, vol. 25, No. 17, 3389-3402.

Cannon CP, et al. Efficacy and safety of alirocumab in high cardiovascular risk patients with inadequately controlled hypercholesterolaemia on maximally tolerated daily statin: results from the ODYSSEY Combo II study; presented at ESC Congress; Aug. 31, 2014, abstract not published.

Cannon CP, et al. Efficacy and safety of alirocumab in high cardiovascular risk patients with inadequately controlled hypercholesterolaemia on maximally tolerated doses of statins: the ODYSSEY Combo II randomized controlled trial Eur Heart J.; May 14, 2015;36(19):1186-94.

Catapano AL, et al. The safety of therapeutic monoclonal antibodies: implications for cardiovascular disease and targeting the PCSK9 pathway. Atherosclerosis 2013;228(1):18-28.

Chan et al., 'A Proprotein Convertase subtilisin/kexin type 9 Neutralizing Antibody Reduces Serum Cholesterol in Mice and Nonhuman primates.' PNAS. 2009, vol. 106, No. 24, pp. 9820-9825.

Chaparro-Riggers et al., 'Increasing serum half-life and extending cholesterol lowering in vivo by engineering antibody with pH-sensitive binding to PCSK9.' J. Biological Chemistry. 2012, 287(14):11090-11097.

Chinese Patent Application No. 201280015477.6, Office Action dated Dec. 2, 2014 with English summary, 12 pages.

(56) References Cited

OTHER PUBLICATIONS

Chinese Patent Application No. 201280015571.1, Office Action dated Sep. 3, 2014 with English summary, 12 pages.
Colhoun HM, et al. Efficacy and safety of alirocumab, a fully human PCSK9 monoclonal antibody, in high cardiovascular risk patients with poorly controlled hypercholesterolemia on maximally tolerated doses of statins: rationale and design of the ODYSSEY Combo I and II trials. BMC Cardiovasc Disord. 2014;14(1):121.
Costet, PCSK9 inhibitors as LDL cholesterol-lowering agents: Rationale, concerns and preliminary outcomes. Drugs of the Future. May 1, 2012. vol. 37, No. 5, pp. 331-341.
Duff et al. Biochem Journal, the Biochemical Society, vol. 419, No. 3, May 1, 2009; pp. 577-584.
Dufour R, et al. Effect of REGN727/SAR236553 PCSK9 fully human monoclonal antibody in patients with elevated triglycerides/low high-density lipoprotein cholesterol: data from three phase 2 studies. Circulation 2012;126:Abstract A16127.
European Patent Application No. 12701015.5, Communication pursuant to Article 94(3) EPC dated May 30, 2014, 8 pages.
European Patent Application No. 12701015.5, Communication pursuant to Article 94(3) EPC dated Apr. 24, 2015, 9 pages.
European Patent Application No. 12701742.4, Communication pursuant to Article 94(3) EPC dated Jun. 1, 2015, 10 pages.
European Patent Application No. 12701742.4, Communication pursuant to Article 94(3) EPC dated May 28, 2014, 8 pages.
Fallon et al., 'Increased endosomal sorting of ligand to recycling enhances potency of an intereukin-2 analog.' J. Biological Chemistry. 2000, 275(10):6790-6797.
Farnier M, et al. Relationship between alirocumab, PCSK9 and LDL-C levels: results from the ODYSSEY Mono Phase 3 trial of alirocumab 75 mg every 2 weeks. Atherosclerosis. 2014;235(2):e34—e35; Abstract MP02E.
Farnier, Michel, 'The role of proprotein convertase subtilisin/kexin type 9 in hyperlipidemia: Focus on therapeutic implications.' American Journal of Cardiovascular Drugs. 2011, 11(3):145-152.
Fasano et al., 'Activity of Gain-of-Function PCSK9 Mutants on LDLR Correlates with Total-Cholesterol Values in ADH patients.' NMCD Nutrition Metabolism and Cardiovascular Diseases. 2008, 18(1):S46.
Foody J, et al. Attainment of low-density lipoprotein cholesterol goals in patients at high cardiovascular risk: results from a managed care population study. Circulation. 2013;128: A17254.
Foote et al., 'Antibody Framework Residues Affecting the Conformation of the Hypervariable Loops.' J. Mol. Biol. 1992, 224:487-499.
Gaudet D, et al. Alirocumab, a fully human monoclonal antibody to PCSK9, reduces high plasma Lp(a) concentration: pooled analysis of 352 patients from phase 2. J Clin Lipidol 2013:7(3): 283-284.
Gaudet D, et al. Effect of Alirocumab, a Monoclonal Proprotein Convertase Subtilisin/Kexin 9 Antibody, on Lipoprotein(a) Concentrations (a Pooled Analysis of 150 mg Every 2 Weeks Dosing from Phase 2 Trials). Am J Cardiol. 2014;114(5):711-715.
Gaudet D, et al. Effect of SAR236553/REGN727 fully human monoclonal anti-proprotein convertase subtilisin/kexin type 9 antibody on plasma lipoprotein(a) concentrations: pooled analysis from three phase 2 studies (NCT:01266876; 01288469; 01288443). Circulation 2012;126:Abstract A16125.
Ginsberg HN, et al. ODYSSEY High FH: efficacy and safety of alirocumab in patients with severe heterozygous familial hypercholesterolemia. Circulation. 2014;130:2119.
Gonnet et al. 'Exhaustive matching of the entire protein sequence database.' Science. 1992, vol. 256, No. 5062, pp. 1443-1445.
Grozdanov et al., 'Expression and localization of PCSK9 in rat hepatic cells.' Biochem. Cell. Biol., 2006, 84:80-92.
Gusarova V, et al. Fully human antibody that blocks PCSK9 demonstrates reduction in LDL-C preclinically and in early clinical trials.Abstract of oral presentation at the Keystone Symposia on Molecular and Cellular Biology, Mar. 25-30, 2012, Montana, USA.

Gusarova V, et al. Reduction of LDL cholesterol by a monoclonal antibody to PCSK9 in rodents and nonhuman primates. Clin Lipidol 2012;7(6):737-743.
Haddley et al. Alirocumab Anti-Proprotein Convertase 9 (PCSK9) Mab Treatment of Hypercholesterolemia. Drugs of the Future; Apr. 1, 2013. vol. 38, No. 4. pp. 214-219.
Heap et al., 'Analysis of a 17-amino acid residue, virus-neutralizing microantibody.' Journal of General Virology. 2005, vol. 86, No. 6, pp. 1791-1800.
Hochleitner et al. 'Characterization of a discontinuous epitope of the human immunodeficiency virus (HIV) core protein p24 by epitope excision and differential chemical modification followed by mass spectrometric peptide mapping analysis.' Protein Science. 2000, vol. 9, No. 3, pp. 487-496.
Holliger et al., 'Diabodies : small bivalent and bispecific antibody fragments.' Proceedings of the National Academy of Sciences. 1993, vol. 90,No. 14, pp. 6444-6448.
Bambauer et al. (2003) "Low-density Lipoprotein Apheresis: An Overview," Therapuetic Apherisis and Dialysis. 7(4):382-390.
Bee et al. (2009) "Precipitation of a monoclonal antibody by soluble tungsten," Journal of Pharmaceutical Sciences. 98(9):3290-3301.
Beliard et al. (Mar. 3, 2014) "Improvement in LDL-cholesterol levels of patients with familial hypercholesterolemia: can we do better? Analysis of results obtained during the past two decades in 1669 French subjects," Atherosclerosis. 234:136-141.
Berthold et al. (Jan. 2013) "Hyperlipoproteinemia(a): Clinical significance and treatment options," Atherosclerosis Supplements 14:1-5.
Boerwinkle et al. (1992) "Apolipoprotein(a) Gene Accounts for Greater Than 90% of the Variation in Plasma Lipoprotein(a) Concentrations," J. Clin. Invest. 90:52-60.
Borberg (Apr. 2013) "The lower the better: Target values after LDL-Apheresis and semi-selective LDL-elimination therapies," Transfusion and Apheresis Science. 48:203-206.
Demant et al. (2001) "The metabolism of lipoprotein(a) and other apolipoprotein B-containing lipoproteins: a kinetic study in humans," Atherosclerosis. 157:325-339.
Gaudet et al. (Sep. 29, 2016) "Effect of Alirocumab on Lipoprotein(a) Over ≥1.5 Years (from the Phase 3 ODYSSEY Program)," Am. J. Cardiol. 119:40-46.
Hopkins et al. (2007) "The Lund-Mackay staging system for chronic rhinosinusitis: How is it used and what does it predict?" Otolaryngology—Head and Neck Surgery. 137(4):555-561.
Huijgen et al. (2010) "Two years after molecular diagnosis of familial hypercholesterolemia: majority on cholesterol-lowering treatment but a minority reaches treatment goal," PLoS One. 5(2):e9220. pp. 1-7.
Kolata (Jul. 27, 2015) "Praluent Looks Cheap to Those with Extreme Cholesterol" The New York Times. Accessible on the Internet at URL: www.nytimes.com/2015/07/28/health/praluent-looks-cheap-to-those-with-extreme-cholesterol.html. [Last Accessed on Sep. 5, 2017].
Koschinsky et al. (2009) Clinical Lipidology: A Companion to Braunwald's Heart Disease. Ed: Ballantyne. pp. 136-143.
Leebmann et al. (Dec. 17, 2013) Circulation "Lipoprotein Apheresis in Patients With Maximally Tolerated Lipid-Lowering Therapy, Lipoprotein(a)—Hyperlipoproteinemia, and Progressive Cardiovascular Disease," Circulation. 128(24):2567-2576.
McPherson (2013) "Remnant Cholesterol: Non-(HDL-C + LDL-C) as a Coronary Artery Disease Risk Factor," Journal of the American College of Cardiology. 61(4):437-439.
Meehan et al. (1996) "A microinfusor device for the delivery of therapeutic levels of peptides and macromolecules," Ccontrolled Release 46:107-116.
Moon (2007) "Lipoprotein(a) and LDL Particle Size are Related to the Severity of Coronary Artery Disease", Cardiology 108:282-289.
Moriarty (May 2015) "PCSK9 Inhibitors and their Effect on Patients who are Stalin Intolerant or Receiving Lipoprotein-apheresis," The 10th International Society for Apheresis Congress. May 13-16, 2015. Cancun, Mexico.
Neil et al. (2004) "Established and emerging coronary risk factors in patients with heterozygous familial hypercholesterolaemia," Heart. 90(12):1431-1437.

(56) References Cited

OTHER PUBLICATIONS

Pijlman et al. (2010) "Evaluation of cholesterol lowering treatment of patients with familial hypercholesterolemia: a large cross-sectional study in The Netherlands," Atherosclerosis. 209:189-194.
Regeneron and Sanofi (Nov. 5, 2012) "IR Conference Call on PCSK9: SAR236553/REGN727 PCSK9 Antibody for Hypercholesterolemia Phase 3 ODYSSEY Program Underway," Accessible on the Internet at URL: www.sanofi.com/Images/31341_2012-11-05_PCSK9_call.pdf. pp. 1-30. [Last Accessed on Sep. 5, 2017].
Saeedi et al. (Mar. 31, 2016) "Lipoprotein (a), an independent cardiovascular risk marker," Clinical Diabetes and Endocrinology. 2:7. pp. 1-6.
Sahebkar et al. (Aug. 8, 2013) "New LDL-Cholesterol Lowering Therapies: Pharmacology, Clinical Trials, and Relevance to Acute Coronary Syndromes," Clinical Therapeutics. 35(8)1082-1098.
Shoji et al. (1998) "Intermediate-Density Lipoprotein as an Independent Risk Factor for Aortic Atherosclerosis in Hemodialysis Patients," J. Am. Soc. Nephrol. 9:1277-1284.
Tavori et al. (Oct. 11, 2013) "Loss of Plasma Proprotein Convertase Subtilisin/Kevin 9 (PCSK9) After Lipoprotein Apheresis," Circulation Research. 113(12):1290-1295.
Van Wissen et al. (2003) "Long term statin treatment reduces lipoprotein(a) concentrations in heterozygous familial hypercholesterolaemia," Heart. 89(8):893-896.
Walji (2013) "Lipoprotein Apheresis for the Treatment of Familial Hypercholesterolemia," Clinical Lipidology. 8(5):573-586.
Wang et al. (2007) "Antibody Structure, Instability, and Formulation," Journal of Pharmaceutical Sciences. 96(1):1-26.
Warnick et al. (2008) "Standardization of Measurements for Cholesterol, Triglycerides, and Major Lipoproteins," Lab Med. 39(8):481-490.
International Search Report with Written Opinion corresponding to International Patent Application No. PCT/US2014/040050, dated Oct. 6, 2014.
Rahilly-Tierney et al. (2009) "Low-Density Lipoprotein Reduction and Magnitude of Cardiovascular Risk Reduction," Prev. Cardiol. 12(2):80-87.
Sanofi and Regeneron Report Positive Top-line Results with Alirocumab from First Phase 3 Study of a PCSK9 Inhibitor for LDL Cholesterol Reduction, Oct. 16, 2013, Retrieved from the Internet, [Last accessed Dec. 4, 2018: http://www.epresspack.net/mmr/sanofi-pcsk9-1st-phase3-results/].
Sanofi and Regeneron Announce Collaboration with American College of Cardiology for PCSK9 Inhibitor Clinical Program, Dec. 19, 2013, Retrieved from the Internet, [Last accessed Dec. 4, 2018: https://newsroom.regeneron.com/news-releases/news-release-details/sanofi-and-regeneron-announce-collaboration-american-college].
Australian Public Assessment Report for Alirocumab (rch) (2016) Australian Government Department of Health, Therapeutic Goods Administration. Sponsor: Sanofi-Aventis Australia Pty Ltd. 93 pp.
Ni et al. (2010) "A proprotein convertase subtilisin-like/kexin type 9 (PCSK9) C-terminal domain antibody antigen-binding fragment inhibits PCSK9 internalization and restores low density lipoprotein uptake," J Biol Chem. 285(17):12882-91.

* cited by examiner

METHODS FOR TREATING PATIENTS WITH HETEROZYGOUS FAMILIAL HYPERCHOLESTEROLEMIA (HEFH) WITH AN ANTI-PCSK9 ANTIBODY

RELATED APPLICATIONS

This application claims the benefit of U.S. Provisional Application No. 62/080,717, filed on Nov. 17, 2014, U.S. Provisional Application No. 62/043,144, filed on Aug. 28, 2014, U.S. Provisional Application No. 62/025,362, filed on Jul. 16, 2014, and European Patent Application No. 15305419.2, filed on Mar. 23, 2015, the contents of which are incorporated herein by reference in their entirety.

FIELD OF THE INVENTION

The present invention relates to the field of therapeutic treatments of diseases and disorders that are associated with elevated levels of lipids and lipoproteins. More specifically, the invention relates to the use of PCSK9 inhibitors to treat patients with heterozygous familial hypercholesterolemia who are not adequately controlled by maximum tolerated dose statin therapy with or without other lipid lowering therapy.

BACKGROUND

Heterozygous familial hypercholesterolemia (heFH) is a hereditary lipid metabolism disorder that predisposes affected individuals to cardiovascular (CV) disease. Patients with heFH typically have very high low-density lipoprotein cholesterol (LDL-C) levels—often >190 mg/dL at the time of diagnosis—that are associated with high risk for premature CV disease. Findings from observational studies have shown that the risk of coronary heart disease (CHD) is reduced in heFH patients receiving statin therapy; however, even with treatment, the risk of CHD is still greater in heFH patients than in the general population. Despite the availability of lipid-lowering therapy (LLT), approximately 80% of patients with heFH do not reach the recommended levels of LDL-C. Given the increased CV risk in the heFH population, there is a need to provide patients with more intensive cholesterol-lowering therapy.

Current LDL-C lowering medications include statins, cholesterol absorption inhibitors (e.g., ezetimibe [EZE]), fibrates, niacin, and bile acid sequestrants. Statins are the most commonly prescribed, as they have shown a greater ability to lower LDL-C and reduce CHD events. However, many patients at risk of cardiovascular disease (CVD) have poorly controlled low-density lipoprotein cholesterol (LDL-C) despite statin therapy.

BRIEF SUMMARY OF THE INVENTION

The present invention provides methods for treating hypercholesterolemia. In particular, the methods of the present invention are useful for treating patients with heterozygous familial hypercholesterolemia who are not adequately controlled by maximum tolerated dose statin therapy with or without other lipid lowering therapy.

According to one aspect, the methods of the present invention comprise administering one or more doses of a PCSK9 inhibitor to a patient with heterozygous familial hypercholesterolemia who is not adequately controlled by maximum tolerated dose statin therapy with or without other lipid lowering therapy (i.e., hypercholesterolemia that is not adequately controlled by maximum tolerated dose statin therapy in the absence of a PCSK9 inhibitor, with or without other lipid modifying therapy). According to certain embodiments of the present invention, the PCSK9 inhibitor is administered to the patient with heterozygous familial hypercholesterolemia as an add-on therapy to the patient's existing statin therapy with or without other lipid lowering therapy.

According to another aspect, the methods of the present invention comprise selecting a patient with heterozygous familial hypercholesterolemia who is not adequately controlled by maximum tolerated dose statin therapy with or without other lipid lowering therapy (e.g., a maximum tolerated dose statin therapy), and administering to the patient one or more doses of a PCSK9 inhibitor in combination with (i.e., "on top of") the statin therapy.

Another aspect of the invention includes a method for treating a patient with heterozygous familial hypercholesterolemia (heFH) who is not adequately controlled by maximum tolerated dose statin therapy with or without other lipid lowering therapy by administering one or more doses of a proprotein convertase subtilisin/kexin type 9 (PCSK9) inhibitor to the patient, wherein the patient exhibits inadequate control of the hypercholesterolemia despite treatment with the maximum tolerated dose statin therapy with or without other lipid lowering therapy in the absence of the PCSK9 inhibitor.

Another aspect of the invention includes a method for reducing low-density lipoprotein cholesterol (LDL-C) in a patient with heterozygous familial hypercholesterolemia (heFH) who is not adequately controlled by maximum tolerated dose statin therapy with or without other lipid lowering therapy by administering one or more doses of a proprotein convertase subtilisin/kexin type 9 (PCSK9) inhibitor to the patient, wherein the patient exhibits inadequate control of the hypercholesterolemia despite treatment with the maximum tolerated dose statin therapy with or without other lipid lowering therapy in the absence of the PCSK9 inhibitor.

Another aspect of the invention includes a method for treating hypercholesterolemia in a patient with heterozygous familial hypercholesterolemia (heFH) who is not adequately controlled by maximum tolerated dose statin therapy with or without other lipid lowering therapy by administering one or more doses of a proprotein convertase subtilisin/kexin type 9 (PCSK9) inhibitor to the patient, wherein the patient exhibits inadequate control of the hypercholesterolemia despite treatment with the maximum tolerated dose statin therapy with or without other lipid lowering therapy in the absence of the PCSK9 inhibitor.

Another aspect of the invention includes a method for improving the serum level of one or more lipid components in a patient with heterozygous familial hypercholesterolemia (heFH) who is not adequately controlled by maximum tolerated dose statin therapy with or without other lipid lowering therapy by administering one or more doses of a proprotein convertase subtilisin/kexin type 9 (PCSK9) inhibitor to the patient, wherein the patient exhibits inadequate control of the lipid component despite treatment with the maximum tolerated dose statin therapy with or without other lipid lowering therapy in the absence of the PCSK9 inhibitor. In certain aspects, the invention provides a decrease in the serum level of a lipid component selected from the group consisting of LDL-C, Apo B, non-HDL-C, total cholesterol, Lp(a), and triglycerides. In certain aspects, the invention provides an increase in the serum level of a lipid component selected from the group consisting of HDL-C and Apo A1.

In certain aspects of the invention, the diagnosis of heFH is made by either genotyping or by clinical criteria. In some aspects, the clinical criteria is either the Simon Broome Register Diagnostic Criteria for Heterozygous Familial Hypercholesterolemia, or the WHO/Dutch Lipid Network criteria with a score >8.

In certain aspects of the invention, the PCSK9 inhibitor is an antibody or an antigen-binding fragment thereof that specifically binds PCSK9.

In certain aspects of the invention, the antibody or antigen-binding fragment thereof comprises the heavy and light chain complementarity determining regions (CDRs) of a heavy chain variable region/light chain variable region (HCVR/LCVR) amino acid sequence pair selected from the group consisting of SEQ ID NOs: 1/6 and 11/15. In some aspects, the antibody or antigen-binding fragment thereof comprises heavy and light chain CDR amino acid sequences having SEQ ID NOs:12, 13, 14, 16, 17, and 18. In some aspects, the antibody or antigen-binding fragment thereof comprises an HCVR having the amino acid sequence of SEQ ID NO:11 and an LCVR having the amino acid sequence of SEQ ID NO:15. In some aspects, the antibody or antigen-binding fragment thereof comprises heavy and light chain CDR amino acid sequences having SEQ ID NOs:2, 3, 4, 7, 8, and 10. In some aspects, the antibody or antigen-binding fragment thereof comprises an HCVR having the amino acid sequence of SEQ ID NO:1 and an LCVR having the amino acid sequence of SEQ ID NO:6.

In certain aspects of the invention, the antibody or antigen-binding fragment thereof binds to the same epitope on PCSK9 as an antibody comprising heavy and light chain CDR amino acid sequences having SEQ ID NOs:12, 13, 14, 16, 17, and 18; or SEQ ID NOs: 2, 3, 4, 7, 8, and 10.

In certain aspects of the invention, the antibody or antigen-binding fragment thereof competes for binding to PCSK9 with an antibody comprising heavy and light chain CDR amino acid sequences having SEQ ID NOs:12, 13, 14, 16, 17, and 18; or SEQ ID NOs: 2, 3, 4, 7, 8, and 10.

In certain aspects of the invention, the antibody or antigen-binding fragment thereof that specifically binds PCSK9 is administered to the patient at a dose of about 75 mg at a frequency of once every two weeks. In some aspects, the about 75 mg dose is maintained if the patient's LDL-C measured after five or more doses is <70 mg/dL. In some aspects, the about 75 mg dose is discontinued if the patient's LDL-C measured after five or more doses remains ≥70 mg/dL, and the antibody or antigen-binding fragment thereof that specifically binds PCSK9 is subsequently administered to the patient at a dose of about 150 mg at a frequency of once every two weeks. In some aspects, the antibody or antigen-binding fragment thereof that specifically binds PCSK9 is administered to the patient at a dose of about 150 mg at a frequency of once every two weeks.

In certain aspects of the invention, the PCSK9 inhibitor is administered to the patient in combination with the maximum tolerated dose statin therapy. In some aspects, the maximum tolerated dose statin therapy comprises a daily dose of about 40 mg to about 80 mg of atorvastatin. In some aspects, the maximum tolerated dose statin therapy comprises a daily dose of about 20 mg to about 40 mg of rosuvastatin. In some aspects, the maximum tolerated dose statin therapy comprises a daily dose of about 80 mg of simvastatin.

In certain aspects of the invention, the PCSK9 inhibitor is administered to the patient in combination with the other lipid lowering therapy.

In certain aspects of the invention, the method improves at least one hypercholesterolemia-associated parameter selected from the group consisting of: (a) reduction of the patient's low density lipoprotein cholesterol (LDL-C) by at least 40%; (b) reduction of the patient's apolipoprotein B (ApoB) by at least 30%; (c) reduction of the patient's non-high density lipoproprotein cholesterol (non-HDL-C) by at least 40%; (d) reduction of the patient's total cholesterol by at least 20%; (e) increase of the patient's high density lipoprotein cholesterol (HDL-C) by at least 3%; (f) reduction of the patient's triglycerides by at least 5%; (g) reduction of the patient's lipoprotein a (Lp(a)) by at least 20%; and (h) increase of the patient's apolipoprotein A1 by at least 1%.

Other embodiments of the present invention will become apparent from a review of the ensuing detailed description.

(alirocumab vs. placebo) according to demographics and baseline characteristics (FIG. 11A), statin/LLT use (FIG. 11B), and baseline lipids (FIG. 11C) (ITT analysis; pooled data from FH I and FH II). Moderate chronic kidney disease (CKD) was defined as an estimated glomerular filtration rate of ≥30 and ≤60 mL/min/1.73 m2. In FH I, 20/323 and 9/163 patients in alirocumab and placebo arms had moderate CKD at baseline. Corresponding values in FH II were 2/167 and 1/82. "High intensity" statin dose refers to atorvastatin 40-80 mg or rosuvastatin 20-40 mg.

Figure 12:
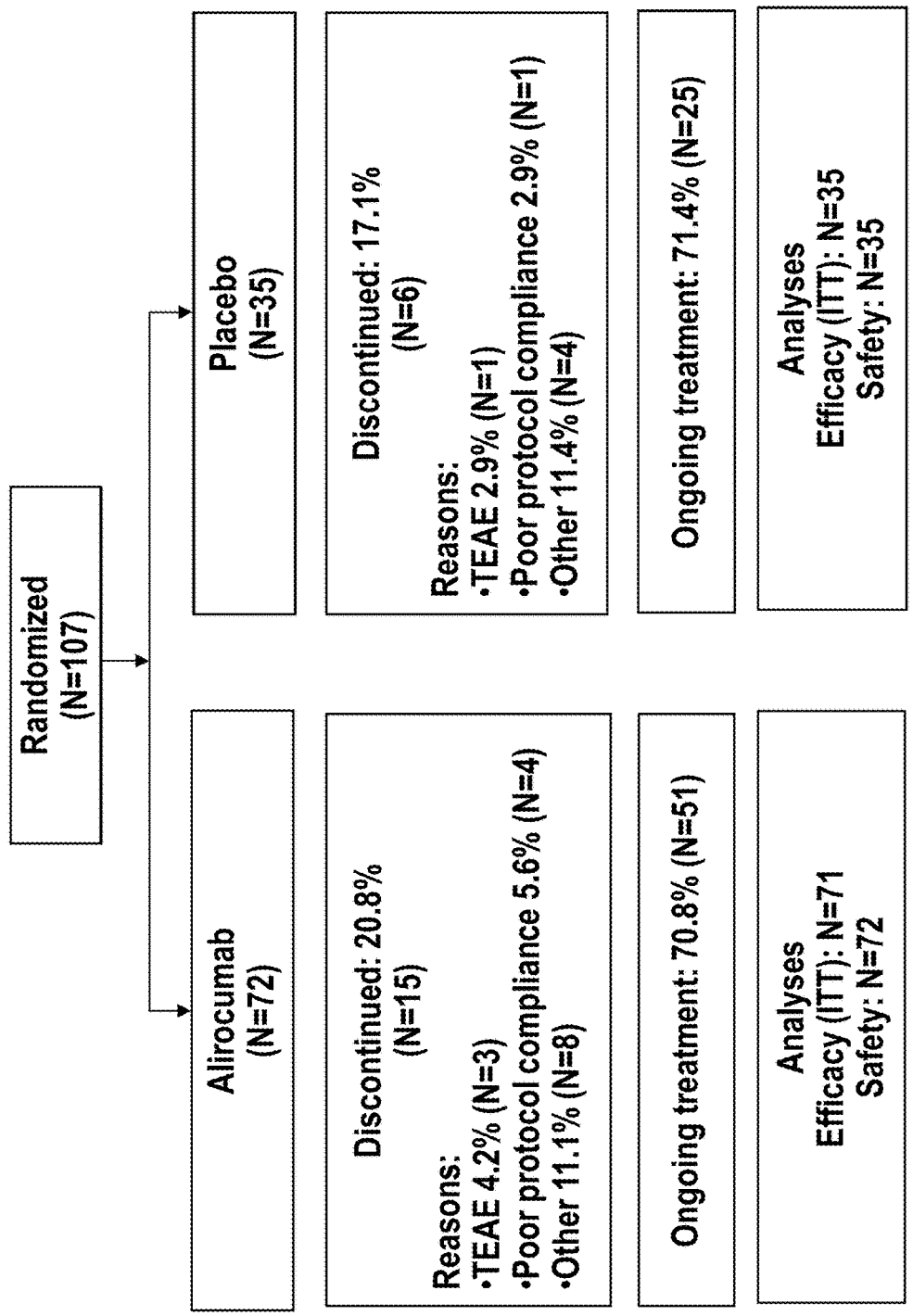

FIG. 12 is a graphic representation of patient disposition in the ODYSSEY HIGH FH study.

Figure 13:
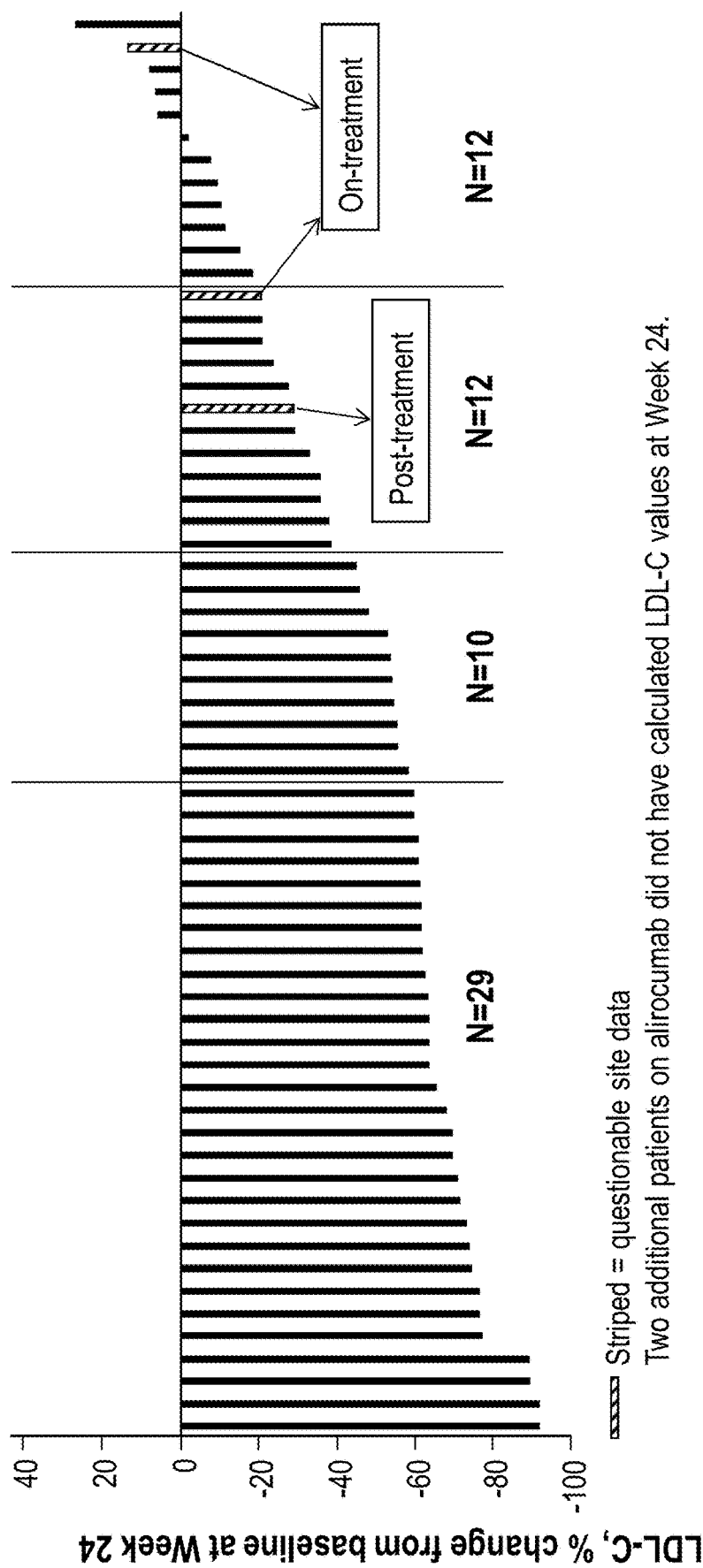

FIG. 13 is a graph showing the percent change from baseline to week 24 in LDL-C levels by individual patients in the ODYSSEY HIGH FH study. All patients were on a background statin (at the maximum tolerated level). A subset of patients also received a further lipid lowering therapy.

Figure 14A:
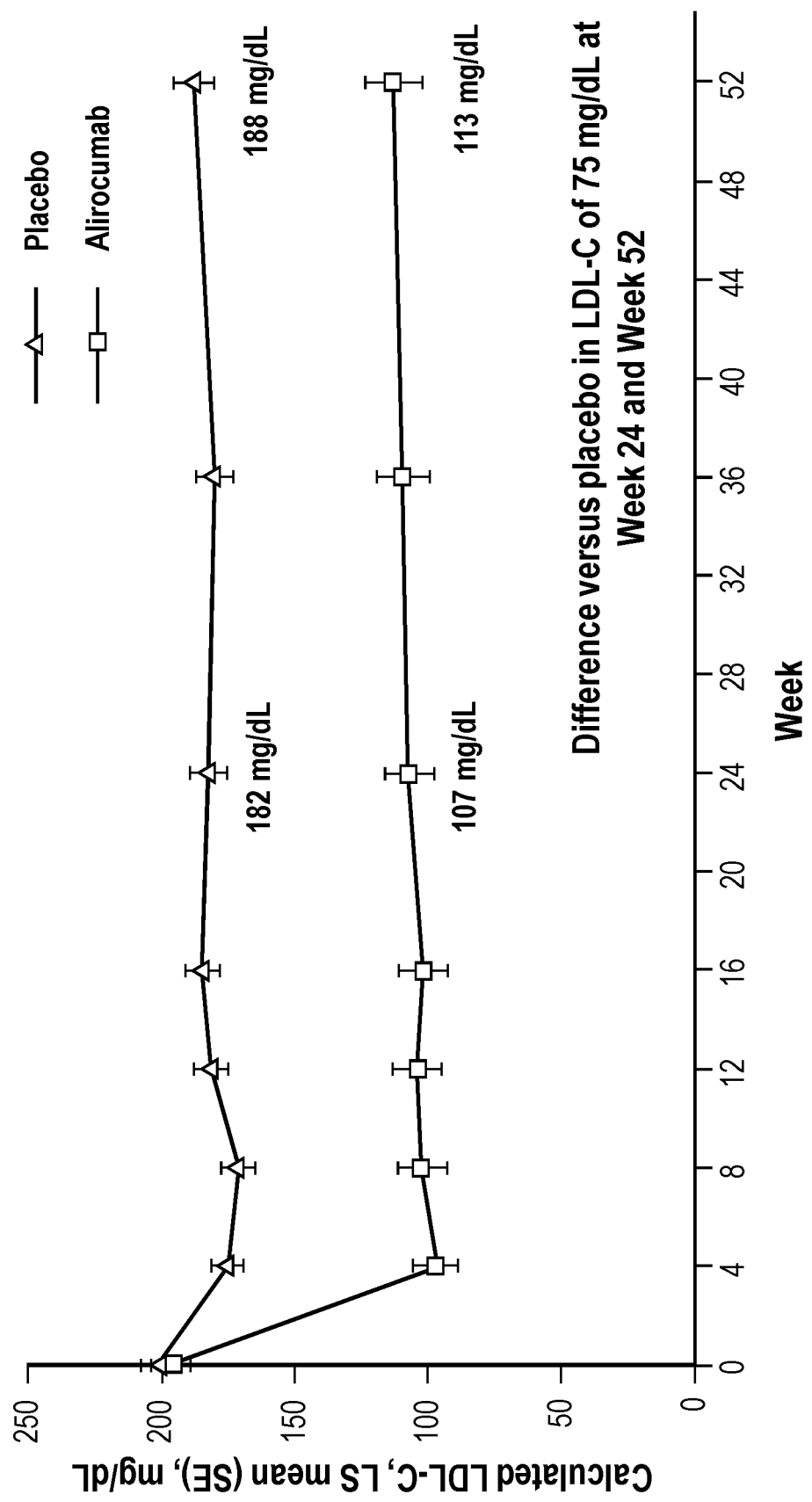
Figure 14B:
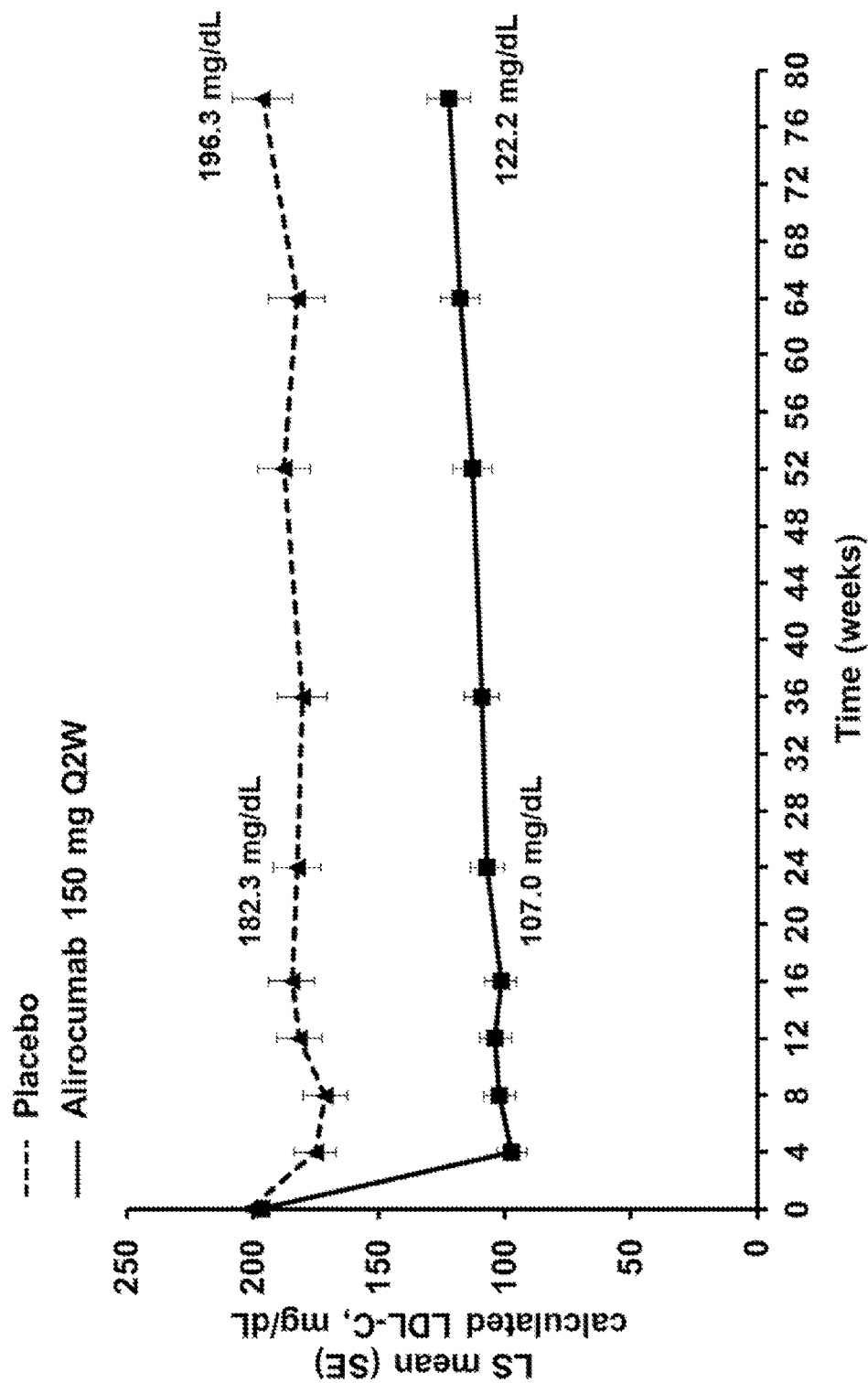

FIGS. 14A-14B depict graphs showing the LS mean (SE) calculated LDL-C values versus time for the ODYSSEY HIGH FH study. In FIG. 14A, the values indicted on the graph are the LS mean % values (in mg/dL) at week 24 and week 52. In FIG. 14B, the values indicated on the graph are the LS mean % values (in mg/dL) at week 24 and week 78. All patients were on a background statin (at the maximum tolerated level). A subset of patients also received a further lipid lowering therapy.

DETAILED DESCRIPTION

Before the present invention is described, it is to be understood that this invention is not limited to the particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice of the present invention, the preferred methods and materials are now described. All publications mentioned herein are incorporated herein by reference to describe in their entirety.

Heterozygous Familial Hypercholesterolemia not Adequately Controlled by Maximum Tolerated Dose Statin Therapy with or without Other Lipid Lowering Therapy The present invention relates generally to methods and compositions for treating patients with heterozygous familial hypercholesterolemia who are not adequately controlled by maximum tolerated dose statin therapy with or without other lipid lowering therapy, i.e., hypercholesterolemia not adequately controlled by a therapeutic regimen comprising a daily maximum tolerated dose of a statin. As used herein, the expression "not adequately controlled," in reference to hypercholesterolemia, means that the patient's serum low-density lipoprotein cholesterol (LDL-C) concentration, total cholesterol concentration, and/or triglyceride concentration is not reduced to a recognized, medically-acceptable level (taking into account the patient's relative risk of coronary heart disease) after at least 4 weeks on a therapeutic regimen comprising a stable daily dose of a statin. For example, "a patient with hypercholesterolemia that is not adequately controlled by a statin" includes patients with a serum LDL-C concentration of greater than about 70 mg/dL, 100 mg/dL, 130 mg/dL, 140 mg/dL, or more (depending on the patient's underlying risk of heart disease) after the patient has been on a stable daily statin regimen for at least 4 weeks.

According to certain embodiments, the patients with heterozygous familial hypercholesterolemia who are not adequately controlled by maximum tolerated dose statin therapy with or without other lipid lowering therapy who are treatable by the methods of the present invention have hypercholesterolemia (e.g., a serum LDL-C concentration of greater than or equal to 70 mg/dL in patients with a history of documented cardiovascular disease or a serum LDL-C≥100 mg/dL in patients without a history of documented cardiovascular disease) despite taking a stable daily dose of a statin (with or without other lipid modifying therapy) for at least 4 weeks, 5 weeks, 6 weeks, or more. In certain embodiments, the heterozygous familial hypercholesterolemia patient's hypercholesterolemia is inadequately controlled by a maximum tolerated dose statin therapy (also referred to herein as "a daily maximum tolerated dose therapeutic statin regimen").

As used herein, "maximum tolerated dose statin therapy" means a therapeutic regimen comprising the administration of daily dose of a statin that is the maximally tolerated dose for a particular patient. Maximally tolerated dose means the highest dose of statin that can be administered to a patient without causing unacceptable adverse side effects in the patient. Maximum tolerated dose statin therapy includes, but is not limited to, e.g., 40-80 mg of atorvastatin daily, 20-40 mg of rosuvastatin daily, or 80 mg of simvastatin (if already on this dose for >1 year). However, patients not able to tolerate the above statin doses could take a lower dose of daily atorvastatin, rosuvastatin, or simvastatin provided there was an acceptable reason for not using the higher dose. Some examples of acceptable reasons for a patient taking a lower statin dose include: adverse effects on higher doses, advanced age, low body mass index (BMI), regional practices, local prescribing information, concomitant medications, and comorbid conditions such as impaired glucose tolerance/impaired fasting glucose.

The present invention also includes methods for treating patients with heterozygous familial hypercholesterolemia that are not adequately controlled by maximum tolerated dose statin therapy with or without other lipid lowering therapy comprising daily administration of other statins such as cerivastatin, pitavastatin, fluvastatin, lovastatin, and pravastatin.

Patient Selection

The present invention includes methods and compositions useful for treating patients with heterozygous familial hypercholesterolemia who are not adequately controlled by maximum tolerated dose statin therapy with or without other lipid lowering therapy.

Diagnosis of heFH must be made either by genotyping or by clinical criteria. For those patients not genotyped, the clinical diagnosis may be based on either the Simon Broome criteria with a criteria for definite FH or the WHO/Dutch Lipid Network criteria with a score >8 points.

According to the Simon Broome Register Diagnostic Criteria for Heterozygous Familial Hypercholesterolemia, definite familial hypercholesterolemia is defined as: 1) total-C>6.7 mmol/l (260 mg/dL) or LDL cholesterol above 4.0 mmol/l (155 mg/dL) in a child <16 years or Total-C>7.5 mmol/l (290 mg/dL) or LDL cholesterol above 4.9 mmol/l (190 mg/dL) in an adult. (Levels either pre-treatment or highest on treatment); plus either A) tendon xanthomas in patient, or in 1 st degree relative (parent, sibling, child), or in 2nd degree relative (grandparent, uncle, aunt); or B) DNA-based evidence of an LDL receptor mutation or familial defective apo B-100.

According to the Simon Broome Register Diagnostic Criteria for Heterozygous Familial Hypercholesterolemia, possible familial hypercholesterolemia is defined as: 1) total-C>6.7 mmol/l (260 mg/dL) or LDL cholesterol above 4.0 mmol/l (155 mg/dL) in a child <16 years or Total-C>7.5 mmol/l (290 mg/dL) or LDL cholesterol above 4.9 mmol/l (190 mg/dL) in an adult. (Levels either pre-treatment or highest on treatment); and at least one of the following: A) family history of MI below 50 years of age in 2nd degree relative or below 60 years of age in 1 st degree relative; and B) family history of raised cholesterols >7.5 mmol/l (290 mg/dL) in adult 1st or 2nd degree relative or >6.7 mmol/l (260 mg/dL) in child or sibling under 16 years of age.

The WHO Criteria (Dutch Lipid Network clinical criteria) for diagnosis of Heterozygous Familial Hypercholesterolemia (heFH) is set forth in the Examples, such as in Table 2.

According to certain embodiments, the heterozygous familial hypercholesterolemia patient may be selected on the basis of having one or more additional risk factors selected from the group consisting of age (e.g., older than 40, 45, 50, 55, 60, 65, 70, 75, or 80 years), race, national origin, gender (male or female), exercise habits (e.g., regular exerciser, non-exerciser), other preexisting medical conditions (e.g., type-II diabetes, high blood pressure, myocardial infarction, ischemic stroke, etc.), and current medication status (e.g., currently taking beta blockers, niacin, ezetimibe, fibrates, omega-3 fatty acids, bile acid resins, etc.).

According to the present invention, heterozygous familial hypercholesterolemia patients may be selected on the basis of a combination of one or more of the foregoing selection criteria or therapeutic characteristics.

Administration of a PCSK9 Inhibitor as Add-On Therapy to Maximum Tolerated Dose Statin Therapy The present invention includes methods wherein a heterozygous familial hypercholesterolemia patient who is not adequately controlled by maximum tolerated dose statin therapy with or without other lipid lowering therapy in the absence of a PCSK9 inhibitor is administered a PCSK9 inhibitor according to a particular dosing amount and frequency, and wherein the PCSK9 inhibitor is administered as an add-on to the patient's therapeutic statin regimen. For example, according to certain embodiments, if a patient with heterozygous familial hypercholesterolemia who is not adequately controlled by maximum tolerated dose statin therapy with or without other lipid lowering therapy comprising, e.g., 40-80 mg of atorvastatin, the patient with heterozygous familial hypercholesterolemia may be administered a PCSK9 inhibitor at a particular amount and dosing interval while the patient continues his or her stable daily therapeutic statin regimen.

The methods of the present invention include add-on therapeutic regimens wherein the PCSK9 inhibitor is administered as add-on therapy to the same stable daily maximum tolerated dose therapeutic statin regimen (i.e., same dosing amount of statin) that the heterozygous familial hypercholesterolemia risk patient was on prior to receiving the PCSK9 inhibitor. In other embodiments, the PCSK9 inhibitor is administered as add-on therapy to a daily maximum tolerated dose therapeutic statin regimen comprising a statin in an amount that is more than or less than the dose of statin the patient was on prior to receiving the PCSK9 inhibitor. For example, after starting a therapeutic regimen comprising a PCSK9 inhibitor administered at a particular dosing frequency and amount, the daily dose of statin administered or prescribed to the patient may (a) stay the same, (b) increase, or (c) decrease (e.g., up-titrate or down-titrate) in comparison to the daily statin dose the high cardiovascular risk patient was taking before starting the PCSK9 inhibitor therapeutic regimen, depending on the therapeutic needs of the patient.

Therapeutic Efficacy

The methods of the present invention will result in the improvement in the serum level of one or more lipid components selected from the group consisting of LDL-C, ApoB, non-HDL-C, total cholesterol, HDL-C, triglycerides, Apo A-1, and Lp(a). For example, according to certain embodiments of the present invention, administration of a pharmaceutical composition comprising a PCSK9 inhibitor to a heterozygous familial hypercholesterolemia patient who is not adequately controlled by a stable daily maximum tolerated dose therapeutic statin regimen (e.g., administration of the PCSK9 inhibitor on top of the patient's maximum tolerated dose statin therapy) will result in a mean percent reduction from baseline in serum low density lipoprotein cholesterol (LDL-C) of at least about 40%, 41%, 42%, 43%, 44%, 45%, 46%, 47%, 48%, 49%, 50%, 51%, 52%, 53%, 54%, 55%, or greater; a mean percent reduction from baseline in ApoB of at least about 30%, 31%, 32%, 33%, 34%, 35%, 36%, 37%, 38%, 39%, 40%, 41%, 42%, 43%, 44%, 45%, or greater; a mean percent reduction from baseline in non-HDL-C of at least about 40%, 41%, 42%, 43%, 44%, 45%, 46%, 47%, 48%, 49%, 50%, 51%, 52%, 53%, 54%, 55%, or greater; a mean percent reduction from baseline in total cholesterol of at least about 20%, 21%, 22%, 23%, 24%, 25%, 26%, 27%, 28%, 29%, 30%, 31%, 32%, 33%, 34%, 35%, or greater; a mean percent increase from baseline in HDL-C of at least about 1%, 2%, 3%, 4%, 5%, 6%, 7%, 8%, 9%, 10%, 11%, 12%, 13%, 14%, 15% or greater; a mean percent reduction from baseline in triglycerides of at least about 2%, 3%, 4%, 5%, 6%, 7%, 8%, 9%, 10%, 11%, 12%, 13%, 14%, 15%, or greater; a mean percent increase from baseline in Apo A-1 of at least about 1%, 2%, 3%, 4%, 5%, 6%, 7%, 8%, 9%, 10%, or greater; and/or a mean percent reduction from baseline in Lp(a) of at least about 20%, 21%, 22%, 23%, 24%, 25%, 26%, 27%, 28%, 29%, 30%, 31%, 32%, 33%, 34%, 35%, or greater.

PCSK9 Inhibitors

The methods of the present invention comprise administering to a patient with heterozygous familial hypercholesterolemia who is not adequately controlled by maximum tolerated dose statin therapy with or without other lipid lowering therapy a therapeutic composition comprising a PCSK9 inhibitor. As used herein, a "PCSK9 inhibitor" is any agent that binds to or interacts with human PCSK9 and inhibits the normal biological function of PCSK9 in vitro or in vivo. Non-limiting examples of categories of PCSK9 inhibitors include small molecule PCSK9 antagonists, peptide-based PCSK9 antagonists (e.g., "peptibody" molecules), and antibodies or antigen-binding fragments of antibodies that specifically bind human PCSK9.

The term "human proprotein convertase subtilisin/kexin type 9" or "human PCSK9" or "hPCSK9", as used herein, refers to PCSK9 having the nucleic acid sequence shown in SEQ ID NO:197 and the amino acid sequence of SEQ ID NO:198, or a biologically active fragment thereof.

The term "antibody", as used herein, is intended to refer to immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementarity determining regions (CDRs), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-PCSK9 antibody (or antigen-binding portion thereof) may be identical to the human germline sequences, or may be naturally or artificially modified. An amino acid consensus sequence may be defined based on a side-by-side analysis of two or more CDRs.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a VH domain associated with a VL domain, the VH and VL domains may be situated relative to one another in any suitable arrangement. For example, the variable region may be dimeric and contain VH-VH, VH-VL or VL-VL dimers. Alternatively, the antigen-binding fragment of an antibody may contain a monomeric VH or VL domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) VH-CH1; (ii) VH-CH2; (iii) VH-CH3; (iv) VH-CH1-CH2; (v) VH-CH1-CH2-CH3; (vi) VH-CH2-CH3; (vii) VH-CL; (viii) VL-CH1; (ix) VL-CH2; (x) VL-CH3; (xi) VL-CH1-CH2; (xii) VL-CH1-CH2-CH3; (xiii) VL-CH2-CH3; and (xiv) VL-CL. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric VH or VL domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The term "human antibody", as used herein, is intended to include antibodies having variable and constant regions derived from human germline immunoglobulin sequences. The human antibodies of the invention may nonetheless include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, CH2 or CH3 region which may be desirable, for example, in production, to improve the yield of the desired antibody form.

An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" PCSK9, as used in the context of the present invention, includes antibodies that bind PCSK9 or portion thereof with a KD of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or less than about 0.5 nM, as measured in a surface plasmon resonance assay. An isolated antibody that specifically binds human PCSK9, however, have cross-reactivity to other antigens, such as PCSK9 molecules from other (non-human) species.

The anti-PCSK9 antibodies useful for the methods of the present invention may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes methods involving the use of antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the VH and/or VL domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. The use of antibodies and antigen-binding fragments obtained in this general manner are encompassed within the present invention.

The present invention also includes methods involving the use of anti-PCSK9 antibodies comprising variants of any of the HCVR, LCVR, and/or CDR amino acid sequences disclosed herein having one or more conservative substitutions. For example, the present invention includes the use of anti-PCSK9 antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, N.J.).

The term "KD", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstances, an epitope may include moieties of saccharides, phosphoryl groups, or sulfonyl groups on the antigen.

According to certain embodiments, the anti-PCSK9 antibody used in the methods of the present invention is an antibody with pH-dependent binding characteristics. As used herein, the expression "pH-dependent binding" means that the antibody or antigen-binding fragment thereof exhibits "reduced binding to PCSK9 at acidic pH as compared to neutral pH" (for purposes of the present disclosure, both expressions may be used interchangeably). For example, antibodies "with pH-dependent binding characteristics" includes antibodies and antigen-binding fragments thereof that bind PCSK9 with higher affinity at neutral pH than at acidic pH. In certain embodiments, the antibodies and antigen-binding fragments of the present invention bind PCSK9 with at least 3, 5, 10, 15, 20, 25, 30, 35, 40, 45, 50, 55, 60, 65, 70, 75, 80, 85, 90, 95, 100, or more times higher affinity at neutral pH than at acidic pH.

According to this aspect of the invention, the anti-PCSK9 antibodies with pH-dependent binding characteristics may possess one or more amino acid variations relative to the parental anti-PCSK9 antibody. For example, an anti-PCSK9 antibody with pH-dependent binding characteristics may contain one or more histidine substitutions or insertions, e.g., in one or more CDRs of a parental anti-PCSK9 antibody. Thus, according to certain embodiments of the present invention, methods are provided comprising administering an anti-PCSK9 antibody which comprises CDR amino acid sequences (e.g., heavy and light chain CDRs) which are identical to the CDR amino acid sequences of a parental anti-PCSK9 antibody, except for the substitution of one or more amino acids of one or more CDRs of the parental antibody with a histidine residue. The anti-PCSK9 antibodies with pH-dependent binding may possess, e.g., 1, 2, 3, 4, 5, 6, 7, 8, 9, or more histidine substitutions, either within a single CDR of a parental antibody or distributed throughout multiple (e.g., 2, 3, 4, 5, or 6) CDRs of a parental anti-PCSK9 antibody. For example, the present invention includes the use of anti-PCSK9 antibodies with pH-dependent binding comprising one or more histidine substitutions in HCDR1, one or more histidine substitutions in HCDR2, one or more histidine substitutions in HCDR3, one or more histidine substitutions in LCDR1, one or more histidine substitutions in LCDR2, and/or one or more histidine substitutions in LCDR3, of a parental anti-PCSK9 antibody.

As used herein, the expression "acidic pH" means a pH of 6.0 or less (e.g., less than about 6.0, less than about 5.5, less than about 5.0, etc.). The expression "acidic pH" includes pH values of about 6.0, 5.95, 5.90, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

Preparation of Human Antibodies

Methods for generating human antibodies in transgenic mice are known in the art. Any such known methods can be used in the context of the present invention to make human antibodies that specifically bind to human PCSK9.

Using VELOCIMMUNE® technology (see, for example, U.S. Pat. No. 6,596,541, Regeneron Pharmaceuticals) or any other known method for generating monoclonal antibodies, high affinity chimeric antibodies to PCSK9 are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. The antibodies are characterized and selected for desirable characteristics, including affinity, selectivity, epitope, etc, using standard procedures known to those skilled in the art. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

In general, the antibodies that can be used in the methods of the present invention possess high affinities, as described above, when measured by binding to antigen either immobilized on solid phase or in solution phase. The mouse constant regions are replaced with desired human constant regions to generate the fully human antibodies of the invention. While the constant region selected may vary according to specific use, high affinity antigen-binding and target specificity characteristics reside in the variable region.

Specific examples of human antibodies or antigen-binding fragments of antibodies that specifically bind PCSK9 which can be used in the context of the methods of the present invention include any antibody or antigen-binding fragment which comprises the three heavy chain CDRs (HCDR1, HCDR2 and HCDR3) contained within a heavy chain variable region (HCVR) having an amino acid sequence selected from the group consisting of SEQ ID NOs: 1 and 11, or a substantially similar sequence thereof having at least 90%, at least 95%, at least 98% or at least 99% sequence identity. Alternatively, specific examples of human antibodies or antigen-binding fragments of antibodies that specifically bind PCSK9 which can be used in the context of the methods of the present invention include any antibody or antigen-binding fragment which comprises the three heavy chain CDRs (HCDR1, HCDR2 and HCDR3) contained within a heavy chain variable region (HCVR) having an amino acid sequence selected from the group consisting of SEQ ID NOs 37, 45, 53, 61, 69, 77, 85, 93, 101, 109, 117, 125, 133, 141, 149, 157, 165, 173, 181, and 189, or a substantially similar sequence thereof having at least 90%, at least 95%, at least 98% or at least 99% sequence identity. The antibody or antigen-binding fragment may comprise the three light chain CDRs (LCVR1, LCVR2, LCVR3) contained within a light chain variable region (LCVR) having an amino acid sequence selected from the group consisting of SEQ ID NOs: 6 and 15, or a substantially similar sequence thereof having at least 90%, at least 95%, at least 98% or at least 99% sequence identity. Alternatively, the antibody or antigen-binding fragment may comprise the three light chain CDRs (LCVR1, LCVR2, LCVR3) contained within a light chain variable region (LCVR) having an amino acid sequence selected from the group consisting of SEQ ID NOs 41, 49, 57, 65, 73, 81, 89, 97, 105, 113, 121, 129, 137, 145, 153, 161, 169, 177, 185, and 193, or a substantially similar sequence thereof having at least 90%, at least 95%, at least 98% or at least 99% sequence identity.

In certain embodiments of the present invention, the antibody or antigen-binding fragment thereof comprises the six CDRs (HCDR1, HCDR2, HCDR3, LCDR1, LCDR2 and LCDR3) from the heavy and light chain variable region amino acid sequence pairs (HCVR/LCVR) selected from the group consisting of SEQ ID NOs:1/6 and 11/15. Alternatively, in certain embodiments of the present invention, the antibody or antigen-binding protein comprises the six CDRs (HCDR1, HCDR2, HCDR3, LCDR1, LCDR2 and LCDR3) from the heavy and light chain variable region amino acid sequence pairs (HCVR/LCVR) selected from the group consisting of SEQ ID NOs:37/41, 45/49, 53/57, 61/65, 69/73, 77/81, 85/89, 93/97, 101/105, 109/113, 117/121, 125/129, 133/137, 141/145, 149/153, 157/161, 165/169, 173/177, 181/185, and 189/193.

In certain embodiments of the present invention, the anti-PCSK9 antibody, or antigen-binding fragment thereof, that can be used in the methods of the present invention has HCDR1/HCDR2/HCDR3/LCDR1/LCDR2/LCDR3 amino acid sequences selected from SEQ ID NOs: 2/3/4/7/8/10 (mAb316P) and 12/13/14/16/17/18 (mAb300N) (See US Patent App. Publ No. 2010/0166768).

In certain embodiments of the present invention, the antibody or antigen-binding fragment thereof comprises HCVR/LCVR amino acid sequence pairs selected from the group consisting of SEQ ID NOs: 1/6 and 11/15. Alternatively, in certain embodiments of the present invention, the antibody or antigen-binding protein comprises HCVR/LCVR amino acid sequence pairs selected from the group consisting of SEQ ID NOs:37/41, 45/49, 53/57, 61/65, 69/73, 77/81, 85/89, 93/97, 101/105, 109/113, 117/121, 125/129, 133/137, 141/145, 149/153, 157/161, 165/169, 173/177, 181/185, and 189/193.

Pharmaceutical Compositions and Methods of Administration

The present invention includes methods which comprise administering a PCSK9 inhibitor to a patient with heterozygous familial hypercholesterolemia who is not adequately controlled by maximum tolerated dose statin therapy with or without other lipid lowering therapy, wherein the PCSK9 inhibitor is contained within a pharmaceutical composition. The pharmaceutical compositions of the invention are formulated with suitable carriers, excipients, and other agents that provide suitable transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of administration include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by known methods. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc.

Dosage

The amount of PCSK9 inhibitor (e.g., anti-PCSK9 antibody) administered to a patient with heterozygous familial hypercholesterolemia who is not adequately controlled by maximum tolerated dose statin therapy with or without other lipid lowering therapy according to the methods of the present invention is, generally, a therapeutically effective amount. As used herein, the phrase "therapeutically effective amount" means a dose of PCSK9 inhibitor that results in a detectable improvement (at least about 5%, 10%, 15%, 20%, 25%, 30%, 35%, 40%, 45%, 50%, 55%, 60%, 65%, 70%, 75%, or more from baseline) in one or more parameters selected from the group consisting of LDL-C, ApoB, non-HDL-C, total cholesterol, HLDL-C, triglycerides, Apo A-1, and Lp(a).

In the case of an anti-PCSK9 antibody, a therapeutically effective amount can be from about 0.05 mg to about 600 mg, e.g., about 0.05 mg, about 0.1 mg, about 1.0 mg, about 1.5 mg, about 2.0 mg, about 10 mg, about 20 mg, about 30 mg, about 40 mg, about 50 mg, about 60 mg, about 70 mg, about 75 mg, about 80 mg, about 90 mg, about 100 mg, about 110 mg, about 120 mg, about 130 mg, about 140 mg, about 150 mg, about 160 mg, about 170 mg, about 180 mg, about 190 mg, about 200 mg, about 210 mg, about 220 mg, about 230 mg, about 240 mg, about 250 mg, about 260 mg, about 270 mg, about 280 mg, about 290 mg, about 300 mg, about 310 mg, about 320 mg, about 330 mg, about 340 mg, about 350 mg, about 360 mg, about 370 mg, about 380 mg, about 390 mg, about 400 mg, about 410 mg, about 420 mg, about 430 mg, about 440 mg, about 450 mg, about 460 mg, about 470 mg, about 480 mg, about 490 mg, about 500 mg, about 510 mg, about 520 mg, about 530 mg, about 540 mg, about 550 mg, about 560 mg, about 570 mg, about 580 mg, about 590 mg, or about 600 mg, of the anti-PCSK9 antibody.

The amount of anti-PCSK9 antibody contained within the individual doses may be expressed in terms of milligrams of antibody per kilogram of patient body weight (i.e., mg/kg). For example, the anti-PCSK9 antibody may be administered to a patient at a dose of about 0.0001 to about 10 mg/kg of patient body weight.

Combination Therapies

As described elsewhere herein, the methods of the present invention may comprise administering a PCSK9 inhibitor to patients with heterozygous familial hypercholesterolemia in combination with the patient's previously prescribed stable daily maximum tolerated dose therapeutic statin regimen. According to certain embodiments of the present invention, additional therapeutic agents, besides a statin, may be administered to the patient in combination with the PCSK9 inhibitor. Examples of such additional therapeutic agents include e.g., (1) an agent which inhibits cholesterol uptake and or bile acid re-absorption (e.g., ezetimibe); (2) an agent which increases lipoprotein catabolism (such as niacin); and/or (3) activators of the LXR transcription factor that plays a role in cholesterol elimination such as 22-hydroxycholesterol.

Administration Regimens

According to certain embodiments of the present invention, multiple doses of a PCSK9 inhibitor (i.e., a pharmaceutical composition comprising a PCSK9 inhibitor) may be administered to a subject over a defined time course (e.g., on top of a daily therapeutic statin regimen). The methods according to this aspect of the invention comprise sequentially administering to a patient with heterozygous familial hypercholesterolemia who is not adequately controlled by maximum tolerated dose statin therapy with or without other lipid lowering therapy multiple doses of a PCSK9 inhibitor. As used herein, "sequentially administering" means that each dose of PCSK9 inhibitor is administered to the subject at a different point in time, e.g., on different days separated by a predetermined interval (e.g., hours, days, weeks or months). The present invention includes methods which comprise sequentially administering to the patient with heterozygous familial hypercholesterolemia a single initial dose of a PCSK9 inhibitor, followed by one or more secondary doses of the PCSK9 inhibitor, and optionally followed by one or more tertiary doses of the PCSK9 inhibitor.

The terms "initial dose," "secondary doses," and "tertiary doses," refer to the temporal sequence of administration of the individual doses of a pharmaceutical composition comprising a PCSK9 inhibitor. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of the PCSK9 inhibitor, but generally may differ from one another in terms of frequency of administration. In certain embodiments, however, the amount of PCSK9 inhibitor contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

According to exemplary embodiments of the present invention, each secondary and/or tertiary dose is administered 1 to 26 (e.g., 1, 1 1/2, 2, 2 1/2, 3, 3 1/2, 4, 4 1/2, 5, 5 1/2, 6, 6 1/2, 7, 7 1/2, 8, 8 1/2, 9, 9 1/2, 10, 10 1/2, 11, 11 1/2, 12, 12 1/2, 13, 13 1/2, 14, 14 1/2, 15, 15 1/2, 16, 16 1/2, 17, 17 1/2, 18, 18 1/2, 19, 19 1/2, 20, 20 1/2, 21, 21 1/2, 22, 22 1/2, 23, 23 1/2, 24, 24 1/2, 25, 25 1/2, 26, 26 1/2, or more) weeks after the immediately preceding dose. The phrase "the immediately preceding dose," as used herein, means, in a sequence of multiple administrations, the dose of antigen-binding molecule which is administered to a patient prior to the administration of the very next dose in the sequence with no intervening doses.

The methods according to this aspect of the invention may comprise administering to a patient with heterozygous familial hypercholesterolemia any number of secondary and/or tertiary doses of a PCSK9 inhibitor. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient with heterozygous familial hypercholesterolemia 1 to 2, 4, 6, 8 or more weeks after the immediately preceding dose. Similarly, in embodiments involving multiple tertiary doses, each tertiary dose may be administered at the same frequency as the other tertiary doses. For example, each tertiary dose may be administered to the patient 1 to 2, 4, 6, 8 or more weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

The present invention includes administration regimens comprising an up-titration option (also referred to herein as "dose modification"). As used herein, an "up-titration option" means that, after receiving a particular number of doses of a PCSK9 inhibitor, if a patient has not achieved a specified reduction in one or more defined therapeutic parameters, the dose of the PCSK9 inhibitor is thereafter increased. For example, in the case of a therapeutic regimen comprising administration of 75 mg doses of an anti-PCSK9 antibody to a patient with heterozygous familial hypercholesterolemia who is not adequately controlled by maximum tolerated dose statin therapy with or without other lipid lowering therapy at a frequency of once every two weeks, if after 8 weeks (i.e., 5 doses administered at Week 0, Week 2 and Week 4, Week 6 and Week 8), the patient has not achieved a serum LDL-C concentration of less than 70 mg/dL, then the dose of anti-PCSK9 antibody is increased to e.g., 150 mg administered once every two weeks thereafter (e.g., starting at Week 12).

In certain embodiments, the anti-PCSK9 antibody is administered to a subject at a dose of about 75 mg every two weeks, for example for at least six doses.

In some embodiments, the antibody is administered to a subject at a dose of about 75 mg every two weeks for 12 weeks, and the dose remains at 75 mg every two weeks if, at week 8, the subject's LDL-C value was less than 70 mg/dl.

In other embodiments, the antibody is administered to a subject at a dose of about 75 mg every two weeks for 12 weeks, and the dose is titrated up to about 150 mg every two weeks if, at week 8, the subject's LDL-C value was greater than or equal to 70 mg/dl. In certain embodiments, the anti-PCSK9 antibody is administered to a subject at a dose of about 150 mg every two weeks, for example for at least six doses.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1. Generation of Human Antibodies to Human PCSK9

Human anti-PCSK9 antibodies were generated as described in U.S. Pat. No. 8,062,640. The exemplary PCSK9 inhibitor used in the following Examples is the human anti-PCSK9 antibody designated "mAb316P," also known as "Alirocumab." mAb316P has the following amino acid sequence characteristics: heavy chain variable region (HCVR) comprising SEQ ID NO:1; light chain variable domain (LCVR) comprising SEQ ID NO:6; heavy chain complementarity determining region 1 (HCDR1) comprising SEQ ID NO:2; HCDR2 comprising SEQ ID NO:3; HCDR3 comprising SEQ ID NO:4; light chain complementarity determining region 1 (LCDR1) comprising SEQ ID NO:7; LCDR2 comprising SEQ ID NO:8; and LCDR3 comprising SEQ ID NO:10.

Example 2: A Randomized, Double-Blind, Placebo-Controlled, Parallel Group Study to Evaluate the Efficacy and Safety of Alirocumab in Patients with Heterozygous Familial Hypercholesterolemia not Adequately Controlled with their Lipid-Modifying Therapy Introduction This study included patients with heterozygous familial hypercholesterolemia (heFH) with or without a history of documented myocardial infarction (MI) or ischemic stroke.

The objective of the study was to assess the efficacy and safety of Alirocumab in patients with heFH and who require additional pharmacological management since their current lipid-modifying therapy (LMT) failed to achieve the LDL-C treatment goal.

Figure 1:
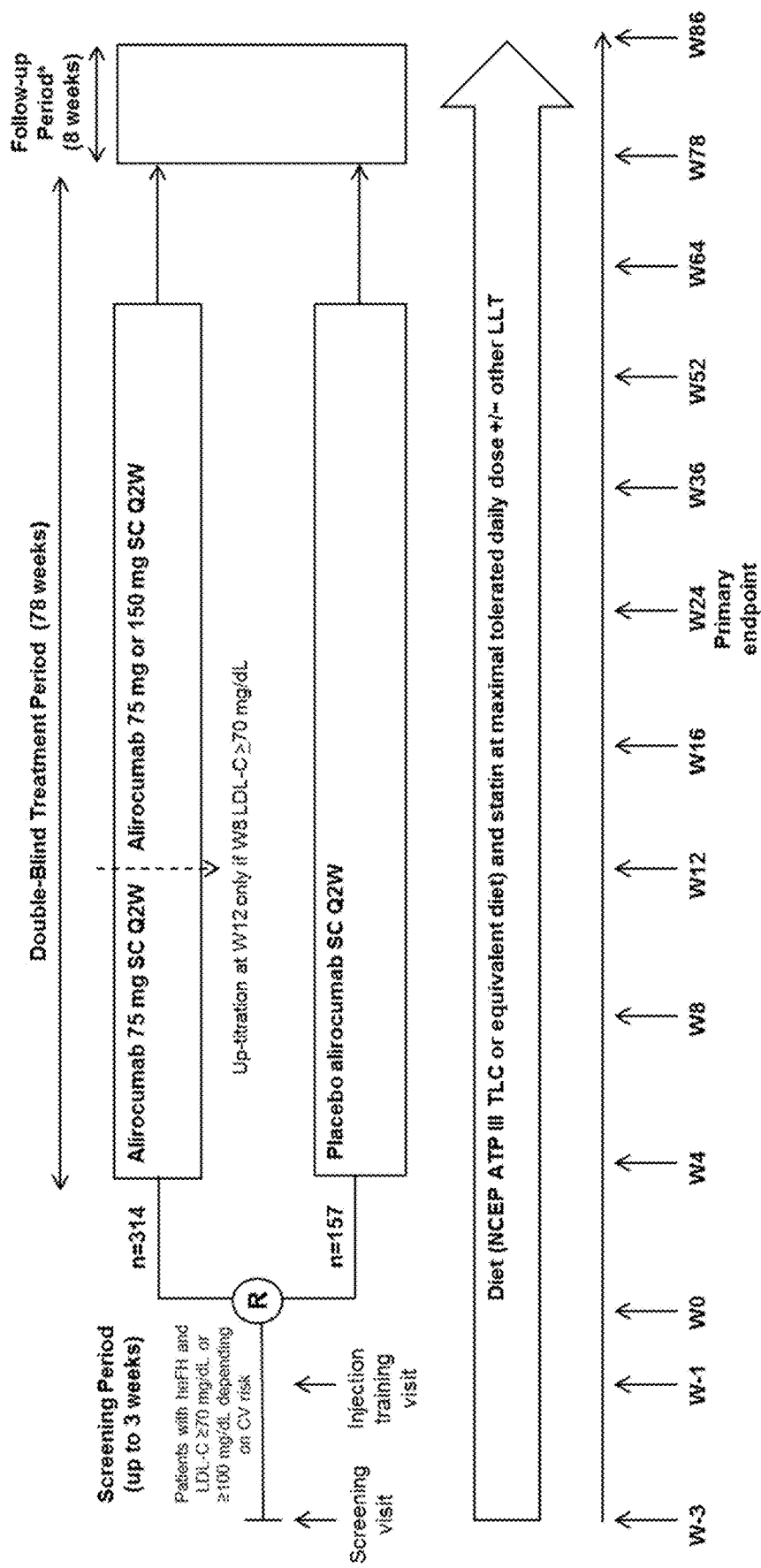
FIG. 1 is a graphic representation of the study design for ODYSSEY FH I (Example 2).

This study (FIG. 1) was undertaken to demonstrate in heFH patients who are not at their LDL-C goal that Alirocumab 75 mg Q2W or 75 mg Q2W/150 mg Q2W as add-on therapy to statin ±other LMT causes a statistically significant and clinically meaningful reduction in LDL-C. This population that is not at LDL-C goal on optimized LMT represents the highest risk group with a well identified unmet medical need that can be addressed by adding Alirocumab to their LDL-C lowering therapies.

Study Objectives

The primary objective of the study was to demonstrate the reduction of LDL-C by Alirocumab as add-on therapy to stable maximally tolerated daily statin therapy with or without other LMT in comparison with placebo after 24 weeks of treatment in patients with heFH.

The secondary objectives of the study were: 1) to evaluate the effect of Alirocumab 75 mg in comparison with placebo on LDL-C after 12 weeks of treatment; 2) to evaluate the effect of Alirocumab on other lipid parameters (i.e., Apo B, non-HDL-C, total-C, Lp (a), HDL-C, TG levels, and Apo A-1 levels); 3) to evaluate the long-term effect of Alirocumab on LDL-C; 4) to evaluate the safety and tolerability of Alirocumab; 5) to evaluate the development of anti-Alirocumab antibodies; and 6) to evaluate the PK of Alirocumab.

Study Design

This was a randomized, double-blind, placebo-controlled, parallel-group, unbalanced (2:1, Alirocumab:placebo), multi-center, multi-national study to assess the efficacy and the safety of Alirocumab in patients with heFH not adequately controlled with their LMT (i.e., stable maximally tolerated daily statin therapy ±other LMT). Not adequately controlled was defined as an LDL-C≥70 mg/dL (1.81 mmol/L) at the screening visit (Week-3) in patients with a history of documented cardiovascular disease or LDL-C≥100 mg/dL (2.59 mmol/L) at the screening visit (Week-3) in patients without a history of documented cardiovascular disease. Randomization was stratified according to prior history of MI or ischemic stroke [Yes/No], statin treatment (atorvastatin 40 to 80 mg daily or rosuvastatin 20 to 40 mg daily vs. simvastatin whatever the daily dose, atorvastatin below 40 mg daily or rosuvastatin below 20 mg daily) and geographic region. After randomization, patients received double-blind study treatment (either Alirocumab or placebo) Q2W over a period of 18 months (78 weeks) on top of stable maximally tolerated daily statin therapy ±other LMT. A dose up-titration depending on Week 8 LDL-C levels may occur at Week 12 for patients randomized to Alirocumab. After completion of the 18-month double-blind treatment period, all patients who successfully completed the study had the opportunity to participate in an open-label extension study. Consequently all patients received Alirocumab at entry in the open-label extension study regardless of the study treatment they received during the 18-month double-blind treatment period.

The study consisted of 3 periods: screening, double-blind treatment, and follow-up.

The screening period was up to 3 weeks in duration including an intermediate visit during which the patient (or another designated person such as spouse, relative, etc.) was trained to self-inject/inject with placebo for Alirocumab. Eligibility assessments were performed to permit the randomization of patients into the study.

The double blind treatment period (DBTP) was a randomized, double-blind study treatment period of 18 months. The first injection during the double-blind period was done at the site on the day of randomization (Week 0 [D1]-V3). The subsequent injections were done by the patient (self-injection) or another designated person (such as spouse, relative, etc.) at a patient-preferred location (home . . . ). Patients randomized to Alirocumab received a dose of 75 mg of the Investigational Medicinal Product (IMP) from randomization (V3) up to Week 12 (V6) (i.e., Weeks 0, 2, 4, 6, 8, and 10). At the Week 12 visit (V6) these patients, in a blinded manner, either: 1) continued Alirocumab 75 mg Q2W from Week 12 onwards until the last injection at Week 76, if the Week 8 LDL-C was <70 mg/dL (1.81 mmol/L); OR 2) dose up-titrated to Alirocumab 150 mg Q2W from Week 12 onwards until the last injection at Week 76, if the Week 8 LDL-C was ≥70 mg/dL (1.81 mmol/L).

The follow-up period (if applicable) was a period of 8 weeks after the end of the DBTP for patients not consenting to participate in the open-label extension study or if prematurely discontinuing study treatment.

The laboratory measurement of lipid parameters were performed by a central laboratory (central lab) during the study.

Patients who achieved 2 consecutive calculated LDL-C levels <25 mg/dL (0.65 mmol/L) during the study were monitored and managed.

Statin and other LMT (if applicable) should be stable (including dose) during the first 24 weeks of the DBTP barring exceptional circumstances whereby overriding concerns warrant such changes. At Week 24 onwards, background LMT may be modified only under certain conditions as described below.

Patients should be on a stable diet (NCEP-ATPIII therapeutic lifestyle changes [TLC] diet or equivalent) throughout the entire study duration from screening. Table 1 provides a summary of the TLC diet for high cholesterol.

TABLE 1

| | |
|---|---|
| Total Fat | 25%-35% total calories* |
| Saturated fat* | <7% total calories |
| Polyunsaturated fat | up to 10% total calories |
| Monounsaturated fat | up to 20% total calories |
| Carbohydrates† | 50%-60% total calories* |
| Protein | ~15% total calories |
| Cholesterol | <200 mg/day (5.172 mmol/day) |
| Plant Sterols | 2 g |
| Soluble Fiber such as psyllium | 10 g-25 g |

*ATP III allows an increase of total fat to 35 percent of total calories and a reduction in carbohydrate to 50 percent for persons with the metabolic syndrome. Any increase in fat intake should be in the form of either polyunsaturated or monounsaturated fat. Trans-fatty acids are another LDL-raising fat that should be kept at a low intake.
†Carbohydrate should derive predominantly from foods rich in complex carbohydrates including grains-especially whole grains-fruits, and vegetables.

The study duration included a screening period of up to 3 weeks, a 78-week DBTP for efficacy and safety assessment, and an 8-week post-treatment follow-up period after the last visit of the DBTP for patients not consenting to participate in the open-label extension study or if prematurely discontinuing study treatment. Thus, the maximum study duration per patient was about 89 weeks (i.e., 20 months) (up to 3 weeks screening+78 weeks double-blind treatment+8 weeks follow-up). The end of the study per patient was the last protocol planned visit or the resolution/stabilization of all SAEs, and AESI, whichever came last.

Selection of Patients

The inclusion criteria were: 1) patients with heFH* who were not adequately controlled with a maximally tolerated daily dose of statin** with or without other LMT, at stable dose prior to the screening visit (Week-3).

*Diagnosis of heFH must be made either by genotyping or by clinical criteria. For those patients not genotyped, the clinical diagnosis may be based on either the Simon Broome criteria with a criteria for definite FH or the WHO/Dutch Lipid Network criteria with a score >8 points.

According to the Simon Broome Register Diagnostic Criteria for Heterozygous Familial Hypercholesterolemia, definite familial hypercholesterolemia is defined as: 1) total-C>6.7 mmol/l (260 mg/dL) or LDL cholesterol above 4.0 mmol/l (155 mg/dL) in a child <16 years or Total-C>7.5 mmol/l (290 mg/dL) or LDL cholesterol above 4.9 mmol/l (190 mg/dL) in an adult. (Levels either pre-treatment or highest on treatment); plus either A) tendon xanthomas in patient, or in 1 st degree relative (parent, sibling, child), or in 2nd degree relative (grandparent, uncle, aunt); or B) DNA-based evidence of an LDL receptor mutation or familial defective Apo B.

According to the Simon Broome Register Diagnostic Criteria for Heterozygous Familial Hypercholesterolemia, possible familial hypercholesterolemia is defined as: 1) total-C>6.7 mmol/l (260 mg/dL) or LDL cholesterol above 4.0 mmol/l (155 mg/dL) in a child <16 years or Total-C>7.5 mmol/l (290 mg/dL) or LDL cholesterol above 4.9 mmol/l (190 mg/dL) in an adult. (Levels either pre-treatment or highest on treatment); and at least one of the following: A) family history of MI below 50 years of age in 2nd degree relative or below 60 years of age in 1 st degree relative; and B) family history of raised cholesterols >7.5 mmol/l (290 mg/dL) in adult 1st or 2nd degree relative or >6.7 mmol/l (260 mg/dL) in child or sibling under 16 years of age.

The WHO Criteria (Dutch Lipid Network clinical criteria) for diagnosis of Heterozygous Familial Hypercholesterolemia (heFH) is set forth in Table 2.

TABLE 2

| Diagnostic Scoring for Heterozygous Familial Hypercholesterolemia | |
|---|---|
| Family history | |
| a First degree relative with known premature (men < 55 yrs, women <60 yrs) coronary and vascular disease. | 1 |
| b First degree relative with known LDL-cholesterol > 95th percentile for age and sex. and/or | |
| a First degree relative with tendon xanthomata and/or arcus cornealis. | 2 |
| b Children below 18 yrs. with LDL-cholesterol > 95th percentile for age and sex. | |
| Clinical history | |
| a Patient has premature (men < 55 yrs, women < 60 yrs) coronary artery disease | 2 |
| b Patient has premature (men < 55 yrs, women < 60 yrs) cerebral or peripheral vascular disease. | 1 |
| Physical examination | |
| a Tendon xanthomata | 6 |
| b Arcus cornealis below the age of 45 yrs. | 4 |

TABLE 2-continued

| Diagnostic Scoring for Heterozygous Familial Hypercholesterolemia | | | |
|---|---|---|---|
| Laboratory analysis | mmol/L | mg/dL | |
| a LDL-cholesterol | >8.5 | >330 | 8 |
| b LDL-cholesterol | 6.5-8.4 | 250-329 | 5 |
| c LDL-cholesterol | 5.0-6.4 | 190-249 | 3 |
| d LDL-cholesterol | 4.0-4.9 | 155-189 | 1 |
| (HDL-cholesterol and triglycerides are normal) | | | |
| DNA-analysis | | | |
| a Functional mutation low-density lipoprotein receptor gene present | | | 8 |
| Diagnosis of heFH is: | | | |
| Certain When | >8 points | | |
| Probable When | 6-8 points | | |
| Possible When | 3-5 points | | |

**Definition of maximally tolerated dose (any of the following were acceptable): 1) rosuvastatin 20 mg or 40 mg daily; 2) atorvastatin 40 mg or 80 mg daily; 3) simvastatin 80 mg daily (if already on this dose for >1 year); or 4) patients not able to be on any of the above statin doses, should be treated with the dose of daily atorvastatin, rosuvastatin or simvastatin that is considered appropriate for the patient as per the investigator's judgment or concerns. Some examples of acceptable reasons for a patient taking a lower statin dose included, but were not limited to: adverse effects on higher doses, advanced age, low body mass index, regional practices, local prescribing information, concomitant medications, co-morbid conditions such as impaired glucose tolerance/impaired fasting glucose.

Patients who met all of the above inclusion criteria were screened for the following exclusion criteria, which are sorted and numbered in the following 3 subsections: exclusion criteria related to study methodology, exclusion criteria related to the active comparator and/or mandatory background therapies, and exclusion criteria related to Alirocumab.

Exclusion criteria related to study methodology were: 1) patient without diagnosis of heFH made either by genotyping or by clinical criteria; 2) LDL-C<70 mg/dL (<1.81 mmol/L) at the screening visit (Week-3) and patient with history of documented cardiovascular disease. Cardiovascular disease was defined as coronary heart disease, ischemic stroke or peripheral arterial disease; 3) LDL-C<100 mg/dL (<2.59 mmol/L) at the screening visit (Week-3) and patient without history of documented cardiovascular disease; 4) not on a stable dose of LMT (including statin) for at least 4 weeks and/or fenofibrate for at least 6 weeks, as applicable, prior to the screening visit (Week −3) and from screening to randomization; 5) currently taking a statin other than simvastatin, atorvastatin, or rosuvastatin; 6) simvastatin, atorvastatin, or rosuvastatin is not taken daily or not taken at a registered dose; 7) daily doses above atorvastatin 80 mg, rosuvastatin 40 mg, or simvastatin 40 mg (except for patients on simvastatin 80 mg for more than one year, who are eligible); 8) use of fibrates, other than fenofibrate within 6 weeks of the screening visit (Week-3) or between screening and randomization visits; 9) use of nutraceutical products or over-the-counter therapies that may affect lipids which have not been at a stable dose/amount for at least 4 weeks prior to the screening visit (Week −3) or between screening and randomization visits; 10) use of red yeast rice products within 4 weeks of the screening visit (Week-3) or between screening and randomization visits; 11) patient who has received plasmapheresis treatment within 2 months prior to the screening visit (Week −3), or has plans to receive it during the study; 12) recent (within 3 months prior to the screening visit [Week −3] or between screening and randomization visits) MI, unstable angina leading to hospitalization, percutaneous coronary intervention (PCI), coronary artery bypass graft surgery (CABG), uncontrolled cardiac arrhythmia, stroke, transient ischemic attack (TIA), carotid revascularization, endovascular procedure or surgical intervention for peripheral vascular disease; 13) planned to undergo scheduled PCI, CABG, carotid, or peripheral revascularization during the study; 14) systolic BP>160 mmHg or diastolic BP>100 mmHg at screening visit or randomization visit; 15) history of New York Heart Association (NYHA) Class III or IV heart failure within the past 12 months; 16) known history of a hemorrhagic stroke; 17) age <18 years or legal age of majority at the screening visit (Week-3), whichever is greater; 18) patients not previously instructed on a cholesterol-lowering diet prior to the screening visit (Week-3); 19) newly diagnosed (within 3 calendar months prior to randomization visit [Week 0]) or poorly controlled (glycated haemoglobin A1c [HbA$_{1c}$]>9% at the screening visit [Week-3] diabetes); 20) presence of any clinically significant uncontrolled endocrine disease known to influence serum lipids or lipoproteins. Note that patients on thyroid replacement therapy can be included if the dosage has been stable for at least 12 weeks prior to screening and between screening and randomization visits, and TSH level is within the normal range of the Central Laboratory at the screening visit; 21) history of bariatric surgery within 12 months prior to the screening visit (Week-3); 22) unstable weight defined by a variation >5 kg within 2 months prior to the screening visit (Week-3); 23) known history of homozygous FH; 24) known history of loss of function of PCSK9 (i.e., genetic mutation or sequence variation); 25) use of systemic corticosteroids, unless used as replacement therapy for pituitary/adrenal disease with a stable regimen for at least 6 weeks prior to randomization visit (Week 0). Note that topical, intra-articular, nasal, inhaled and ophthalmic steroid therapies were not considered as 'systemic' and were allowed; 26) use of continuous estrogen or testosterone hormone replacement therapy unless the regimen has been stable in the past 6 weeks prior to the Screening visit (Week-3) and no plans to change the regimen during the study; 27) history of cancer within the past 5 years, except for adequately treated basal cell skin cancer, squamous cell skin cancer or in situ cervical cancer; 28) known history of a positive HIV test; 29) patient who has taken any investigational drugs other than the Alirocumab training placebo kits within 1 month or 5 half lives, whichever is longer; 30) patient who has been previously treated with at least one dose of Alirocumab or any other anti-PCSK9 monoclonal antibody in other clinical trials; 31) patient who withdraws consent during the screening period (patient who is not willing to continue or fails to return); 32) conditions/situations such as: a) any clinically significant abnormality identified at the time of screening that, in the judgment of the Investigator or any sub-Investigator, would preclude safe completion of the study or constrain endpoints assessment; e.g., major systemic diseases, patients with short life expectancy; or b) considered by the Investigator or any sub-Investigator as inappropriate for this study for any reason, e.g.: deemed unable to meet specific protocol requirements, such as scheduled visits; deemed unable to administer or tolerate long-term injections as per the patient or the Investigator; Investigator or any sub-Investigator, pharmacist, study coordinator, other study staff or relative thereof directly involved in the conduct of the protocol, etc; presence of any other conditions (eg, geographic or social), either actual or anticipated, that the Investigator feels would restrict or limit the patient's participation for the duration of the study; or 33) laboratory findings during screening period (not including randomization Week 0 labs): positive test for Hepatitis B surface antigen or Hepatitis C antibody; positive serum beta-hCG or urine pregnancy test (including Week 0) in women of childbearing potential (WOCBP); triglycerides >400 mg/dL (>4.52 mmol/L) (1 repeat lab is allowed); estimated glomerular filtration rate (eGFR)<30 mL/min/1.73 m2 according to 4-variable modification of diet in renal disease (MDRD) Study equation (calculated by central lab); alanine aminotransferase (ALT) or aspartate aminotransferase (AST)>3×upper limit of normal range (ULN) (1 repeat lab is allowed); CPK>3×ULN (1 repeat lab is allowed); TSH<lower limit of normal (LLN) or >ULN (1 repeat lab is allowed).

Exclusion criteria related to the active comparator and/or mandatory background therapies were: 1) all contraindications to the background therapies or warnings/precautions of use (when appropriate) as displayed in the respective National Product Labeling.

Exclusion criteria related to Alirocumab were: 1) known hypersensitivity to monoclonal antibody or any component of the drug product; 2) pregnant or breast-feeding women; or 3) women of childbearing potential not protected by highly-effective method(s) of birth control (as defined in the informed consent form and/or in a local protocol addendum) and/or who are unwilling or unable to be tested for pregnancy. Note that women of childbearing potential must have a confirmed negative pregnancy test at screening and randomization visits. They must use an effective contraceptive method throughout the entire duration of the study treatment, and for 10 weeks after the last intake of IMP, and agree to repeat urine pregnancy test at designated visits. Postmenopausal women must be amenorrheic for at least 12 months.

Coronary heart disease, ischemic stroke, and peripheral arterial disease, as defined in exclusion criteria number 2 related to study methodology was as follows. Documented history of CHD (includes one or more of the following): acute myocardial infarction (MI); silent myocardial infarction; unstable angina; coronary revascularization procedure (eg, percutaneous coronary intervention [PCI] or coronary artery bypass graft surgery [CABG]); clinically significant CHD diagnosed by invasive or non-invasive testing (such as coronary angiography, stress test using treadmill, stress echocardiography or nuclear imaging).

Documented previous ischemic stroke with a focal ischemic neurological deficit that persisted more than 24 hours, considered as being of atherothrombotic origin. CT or MRI must have been performed to rule out hemorrhage and non-ischemic neurological disease.

Documented peripheral arterial disease (one of the following criteria must be satisfied): 1) current intermittent claudication (muscle discomfort in the lower limb produced by exercise that is both reproducible and relieved by rest within 10 minutes) of presumed atherosclerotic origin together with ankle-brachial index equal to or less than 0.90 in either leg at rest or 2) history of intermittent claudication (muscle discomfort in the lower limb produced by exercise that is both reproducible and relieved by rest within 10 minutes) together with endovascular procedure or surgical intervention in one or both legs because of atherosclerotic disease or 3) history of critical limb ischemia together with thrombolysis, endovascular procedure or surgical intervention in one or both legs because of atherosclerotic disease.

Study Treatments

Sterile Alirocumab drug product was supplied at a concentration of 75 mg/mL and 150 mg/mL both as 1 mL volume in an auto-injector. The drug substance was formulated in histidine, pH 6.0, polysorbate 20, and sucrose.

Sterile placebo for Alirocumab was prepared in the same formulation as Alirocumab without the addition of protein as 1 mL volume in an auto-injector.

During the double-blind treatment period, Alirocumab or placebo was administered subcutaneously Q2W, starting at Week 0 continuing up to the last injection (Week 76) 2 weeks before the end of the double blind treatment period (DBTP). If the injection was scheduled to take place on the same date as the site visit, then the IMP was administered after the blood sampling was completed.

Investigational Medicinal Product (IMP) should ideally have been administered Q2W subcutaneously at approximately the same time of the day; however it was acceptable to have a window period of ±3 days. The time of the day was based on the patient's preference.

The following classes of drugs were identified as non-NIMP because the medication was either a background therapy or a potential rescue medication: statins (rosuvastatin, atorvastatin, simvastatin); cholesterol absorption inhibitors (ezetimibe); bile acid-binding sequestrants (such as cholestyramine, colestipol, colesevelam); nicotinic acid; fenofibrate; and omega-3 fatty acids (≥1000 mg daily).

Patients were randomized to receive either placebo or Alirocumab during the double-blind study treatment period using a ratio 1:2, with permuted-block randomization. Randomization was stratified according to prior history of MI or ischemic stroke [Yes/No], statin treatment (atorvastatin 40 to 80 mg daily or rosuvastatin 20 to 40 mg daily vs. simvastatin whatever the daily dose, atorvastatin below 40 mg daily or rosuvastatin below 20 mg daily) and geographic region.

A concomitant medication was any treatment received by the patient concomitantly to the study (until follow-up visit). Concomitant medications should be kept to a minimum during the study. However, if these are considered necessary for the patient's welfare and are unlikely to interfere with the IMP, they may be given at the discretion of the Investigator, with a stable dose (when possible). Besides the specific information related to concomitant medications provided in this section, any other concomitant medication(s) will be allowed. If the patient has an LDL-C≥160 mg/dL (4.14 mmol/L) at the screening visit (Week-3) and is treated with a statin only, i.e., without additional LMT, the investigator will have to report the reason for the patient not being on a second LMT. For background LMT, including statins, sites must follow the national product label for the safety monitoring and management of patients.

Nutraceutical products or over-the-counter therapies that may affect lipids were allowed only if they had been used at a stable dose for at least 4 weeks prior to screening visit, during the screening period and maintained during the first 24 weeks of the double-blind treatment period. After the Week 24 visit, modification to these nutraceutical products or over-the-counter therapies was allowed but in general should be avoided. Examples of such nutraceutical products or over-the-counter therapies include omega-3 fatty acids at doses <1000 mg, plant stanols such as found in Benecol, flax seed oil, and *psyllium*.

Patients must have been on stable maximally tolerated daily registered doses of statins with or without other LMT for at least 4 weeks (6 weeks for fenofibrate) before screening visit. During the study, the patients should stay on these stable maximally tolerated registered daily doses of statins with or without other LMT. From the screening visit (Week-3) until Week 24 of the double-blind treatment period, the background LMT should not be changed. No dose adjustment, discontinuation or initiation of other statins or other LMT should take place during this time, barring exceptional circumstances whereby overriding concerns (including but not limited to triglyceride alert posted by the central lab) warrant such changes, as per the Investigator's judgment.

For a rescue notification of LDL-C at the Week 24 visit and later, i.e., LDL-C increase >25% as compared to randomization visit LDL-C on two consecutive occasions, the Investigator should have ensured that no reasonable explanation existed for insufficient LDL-C control (such as an alternative medical cause like corticosteroid use, etc) and in particular that: compliance with diet was appropriate; compliance with background LMT was appropriate; and study treatment was given as planned. If any of the above could reasonably explain the insufficient LDL-C control, the Investigator should have undertaken appropriate action, i.e., stress on the absolute need to be compliant with treatment, if needed organize a specific interview with a qualified nutrition professional and stress on the absolute need to be compliant with diet, and perform a blinded LDL-C assessment within 1 to 2 months. If none of the above mentioned reasons were found, or if appropriate action failed to decrease LDL-C under the alert value, rescue medication may have been introduced.

If no reason for LDL-C above the threshold value could be found, or if appropriate action failed to decrease LDL-C below the threshold value, rescue medication may have been introduced. The effectiveness of any such changes was to be made based on lack of rescue threshold from blinded lipid testing at the next routinely scheduled lab draw. Patients per protocol already received a maximum tolerated dose of statin, so statin uptitration or switch was not an option. For further LDL-C lowering, the investigator could consider adding: a cholesterol absorption inhibitor (ezetimibe), or a bile acid-binding sequestrant (the resins cholestyramine and colestipol, or colesevelam, a nonabsorbable polymer). The following lipid-modifying agents could also be considered: fibrate (Note: Caution should be exercised when combining fibrates with other cholesterol-lowering medications such as statins because of the risk of myopathy. When a fibrate is combined with a statin, fenofibrate is the fibrate of choice because it does not affect statin glucuronidation. The only fibrate allowed per protocol was fenofibrate); nicotinic acid (niacin) (Note: Niacin raises blood glucose but has been shown to be effective in modifying lipid disorders in people with diabetes if glucose control is maintained).

In summary, background LMT should not be modified from screening to the follow-up visit. However, up to Week 24, if a confirmed TG alert was reached or if there was an overwhelming clinical concern (at the discretion of the Investigator) then modification of the background LMT was allowed. At Week 24 onwards, if a confirmed TG alert was reached, or if a rescue threshold for LDL-C was attained (and no other reasonable explanation exists), or if there was an overwhelming clinical concern (at the discretion of the Investigator) then modification of the background LMT was allowed.

Women of childbearing potential must take an effective contraceptive method throughout the study treatment and for 10 weeks after the last IMP injection (e.g., Follow-up visit).

Forbidden concomitant medications from the initial screening visit until the follow-up visit included the following: statins other than simvastatin, atorvastatin and rosuvastatin; fibrates, other than fenofibrate; and red yeast rice products.

Study Endpoints

The primary efficacy endpoint was the percent change in calculated LDL-C from baseline to Week 24, which was defined as: 100× (calculated LDL-C value at Week 24–calculated LDL-C value at baseline)/calculated LDL-C value at baseline. The baseline calculated LDL-C value was the last LDL-C level obtained before the first double-blind IMP injection. The calculated LDL-C at Week 24 was the LDL-C level obtained within the Week 24 analysis window and during the main efficacy period. The main efficacy period was defined as the time from the first double-blind IMP injection up to 21 days after the last double-blind IMP injection or up to the upper limit of the Week 24 analysis window, whichever came first. All calculated LDL-C values (scheduled or unscheduled, fasting or not fasting) may be used to provide a value for the primary efficacy endpoint if appropriate according to above definition.

The key secondary efficacy endpoints were: 1) the percent change in calculated LDL-C from baseline to Week 12: similar definition and rules as for primary efficacy endpoint, except that the calculated LDL-C at Week 12 was the LDL-C level obtained within the Week 12 analysis window and during the 12-week efficacy period. The 12-week efficacy period was defined as the time from the first double-blind IMP injection up to the Visit 6 re-supply IVRS contact or up to 21 days after the last double-blind IMP injection, whichever came first. Blood sampling collected the day of the Visit 6 re-supply IVRS contact was considered as before titration; 2) the percent change in Apo B from baseline to Week 24, using the same definition and rules as for the primary endpoint; 3) the percent change in non-HDL-C from baseline to Week 24, using the same definition and rules as for the primary endpoint; 4) the percent change in total-C from baseline to Week 24, using the same definition and rules as for the primary endpoint; 5) the percent change in Apo B from baseline to Week 12, using the same definition and rules as for the percent change in calculated LDL-C from baseline to Week 12; 6) the percent change in non-HDL-C from baseline to Week 12, using the same definition and rules as for the percent change in calculated LDL-C from baseline to Week 12; 7) the percent change in total-C from baseline to Week 12, using the same definition and rules as for the percent change in calculated LDL-C from baseline to Week 12; 8) the percent change in calculated LDL-C from baseline to Week 52, using definitions and rules that were similar to the ones used for the primary endpoint replacing Week 24 by Week 52. Note that the 52-week efficacy period was defined as the time from the first double-blind IMP injection up to 21 days after the last double-blind IMP injection, or up to the upper limit of the Week 52 analysis window, whichever came first; 9) the proportion of patients reaching LDL-C goal at Week 24, i.e., LDL-C<70 mg/dL (1.81 mmol/L) in case of prior CVD or <100 mg/dL (2.59 mmol/L) for patients without prior CVD, defined as: (number of patients whose calculated LDL-C value at Week 24 reach LDL-C goal/number of patients in the modified intent-to-treat (mITT) population)*100, using definition and rules used for the primary endpoint; 10) the proportion of patients reaching LDL-C<70 mg/dL (1.81 mmol/L) at Week 24; 11) the percent change in Lp(a) from baseline to Week 24, using the same definition and rules as for the primary endpoint; 12) the percent change in HDL-C from baseline to Week 24, using the same definition and rules as for the primary endpoint; 13) the percent change in HDL-C from baseline to Week 12, using the same definition and rules as for the percent change in calculated LDL-C from baseline to Week 12; 14) the percent change in Lp(a) from baseline to Week 12, using the same definition and rules as for the percent change in calculated LDL-C from baseline to Week 12; 15) the percent change in fasting TG from baseline to Week 24, using the same definition and rules as for the primary endpoint; 16) the percent change in fasting TG from baseline to Week 12, using the same definition and rules as for the percent change in calculated LDL-C from baseline to Week 12; 17) the percent change in Apo A-1 from baseline to Week 24, using the same definition and rules as for the primary endpoint; and 18) the percent change in Apo A-1 from baseline to Week 12, using the same definition and rules as for the percent change in calculated LDL-C from baseline to Week 12.

Other secondary efficacy endpoints were: 1) the percent change in calculated LDL-C from baseline to Week 78, using definitions and rules that were similar to the ones used for the primary endpoint replacing Week 24 by Week 78. The 78-week efficacy period was defined as the time from the first double-blind IMP injection up to 21 days after the last double-blind IMP injection, or up to the upper limit of the Week 78 analysis window, whichever came first; 2) the proportion of patients reaching LDL-C goal at Weeks 12, 52, and 78, i.e., LDL-C<70 mg/dL (1.81 mmol/L) in case of prior CVD or <100 mg/dL (2.59 mmol/L) for patients without prior CVD; 3) the proportion of patients reaching LDL-C<100 mg/dL (2.59 mmol/L) at Week 24; 4) the proportion of patients reaching LDL-C<100 mg/dL (2.59 mmol/L) at Week 12; 5) the proportion of patients reaching LDL-C<70 mg/dL (1.81 mmol/L) at Week 12; 6) the absolute change in calculated LDL-C (mg/dL and mmol/L) from baseline to Weeks 12, 24, 52, and 78; 7) the percent change in Apo B, non-HDL-C, total-C, Lp (a), HDL-C, fasting TG, and Apo A-1 from baseline to Weeks 52 and 78; 8) the change in ratio Apo B/Apo A-1 from baseline to Weeks 12, 24, 52, and 78; 9) the proportion of patients with Apo B<80 mg/dL (0.8 g/L) at Weeks 12, 24, 52, and 78; 10) the proportion of patients with non-HDL-C<100 mg/dL at Weeks 12, 24, 52, and 78; and 11) the proportion of patients with calculated LDL-C<70 mg/dL (1.81 mmol/L) and/or ≥50% reduction in calculated LDL-C(if calculated LDL-C≥70 mg/dL [1.81 mmol/L]) at Weeks 12, 24, 52, and 78.

Other endpoints were: anti-Alirocumab antibody assessments, high-sensitivity C-reactive protein, glycated haemoglobin A1c, EQ-5D Questionnaire, pharmacogenetics, and pharmacokinetics. Anti-Alirocumab antibodies included the antibody status (positive/negative) and antibody titers. Serum samples for anti-Alirocumab antibody determination were drawn periodically throughout the study. The first scheduled sample at randomization visit was obtained before IMP injection (predose). Patients who had a titer at or above 240 for anti-Alirocumab antibody at follow-up visit had additional antibody sample(s), at 6 to 12 months after the last dose and thereafter, about every 3 to 6 months until titer returns below 240. The percent change in high-sensitivity C-reactive protein (hs-CRP) was measured at baseline and Weeks 24, 52, and 78. EQ-5D is a standardized measure of health status developed by the EuroQol Group in order to provide a simple, generic measure of health for clinical and economic appraisal. The EQ-5D as a measure of health-related quality of life defines health in terms of 5 dimensions: mobility, self-care, usual activities, pain/discomfort, anxiety/depression. Each dimension can take one of three responses (3 ordinal levels of severity): "no problem" (1); "some problems" (2); "severe problems" (3); Overall health state is defined as a 5-digit number. Health states defined by the 5-dimensional classification can be converted into corresponding index scores that quantify health status, where 0 represents 'death' and 1 represents "perfect health".

Study Procedures

For all visits after Day 1/Week 0 (randomization visit), a timeframe of a certain number of days was allowed. The window period for visits at Weeks 12 and 24 were ±3 days, at Weeks 52 and 78 was ±5 days, and for all other site visits it was ±7 days during the double-blind treatment period, and follow-up period. A window period of +3 days was allowed for the randomization visit (Day1/Week 0) and ±7 days for the injection training visit during the screening period (Week-1). For all visits after Day 1/randomization visit, if one visit date is changed, then the next visit should take place according to the original schedule.

Safety

Occurrence of treatment emergent adverse events (TEAEs) reported by the patient or noted by the investigator, serious adverse events (SAEs), TEAEs leading to treatment discontinuation, AEs of special interest (local Injection site reactions, allergic events, selected neurological events and cardiovascular events confirmed by adjudication result), occurrence of PCSA (potentially clinically significant abnormalities) in laboratory parameters, exploratory analysis for patients with 2 consecutive calculated LDL-C<25 mg/dL (<0.65 mmo/L) and for changes in blood glucose control, including diabetes.

Statistical Methods

Sample Size Determination:

A total sample size of 45 patients (30 in alirocumab and 15 in placebo) had 95% power to detect a difference in mean percent change in LDL-C of 30% with a 0.05 two-sided significance level and assuming a common standard deviation of 25%, and all these 45 patients having an evaluable primary endpoint. Nevertheless, to meet regulatory requirements across the program, the sample size was increased to assess the safety of alirocumab. In order to have at least 225 patients on alirocumab followed for 12 months in this study, and assuming a drop-out rate of 10% over the first 3-month period and a drop-out rate of 20% over the remaining 9-month period, the final total sample size was increased to 471 with a randomization ratio 2:1 (alirocumab 314: placebo 157).

Timing of Analyses:

The first step analysis included efficacy endpoints up to Week 52 (final efficacy analysis) and interim safety analysis, which was performed on all safety data up to the common study cut-off date (last patient Week 52 visit). Analysis of lipid data beyond Week 52 was descriptive. These results are presented herein.

The second step (final) analysis will be conducted at the end of the study and will consist in the final analysis of efficacy endpoints up to Week 78 and final safety analysis.

Analysis Populations:

The primary efficacy analysis population was the intent-to-treat (ITT) population, defined as all randomized patients who had an evaluable primary endpoint, that is, those with an available baseline calculated LDL-C value, and at least one available calculated LDL-C value within one of the analysis windows up to Week 24 (including all calculated LDL-C values on-treatment and off-treatment).

The secondary efficacy analysis population was the modified intent-to-treat (mITT) population, defined as all randomized patients who took at least one dose or part of a dose of the double-blind investigational medicinal product (IMP) and who had an available calculated LDL-C value at baseline and at least one within one of the analysis windows up to Week 24 during the efficacy treatment period. The efficacy treatment period was defined as the time from the first double-blind IMP injection up to 21 days after the last double-blind injection.

The safety population included all randomized patients who received at least one dose or part of a dose of the double-blind IMP.

Efficacy Analyses:

Primary analyses of efficacy endpoints were conducted using an ITT approach (based on the ITT population defined above), including all lipid data, regardless of whether the patient was continuing therapy or not. This corresponds to ITT estimands, defined for primary and key secondary endpoints. In addition, analyses were also conducted using an on-treatment approach (based on the mITT population defined above), including lipid data collected during the efficacy treatment period. This corresponds to on-treatment estimands of key secondary endpoints.

The ITT approach analyzed all patients, irrespective of their adherence to the treatment; it assessed the benefit of the treatment strategy and reflected as much as possible the effect in a population of patients. The on-treatment approach analyzed the effect of treatment, restricted to the period during which patients actually received the treatment. It assessed the benefit that a treatment would achieve in patients adherent to treatment up to the considered time point.

Efficacy analyses were performed according to treatment as-randomized.

All measurements, scheduled or unscheduled, fasting or not fasting, were assigned to analysis windows in order to provide an assessment for Week 4 to Week 78 time points.

With regards to the primary efficacy analysis (ITT approach), the percent change in calculated LDL-C from baseline to Week 24 was analyzed using a mixed-effect model with repeated measures (MMRM) approach. All post-baseline data available from Week 4 to Week 52 analysis windows were used and missing data were accounted for by the MMRM. The model included the fixed categorical effects of treatment group (placebo versus alirocumab), randomization strata (as per IVRS), time point (Week 4 to Week 52), treatment-by-time point interaction and strata-by-time point interaction, as well as the continuous fixed covariates of baseline LDL-C value and baseline value-by-time-point interaction. This model provided baseline adjusted least-squares means (LSmeans) estimates at Week 24 for both treatment groups with their corresponding standard errors and 95% confidence intervals. To compare the alirocumab to the placebo group, an appropriate contrast statement was used to test the differences of these estimates at the 5% alpha level.

A hierarchical procedure was defined to test key secondary endpoints while controlling for multiplicity (using above order of key secondary endpoints). The first key secondary endpoint was the percent change in calculated LDL-C from baseline to Week 24 using an on-treatment approach.

Continuous secondary variables anticipated to have a normal distribution (i.e., lipids other than TGs and Lp(a)) were analyzed using the same MMRM model as for the primary endpoint. Continuous endpoints anticipated to have a non-normal distribution (i.e., TGs and Lp(a)) were analyzed using multiple imputation approach for handling of missing values followed by robust regression model with endpoint of interest as response variable using M-estimation (using SAS ROBUSTREG procedure) with treatment group, randomization strata (as per IVRS) and corresponding baseline value(s) as effects to compare treatment effects. Combined estimate for mean in both treatment groups, as well as the differences of these estimates, with their corresponding SEs, 95% CIs and p-value were provided (through SAS MIANALYZE procedure).

Binary secondary efficacy endpoints were analyzed using multiple imputation approach for handling of missing values followed by stratified logistic regression with treatment group as main effect and corresponding baseline value(s) as covariate, stratified by randomization factors (as per IVRS). Combined estimates of odds ratio versus placebo, 95% CI, and p-value were provided (through SAS MIANALYZE procedure).

Safety Analyses:

Safety analyses were descriptive, performed on the safety population according to treatment actually received. The safety analysis focused on the TEAE period defined as the time from the first dose of double-blind IMP up to 70 days after the last double-blind injection. TEAE which developed, worsened or became serious or PCSA occurring after the patient inclusion in the open-label extension study (LTS13643) were not considered in the TEAE period. TEAE period was truncated at the common study cut-off date.

Results

Study Patients

Patient Accountability

Of the 486 randomized patients (323 patients and 163 patients in the alirocumab and the placebo groups, respectively), one patient in the alirocumab group was not treated and was therefore not included in the safety population. This patient was also excluded from the ITT population (no LDL-C value within one of the analysis windows up to Week 24 as the patient withdrew consent on Day 1).

Two randomized patients in the alirocumab group were excluded from the mITT population (one patient excluded from the ITT population and one patient with no LDL-C value within one of the analysis windows up to Week 24 during the efficacy treatment period).

TABLE 3

Analysis populations

| | Placebo | Alirocumab 75 Q2W/Up150 Q2W | All |
|---|---|---|---|
| Randomized population | 163 (100%) | 323 (100%) | 486 (100%) |
| Efficacy populations | | | |
| Intent-to-Treat (ITT) | 163 (100%) | 322 (99.7%) | 485 (99.8%) |
| Modified Intent-to-Treat (mITT) | 163 (100%) | 321 (99.4%) | 484 (99.6%) |
| Safety population | 163 | 322 | 485 |

Note:
The safety population patients are tabulated according to treatment actually received (as treated).
For the other populations, patients are tabulated according to their randomized treatment.

In the alirocumab group, among the 311 patients who received at least one injection after Week 12, 135 (43.4%) patients received automatic up-titration at Week 12 from alirocumab 75 mg Q2W to 150 mg Q2W in a blinded manner.

Study Disposition

Study disposition, exposure and safety analyses were assessed using all data up to the study common cut-off date (defined as the date of the last patient's Week 52 visit). Therefore, this first step analysis includes data beyond Week 52 and up to Week 78 or Follow-up visit for some patients.

There were in total 7 (1.4%) randomized patients who completed the 78-week double-blind study treatment period and 424 (87.2%) randomized patients with treatment ongoing at the time of the first-step analysis cut-off date. The double-blind IMP was prematurely discontinued before Week 78 for 18 (11.0%) randomized patients in the placebo group and 36 (11.1%) randomized patients in the alirocumab group. The main reasons for study treatment discontinuation were adverse event and other reasons.

In addition, among these patients 34 (10.5%) randomized patients had prematurely discontinued the double-blind IMP before the Week 52 visit in the alirocumab group and 15 (9.2%) patients in the placebo group.

In this first step analysis, final results are available for the primary efficacy endpoint at Week 24 and key secondary efficacy endpoints were assessed at Week 12, Week 24 and Week 52. The primary endpoint was missing for 46 patients at the week 24 visit for the following reasons: 18 samples were not done due to earlier study discontinuation, 14 samples were done outside the analysis time window, 4 missing samples while visit Week 24 was done, and 10 samples were done but the measurement could not be done (lipemia, insufficient quantity, TGs>400 mg/dL[>4.52 mmol/L], sample lost, . . . ).

Demographics, Baseline, and Summary Population Characteristics

Demographic characteristics, disease characteristics and lipid parameters at baseline were similar in the alirocumab group as compared to the placebo group (see Table 4). 486 heFH patients diagnosed by genotyping (39%) or WHO or Simon Broome criteria (61%) were randomized (2:1) to alirocumab (75 mg Q2W potentially uptitrated to 150 mg Q2W) or placebo (323 versus 163, respectively). Half of the randomized population (51%) had a history of at least one coronary heart disease (CHD) or multiple CHD risk factors that defined these patients being at very high cardiovascular risk. Demographics characteristics, disease characteristics and lipid parameters at baseline were similar in the alirocumab group as compared to the placebo group. All patients were treated with a statin, 82% receiving a dose defined as high intensity statin (atorvastatin 40 to 80 mg daily or rosuvastatin 20 to 40 mg daily) and 57% receiving ezetimibe in addition to the statin. Mean (SD) calculated LDL-C at baseline was 144.6 (49.7) mg/dL [3.75 (1.29) mmol/L].

Exposure to injections was similar across treatment groups with a mean exposure of 59 weeks. In the alirocumab group, among the 311 patients who received at least one injection after Week 12, 135 (43.4%) patients received automatic up-titration at Week 12 from alirocumab 75 mg Q2W to 150 mg Q2W in a blinded manner.

TABLE 4

Baseline Characteristics of FHI Patient Population

| Characteristic | Alirocumab (N = 323) | Placebo (N = 163) |
|---|---|---|
| Diagnosis of heFH[†], % (n) | | |
| Genotyping | 39.9% (129) | 38.0% (62) |
| Clinical criteria | 59.8% (193) | 62.0% (101) |
| Age, mean (SD), yrs | 52.1 (12.9) | 51.7 (12.3) |
| Male | 55.7% (180) | 57.7% (94) |
| Race, white | 92.9% (300) | 88.3% (144) |
| BMI, mean (SD), kg/m² | 29.0 (4.6) | 30.0 (5.4) |
| CHD history | 45.5% (147) | 47.9% (78) |
| CHD risk equivalents[†] | 16.7% (54) | 15.3% (25) |
| Current smoker | 12.1% (39) | 18.4% (30) |
| Hypertension | 43.0% (139) | 43.6% (71) |
| Type 2 diabetes | 9.6% (31) | 15.3% (25) |

% (N) of patients unless statedAll pts on background of max tolerated statin ± other lipid-lowering therapy.
[†]Diagnosis of heFH must be made either by genotyping or by clinical criteria. For those patients not genotyped, the clinical diagnosis may be based on either the Simon Broome criteria for definite FH or the WHO/Dutch Lipid Network criteria with a score of >8 points. In FH I, one patient was categorised as "probable" FH by clinical criteria - genotyping results for this patient are pending.

TABLE 5

Disease characteristics and other relevant baseline data - Randomized population

|  | Placebo (N = 163) | Alirocumab 75 Q2W/Up150 Q2W (N = 323) | All (N = 486) |
|---|---|---|---|
| Type of hypercholesterolemia | | | |
| Heterozygous Familial Hypercholesterolemia (heFH) | 163 (100%) | 323 (100%) | 486 (100%) |
| Non-Familial Hypercholesterolemia (non-FH) | 0 | 0 | 0 |
| Time from hypercholesterolemia diagnosis (years) | | | |
| Number | 163 | 323 | 486 |
| Mean (SD) | 13.28 (11.38) | 12.19 (11.38) | 12.55 (11.38) |
| Median | 9.43 | 8.82 | 9.03 |
| Min:Max | 0.0:42.6 | 0.0:60.7 | 0.0:60.7 |
| Confirmation of diagnosis | | | |
| By genotyping | 62 (38.0%) | 129 (39.9%) | 191 (39.3%) |
| By WHO/Simon Broome[a] | 101 (62.0%) | 193 (59.8%) | 294 (60.5%) |

[a] for heFH diagnosis not confirmed by genotyping.

Note: at time of screening, one patient was included based on clinical criteria with a score of 8 for the WHO criteria. As the clinical score characterized the patient as probable heFH rather than certain, a genotyping was performed to confirm heFH status but these results are still pending.

TABLE 6

Cardiovascular History and Risk Factors Breakdown

| Characteristic | Alirocumab (N = 323) | Placebo (N = 163) |
|---|---|---|
| CHD history | 45.5% (147) | 47.9% (78) |
| Acute MI | 22.0% (71) | 26.4% (43) |
| Silent MI | 2.5% (8) | 1.2% (2) |
| Unstable angina | 11.1% (36) | 15.3% (25) |
| Coronary revasc. | 31.6% (102) | 34.4% (56) |
| Other clinically significant CHD | 26.9% (87) | 29.4% (48) |
| CHD risk equivalents | 16.7% (54) | 15.3% (25) |
| Ischemic stroke | 4.0% (13) | 1.8% (3) |
| Peripheral arterial disease | 2.8% (9) | 2.5% (4) |
| Moderate CKD | 6.2% (20) | 5.5% (9) |
| Diabetes + 2 or more risk factors | 5.9% (19) | 6.1% (10) |

% (N) of patients unless stated. All pts on background of max tolerated statin ± other lipid-lowering therapy

TABLE 7

Background LMT at randomization - Randomized population

|  | Placebo (N = 163) | Alirocumab 75 Q2W/Up150 Q2W (N = 323) | All (N = 486) |
|---|---|---|---|
| Any statin | 163 (100%) | 323 (100%) | 486 (100%) |
| Taking high intensity statin | 135 (82.8%) | 261 (80.8%) | 396 (81.5%) |
| Atorvastatin daily dose (mg) | 64 (39.3%) | 113 (35.0%) | 177 (36.4%) |
| 10 | 1 (0.6%) | 3 (0.9%) | 4 (0.8%) |
| 20 | 2 (1.2%) | 7 (2.2%) | 9 (1.9%) |
| 40 | 23 (14.1%) | 23 (7.1%) | 46 (9.5%) |
| 80 | 38 (23.3%) | 77 (23.8%) | 115 (23.7%) |
| Other doses | 0 | 3 (0.9%) | 3 (0.6%) |
| Rosuvastatin daily dose (mg) | 81 (49.7%) | 172 (53.3%) | 253 (52.1%) |
| 5 | 4 (2.5%) | 7 (2.2%) | 11 (2.3%) |
| 10 | 2 (1.2%) | 5 (1.5%) | 7 (1.4%) |
| 20 | 19 (11.7%) | 44 (13.6%) | 63 (13.0%) |
| 40 | 55 (33.7%) | 116 (35.9%) | 171 (35.2%) |
| Other doses | 1 (0.6%) | 0 | 1 (0.2%) |
| Simvastatin daily dose (mg) | 18 (11.0%) | 38 (11.8%) | 56 (11.5%) |
| 10 | 2 (1.2%) | 2 (0.6%) | 4 (0.8%) |
| 20 | 1 (0.6%) | 5 (1.5%) | 6 (1.2%) |
| 40 | 10 (6.1%) | 25 (7.7%) | 35 (7.2%) |
| 80 | 3 (1.8%) | 6 (1.9%) | 9 (1.9%) |
| Other doses | 2 (1.2%) | 0 | 2 (0.4%) |
| Any LMT other than statins[a] | 107 (65.6%) | 198 (61.3%) | 305 (62.8%) |
| Any LMT other than nutraceuticals | 105 (64.4%) | 192 (59.4%) | 297 (61.1%) |
| Ezetimibe | 97 (59.5%) | 180 (55.7%) | 277 (57.0%) |
| Nutraceuticals | 8 (4.9%) | 20 (6.2%) | 28 (5.8%) |

[a] in combination with statins or not.

High intensity statin corresponds to atorvastatin 40 to 80 mg daily or rosuvastatin 20 to 40 mg daily.

TABLE 8

Lipid efficacy parameters at baseline - Quantitative summary in conventional units - Randomized population

|  | Placebo (N = 163) | Alirocumab 75 Q2W/Up150 Q2W (N = 323) | All (N = 486) |
|---|---|---|---|
| Calculated LDL-C (mg/dL) | | | |
| Number | 163 | 323 | 486 |
| Mean (SD) | 144.4 (46.8) | 144.8 (51.1) | 144.6 (49.7) |

TABLE 8-continued

Lipid efficacy parameters at baseline - Quantitative summary in conventional units - Randomized population

| | Placebo (N = 163) | Alirocumab 75 Q2W/Up150 Q2W (N = 323) | All (N = 486) |
|---|---|---|---|
| Median | 138.0 | 135.0 | 135.5 |
| Q1:Q3 | 112.0:166.0 | 112.0:163.0 | 112.0:165.0 |
| Min:Max | 66:354 | 39:384 | 39:384 |
| Measured LDL-C (mg/dL) | | | |
| Number | 140 | 272 | 412 |
| Mean (SD) | 140.0 (43.5) | 140.2 (49.7) | 140.1 (47.6) |
| Median | 135.0 | 130.5 | 132.0 |
| Q1:Q3 | 111.0:164.0 | 108.0:159.5 | 108.5:161.0 |
| Min:Max | 68:356 | 37:378 | 37:378 |
| Non-HDL-C (mg/dL) | | | |
| Number | 163 | 323 | 486 |
| Mean (SD) | 169.6 (50.6) | 170.3 (54.6) | 170.1 (53.3) |
| Median | 161.0 | 158.0 | 160.0 |
| Q1:Q3 | 132.0:195.0 | 134.0:198.0 | 133.0:196.0 |
| Min:Max | 78:390 | 58:426 | 58:426 |
| Total-C (mg/dL) | | | |
| Number | 163 | 323 | 486 |
| Mean (SD) | 217.6 (50.3) | 221.1 (54.3) | 219.9 (53.0) |
| Median | 210.0 | 212.0 | 211.0 |
| Q1:Q3 | 185.0:240.0 | 184.0:244.0 | 185.0:243.0 |
| Min:Max | 137:445 | 123:482 | 123:482 |
| HDL-C (mg/dL) | | | |
| Number | 163 | 323 | 486 |
| Mean (SD) | 48.0 (14.4) | 50.8 (15.7) | 49.8 (15.3) |
| Median | 45.0 | 47.0 | 46.5 |
| Q1:Q3 | 36.0:56.0 | 39.0:59.0 | 38.0:58.0 |
| Min:Max | 24:116 | 22:115 | 22:116 |
| Fasting TGs (mg/dL) | | | |
| Number | 163 | 323 | 486 |
| Mean (SD) | 126.5 (62.9) | 128.4 (66.7) | 127.8 (65.4) |
| Median | 111.0 | 113.0 | 112.0 |
| Q1:Q3 | 85.0:151.0 | 82.0:153.0 | 83.0:152.0 |
| Min:Max | 45:431 | 35:566 | 35:566 |
| Lipoprotein-(a)(mg/dL) | | | |
| Number | 161 | 317 | 478 |
| Mean (SD) | 47.2 (51.6) | 51.7 (50.2) | 50.2 (50.7) |
| Median | 23.0 | 34.0 | 28.0 |
| Q1:Q3 | 8.0:72.0 | 12.0:82.0 | 11.0:80.0 |
| Min:Max | 2:223 | 2:229 | 2:229 |
| Apo-B (mg/dL) | | | |
| Number | 161 | 317 | 478 |
| Mean (SD) | 113.4 (28.5) | 114.4 (30.8) | 114.1 (30.0) |
| Median | 109.0 | 108.0 | 109.0 |
| Q1:Q3 | 94.0:128.0 | 94.0:130.0 | 94.0:129.0 |
| Min:Max | 64:249 | 45:250 | 45:250 |
| Apo-A1 (mg/dL) | | | |
| Number | 161 | 317 | 478 |
| Mean (SD) | 137.6 (27.2) | 142.8 (27.4) | 141.1 (27.4) |
| Median | 134.0 | 138.0 | 137.0 |
| Q1:Q3 | 121.0:151.0 | 124.0:158.0 | 122.0:155.0 |
| Min:Max | 84:292 | 79:278 | 79:292 |
| Apo-B/Apo-A1 (ratio) | | | |
| Number | 161 | 317 | 478 |
| Mean (SD) | 0.859 (0.292) | 0.830 (0.269) | 0.839 (0.277) |
| Median | 0.810 | 0.780 | 0.800 |
| Q1:Q3 | 0.640:0.990 | 0.650:0.960 | 0.650:0.970 |
| Min:Max | 0.36:2.42 | 0.26:1.84 | 0.26:2.42 |
| Total-C/HDL-C (ratio) | | | |
| Number | 163 | 323 | 486 |
| Mean (SD) | 4.907 (1.838) | 4.707 (1.756) | 4.774 (1.785) |
| Median | 4.658 | 4.321 | 4.444 |

TABLE 8-continued

Lipid efficacy parameters at baseline - Quantitative summary in conventional units - Randomized population

|  | Placebo (N = 163) | Alirocumab 75 Q2W/Up150 Q2W (N = 323) | All (N = 486) |
|---|---|---|---|
| Q1:Q3 | 3.661:5.658 | 3.537:5.649 | 3.542:5.649 |
| Min:Max | 1.86:13.64 | 1.73:15.14 | 1.73:15.14 |

Note:
Measured LDL-C was assessed via the beta-quantification method.

The collection of measured LDL-C was not planned in the initial protocol and was added in an amendment. Therefore, measured LDL-C values are available for fewer patients compared to calculated LDL-C values.

Dosage and Duration

Exposure to injections was similar across treatment groups with a mean exposure of 59 weeks.

In the alirocumab group, among the 311 patients who received at least one injection after Week 12, 135 (43.4%) patients received automatic up-titration from 75 mg Q2W to 150 mg Q2W at Week 12 in a blinded manner.

Efficacy

Primary Efficacy Endpoint

The ITT analysis includes all calculated LDL-C values collected on-treatment and off-treatment up to Week 52. The primary endpoint (percent change in calculated LDL-C from baseline to Week 24) analysis is provided based on a MMRM model on the ITT population, using LS means estimates at Week 24. Thirty-two (9.9%) patients in the alirocumab group and 14 (8.6%) patients in the placebo group did not have a calculated LDL-C value at Week 24. These missing values were accounted for by the MMRM model.

Results of the primary endpoint analysis are presented in Table 9, in mmol/L and mg/dL.

Primary Efficacy Analysis

Figure 2:
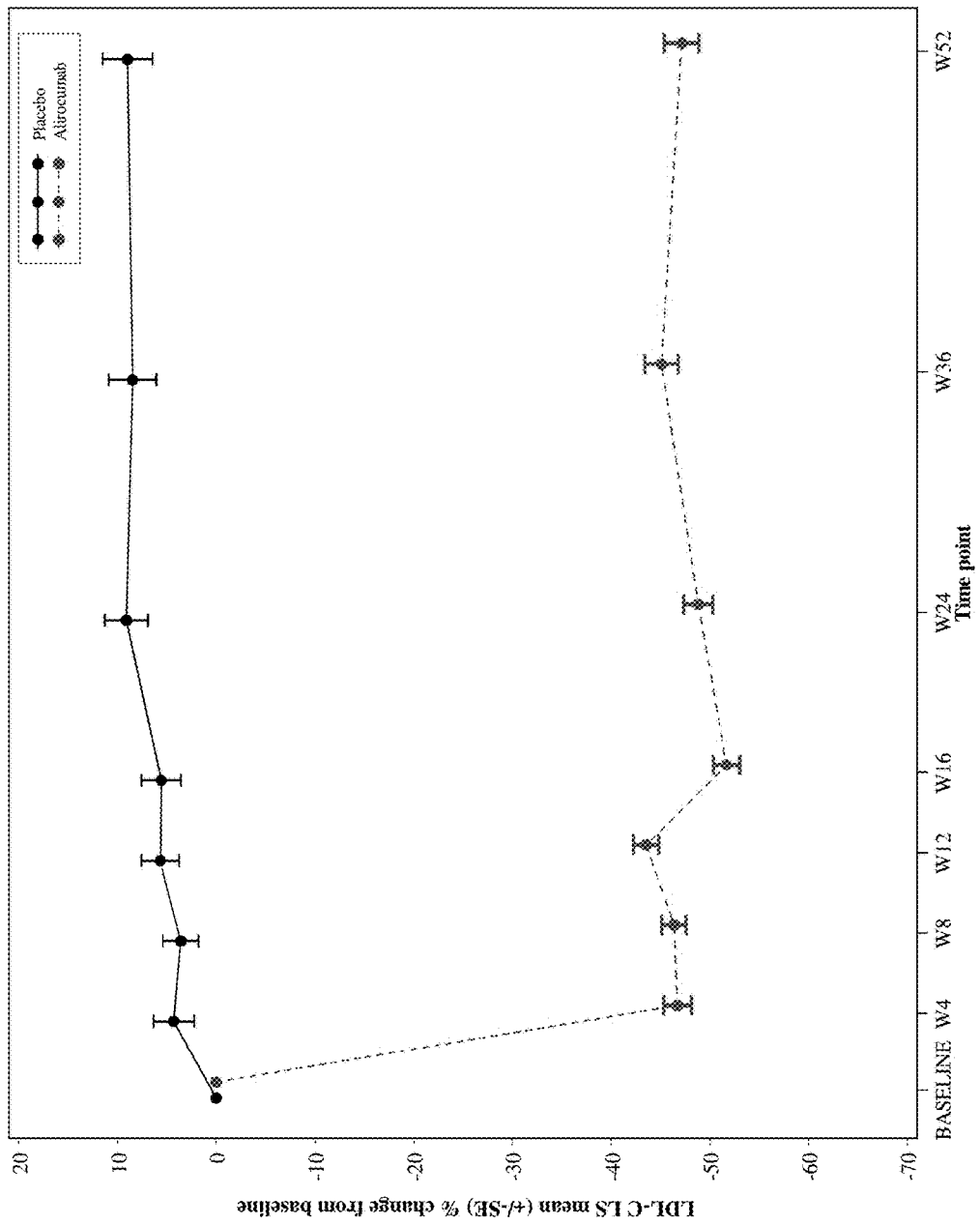
FIG. 2 is a graph showing the calculated LDL-C LS mean percent change from baseline over time for treatment with alirocumab or placebo in the ITT population in the ODYSSEY FH I study (Example 2). The least-squares (LS) means and standard errors (SD) are taken from MMRM (mixed-effect model with repeated measures) analysis.

A statistically significant decrease in percent change in LDL-C from baseline to Week 24 was observed in the alirocumab group (LS mean versus baseline−48.8%) compared to the placebo group (LS mean versus baseline+9.1%) (LS mean difference vs. placebo of −57.9%, p<0.0001). In the alirocumab group, LDL-C reduction from baseline was observed from Week 4 and maintained throughout the study up to Week 78 (see FIG. 2 and Table 10).

TABLE 9

Percent change from baseline in calculated LDL-C at Week 24: MMRM - ITT analysis - ITT population

| Calculated LDL Cholesterol | Placebo (N = 163) | Alirocumab 75 Q2W/Up150 Q2W (N = 322) |
|---|---|---|
| Baseline (mmol/L) | | |
| Number | 163 | 322 |
| Mean (SD) | 3.739 (1.213) | 3.748 (1.326) |
| Median | 3.574 | 3.497 |
| Min:Max | 1.71:9.17 | 1.01:9.95 |
| Baseline (mg/dL) | | |
| Number | 163 | 322 |
| Mean (SD) | 144.4 (46.8) | 144.7 (51.2) |
| Median | 138.0 | 135.0 |
| Min:Max | 66:354 | 39:384 |
| Week 24 percent change from baseline (%) | | |
| LS Mean (SE) | 9.1 (2.2) | −48.8 (1.6) |
| LS mean difference (SE) vs placebo | | −57.9 (2.7) |
| 95% CI | | (−63.3 to −52.6) |
| p-value vs placebo | | <0.0001* |

Note:
Least-squares (LS) means, standard errors (SE) and p-value taken from MMRM (mixed-effect model with repeated measures) analysis. The model includes the fixed categorical effects of treatment group, randomization strata as per IVRS, time point, treatment-by-time point and strata-by-time point interaction, as well as the continuous fixed covariates of baseline calculated LDL-C value and baseline calculated LDL-C value-by-time point interaction
MMRM model and baseline description run on patients with a baseline value and a post-baseline value in at least one of the analysis windows used in the model.
The p-value is followed by a '*' if statistically significant according to the fixed hierarchical approach used to ensure a strong control of the overall type-I error rate at the 0.05 level

TABLE 10

Calculated LDL-C over time - ITT analysis - ITT population

| | Placebo (N = 163) | | | Alirocumab 75 Q2W/Up150 Q2W (N = 322) | | |
|---|---|---|---|---|---|---|
| Calculated LDL-C | Value | Change from baseline | Percent change from baseline | Value | Change from baseline | Percent change from baseline |
| LS Mean (SE) (mmol/L) | | | | | | |
| Baseline[a] | 3.739 (0.095) | NA | NA | 3.748 (0.074) | NA | NA |

TABLE 10-continued

Calculated LDL-C over time - ITT analysis - ITT population

| Calculated LDL-C | Placebo (N = 163) | | | Alirocumab 75 Q2W/Up150 Q2W (N = 322) | | |
|---|---|---|---|---|---|---|
| | Value | Change from baseline | Percent change from baseline | Value | Change from baseline | Percent change from baseline |
| Week 4 | 3.819 (0.070) | 0.074 (0.070) | 4.3 (2.1) | 1.996 (0.050) | −1.749 (0.050) | −46.7 (1.5) |
| Week 8 | 3.805 (0.073) | 0.059 (0.073) | 3.6 (1.8) | 1.986 (0.052) | −1.759 (0.052) | −46.4 (1.3) |
| Week 12 | 3.898 (0.074) | 0.153 (0.074) | 5.7 (2.0) | 2.078 (0.053) | −1.668 (0.053) | −43.5 (1.4) |
| Week 16 | 3.892 (0.080) | 0.147 (0.080) | 5.6 (2.1) | 1.763 (0.057) | −1.982 (0.057) | −51.7 (1.5) |
| Week 24 | 4.029 (0.084) | 0.284 (0.084) | 9.1 (2.2) | 1.846 (0.060) | −1.899 (0.060) | −48.8 (1.6) |
| Week 36 | 3.965 (0.091) | 0.220 (0.091) | 8.5 (2.4) | 1.997 (0.066) | −1.748 (0.066) | −45.1 (1.8) |
| Week 52 | 4.000 (0.092) | 0.255 (0.092) | 9.0 (2.6) | 1.925 (0.066) | −1.821 (0.066) | −47.1 (1.9) |
| Week 64 | 3.947 (0.086) | | | 1.962 (0.063) | | |
| Week 78 | 4.082 (0.101) | | | 2.177 (0.073) | | |
| LS Mean (SE) (mg/dL) | | | | | | |
| Baseline[a] | 144.4 (3.7) | NA | NA | 144.7 (2.9) | NA | NA |
| Week 4 | 147.5 (2.7) | 2.9 (2.7) | 4.3 (2.1) | 77.1 (1.9) | −67.5 (1.9) | −46.7 (1.5) |
| Week 8 | 146.9 (2.8) | 2.3 (2.8) | 3.6 (1.8) | 76.7 (2.0) | −67.9 (2.0) | −46.4 (1.3) |
| Week 12 | 150.5 (2.9) | 5.9 (2.9) | 5.7 (2.0) | 80.2 (2.0) | −64.4 (2.0) | −43.5 (1.4) |
| Week 16 | 150.3 (3.1) | 5.7 (3.1) | 5.6 (2.1) | 68.1 (2.2) | −76.5 (2.2) | −51.7 (1.5) |
| Week 24 | 155.6 (3.2) | 11.0 (3.2) | 9.1 (2.2) | 71.3 (2.3) | −73.3 (2.3) | −48.8 (1.6) |
| Week 36 | 153.1 (3.5) | 8.5 (3.5) | 8.5 (2.4) | 77.1 (2.5) | −67.5 (2.5) | −45.1 (1.8) |
| Week 52 | 154.4 (3.5) | 9.8 (3.5) | 9.0 (2.6) | 74.3 (2.6) | −70.3 (2.6) | −47.1 (1.9) |
| Week 64 | 152.4 (3.3) | | | 75.8 (2.4) | | |
| Week 78 | 157.6 (3.9) | | | 84.0 (2.8) | | |

[a]Baseline is described using means and standard errors.

Note:
Least-squares (LS) means, standard errors (SE) and p-value taken from MMRM (mixed-effect model with repeated measures) analysis. The model includes the fixed categorical effects of treatment group, randomization strata as per IVRS, time point, treatment-by-time point interaction, strata-by-time point interaction, as well as the continuous fixed covariates of baseline LDL-C value and baseline LDL-C value-by-time point interaction
MMRM model and baseline description run on patients with a baseline value and a post-baseline value in at least one of the analysis windows used in the model.

Key Secondary Efficacy Endpoints

Table 11 summarizes analysis results on key secondary endpoints in the hierarchical order. All key secondary endpoints are statistically significant according to the hierarchical testing procedure.

TABLE 11

| Endpoint | Analysis | Results | P-value |
|---|---|---|---|
| Calculated LDL-C - Percent change from baseline to Week 24 | On-treatment | LS mean difference vs. placebo of −58.1% | <0.0001 |
| Calculated LDL-C - Percent change from baseline to Week 12 | ITT | LS mean difference vs. placebo of −49.2% | <0.0001 |
| Calculated LDL-C - Percent change from baseline to Week 12 | On-treatment | LS mean difference vs. placebo of −49.5% | <0.0001 |
| Apo-B - Percent change from baseline to Week 24 | ITT | LS mean difference vs. placebo of −45.8% | <0.0001 |
| Apo-B - Percent change from baseline to Week 24 | On-treatment | LS mean difference vs. placebo of −45.9% | <0.0001 |
| Non-HDL-C - Percent change from baseline to Week 24 | ITT | LS mean difference vs. placebo of −52.4% | <0.0001 |
| Non-HDL-C - Percent change from baseline to Week 24 | On-treatment | LS mean difference vs. placebo of −52.6% | <0.0001 |
| Total-C - Percent change from baseline to Week 24 | ITT | LS mean difference vs. placebo of −38.7% | <0.0001 |
| Apo-B - Percent change from baseline to Week 12 | ITT | LS mean difference vs. placebo of −37.5% | <0.0001 |

TABLE 11-continued

| Endpoint | Analysis | Results | P-value |
|---|---|---|---|
| Non-HDL-C - Percent change from baseline to Week 12 | ITT | LS mean difference vs. placebo of −43.7% | <0.0001 |
| Total-C - Percent change from baseline to Week 12 | ITT | LS mean difference vs. placebo of −32.5% | <0.0001 |
| Calculated LDL-C - Percent change from baseline to Week 52 | ITT | LS mean difference vs. placebo of −56.2% | <0.0001 |
| Proportion of very high CV risk patients reaching calculated LDL-C < 70 mg/dL (1.81 mmol/L) or high CV risk patients reaching calculated LDL-C < 100 mg/dL (2.59 mmol/L) at Week 24 | ITT | combined estimate for odds-ratio vs. placebo of 155.1 | <0.0001 |
| Proportion of very high CV risk patients reaching calculated LDL-C < 70 mg/dL (1.81 mmol/L) or high CV risk patients reaching calculated LDL-C < 100 mg/dL (2.59 mmol/L) at Week 24 | On-treatment | combined estimate for odds-ratio vs. placebo of 149.1 | <0.0001 |
| Proportion of patients reaching calculated LDL-C < 70 mg/dL (1.81 mmol/L) at Week 24 | ITT | combined estimate for odds-ratio vs. placebo of 237.1 | <0.0001 |
| Proportion of patients reaching calculated LDL-C < 70 mg/dL (1.81 mmol/L) at Week 24 | On-treatment | combined estimate for odds-ratio vs. placebo of 237.9 | <0.0001 |
| Lp(a) - Percent change from baseline to Week 24 | ITT | combined estimate for adjusted mean difference vs. placebo of −17.7% | <0.0001 |
| HDL-C - Percent change from baseline to Week 24 | ITT | LS mean difference vs. placebo of 8% | <0.0001 |
| Fasting TGs - Percent change from baseline to Week 24 | ITT | combined estimate for adjusted mean difference vs. placebo of −16.1% | <0.0001 |
| Apolipoprotein A1 - Percent change from baseline to Week 24 | ITT | LS mean difference vs. placebo of 4.7% | <0.05 |

The on-treatment analysis of LDL-C percent change from baseline to Week 24 shows very consistent results with the ITT analysis (LS mean difference vs. placebo of −58.1% in the on-treatment analysis versus—57.9% in the ITT analysis). Indeed, few patients had LDL-C values collected post-treatment (i.e., more than 21 days after last injection) at Week 24: 6 patients (3.7%) in the placebo group and 2 patients (0.6%) in the alirocumab group. A statistically significant decrease in percent change in LDL-C from baseline to Week 12 (i.e. before possible up-titration) in the ITT analysis was observed in the alirocumab group (LS mean versus baseline−43.5%) compared to the placebo group (LS mean versus baseline+5.7%) (LS mean difference vs. placebo of −49.2%, p<0.0001).

The key secondary endpoints of Apo B, non-HDL-C, Total-C, Lp(a), HDL-C, and TGs at various time points as well as the proportion of patients reaching their LDL-C goals and the proportion of patients reaching calculated LDLD-C<70 mg/dL at Week 24 were statistically significant according to the hierarchical testing procedure. For the alirocumab group the baseline mean (SD) LDL-C, Non-LDL-C, ApoB and the median (IQR) Lp(a) levels were 144.7 (51.3), 170.3 (54.6), 114.3 (30.8), and 34 (12:82) mg/dl respectively. For the placebo group the baseline mean (SD) LDL-C, Non-LDL-C, ApoB and the median (IQR) Lp(a) levels were 144.4 (46.8), 169.6 (50.6), 113.4 (28:5), and 23 (8.72) mg/dl respectively. After 24 weeks, LS mean (SE) % change from baseline to Week 24 for Non-LDL-C, ApoB Lp(a) levels in the alirocumab group was −42.8%, −41.1%, and −25.2%, respectively. The LS mean (SE) % change from baseline to Week 24 for Non-LDL-C, ApoB Lp(a) levels for the placebo group was 9.6%, 4.7%, and −7.5%, respectively. The LS mean difference vs. placebo for Non-LDL-C, ApoB and Lp(a) was −52.4%, −45.8%, and 17.7%, respectively.

The proportion of very high cardiovascular (CV) risk patients reaching calculated LDL-C<70 mg/dL (1.81 mmol/L) or high CV risk patients reaching calculated LDL-C<100 mg/dL (2.59 mmol/L) at Week 24 was significantly higher in the alirocumab than in the placebo group (combined estimate for proportion of 72.1% in the alirocumab group vs 2.4% in the placebo group, p<0.0001).

Two consecutive calculated LDL-C values <25 mg/dL (<0.65 mmol/L) were observed in 16 (5.0%) patients. No particular safety concern has been observed in these patients.

TABLE 12

Number (%) of patients with 2 consecutive calculated LDL-C < 25 mg/dL (<0.65 mmol/L) during the treatment period- Safety population

| | Placebo (N = 163) | Alirocumab 75 Q2W/Up150 Q2W (N = 322) |
|---|---|---|
| Patients with 2 consecutive calculated LDL-C value < 25 mg/dL [1] | 0/163 | 16/317 (5.0%) |
| Time to the first calculated LDL-C value < 25 mg/dL (weeks) [2] | | |
| Number | 0 | 16 |
| Mean (SD) | | 14.79 (11.37) |
| Median | | 14.14 |
| Min:Max | | 3.1:36.1 |
| Patients with 2 consecutive calculated LDL-C value < 15 mg/dL [1] | 0/163 | 6/317 (1.9%) |
| Time to the first calculated LDL-C value < 15 mg/dL (weeks) [2] | | |
| Number | 0 | 6 |
| Mean (SD) | | 18.31 (12.35) |

TABLE 12-continued

Number (%) of patients with 2 consecutive calculated LDL-C < 25 mg/dL (<0.65 mmol/L) during the treatment period- Safety population

|  | Placebo (N = 163) | Alirocumab 75 Q2W/Up150 Q2W (N = 322) |
|---|---|---|
| Median |  | 20.14 |
| Min:Max |  | 4.6:36.1 |

The number (n) represents the subset of the total number of patients who met the criteria
The denominator (/N) within a treatment group is the number of patients for the treatment group who had at least two calculated LDL-C values assessed at least 21 days apart in the efficacy period
[1] 2 consecutive values are considered if spaced out by at least 21 days
[2] First calculated LDL-C value < 25 or < 15 mg/dL among the first 2 consecutive calculated LDL-C values < 25 or < 15 mg/dL per patient Summary Safety Results:

Alirocumab was well tolerated during the treatment period.

TABLE 13

Overview of adverse event profile: Treatment emergent adverse events - Safety population

| n(%) | Placebo (N = 163) | Alirocumab 75 Q2W/Up150 Q2W (N = 322) |
|---|---|---|
| Patients with any TEAE | 122 (74.8%) | 249 (77.3%) |
| Patients with any treatment emergent SAE | 15 (9.2%) | 39 (12.1%) |
| Patients with any TEAE leading to death | 0 | 4 (1.2%) |
| Patients with any TEAE leading to permanent treatment discontinuation | 8 (4.9%) | 10 (3.1%) | n(%) = number and percentage of patients with at least one TEAE

Overall, the proportions of patients reporting at least one treatment emergent adverse event (TEAE) (77.3% in the alirocumab group and 74.8% in the placebo group) or at least one TEAE leading to permanent discontinuation (3.1% in the alirocumab group and 4.9% in the placebo group) were similar in both groups. "Musculoskeletal and connective tissue disorders" SOC was reported in 22.4% of patients in the alirocumab group vs. 25.2% in the placebo group. The most frequently reported TEAEs in both treatment groups were "injection site reaction" (11.8% vs. 9.8% in alirocumab vs. placebo group, respectively) and "nasopharyngitis" (9.9% vs 6.7% in alirocumab vs. placebo group, respectively). Among the events of interest, no particular signal was detected for TEAEs related to allergic events, neurological events, neurocognitive disorders and diabetes. The SOC "neoplasms begnin, malignant and unspecified" was observed in 2.8% of patients in the alirocumab group vs 0.6% in the placebo group with no particular clinical pattern on individual events (all these events were reported as not related to IMP by the investigator). TEAEs "cardiovascular events confirmed by adjudication" were reported for 1.9% of patients in the alirocumab group and 1.2% in the placebo group.

Six deaths (1.9%) were reported as not related to IMP by the investigator in the alirocumab group versus none in the placebo group: two myocardial infarctions (MI) (one classified as acute MI and one classified as sudden cardiac death), two metastatic cancers (non-small cell lung cancer and pancreatic carcinoma with secondary Trousseau syndrome causing multiple embolic strokes), a colonic pseudo-obstruction following abdominal surgery in one patient, and sudden cardiac death in one patient due to congestive cardiac failure and coronary artery disease. Both patients with MI had multiple risk factors for coronary artery disease. With regards to cancers, the time to onset of first symptoms (about 3.5 and 7.5 months after starting the investigational product) is not suggestive of a causal role of the investigational product.

No relevant abnormalities were observed for PCSA.

Example 3: A Randomized, Double-Blind, Placebo-Controlled, Parallel-Group Study to Evaluate the Efficacy and Safety of Alirocumab in Patients with Heterozygous Familial Hypercholesterolemia not Adequately Controlled with their Lipid-Modifying Therapy Introduction The objective of the study was to assess the efficacy and safety of Alirocumab in improving lipid parameters in patients with heterozygous familial hypercholesterolemia (heFH) who have failed to reach their LDL-C treatment goal on maximally-tolerated statin therapy, with or without additional lipid-modifying therapy (LMT). Patients not at goal on a maximally-tolerated dose of daily statin therapy, with or without other LMT, were enrolled in this study, and that their background treatment was maintained throughout the study.

Figure 3:
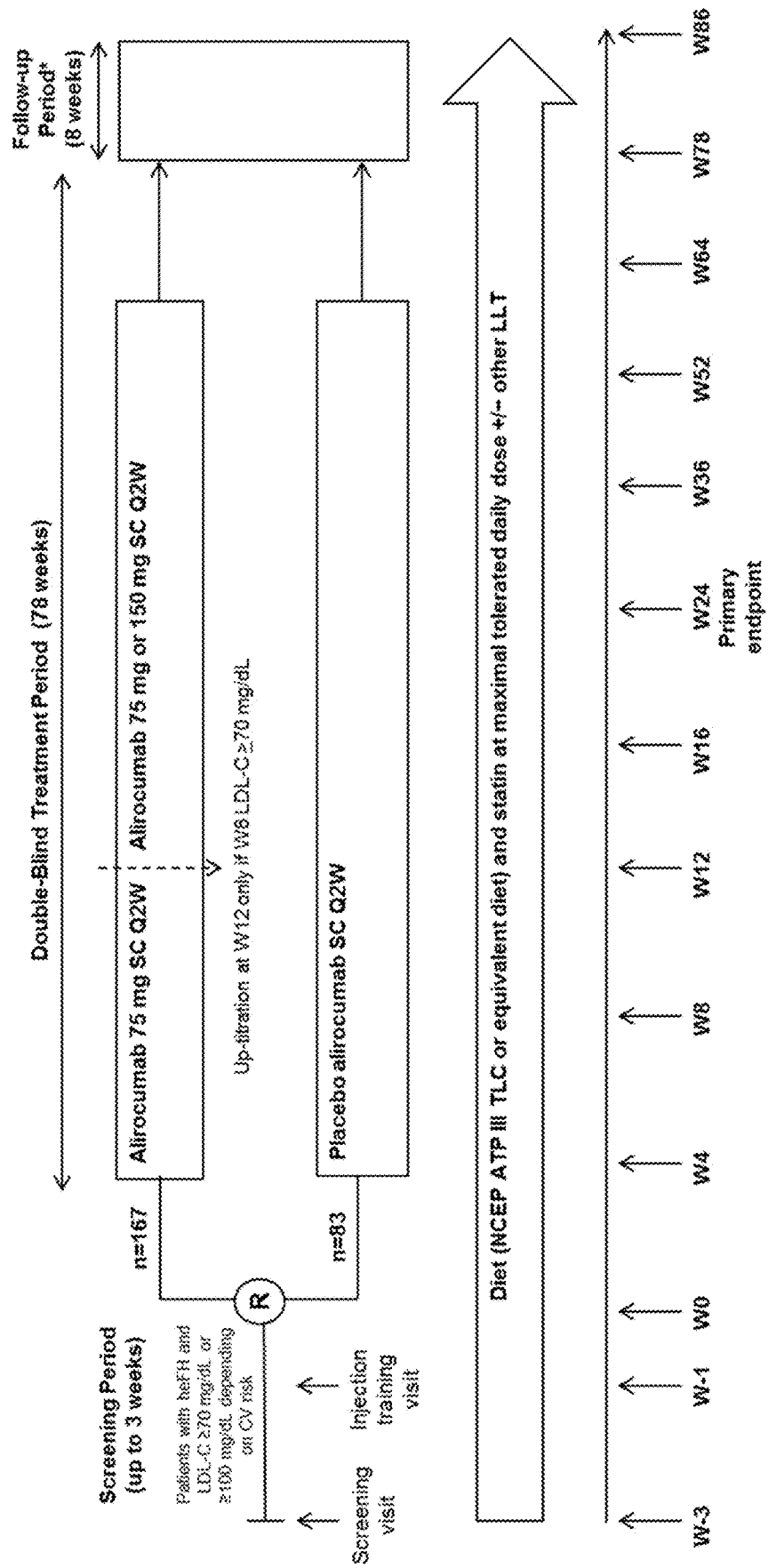
FIG. 3 is a graphic representation of the study design for ODYSSEY FH II (Example 3).

This specific study (FIG. 3) was undertaken to demonstrate in heFH patients who were not at their LDL-C goal, that Alirocumab 75 mg q2w or 75 mg q2w/150 mg q2w as add-on therapy to statin+/−other LMT, causes a statistically significant and clinically meaningful reduction in LDL-C. This population that is not at LDL-C goal on optimized LMT represents a highest risk group with a well-identified unmet medical need that can be addressed by adding Alirocumab to their LDL-C lowering therapies.

Study Objectives

The primary objective of the study was to demonstrate the reduction of LDL-C by Alirocumab as add-on therapy to stable, maximally-tolerated daily statin therapy with or without other LMT in comparison with placebo after 24 weeks of treatment in patients with heFH.

The secondary objectives of the study were: 1) to evaluate the effect of Alirocumab 75 mg in comparison with placebo on LDL-C after 12 weeks of treatment; 2) to evaluate the effect of Alirocumab on other lipid parameters (e.g., ApoB, non-HDL-C, total-C, Lp[a], HDL-C, TG levels, and ApoA-1 levels); 3) to evaluate the long-term effect of Alirocumab on LDL-C; 4) to evaluate the safety and tolerability of Alirocumab; and 5) to evaluate the development of anti-Alirocumab antibodies.

Study Design

This was a randomized, double-blind, placebo-controlled, parallel-group, multi-national study in patients with heFH who were not adequately controlled with their LMT (i.e., stable maximally-tolerated daily statin therapy+/−other LMT). Not adequately controlled was defined as an LDL-C≥70 mg/dL (1.81 mmol/L) at the screening visit (week 2) in patients with a history of documented CVD or LDL-C≥100 mg/dL (2.59 mmol/L) at the screening visit (week −2) in patients without a history of documented CVD. Patients were randomized in a 2:1 ratio to receive either 75 mg of Alirocumab or placebo by SC injection, every 2 weeks, on top of stable, maximally-tolerated daily statin therapy (atorvastatin, rosuvastatin, or simvastatin) with or without other LMT. Randomization was stratified according to prior history of either myocardial infarction (MI) or ischemic stroke, and statin treatment (atorvastatin 40 mg to 80 mg daily or rosuvastatin 20 mg to 40 mg daily vs. simvastatin whatever the daily dose, atorvastatin below 40 mg daily, or rosuvastatin below 20 mg daily).

The study consisted of three periods: a screening period, a treatment period, and a follow-up period.

The screening period was up to 2 weeks, including an intermediate visit during which the patient or caregiver was trained to self-inject/inject using a dose of placebo.

The double-blind treatment period was 78 weeks. The first injection of study drug was administered at the clinical site on day 1, after study assessments were completed, and as soon as possible after the patient was randomized into the study. The patient/caregiver administered subsequent injections outside of the clinic according to the dosing schedule. On days where the clinic study visit coincides with dosing, the dose of study drug was administered after all study assessments were performed and all laboratory samples collected. The last dose of study drug was administered at week 76. At week 12, patients randomized to Alirocumab were, in a blinded manner, either: 1) continued Alirocumab 75 mg every 2 weeks, if the week 8 LDL-C was <70 mg/dL (1.81 mmol/L), or 2) dose up-titrated to Alirocumab 150 mg every 2 weeks, if the week 8 LDL-C was ≥70 mg/dL (1.81 mmol/L).

The follow-up period (if applicable) was 8 weeks after the end of the DBTP for patients not consenting to participate in the open-label extension study, or if prematurely discontinuing study treatment.

Patients were asked to follow a stable diet (equivalent to the National Cholesterol Education Program Adult Treatment Panel III Therapeutic Lifestyle Changes [NCEP ATP III TLC] diet/Appendix 5) from screening to the end of study visit. The daily dose of statin or other LMT (if applicable) should remain stable from screening to the end of study visit. Starting at week 24, background LMT may be modified under certain conditions as described later. Table 1 from Example 2 is relevant to this Example and provides a summary of the TLC diet for high cholesterol.

An independent external physician was notified by the central laboratory for any patient who achieved 2 consecutive calculated LDL-C levels <25 mg/dL (0.65 mmol/L). Patients who meet this criterion were monitored.

Selection of Patients

The study population consisted of patients with heFH who were not adequately controlled with a maximally-tolerated stable daily dose of a statin for at least 4 weeks before the screening visit (week −2), with or without other LMT.

A patient must have met the following criteria to be eligible for inclusion in the study: 1) patients with heFH* who were not adequately controlled with a maximally-tolerated daily dose* of statin with or without other LMT, at a stable dose prior to the screening visit (week −2).

*Diagnosis of heFH must be made either by genotyping or by clinical criteria. For those patients not genotyped, the clinical diagnosis may be based on either the Simon Broome criteria for definite FH or the WHO/Dutch Lipid Network criteria with a score of >8 points.

Definite familial hypercholesterolemia was defined herein the same as it was in Example 2. Possible familial hypercholesterolemia was defined herein the same as it was in Example 2. The WHO Criteria (Dutch Lipid Network clinical criteria) for Diagnosis of Heterozygous Familial Hypercholesterolemia (heFH) set forth in Table 2 in Example 2 was the same for this Example.

**"Not adequately controlled" was defined herein the same as it was in Example 2.

A Documented History of CHD was defined herein the same as in Example 2.

CHD Risk Equivalents (includes 1 or more of the following criteria): 1) documented peripheral arterial disease (one of the following criteria must be satisfied): A) current intermittent claudication (muscle discomfort in the lower limb produced by exercise that is both reproducible and relieved by rest within 10 minutes) of presumed atherosclerotic origin together with ankle-brachial index equal to or less than 0.90 in either leg at rest, or B) history of intermittent claudication (muscle discomfort in the lower limb produced by exercise that is both reproducible and relieved by rest within 10 minutes) together with endovascular procedure or surgical intervention in one or both legs because of atherosclerotic disease, or C) history of critical limb ischemia together with thrombolysis, endovascular procedure or surgical intervention in one or both legs because of atherosclerotic disease; 2) documented previous ischemic stroke with a focal ischemic neurological deficit that persisted more than 24 hours, considered as being of atherothrombotic origin. CT or MRI must have been performed to rule out hemorrhage and non-ischemic neurological disease.

***"Maximally-tolerated dose" was defined herein the same as it was in Example 2.

Patients who met all of the above inclusion criteria were screened for the following exclusion criteria, which are sorted in the following three subsections: exclusion criteria related to study methodology, exclusion criteria related to the active comparator and/or mandatory background therapies, and exclusion criteria related to the current knowledge of Alirocumab.

Exclusion criteria related to the study methodology were: 1) patient without diagnosis of heFH made either by genotyping or by clinical criteria; 2) LDL-C<70 mg/dL (<1.81 mmol/L) at the screening visit (week −2) in patients with history of documented CVD. NOTE: CVD is defined as CHD, ischemic stroke, or peripheral arterial disease as described above; 3) LDL-C<100 mg/dL (<2.59 mmol/L) at the screening visit (week −2) in patients without history of documented CVD; 4) not on a stable dose of LMT (including statin) for at least 4 weeks and/or fenofibrate for at least 6 weeks, as applicable, prior to the screening visit (week −2) and from screening to randomization; 5) currently taking another statin than simvastatin, atorvastatin, or rosuvastatin; 6) simvastatin, atorvastatin, or rosuvastatin is not taken daily or not taken at a registered dose; 7) daily doses above atorvastatin 80 mg, rosuvastatin 40 mg, or simvastatin 40 mg (except for patients on simvastatin 80 mg for more than 1 year, who are eligible); 8) use of fibrates, other than fenofibrate within 6 weeks of the screening visit (week −2) or between screening and randomization visits; 9) use of nutraceutical products or over-the-counter therapies that may affect lipids which have not been at a stable dose/amount for at least 4 weeks prior to the screening visit (week −2) or between screening and randomization visits; 10) use of red yeast rice products within 4 weeks of the screening visit (week −2), or between screening and randomization visits; 11) patient who has received plasmapheresis treatment within 2 months prior to the screening visit (week −2), or has plans to receive it during the study; 12) recent (within 3 months prior to the screening visit [week −2] or between screening and randomization visits) MI, unstable angina leading to hospitalization, percutaneous coronary intervention (PCI), coronary artery bypass graft surgery (CABG), uncontrolled cardiac arrhythmia, stroke, transient ischemic attack, carotid revascularization, endovascular procedure or surgical intervention for peripheral vascular disease; 13) planned to undergo scheduled PCI, CABG, carotid, or peripheral revascularization during the study; 14) systolic blood pressure >160 mm Hg or diastolic blood pressure >100 mm Hg at screening visit or randomization visit; 15) history of New York Heart Association (NYHA) Class III or IV heart failure within the past 12 months; 16) known history of a hemorrhagic stroke; 17) age <18 years or legal age of majority at the screening visit (week −2), whichever is greater; 18) patients not previously instructed on a cholesterol-lowering diet prior to the screening visit (week −2); 19) newly diagnosed (within 3 calendar months prior to randomization visit [week 0]) or poorly controlled (hemoglobin A1c [HbA1c]>9% at the screening visit [week −2]) diabetes; 20) presence of any clinically significant uncontrolled endocrine disease known to influence serum lipids or lipoproteins. Note: Patients on thyroid replacement therapy can be included if the dosage has been stable for at least 12 weeks prior to screening and between screening and randomization visits, and thyroid-stimulating hormone (TSH) level is within the normal range of the central laboratory at the screening visit; 21) history of bariatric surgery within 12 months prior to the screening visit (week −2); 22) unstable weight defined by a variation >5 kg within 2 months prior to the screening visit (week −2); 23) known history of homozygous FH; 24) known history of loss-of-function of PCSK9 (ie, genetic mutation or sequence variation); 25) use of systemic corticosteroids, unless used as replacement therapy for pituitary/adrenal disease with a stable regimen for at least 6 weeks prior to randomization visit (week 0). Note: Topical, intra-articular, nasal, inhaled and ophthalmic steroid therapies are not considered as 'systemic' and are allowed; 26) use of continuous estrogen or testosterone hormone replacement therapy unless the regimen has been stable in the past 6 weeks prior to the screening visit (week −2) and no plans to change the regimen during the study; 27) history of cancer within the past 5 years, except for adequately treated basal cell skin cancer, squamous cell skin cancer, or in situ cervical cancer; 28) known history of a positive HIV test; 29) patient who has taken any investigational drugs other than the Alirocumab training placebo kits within 1 month or 5 half-lives, whichever is longer; 30) patient who has been previously treated with at least 1 dose of Alirocumab or any other anti-PCSK9 monoclonal antibody in other clinical studies; 31) conditions/situations such as: a) any clinically significant abnormality identified at the time of screening that, in the judgment of the investigator or any sub-investigator, would preclude safe completion of the study or constrain endpoints assessment; eg, major systemic diseases, patients with short life expectancy; or b) considered by the investigator or any sub-investigator as inappropriate for this study for any reason, e.g.: i) deemed unable to meet specific protocol requirements, such as scheduled visits; ii) those deemed unable to administer or tolerate long-term injections as per the patient or the investigator; iii) investigator or any sub-investigator, pharmacist, study coordinator, other study staff or relative thereof directly involved in the conduct of the protocol, etc.; iv) presence of any other conditions (eg, geographic or social), either actual or anticipated, that the investigator feels would; 32) laboratory findings during screening period (not including randomization week 0 labs, unless otherwise noted): i) positive test for hepatitis B surface antigen or hepatitis C antibody (confirmed by reflexive testing); ii) positive serum beta-hCG or urine pregnancy test (including week 0) in women of childbearing potential; iii) TG>400 mg/dL (>4.52 mmol/L) (1 repeat lab is allowed); iv) eGFR<30 mL/min/1.73 m2 according to 4-variable MDRD study equation (calculated by central lab); v) alanine aminotransferase (ALT) or aspartate aminotransferase (AST)>3×upper limit of normal (ULN) (1 repeat lab is allowed); vi) CPK>3×ULN (1 repeat lab is allowed); vii) TSH<lower limit of normal (LLN) or >ULN (1 repeat lab is allowed).

Exclusion criteria related to the active comparator and/or mandatory background therapies were: 1) all contraindications to the background therapies or warnings/precautions of use (when appropriate) as displayed in the respective National Product Labeling.

Exclusion criteria related to the current knowledge of Alirocumab were: 1) known hypersensitivity to monoclonal antibody or any component of the drug product; 2) pregnant or breast-feeding women; 3) women of childbearing potential who are not protected by highly-effective method(s) of birth control (as defined in the informed consent form and/or in a local protocol addendum) and/or who are unwilling or unable to be tested for pregnancy. Note: Women of childbearing potential must have a confirmed negative pregnancy test at screening and randomization visits. They must use an effective contraceptive method throughout the entire duration of study treatment and for 10 weeks after the last dose of study drug, and agree to repeat urine pregnancy test at designated visits. The applied methods of contraception have to meet the criteria for a highly effective method of birth control according to the "Note for guidance on nonclinical safety studies for the conduct of human clinical trials for pharmaceuticals (CPMP/ICH/286/95)". Postmenopausal women must be amenorrheic for at least 12 months.

Study Treatments

The study treatment was a single SC injection of 1 mL for a 75 mg or 150 mg dose of Alirocumab or placebo provided in an auto-injector, administered in the abdomen, thigh, or outer area of the upper arm. The first injection of study drug was administered at the clinical site, as soon as possible after the patient was randomized into the study. The patient was monitored at the clinical site for 30 minutes following the first injection. The patient/caregiver administered subsequent injections outside of the clinic, according to the dosing schedule. On days where the clinic study visit coincided with dosing, the dose of study drug was administered after all study assessments were performed and all laboratory samples collected. Subcutaneous dosing of study drug should be administered every 2 weeks at approximately the same time of day (based upon patient preference); it was acceptable for dosing to fall within a window of +/−3 days.

Sterile Alirocumab drug product was supplied at a concentration of 75 mg/mL or 150 mg/mL in histidine, pH 6.0, polysorbate 20, and sucrose in an auto-injector.

Placebo matching Alirocumab was supplied in the same formulation as Alirocumab, without the addition of protein, in an auto-injector.

All patients were on a maximally-tolerated stable daily statin (atorvastatin, rosuvastatin, or simvastatin)+/−other LMT throughout the duration of the study. Statin dose and the dose of other LMT (if applicable) should have remained stable throughout the whole study duration, from screening to the end of study visit.

During the double-blind treatment period, modification to the background LMT was allowed before week 24 only under certain conditions: 1) exceptional circumstances −overriding concerns (including, but not limited to, TG alert, below, posted by the central lab) warrant such changes, per the investigator's judgment; or 2) a confirmed TG alert—the patient meets the pre-specified TG alert (TG≥500 mg/dL [5.65 mmol/L]).

During the double-blind treatment period, modification to the background LMT was allowed after week 24 only under certain conditions: 1) exceptional circumstances, per the investigator's judgment; 2) a confirmed TG alert—the patient meets the pre-specified TG alert (TG≥500 mg/dL [5.65 mmol/L], or 3) LDL-C increased by at least 25% as compared to the randomization visit LDL-C(and no other reasonable explanation exists).

For a laboratory rescue alert of LDL-C increase >25% as compared to the randomization visit LDL-C on 2 consecutive occasions, the investigator should have ensured that no reasonable explanation exists for insufficient LDL-C control (such as an alternative medical cause like corticosteroid use, etc.) and in particular that: compliance with diet was appropriate; compliance with background LMT was appropriate; and study treatment was given as planned. If any of the above could reasonably explain the insufficient LDL-C control, the investigator should have stressed the absolute need to be compliant with treatment and, if needed, organized a specific interview with a qualified nutrition professional and stressed the absolute need to be compliant with diet, and performed a blinded LDL-C assessment within 1 to 2 months. Rescue treatment may be initiated in the event that no reason for LDL-C above the threshold value could be found.

If no reason for LDL-C above the threshold value could be found, or if appropriate action failed to decrease LDL-C below the threshold value, rescue medication may have been introduced. The effectiveness of any such changes would be made based on lack of rescue threshold from blinded lipid testing at the next routinely scheduled lab draw. Patients per protocol already received a maximum tolerated dose of statin, so statin up-titration or switch would not be an option. For further LDL-C lowering, the investigator may have considered adding: a cholesterol absorption inhibitor (ezetimibe), or a bile acid-binding sequestrant (the resins cholestyramine and colestipol, or colesevelam, a nonabsorbable polymer). The following lipid modifying agents may have also been considered: fibrate (Note: Caution should be exercised when combining fibrates with other cholesterol-lowering medications such as statins because of the risk of myopathy. When a fibrate is combined with a statin, fenofibrate is the fibrate of choice because it does not affect statin glucuronidation. The only fibrate allowed per protocol was fenofibrate); nicotinic acid (niacin) (Note: Niacin raises blood glucose but has been shown to be effective in modifying lipid disorders in people with diabetes if glucose control is maintained).

The dose of study drug was increased (up-titrated) from 75 mg to 150 mg SC every 2 weeks, starting at week 12, for an individual patient in the event LDL-C≥70 mg/dL at the week 8 visit.

Patients were randomized to receive either Alirocumab or placebo in a ratio of 2:1, with permuted-block randomization. Randomization was stratified according to prior history of MI or ischemic stroke (Yes/No), and statin dose ("Yes" as atorvastatin 40 mg to 80 mg daily or rosuvastatin 20 mg to 40 mg daily and "No" as simvastatin whatever the daily dose, atorvastatin below 40 mg daily or rosuvastatin below 20 mg daily) as fixed effects; and the baseline calculated LDL-C as covariate.

Concomitant medications should have been kept to a minimum during the study. If considered necessary for the patient's welfare and unlikely to interfere with study drug, concomitant medications (other than those that are prohibited during the study) could have been given at the discretion of the investigator, with a stable dose (when possible).

Nutraceutical products or over-the-counter therapies that may affect lipids were allowed only if they had been used at a stable dose for at least 4 weeks before the screening visit, during the screening period, and maintained during the first 24 weeks of the double-blind treatment period. After the week 24 visit, modification to these nutraceutical products or over-the-counter therapies was allowed, but in general should have been avoided. Examples of such nutraceutical products or over-the-counter therapies include omega-3 fatty acids at doses <1000 mg, plant stanols such as found in Benecol, flax seed oil, and *psyllium*.

Women of childbearing potential must have used an effective contraception method throughout study treatment, and for 10 weeks after the last dose of study drug.

Prohibited concomitant medications from the initial screening visit until the end of the study visit included the following: statins, other than atorvastatin, rosuvastatin, or simvastatin; fibrates, other than fenofibrate; and red yeast rice products.

Study Endpoints

Baseline characteristics included standard demography (e.g., age, race, weight, height, etc.), disease characteristics including medical history, and medication history for each patient.

The primary efficacy endpoint was the percent change in calculated LDL-C from baseline to week 24, which was defined as: 100× (calculated LDL-C value at week 24−calculated LDL-C value at baseline)/calculated LDL-C value at baseline. The baseline calculated LDL-C value was the last LDL-C level obtained before the first dose of study drug. The calculated LDL-C at week 24 was the LDL-C level obtained within the week 24 analysis window and during the main efficacy period. The main efficacy period was defined as the time from the first double-blind study drug injection up to 21 days after the last double-blind study drug injection or up to the upper limit of the week 24 analysis window, whichever came first.

The key secondary efficacy endpoints were: 1) the percent change in calculated LDL-C from baseline to week 12: similar definition and rules as for primary efficacy endpoint, except that the calculated LDL-C at week 12 was the LDL-C level obtained within the week 12 analysis window and during the 12-week efficacy period. The 12-week efficacy period was defined as the time from the first double-blind study drug injection up to the visit 6 re-supply IVRS contact or up to 21 days after the last study drug injection, whichever came first. Blood sampling collected the day of the visit 6 re-supply IVRS contact will be considered as before titration; 2) the percent change in ApoB from baseline to week 24. Same definition and rules as for the primary endpoint; 3) the percent change in non-HDL-C from baseline to week 24. Same definition and rules as for the primary endpoint; 4) the percent change in total-C from baseline to week 24. Same definition and rules as for the primary endpoint; 5) the percent change in ApoB from baseline to week 12. Same definition and rules as for the percent change in calculated LDL-C from baseline to week 12; 6) the percent change in non-HDL-C from baseline to week 12. Same definition and rules as for the percent change in calculated LDL-C from baseline to week 12; 7) the percent change in total-C from baseline to week 12. Same definition and rules as for the percent change in calculated LDL-C from baseline to week 12; 8) the percent change in calculated LDL-C from baseline to week 52. Definitions and rules are similar to the ones used for the primary endpoint replacing week 24 by week 52; 9) the proportion of patients reaching LDL-C goal at week 24, i.e., LDL-C<70 mg/dL (1.81 mmol/L) in case of prior CVD or <100 mg/dL (2.59 mmol/L) for patients without prior CVD, defined as: (number of patients whose calculated LDL-C value at week 24 reach LDL-C goal/number of patients in the [modified intent-to-treat (mITT population)] *100, using definition and rules used for the primary endpoint; 10) the proportion of patients reaching LDL-C<70 mg/dL (1.81 mmol/L) at week 24; 11) the percent change in Lp(a) from baseline to week 24. Same definition and rules as for the primary endpoint; 12) the percent change in HDL-C from baseline to week 24. Same definition and rules as for the primary endpoint; 13) the percent change in HDL-C from baseline to week 12. Same definition and rules as for the percent change in calculated LDL-C from baseline to week 12; 14) the percent change in Lp(a) from baseline to week 12. Same definition and rules as for the percent change in calculated LDL-C from baseline to week 12; 15) the percent change in fasting TG from baseline to week 24. Same definition and rules as for the primary endpoint; 16) the percent change in fasting TG from baseline to week 12. Same definition and rules as for the percent change in calculated LDL-C from baseline to week 12; 17) the percent change in ApoA-1 from baseline to week 24. Same definition and rules as for the primary endpoint; 18) the percent change in ApoA-1 from baseline to week 12. Same definition and rules as for the percent change in calculated LDL-C from baseline to week 12.

Other secondary efficacy endpoints were: 1) the percent change in calculated LDL-C from baseline to week 78. Definitions and rules are similar to the ones used for the primary endpoint replacing week 24 by week 78; 2) the proportion of patients reaching LDL-C goal at weeks 12, 52, and 78, i.e., LDL-C<70 mg/dL (1.81 mmol/L) in case of prior CVD or <100 mg/dL (2.59 mmol/L) for patients without prior CVD; 3) the proportion of patients reaching LDL-C<100 mg/dL (2.59 mmol/L) at week 24; 4) the proportion of patients reaching LDL-C<100 mg/dL (2.59 mmol/L) at week 12; 5) the proportion of patients reaching LDL-C<70 mg/dL (1.81 mmol/L) at week 12; 6) the absolute change in calculated LDL-C(mg/dL and mmol/L) from baseline to weeks 12, 24, 52, and 78; 7) the percent change in ApoB, non-HDL-C, total-C, Lp(a), HDL-C, fasting TG, and ApoA-1 from baseline to weeks 52 and 78; 8) the change in ratio ApoB/ApoA-1 from baseline to weeks 12, 24, 52, and 78; 9) the proportion of patients with ApoB<80 mg/dL (0.8 g/L) at weeks 12, 24, 52, and 78; 10) the proportion of patients with non-HDL-C<100 mg/dL at weeks 12, 24, 52, and 78; 11) the proportion of patients with calculated LDL-C<70 mg/dL (1.81 mmol/L) and/or ≥50% reduction in calculated LDL-C(if calculated LDL-C≥70 mg/dL [1.81 mmol/L]) at weeks 12, 24, 52, and 78.

Other endpoints were: 1) anti-Alirocumab antibody status (positive/negative) and titers assessed throughout the study; 2) the percent change in high sensitivity C-reactive protein (hs-CRP) from baseline to weeks 24, 52, and 78; 3) the absolute change in HbA1c (%) from baseline to weeks 24, 52, and 78; and 4) response of each EQ-5D item, index score, and change of index score from baseline through week 52.

Study Visits

The following visits were scheduled:

At Visit 1/Screening/Day −14 to −8; Visit 2/Screening/Day −7 (+/−3 days); Visit 3/Baseline/Week 0/Day 1; Visit 4/Week 4/Day 29 (+/−7 days); Visit 6/Week 12/Day 85 (+/−3 days); Visit 7/Week 16/Day 113 (+/−7 days); Visit 8/Week 24/Day 169 (+/−3 days)/Primary Endpoint Assessment; Visit 9/Week 36/Day 253 (+/−7 days); Visit 10/Week 52/Day 365 (+/−5 days); Visit 11/Week 64/Day 449 (+/−7 days); Visit 12/Week 78/Day 547 (+/−5 days); and the End of Study/Visit 13/Week 86/Day 603 (+/−7 days).

Medical/surgical history, medication history, demographics, height, hepatitis B surface antigen, and serum pregnancy testing were performed for the purpose of determining study eligibility or characterizing the baseline population.

All laboratory samples were collected before the dose of study drug was administered.

Blood samples for lipid panels should be collected in the morning, in fasting condition (i.e., overnight at least 10 hours fast, only water, and refrain from smoking) for all clinic visits. Alcohol consumption within 48 hours, and intense physical exercise and smoking within 24 hours preceding blood sampling were discouraged. Note: if the patient was not in fasting condition, the lipid blood samples were collected and a new appointment was scheduled the day after (or as close as possible to this date), with a reminder for the patient to be fasted.

Sample Size and Power Considerations

A total sample size of 45 patients (30 in alirocumab and 15 in placebo) will have 95% power to detect a difference in mean percent change in LDL-C of 30% with a 0.05 two-sided significance level; assuming a common standard deviation of 25% and that all 45 patients have an evaluable primary endpoint.

To meet regulatory requirements across the program, the sample size was increased to 126 patients on alirocumab, with the intent to understand safety in a larger population. In order to have at least 126 patients on alirocumab treated for 12 months in this study, and assuming a drop-out rate of 10% over the first 3-month period and a drop-out rate of 20% over the remaining 9-month period, the final total sample size was increased and rounded to 250 patients, with a randomization ratio 2:1 (alirocumab: 167, placebo: 83).

Analysis Populations

Intent-to-Treat Population

The randomized population included all randomized patients, and was analyzed according to the treatment allocated by randomization.

The ITT population (also known as the full analysis set [FAS]) was defined as all randomized patients who had an evaluable primary endpoint. The endpoint was evaluable when the following two conditions were met: 1) availability of a baseline calculated LDL-C value; and 2) availability of at least 1 calculated LDL-C value within 1 of the analysis windows up to week 24.

Patients in the ITT population were analyzed according to the treatment group allocated by randomization (i.e., as-randomized treatment group).

Modified Intent-to-Treat

The mITT population was defined as the all randomized population who took at least 1 dose or part of a dose of study drug and had an evaluable primary endpoint. The endpoint was considered as evaluable (i.e. efficacy treatment period) when both of the following conditions were met: 1) availability of a baseline calculated LDL-C value; and 2) availability of at least 1 calculated LDL-C value during the efficacy treatment period and within one of the analysis windows up to week 24. The efficacy treatment period is defined as the time from the first double-blind study drug injection up to 21 days after the last double-blind study drug injection.

Patients in the mITT population were analyzed according to the treatment group allocated by randomization.

Safety Analysis Set

The safety population considered for safety analyses was the randomized population who received at least 1 dose or part of a dose of study drug. Patients were analyzed according to the treatment actually received (i.e. as-treated treatment group, placebo or alirocumab).

Results

Description of Study Populations

A total of 249 patients were randomized (82 to the placebo group and 167 to the alirocumab group) in this study. One patient in the placebo group was randomized but did not receive study treatment due to the reason of withdrew consent prior to receiving the first IMP injection. Therefore, the patient was excluded from the safety population. Two patients among the randomized patients (the one in the placebo group above and one in the alirocumab group) were excluded from the ITT and mITT populations due to lack of post-baseline LDL-C assessments.

TABLE 14

Analysis Populations

| | Placebo (N = 82) | Alirocumab 75 Q2W/Up150 Q2W (N = 167) | All (N = 249) |
|---|---|---|---|
| Randomized population | 82 (100%) | 167 (100%) | 249 (100%) |
| Efficacy population: | | | |
| Intent-to-Treat (ITT) | 81 (98.8%) | 166 (99.4%) | 247 (99.2%) |
| Modified Intent-to-Treat (mITT) | 81 (98.8%) | 166 (99.4%) | 247 (99.2%) |
| Quality-of-life population | 80 (97.6%) | 164 (98.2%) | 244 (98.0%) |
| Anti-alirocumab antibody population | 77 (93.9%) | 166 (99.4%) | 243 (97.6%) |
| Safety population | 81 (98.8%) | 167 (100%) | 248 (99.6%) |

Note:
The safety, and anti-alirocumab antibody population patients are tabulated according to treatment actually received (as treated). For the other populations, patients are tabulated according to their randomized treatment In the alirocumab group, among the 158 patients who received at least one injection after Week 12, 61 (38.6%) patients received automatic up-titration at Week 12 in a blinded manner from alirocumab 75 mg Q2W to 150 mg Q2W.

Subject Dispositions

As of the first-step analyses data cut-off date, patient status is presented below for the 249 randomized patients: 1) 0 (0.0%) patients completed the 78-week double-blind treatment period, due to ongoing patients not yet reaching the week 78 visit; 2) 234 (94.0%) patients were still treatment-ongoing: 78 (95.1%) in the placebo group and 156 (93.4%) in the alirocumab group; 3) 9 (3.6%) randomized and treated patients prematurely discontinued study treatments before Week 24: 1 (1.2%) in the placebo group and 8 (4.8%) in the alirocumab group. 4 (1.6%) patients prematurely terminated study treatments due to adverse events: 0 in the placebo group vs. 4 (2.4%) in the alirocumab group. 3 (1.2%) patients prematurely terminated study treatments due to poor protocol compliance: 1 (1.2%) in the placebo group and 2 (1.2%) in the alirocumab group. 2 (0.8%) patients prematurely terminated study treatments due to various other reasons: 0 in the placebo group vs. 2 (1.2%) in the alirocumab group; 4) 13 (5.2%) randomized and treated patients prematurely discontinued study treatments before Week 52: 2 (2.4%) in the placebo group and 11 (6.6%) in the alirocumab group. 5 (2.0%) patients prematurely terminated study treatments due to adverse events: 0 in the placebo group vs. 5 (3.0%) in the alirocumab group. 3 (1.2%) patients prematurely terminated study treatments due to poor protocol compliance: 1 (1.2%) in the placebo group and 2 (1.2%) in the alirocumab group. 5 (0.8%) patients prematurely terminated study treatments due to various other reasons: 1 (1.2%) in the placebo group and 4 (2.4%) in the alirocumab group; 5) 14 (5.6%) patients prematurely terminated study treatments before completing the 78-week treatment period: 3 (3.7%) in the placebo group and 11 (6.6%) in the alirocumab group. 6 (2.4%) patients prematurely terminated study treatments due to adverse events: 1 (1.2%) in the placebo group and 5 (3.0%) in the alirocumab group. 3 (1.2%) patients prematurely terminated study treatments due to poor protocol compliance: 1 (1.2%) in the placebo group and 2 (1.2%) in the alirocumab group. 5 (2.0%) patients prematurely terminated study treatments due to various other reasons: 1 (1.2%) in the placebo group and 4 (2.4%) in the alirocumab group.

The following table provides the availability of LDL-C values over time. At Week 24, the primary efficacy endpoint was available for 78 (96.3%) patients in the placebo group and 157 (94.5%) in the alirocumab group. There were 77 (95.1%) on-treatment assessments and 1 (1.2%) off-treatment assessments in the placebo group, as compared with 155 (93.4%) on-treatment assessments and 2 (1.2%) off-treatment assessments in the alirocumab group. At Week 52, the key secondary efficacy endpoint was available for 78 (96.3%) patients in the placebo and 158 (95.2%) patients in the alirocumab groups.

TABLE 15

Calculated LDL-C Availability over Time - ITT Population

| | Placebo (N = 81) | | | Alirocumab 75 Q2W/Up150 Q2W (N = 166) | | |
|---|---|---|---|---|---|---|
| Calculated LDL-C | On-treatment value | Post-treatment value | Missing value | On-treatment value | Post-treatment value | Missing value |
| WEEK 4 | 79 (97.5%) | 0 | 2 (2.5%) | 162 (97.6%) | 0 | 4 (2.4%) |
| WEEK 8 | 79 (97.5%) | 0 | 2 (2.5%) | 156 (94.0%) | 0 | 10 (6.0%) |
| WEEK 12 | 76 (93.8%) | 0 | 5 (6.2%) | 151 (91.0%) | 1 (0.6%) | 14 (8.4%) |
| WEEK 16 | 77 (95.1%) | 0 | 4 (4.9%) | 149 (89.8%) | 3 (1.8%) | 14 (8.4%) |
| WEEK 24 | 77 (95.1%) | 1 (1.2%) | 3 (3.7%) | 155 (93.4%) | 2 (1.2%) | 9 (5.4%) |
| WEEK 36 | 73 (90.1%) | 0 | 8 (9.9%) | 153 (92.2%) | 2 (1.2%) | 11 (6.6%) |

TABLE 15-continued

Calculated LDL-C Availability over Time - ITT Population

| Calculated LDL-C | Placebo (N = 81) | | | Alirocumab 75 Q2W/ Up150 Q2W (N = 166) | | |
|---|---|---|---|---|---|---|
| | On-treatment value | Post-treatment value | Missing value | On-treatment value | Post-treatment value | Missing value |
| WEEK 52 | 78 (96.3%) | 0 | 3 (3.7%) | 155 (93.4%) | 3 (1.8%) | 8 (4.8%) |

An on-treatment value was obtained after the first study treatment injection and within 21 days after the last study treatment injection.
A post-treatment value was obtained more than 21 deays after the last study treatment injection.

The primary endpoint was missing for 12 (4.9%) patients at Week 24. At the Week 24 visit, the reasons for missing values were as follows: 1) 4 subjects with samples not obtained due to earlier study discontinuation; 2) 2 subjects were still ongoing, but Week 24 LDL-C was not done; 3) 6 samples were obtained at Week 24, but the LDL-C could not be calculated (5 with TGs>400 mg/dL and measured LDL-C reported, 1 with >400 mg/dL but measured LDL-C not reported).

Demographic and Baseline Characteristics

Overall, demographic characteristics, baseline disease characteristics, baseline efficacy lipid parameters, LMT history and background LMT use were homogeneous between patients randomized to the alirocumab group and patients randomized to the placebo group (see Table 16). Particularly, the mean baseline LDL-C in the alirocumab group was 134.6 mg/dL (SD=41.1 mg/dL) compared to that in the placebo group being 134.0 mg/dL (SD=41.4 mg/dL) with an overall mean of 134.4 mg/dL (SD=41.1 mg/dL). One potentially notable exception is the difference observed in baseline BMI, with a mean BMI of 28.6 kg/m2 (SD=4.6 kg/m2) in the alirocumab group compared to 27.7 kg/m2 (SD=4.7 kg/m2) in the placebo group.

TABLE 16

Baseline Characteristics of FHII Patient Population

| Characteristic | Alirocumab (N = 167) | Placebo (N = 82) |
|---|---|---|
| Age, mean (SD), yrs | 53.2 (12.9) | 53.2 (12.5) |
| Diagnosis of heFH[†], % (n) | | |
| Genotyping | 70.1% (117) | 81.7% (67) |
| Clinical criteria | 29.9% (50) | 18.3% (15) |
| Male | 51.5% (86) | 54.9% (45) |
| Race, white | 98.2% (164) | 97.6% (80) |
| BMI, mean (SD), kg/m² | 28.6 (4.6) | 27.7 (4.7) |
| CHD history | 34.1% (57) | 37.8% (31) |
| CHD risk equivalents[†] | 9.0% (15) | 4.9% (4) |
| Current smoker | 21.6% (36) | 15.9% (13) |
| Hypertension | 34.1% (57) | 29.3% (24) |
| Type 2 diabetes | 4.2% (7) | 3.7% (3) |

% (N) of patients unless stated. All pts on background of max tolerated statin ± other lipid-lowering therapy.
[†]Diagnosis of heFH must be made either by genotyping or by clinical criteria. For those patients not genotyped, the clinical diagnosis may be based on either the Simon Broome criteria for definite FH or the WHO/Dutch Lipid Network criteria with a score of >8 points.

TABLE 17

Disease Characteristics and Other Relevant Baseline Data - Randomized Population

| | Placebo (N = 82) | Alirocumab 75 Q2W/Up150 Q2W (N = 167) | All (N = 249) | P Value vs. Placebo |
|---|---|---|---|---|
| Type of hypercholesterolemia | | | | |
| Heterozygous Familial Hypercholesterolemia (heFH) | 82 (100%) | 167 (100%) | 249 (100%) | |
| Non-Familial Hypercholesterolemia (non-FH) | 0 | 0 | 0 | |
| Time from hypercholesterolemia diagnosis (years) | | | | |
| Number | 82 | 167 | 249 | 0.4938 |
| Mean (SD) | 12.7 (8.8) | 12.9 (7.9) | 12.8 (8.2) | |
| Median | 10.8 | 12.3 | 11.5 | |
| Min:Max | 0:42 | 0:40 | 0:42 | |
| Confirmation of diagnosis* | | | | |
| By genotyping | 67 (81.7%) | 117 (70.1%) | 184 (73.9%) | |
| By WHO/Simon Broome | 18 (22.0%) | 52 (31.1%) | 70 (28.1%) | |
| Definite/Certain | 18 (22.0%) | 52 (31.1%) | 70 (28.1%) | |

*heFH diagnosis can be confirmed by both genotyping and WHO or Simon Broome criteria.
Note:
p-values comparing baseline data between treatment groups are provided for descriptive purpose, as a screening tool, using Fisher exact test for qualitative data and the asymptotic one-way ANOVA test for Wilcoxon scores (Krukal-Wallis test) for continuous data.

TABLE 18

Background LMT at Randomization - Randomized Population

|  | Placebo (N = 82) | Alirocumab 75 Q2W/Up150 Q2W (N = 167) | All (N = 249) | P = Value vs. Placebo |
|---|---|---|---|---|
| Any statin | 82 (100%) | 167 (100%) | 249 (100%) |  |
| Taking high intensity statin | 72 (87.8%) | 144 (86.2%) | 216 (86.7%) | 0.8434 |
| Atorvastatin daily dose (mg) |  |  |  |  |
| 10 | 2 (2.4%) | 2 (1.2%) | 4 (1.6%) |  |
| 20 | 0 | 8 (4.8%) | 8 (3.2%) |  |
| 40 | 13 (15.9%) | 27 (16.2%) | 40 (16.1%) |  |
| 80 | 16 (19.5%) | 28 (16.8%) | 44 (17.7%) |  |
| Other doses | 1 (1.2%) | 0 | 1 (0.4%) |  |
| Rosuvastatin daily dose (mg) |  |  |  |  |
| 5 | 1 (1.2%) | 1 (0.6%) | 2 (0.8%) |  |
| 10 | 2 (2.4%) | 4 (2.4%) | 6 (2.4%) |  |
| 20 | 8 (9.8%) | 30 (18.0%) | 38 (15.3%) |  |
| 40 | 33 (40.2%) | 59 (35.3%) | 92 (36.9%) |  |
| Other doses | 1 (1.2%) | 1 (0.6%) | 2 (0.8%) |  |
| Simvastatin daily dose (mg) |  |  |  |  |
| 10 | 1 (1.2%) | 0 | 1 (0.4%) |  |
| 20 | 1 (1.2%) | 3 (1.8%) | 4 (1.6%) |  |
| 40 | 0 | 3 (1.8%) | 3 (1.2%) |  |
| 80 | 3 (3.7%) | 1 (0.6%) | 4 (1.6%) |  |
| Other doses | 0 | 0 | 0 |  |
| Any LMT other than statins* | 57 (69.5%) | 117 (70.1%) | 174 (69.9%) | 1.0000 |
| Any LMT other than nutraceuticals | 54 (65.9%) | 115 (68.9%) | 169 (67.9%) |  |
| Ezetimibe | 53 (64.6%) | 112 (67.1%) | 165 (66.3%) |  |
| Nutraceuticals | 7 (8.5%) | 8 (4.8%) | 15 (6.0%) |  |

Note:
p = values comparing baseline data between treatment groups are provided for descriptive purpose, as a screening tool, using Fisher exact test.
*in combination with statins or not.

TABLE 19

Cardiovascular History and Risk Factors Breakdown

| Characteristic | Alirocumab (N = 323) | Placebo (N = 163) |
|---|---|---|
| CHD history | 34.1% (57) | 37.8% (31) |
| Acute MI | 16.2% (27) | 17.1% (14) |
| Silent MI | 0.6% (1) | 2.4% (2) |
| Unstable angina | 9.0% (15) | 9.8% (8) |
| Coronary revasc. | 27.5% (46) | 29.3% (24) |
| Other clinically significant CHD | 16.2% (27) | 20.7% (17) |
| CHD risk equivalents | 9.0% (15) | 4.9% (4) |
| Ischemic stroke | 3.0% (5) | 1.2% (1) |
| Peripheral arterial disease | 3.0% (5) | 1.2% (1) |
| Moderate CKD | 1.2% (2) | 1.2% (1) |
| Diabetes + 2 or more risk factors | 3.0% (5) | 2.4% (2) |

% (N) of patients unless stated. All pts on background of max tolerated statin ± other lipid-lowering therapy

TABLE 20

Lipid Efficacy Parameters at Baseline - Quantitative Summary in Conventional Units - Randomized Population

|  | Placebo (N = 82) | Alirocumab 75 Q2W/Up150 Q2W (N = 167) | All (N = 249) | P Value vs. Placebo |
|---|---|---|---|---|
| Calculated LDL-C (mg/dL) |  |  |  |  |
| Number | 82 | 167 | 249 | 0.8507 |
| Mean (SD) | 134.0 (41.4) | 134.6 (41.1) | 134.4 (41.1) |  |
| Median | 126.0 | 128.0 | 126.0 |  |
| Q1:Q3 | 109.0:151.0 | 107.0:154.0 | 108.0:151.0 |  |
| Min:Max | 74:295 | 58:303 | 58:303 |  |

TABLE 20-continued

Lipid Efficacy Parameters at Baseline - Quantitative
Summary in Conventional Units - Randomized Population

|  | Placebo (N = 82) | Alirocumab 75 Q2W/Up150 Q2W (N = 167) | All (N = 249) | P Value vs. Placebo |
|---|---|---|---|---|
| Measured LDL-C (mg/dL) | | | | |
| Number | 70 | 149 | 219 | 0.6375 |
| Mean (SD) | 130.2 (36.6) | 132.6 (40.6) | 131.8 (39.3) | |
| Median | 125.5 | 126.0 | 126.0 | |
| Q1:Q3 | 104.0:145.0 | 104.0:149.0 | 104.0:147.0 | |
| Min:Max | 71:249 | 49:310 | 49:310 | |
| HDL-C (mg/dL) | | | | |
| Number | 82 | 167 | 249 | 0.4437 |
| Mean (SD) | 54.2 (15.7) | 52.6 (15.7) | 53.1 (15.7) | |
| Median | 51.0 | 50.0 | 51.0 | |
| Q1:Q3 | 42.0:63.0 | 42.0:61.0 | 42.0:62.0 | |
| Min:Max | 25:103 | 24:110 | 24:110 | |
| Total-C (mg/dL) | | | | |
| Number | 82 | 167 | 249 | 0.9589 |
| Mean (SD) | 211.7 (45.6) | 211.6 (45.8) | 211.6 (45.6) | |
| Median | 200.0 | 205.0 | 202.0 | |
| Q1:Q3 | 179.0:237.0 | 178.0:242.0 | 179.0:239.0 | |
| Min:Max | 133:376 | 123:391 | 123:391 | |
| Non-HDL-C (mg/dL) | | | | |
| Number | 82 | 167 | 249 | 0.8208 |
| Mean (SD) | 157.5 (43.7) | 159.0 (44.8) | 158.5 (44.4) | |
| Median | 150.5 | 147.0 | 149.0 | |
| Q1:Q3 | 129.0:170.0 | 127.0:181.0 | 127.0:177.0 | |
| Min:Max | 93:320 | 76:326 | 76:326 | |
| Fasting TGs (mg/dL) | | | | |
| Number | 82 | 167 | 249 | 0.6593 |
| Mean (SD) | 116.6 (56.8) | 123.2 (69.3) | 121.0 (65.4) | |
| Median | 100.5 | 105.0 | 104.0 | |
| Q1:Q3 | 81.0:136.0 | 81.0:144.0 | 81.0:141.0 | |
| Min:Max | 47:366 | 46:581 | 46:581 | |
| Apo-B (mg/dL) | | | | |
| Number | 81 | 167 | 248 | 0.9533 |
| Mean (SD) | 107.7 (23.9) | 107.9 (27.4) | 107.9 (26.3) | |
| Median | 103.0 | 102.0 | 102.0 | |
| Q1:Q3 | 91.0:116.0 | 91.0:122.0 | 91.0:121.0 | |
| Min:Max | 74:187 | 57:208 | 57:208 | |
| Apo-A1 (mg/dL) | | | | |
| Number | 81 | 167 | 248 | 0.3472 |
| Mean (SD) | 148.9 (29.6) | 146.3 (29.4) | 147.2 (29.4) | |
| Median | 150.0 | 142.0 | 144.5 | |
| Q1:Q3 | 129.0:166.0 | 127.0:160.0 | 128.0:162.5 | |
| Min:Max | 82:223 | 90:252 | 82:252 | |
| Apo-B/Apo-A1 (ratio) | | | | |
| Number | 81 | 167 | 248 | 0.7518 |
| Mean (SD) | 0.8 (0.2) | 0.8 (0.2) | 0.8 (0.2) | |
| Median | 0.7 | 0.7 | 0.7 | |
| Q1:Q3 | 0.6:0.8 | 0.6:0.9 | 0.6:0.9 | |
| Min:Max | 0:1 | 0:2 | 0:2 | |
| Lipoprotein-(a) (mg/dL) | | | | |
| Number | 81 | 167 | 248 | 0.9910 |
| Mean (SD) | 50.9 (59.7) | 49.8 (69.2) | 50.2 (66.1) | |
| Median | 21.0 | 22.0 | 22.0 | |
| Q1:Q3 | 7.0:76.0 | 8.0:70.0 | 7.5:75.0 | |
| Min:Max | 2:232 | 2:555 | 2:555 | |
| Total-C/HDL-C (ratio) | | | | |
| Number | 82 | 167 | 249 | 0.6572 |
| Mean (SD) | 4.2 (1.3) | 4.3 (1.5) | 4.3 (1.5) | |
| Median | 3.9 | 3.9 | 3.9 | |

TABLE 20-continued

Lipid Efficacy Parameters at Baseline - Quantitative
Summary in Conventional Units - Randomized Population

|  | Placebo (N = 82) | Alirocumab 75 Q2W/Up150 Q2W (N = 167) | All (N = 249) | P Value vs. Placebo |
|---|---|---|---|---|
| Q1:Q3 | 3.3:4.8 | 3.3:5.0 | 3.3:4.9 |  |
| Min:Max | 2:9 | 2:11 | 2:11 |  |

Note:
p-values comparing baseline data between treatment groups are provided for descriptive purpose, as a screening tool, using the asymptotic one-way ANOVA test for Wilcoxon scores (Kruskal-Wallis test).

The collection of measured LDL-C was not planned in the initial protocol and was added in an amendment. Therefore, measured LDL-C values are available for fewer patients compared to calculated LDL-C values.

Extent of Exposure

Exposure to injections was similar across treatment groups with a mean exposure of approximately 58-60 weeks. Alirocumab treated patients were exposed for 2-75.9 weeks and placebo treated patients for 11.6-75.7 weeks. The majority (93.5%:97.5%, alirocumab:placebo, respectively) of patients were treated for more than 52 weeks.

In the alirocumab group, among the 158 patients who received at least one injection after Week 12, 61 (38.6%) patients received automatic up-titration in a blinded manner at Week 12 from alirocumab 75 mg Q2W to 150 mg Q2W. 26 patients were not given the opportunity to up-titrate at Week 12 due to missing Week 8 LDL-C values at the time of the up-titration decision. Of the 26 patients missing the Week 8 LDL-C value, 4 alirocumab patients should have been up-titrated based on the now available Week 8 LDL-C data. The remaining patients were either in the placebo treatment group, or the Week 8 LDL-C visits for the alirocumab patients were below the LDL-C<70 mg/dL cut-off for up-titration.

Efficacy Analyses

Primary Efficacy Analysis in the ITT Population

The primary endpoint (percent change in calculated LDL-C from baseline to Week 24) analysis is provided based on a MMRM model on the ITT population, using LS means estimates at Week 24. This repeated measures approach includes all LDL-C values collected on-treatment and off-treatment up to Week 52. At Week 24, 3 (3.7%) patients in the placebo group and 9 (5.4%) patients in the alirocumab group did not have a calculated LDL-C value (Table 15). These missing values were accounted for by the MMRM model.

The primary efficacy analysis showed a statistically significant decrease in percent change from baseline calculated LDL-C at Week 24 in the ITT analysis for the alirocumab treatment group (LS mean=−48.7%) as compared to placebo (LS mean=2.8%). The LS mean difference between the alirocumab treatment group and the placebo treatment groups is −51.4% (p<0.0001). 81.4% of HeFH patients in the alirocumab group achieved the LDL-C goals at 24 weeks, compared to 11.3% for the placebo group.

TABLE 21

Percent Change from Baseline in Calculated LDL-C at Week
24 (ITT Analysis): MMRM Analysis - ITT Population

| Calculated LDL Cholesterol | Placebo (N = 81) | Alirocumab 75 Q2W/ Up150 Q2W (N = 166) |
|---|---|---|
| Baseline (mmol/L) |  |  |
| Number | 81 | 166 |
| Mean (SD) | 3.470 (1.078) | 3.486 (1.069) |
| Median | 3.263 | 3.289 |
| Min:Max | 1.92:7.64 | 1.50:7.85 |
| Baseline (mg/dL) |  |  |
| Number | 81 | 166 |
| Mean (SD) | 134.0 (41.6) | 134.6 (41.3) |
| Median | 126.0 | 127.0 |
| Min:Max | 74:295 | 58:303 |
| Week 24 percent change from baseline (%) |  |  |
| LS Mean (SE) | 2.8 (2.8) | −48.7 (1.9) |
| LS mean difference (SE) vs Placebo |  | −51.4 (3.4) |
| 95% CI |  | (−58.1 to −44.8) |
| p-value vs. Placebo |  | <.0001 |

Note:
Lean-squares (LS) means, standard errors (SE) and p-value taken from MMRM (mixed-effect model with repeated measures) analysis. The model includes the fixed categorical effects of treatment group, randomization strata as per IVRS, time point, treatment-by-time point interaction, strata-by-time point interaction, as well as the continuous fixed covariates of baseline calculated LDL-C value and baseline value by time-point interaction.

MMRM model and baseline description run on patients with a baseline value and a post-baseline value in at least one of the analysis windows used in the model.

The p-value is followed by a '*' if statistically significant according to the fixed hierarchical approach used to ensure a strong control of the overall type-1 error rate at the 0.05 level.

Calculated LDL-C Over Time

Figure 4:
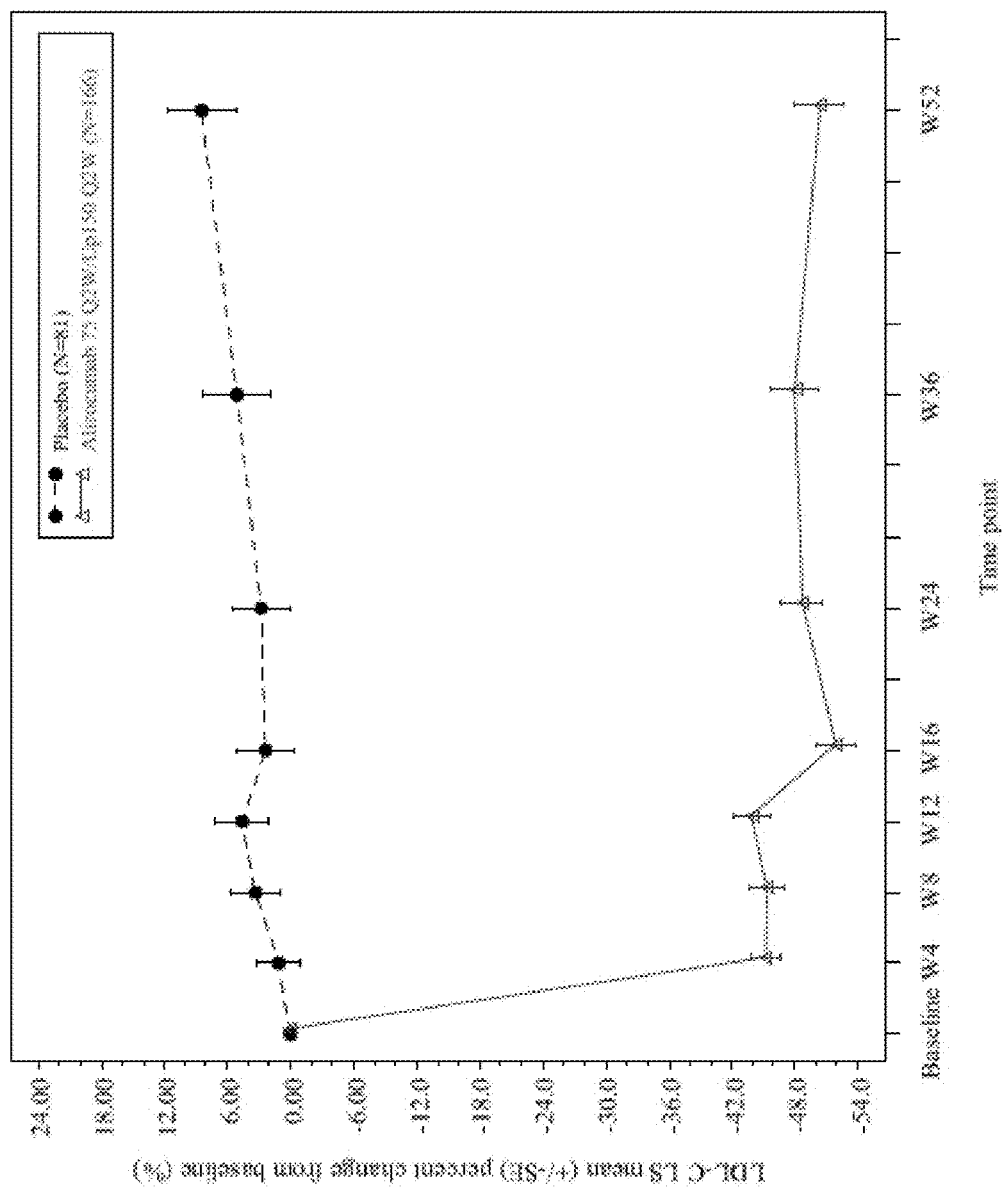
FIG. 4 is a graph showing the LDL-C LS mean (+/−SE) percent change from baseline over time for the ITT population in the ODYSSEY FH II study (Example 3). The Least-squares (LS) means and standard errors (SE) taken from MMRM (mixed-effect model with repeated measures) analysis.

FIG. 4 is a graph that shows the LDL-C LS mean (+/−SE) percent change from baseline over time for the ITT population. Note: Least-squares (LS) means and standard errors (SE) taken from MMRM (mixed-effect model with repeated measures) analysis.

The model includes the fixed categorical effects of treatment group, time point, treatment-by-time point interaction, as well as the continuous fixed covariates of baseline LDL-C value and baseline LDL-C-by-time point interaction.

TABLE 22

Calculated LDL-C Over Time - ITT Population

| Calculated LDL-C | Placebo (N = 81) | | | Alirocumab 75 Q2W/ Up150 Q2W (N = 166) | | |
|---|---|---|---|---|---|---|
| | Value | Change from baseline | Percent change from baseline | Value | Change from baseline | Percent change from baseline |
| LS mean (SE) (mmol/L) | | | | | | |
| Baseline | 3.470 (0.120) | NA | NA | 3.486 (0.083) | NA | NA |
| Week 4 | 3.485 (0.077) | 0.004 (0.077) | 1.1 (2.0) | 1.924 (0.054) | −1.56 (0.054) | −45.2 (1.4) |
| Week 8 | 3.561 (0.090) | 0.081 (0.090) | 3.3 (2.4) | 1.913 (0.063) | −1.57 (0.063) | −45.3 (1.7) |
| Week 12 | 3.585 (0.097) | 0.104 (0.097) | 4.6 (2.6) | 1.960 (0.068) | −1.52 (0.068) | −43.8 (1.8) |
| Week 16 | 3.508 (0.101) | 0.028 (0.101) | 2.4 (2.7) | 1.649 (0.071) | −1.83 (0.071) | −51.9 (1.9) |
| Week 24 | 3.537 (0.103) | 0.057 (0.103) | 2.8 (2.8) | 1.754 (0.072) | −1.73 (0.072) | −48.7 (1.9) |
| Week 36 | 3.603 (0.117) | 0.122 (0.117) | 5.1 (3.2) | 1.788 (0.081) | −1.69 (0.081) | −48.0 (2.2) |
| Week 52 | 3.718 (0.125) | 0.237 (0.125) | 8.4 (3.3) | 1.708 (0.088) | −1.77 (0.088) | −50.3 (2.3) |
| Week 64 | 3.601 (0.107) | | | 1.657 (0.075) | | |
| Week 78 | 3.574 (0.109) | | | 1.806 (0.076) | | |
| LS mean (SE) (mg/dL) | | | | | | |
| Baseline | 134.0 (4.6) | NA | NA | 134.6 (3.2) | NA | NA |
| Week 4 | 134.6 (3.0) | 0.2 (3.0) | 1.1 (2.0) | 74.3 (2.1) | −60.1 (2.1) | −45.2 (1.4) |
| Week 8 | 137.5 (3.5) | 3.1 (3.5) | 3.3 (2.4) | 73.9 (2.4) | −60.5 (2.4) | −45.3 (1.7) |
| Week 12 | 138.4 (3.7) | 4.0 (3.7) | 4.6 (2.6) | 75.7 (2.6) | −58.7 (2.6) | −43.8 (1.8) |
| Week 16 | 135.5 (3.9) | 1.1 (3.9) | 2.4 (2.7) | 63.7 (2.7) | −70.7 (2.7) | −51.9 (1.9) |
| Week 24 | 136.6 (4.0) | 2.2 (4.0) | 2.8 (2.8) | 67.7 (2.8) | −66.7 (2.8) | −48.7 (1.9) |
| Week 36 | 139.1 (4.5) | 4.7 (4.5) | 5.1 (3.2) | 69.0 (3.1) | −65.3 (3.1) | −48.0 (2.2) |
| Week 52 | 143.6 (4.8) | 9.2 (4.8) | 8.4 (3.3) | 65.9 (3.4) | −68.4 (3.4) | −50.3 (2.3) |
| Week 64 | 139.0 (4.1) | | | 64.0 (2.9) | | |
| Week 78 | 138.0 (4.2) | | | 69.7 (2.9) | | |

* Baseline is described using means and standard errors.

Note:
Least-squares (LS) means, standard errors (SE) and p-value taken from MMRM (mixed-effect model with repeated measures) analysis. The model includes the fixed categorical effects of treatment group, randomization strata as per IVRS, time point, treatment-by-time point interaction, strata-by-time point interaction, as well as the continuous fixed covariates of baseline LDL-C value and baseline LDL-C value by time point interaction. MMRM model and baseline description run on patients with a baseline value and a post-baseline value in at least one of the analysis windows used in the model.

Sensitivity to Serious GCP Non-Compliance

There was no site with serious GCP non-compliance in this study.

Key Secondary Efficacy Analysis

The following table summarizes analysis results on all key secondary endpoints in the hierarchical order for statistical testing at the 0.05 significance level. This study has achieved statistically significant effects in favor of the alirocumab treated patients for all but the last one in the hierarchy (i.e., Apo A-1—Percent change from baseline to Week 12) of the key secondary efficacy endpoints.

For clarification, the ITT analysis is defined for patients in the ITT population and includes all endpoint assessments in an analysis window, regardless of study treatment dosing status (i.e. includes post-treatment assessments). The on-treatment analysis is defined for patients in the mITT population and includes all endpoint assessments from the first double-blind study drug injection up to the day of last injection+21 days (i.e. includes assessments in the efficacy treatment period).

TABLE 23

Summary of Key Secondary Efficacy Endpoints

| Endpoint/Analysis | Placebo Result | Alirocumab Result | Comparison | P-value |
|---|---|---|---|---|
| 1. LDL-C at WK 24 - ITT analysis | LS mean: 2.8% | LS mean: −48.7% | Diff: −51.4% | <.0001 |
| 2. LDL-C at WK 24 - on-treatment analysis | LS mean: 2.7% | LS mean: −49.4% | Diff: −52.2% | <.0001 |
| 3. LDL-C at WK 12 - ITT analysis | LS mean: 4.6% | LS mean: −43.8% | Diff: −48.4% | <.0001 |
| 4. LDL-C at WK 12 - on-treatment analysis | LS mean: 4.6% | LS mean: −44.2% | Diff: −48.8% | <.0001 |
| 5. Apo B at WK 24 - ITT analysis | LS mean: −3.5% | LS mean: −42.8% | Diff: −39.3% | <.0001 |
| 6. Apo B at WK 24 - on-treatment analysis | LS mean: −3.5% | LS mean: −43.2% | Diff: −39.8% | <.0001 |
| 7. Non-HDL-C at WK 24 - ITT analysis | LS mean: 3.1% | LS mean: −42.6% | Diff: −45.7% | <.0001 |
| 8. Non-HDL-C at WK 24 - on-treatment analysis | LS mean: 3.1% | LS mean: −43.2% | Diff: −46.4% | <.0001 |
| 9. Total Cholesterol at WK 24 - ITT analysis | LS mean: 2.1% | LS mean: −30.6% | Diff: −32.8% | <.0001 |
| 10. Apo B at WK 12 - ITT analysis | LS mean: −0.9% | LS mean: −35.4% | Diff: −34.5% | <.0001 |
| 11. Non-HDL-C at WK 12 - ITT analysis | LS mean: 4.1% | LS mean: −37.9% | Diff: −42.0% | <.0001 |
| 12. Total Cholesterol at WK 12 - ITT analysis | LS mean: 3.4% | LS mean: −26.6% | Diff: −29.9% | <.0001 |
| 13. LDL-C at WK 52 - ITT analysis | LS mean: 8.4% | LS mean: −50.3% | Diff: −58.8% | <.0001 |
| 14. Very High CV LDL-C < 70 mg/dL OR High CV LDL-C < 100 mg/dL at WK 24 - ITT analysis | Proportion = 11.3% | Proportion = 81.4% | Odds Ratio = 52.2 | <.0001 |
| 15. Very High CV LDL-C < 70 mg/dL OR High CV LDL-C < 100 mg/dL at WK 24 - on-treatment analysis | Proportion = 11.6% | Proportion = 82.1% | Odds Ratio = 53.3 | <.0001 |
| 16. LDL-C < 70 mg/dL at WK 24 - ITT analysis | Proportion = 1.2% | Proportion = 68.2% | Odds Ratio = 239.7 | <.0001 |
| 17. LDL-C < 70 mg/dL at WK 24 - on-treatment analysis | Proportion = 1.3% | Proportion = 68.8% | Odds Ratio = 240.6 | <.0001 |
| 18. Lp(a) at WK 24 - ITT analysis | LS mean: −10.0% | LS mean: −30.3% | Diff: −20.3% | <.0001 |
| 19. HDL-C at WK 24 - ITT analysis | LS mean: −0.8% | LS mean: 6.0% | Diff: 6.8% | 0.0009 |
| 20. Fasting Triglycerides at WK 24 - ITT analysis | LS mean: 0.4% | LS mean: −10.5% | Diff: −10.9% | 0.0017 |
| 19. Apo A-1 at WK 24 - ITT analysis | LS mean: −1.6% | LS mean: 2.8% | Diff: 4.4% | 0.0062 |
| 20. Lp(a) at WK 12 - ITT analysis | LS mean: −5.6% | LS mean: −24.7% | Diff: −19.1% | <.0001 |
| 21. HDL-C at WK 12 - ITT analysis | LS mean: 1.7% | LS mean: 6.0% | Diff: 4.3% | 0.0147 |
| 22. Fasting Triglycerides at WK 12 - ITT analysis | LS mean: 0.9% | LS mean: −8.0% | Diff: −8.9% | 0.0258 |
| Apo A-1 at WK 12 - ITT analysis | LS mean: −1.9% | LS mean: 0.4% | Diff: 2.3% | 0.1475 |

Hierarchical testing terminated

All the key secondary efficacy endpoints, except for percent change in Apo A-1 from baseline to Week 12 in ITT population, achieved statistically significant effects in favor of the alirocumab treated patients according to the hierarchical testing procedure.

The key secondary efficacy analysis for percent change from baseline of calculated LDL-C to week 24 in the mITT population (on-treatment analysis) showed consistent results with the ITT analysis with a statistically significant decrease in calculated LDL-C in the alirocumab treatment group (LS mean=−49.4%) as compared to placebo (LS mean=2.7%). The LS mean treatment difference between the alirocumab-treated patients and the placebo-treated patients is −52.2% (p<0.0001). Indeed, few patients had LDL-C values collected post-treatment (i.e., more than 21 days after last injection) at Week 24: 1 patient (1.2%) in the placebo group and 2 patients (1.2%) in the alirocumab group.

The decrease in percent change in Apo A-1 from baseline to Week 24 in the ITT analysis was non-statistically significant: LS mean versus baseline was 0.4% in the alirocumab group and −1.9% in the placebo group (LS mean difference vs. placebo of 2.3%, p=0.1475).

Calculated Ldl-C Over Time (Includes Observed Data)

Figure 5:
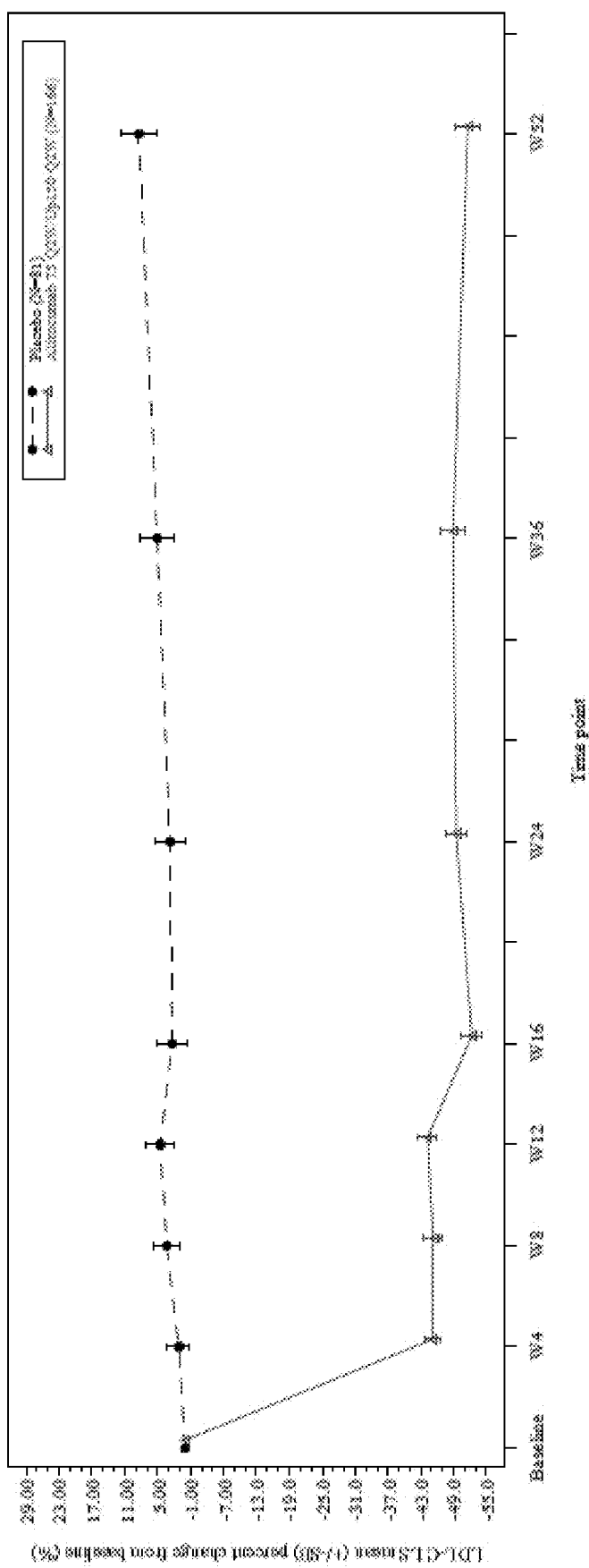
FIG. 5 is a graph showing the LDL-C LS mean (+/−SE) percent change from baseline during efficacy treatment period over time for the mITT Population in the ODYSSEY FH II study (Example 3).

FIG. 5 is a graph that shows the LDL-C LS mean (+/−SE) percent change from baseline during the efficacy treatment period over time for the mITT Population.

Summary

Overall, demographic characteristics, baseline disease characteristics, baseline efficacy lipid parameters, LMT history and background LMT use were comparable between patients randomized to the alirocumab group and patients randomized to the placebo group. Particularly, the mean (SD) baseline LDL-C in the alirocumab group was 134.6 (41.1) mg/dL compared to that in the placebo group being 134.0 (41.4) mg/dL.

The primary efficacy endpoint and all the key secondary endpoints, except for percent change in Apo A-1 from baseline to Week 12 in ITT population (ITT analysis), achieved statistically significant benefit in favor of Alirocumab-treated patients according to the hierarchical testing procedure.

Summary Safety Results

A total of 248 patients were randomized and received at least a partial dose of study treatment (Safety Population). Below is a high-level summary of adverse events and events of interest.

TABLE 24

Overview of Adverse Event Profile: Treatment Emergent Adverse Events - Safety Population

|  | Placebo (N = 81) | Alirocumab 75 Q2W/Up150 Q2W (N = 167) |
| --- | --- | --- |
| Patients with any TEAE | 62 (76.5%) | 117 (70.1%) |
| Patients with any treatment emergent SAE | 7 (8.6%) | 10 (6.0%) |
| Patients with any TEAE leading to death | 0 | 0 |
| Patients with any TEAE leading to permanent treatment discontinuation | 1 (1.2%) | 5 (3.0%) |

TEAE: Treatment emergent adverse event,
SAE: Serious adverse event
n (%) = number and percentage of patients with at least one TEAE Treatment-emergent SAEs occurred in a total of 17 patients, specifically 10 (6.0%) patients in the alirocumab treatment group and 7 (8.6%) patients in the placebo treatment group. There were no more than 2 reports in any SOC for either treatment group and no individual SAE was reported more than once in either treatment group.

No patient deaths were reported at the time of this first-step analysis.

A total of 6 patients prematurely discontinued study treatment due to a TEAE. Specifically, 5 (3.0%) patients in the alirocumab treatment group discontinued treatment early for rectal adenocarcinoma, diarrhoea, nausea, angioedema, asthenia, and alanine aminotransferase increased. One (1.2%) patient in the placebo treatment group discontinued due to syncope.

TEAEs occurred in 117 (70.1%) patients in the alirocumab treatment group and 62 (76.5%) patients in the placebo treatment group. The TEAEs that occurred in ≥5% of patients in any treatment group are: injection site reaction (10.8% vs. 7.4% in alirocumab and placebo group, respectively), headache (8.4% vs. 8.6% in alirocumab and placebo group, respectively), myalgia (6.0% vs. 6.2% in alirocumab and placebo group, respectively), and diarrhoea (5.4% vs. 1.2% in alirocumab and placebo group, respectively).

For TEAEs of special interest (AESIs), results are presented by pre-defined SMQ preferred term groupings.

Treatment-emergent injection site reactions (ISRs) occurred in 18 (10.8%) patients in the alirocumab treatment group and 6 (7.4%) patients in the placebo treatment group. None of the AEs were serious.

General Allergic TEAEs, identified through the MedDRA SMQ of "Hypersensitivity" occurred in 17 (10.2%) patients in the alirocumab treatment group and 6 (7.4%) patients in the placebo treatment group. None of the AEs were serious.

Treatment-emergent neurologic disorders occurred in 7 (4.2%) patients in the alirocumab treatment group and 2 (2.5%) patients in the placebo treatment group. In the alirocumab group, the PTs were: hypoaesthesia in 4 (2.4%) patients, paraesthesia in 2 (1.2%), and balance disorder in 1 (0.6%). None of the AEs were serious.

Treatment-emergent neurocognitive disorders occurred in 0 (0.0%) patients in the alirocumab treatment group and 1 (1.2%) patients in the placebo treatment group. The AE was not serious.

A total of 9 (5.4%) patients in the alirocumab treatment group and 0 (0.0%) patients in the placebo treatment group had 2 consecutive calculated LDL-C measurements below 25 mg/dL. For those patients with 2 consecutive calculated LDL-C measurements below 25 mg/dL, TEAEs occurred in 3 (33.3%) patients in the alirocumab treatment. The PTs were: influenza, influenza like illness, and nasopharyngitis. None of these AEs were serious, nor were they AESIs.

Conclusion

The following conclusions can be drawn from this early review of the study data: 1) the study achieved the primary efficacy endpoint with a statistically significant reduction in calculated LDL-C in the alirocumab treated patients; 2) this study also achieved all of the key secondary efficacy endpoints, except for the last endpoint (Apo A-1 at Week 12 in the ITT population (ITT analysis)); and 3) based on the available data at the time of this first step analysis, subcutaneous administration of alirocumab to patients with heterozygous familial hypercholesterolemia and an LDL-C>70 mg/dL or LDL-C>100 mg/dL, depending on history of MI or stroke at baseline, was generally safe and well tolerated.

Summary of Pooled Data from FH I and FH II Studies

From the pooled data of the FHI and FHII studies the following conclusions can be drawn: 1) self-administered alirocumab produced significantly greater LDL-C reductions vs. placebo after 24 weeks (LS mean difference of 51.4-57.9%); 2) the majority of patients (>70%) achieved their LDL-C goals at Week 24; 3) LDL-C reductions of 47.1-50.3% at Week 52 were achieved with alirocumab; 4) mean LDL-C levels of 1.7-1.9 mmol/L (65.9-74.3 mg/dL) at Week 52 were achieved with alirocumab; 5) approximately 50% of patients did not require uptitration to alirocumab 150 mg Q2W suggesting that 75 mg Q2W may be sufficient for many patients; and 6) TEAEs occurred in a similar frequency in the alirocumab and placebo arms.

Specifically, the combined data of the FHI and FHII studies shows that alirocumab produced a significant reduction in LDL-C at week 24 relative to placebo. The LS mean (SE) % change from baseline at week 24 was −48.8% for the alirocumab group (N=488), compared to 7.1% for the placebo group (N=244). The LS mean difference (SE) vs. placebo was −55.8% (2.1) (P<0.0001). Moreover, only 42% of alirocumab patients required uptitration at Week 12 to the 150 mg Q2W dose.

Figure 8:
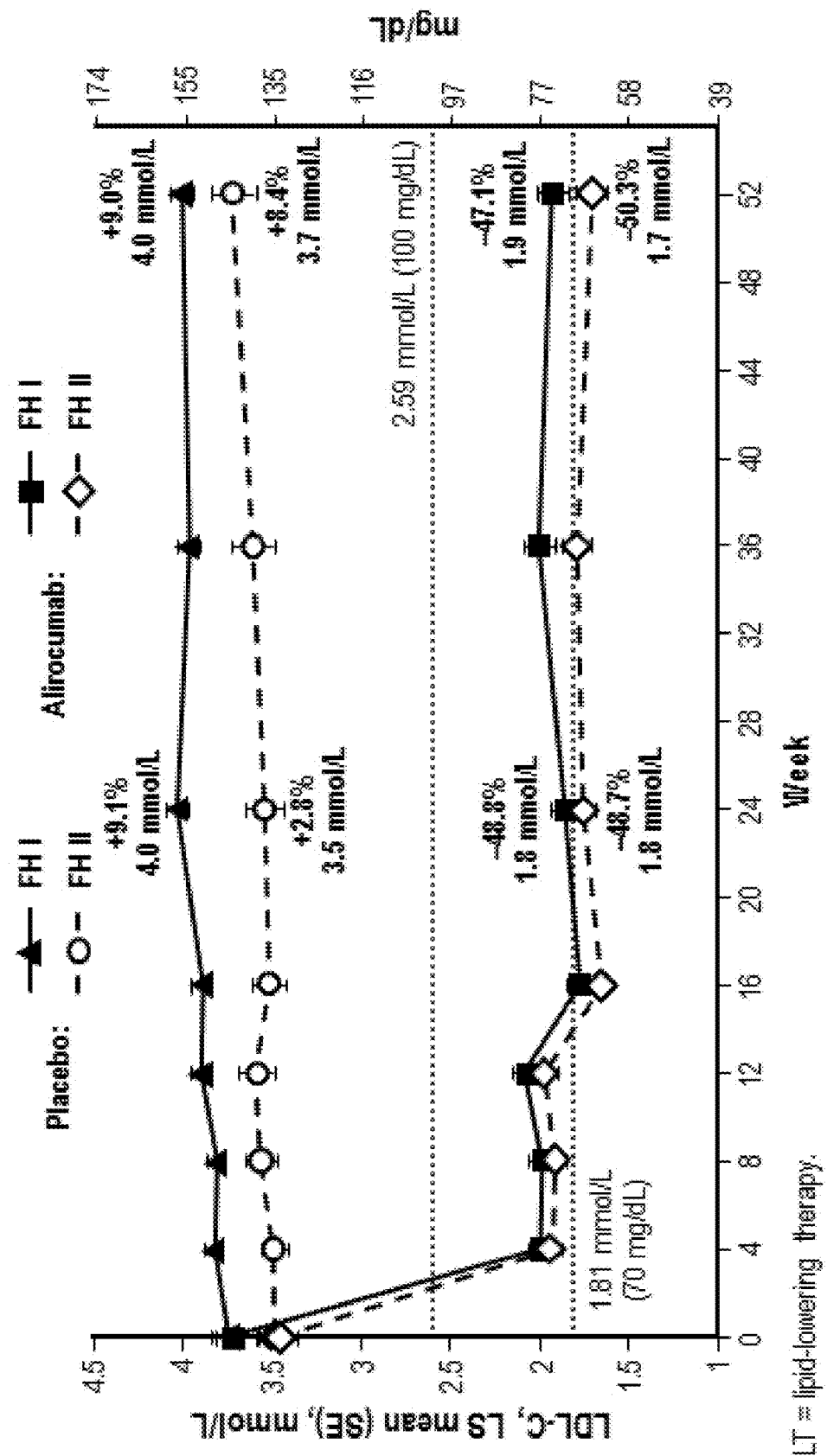
FIG. 8 is a graph showing the LS mean (SE) calculated LDL-C values versus time for the ODYSSEY FH I and FH II studies. The values indicted on the graph are the LS mean % change from baseline to week 24 and week 52.
Figure 9:
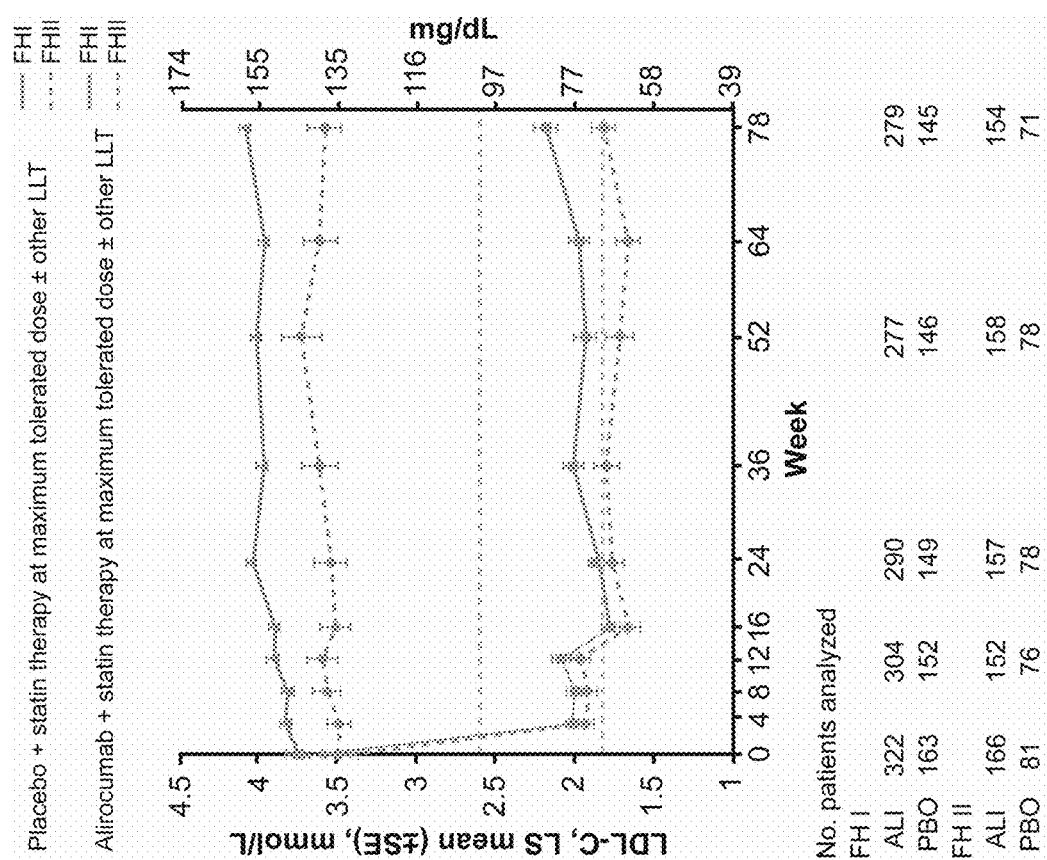
FIG. 9 is a graph showing the LS mean (SE) calculated LDL-C values versus time for the ODYSSEY FH I and FH II studies. The values indicated below the graph are the numbers of patients analyzed at the various timepoints.

The LS mean (SE) calculated LDL-C values versus time for the ODYSSEY FH I and FH II studies are shown in FIG. 8. The values indicted on the graph are the LS mean % change from baseline to week 24 and week 52. FIG. 9 is a graph showing the LS mean (SE) calculated LDL-C values versus time for the ODYSSEY FH I and FH II studies. The values indicted below the graph are the numbers of patients analyzed at the various timepoints.

Figure 10:
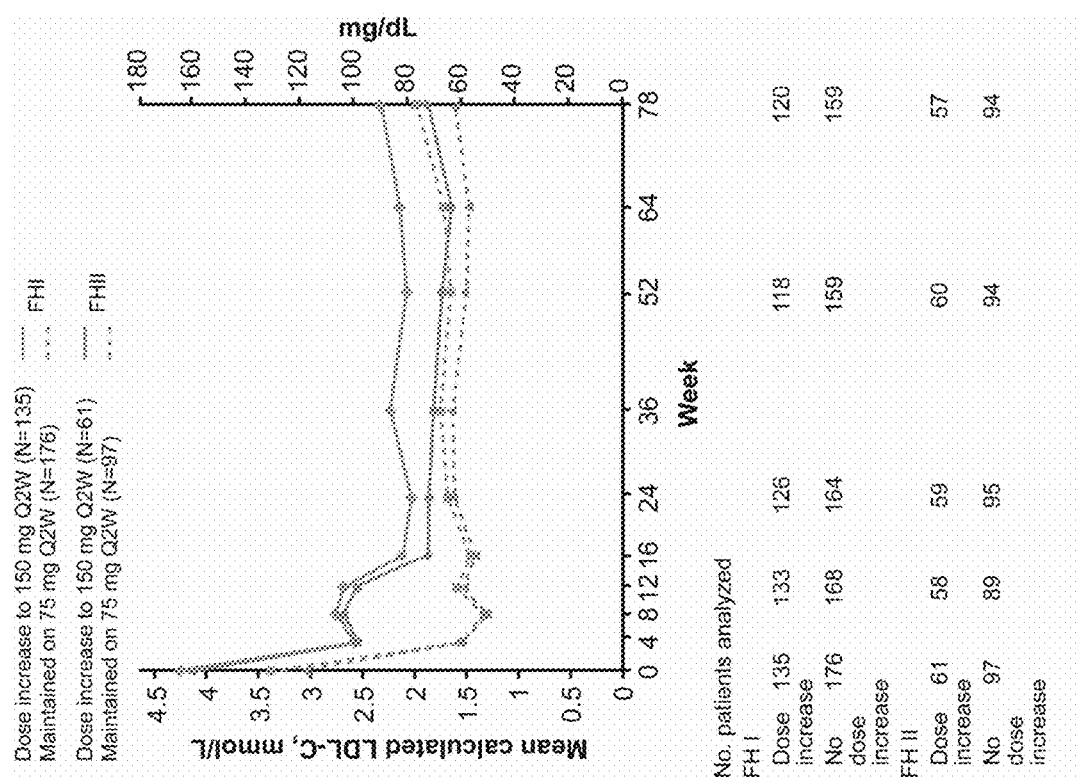
FIG. 10 is a graph showing LDL-C levels over time in alirocumab patients according to whether dose was increased to 150 mg Q2W or maintained at 75 mg Q2W (ITT analysis).

Among patients who received double-blind treatment for at least 12 weeks, 176/311 (56.6%) in FH I and 97/158 (61.4%) in FH II had LDL-C levels <1.8 mmol/L at week 8 and were maintained on alirocumab 75 mg Q2W. LDL-C levels were stable over time in these patients (FIG. 10). For patients in FH I who received dose increase to 150 mg Q2W, mean LDL-C levels were 2.7 mmol/L (104.3 mg/dL) at week 12 and 2.0 mmol/L (78.5 mg/dL) at week 24. Corresponding values in FH II were 2.6 mmol/L (98.6 mg/dL) at week 12 and 1.9 mmol/L (71.8 mg/dL) at week 24.

Figure 11A:
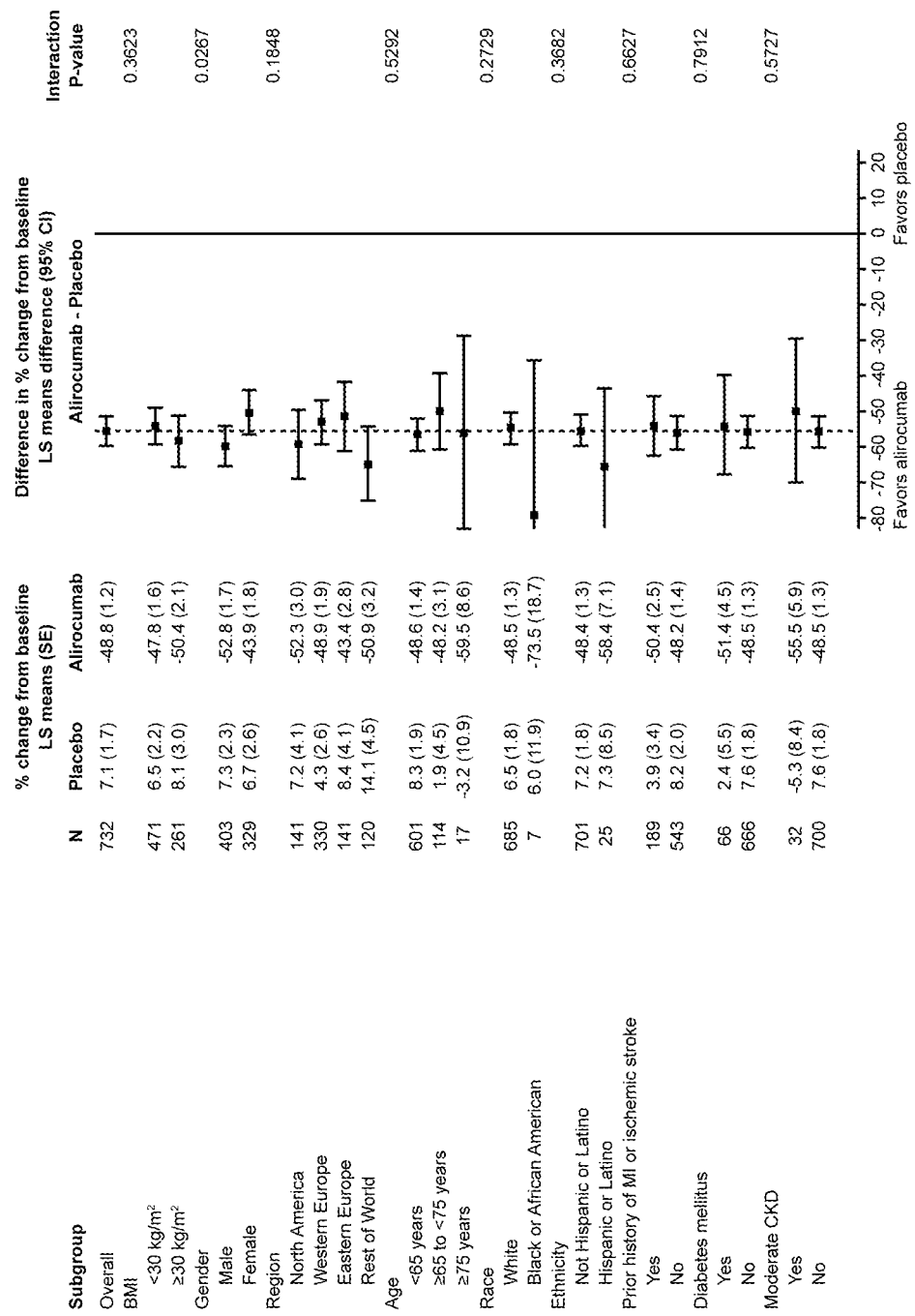
FIGS. 11A, 11B, and 11C depict charts showing subgroup analysis of LDL-C reductions from baseline to week 24
Figure 11B:
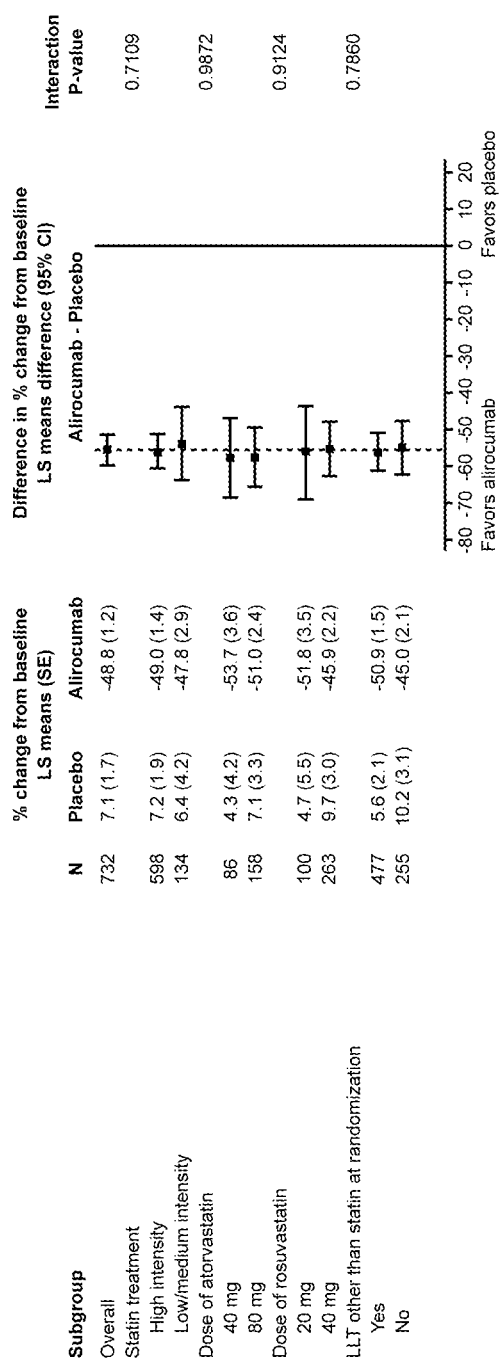
Figure 11C:
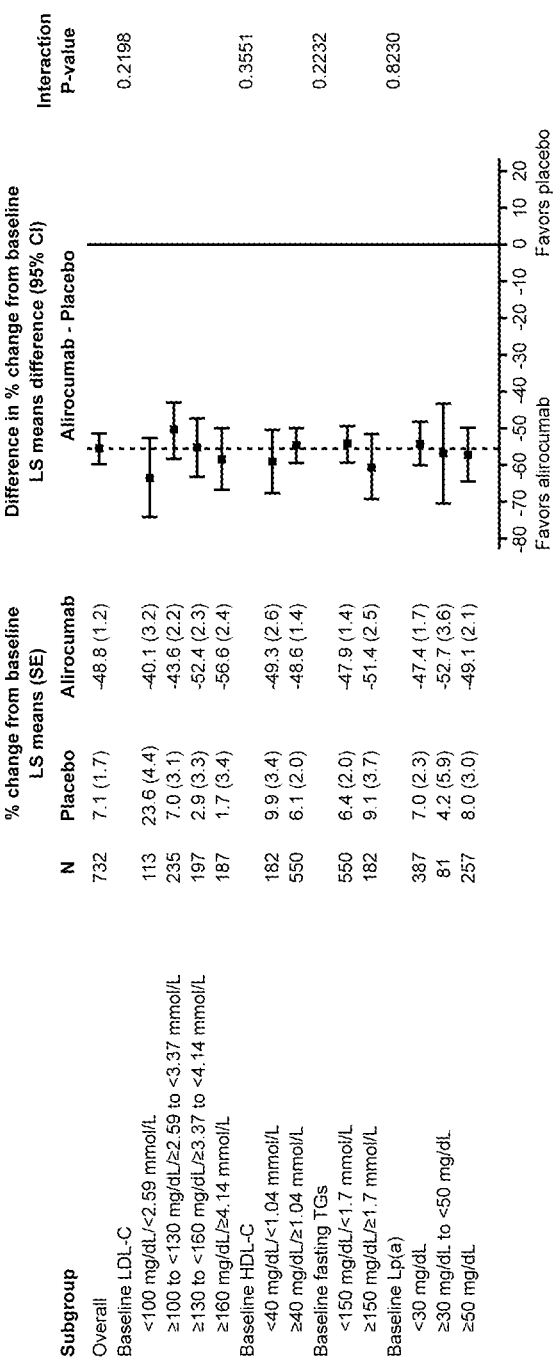

Subgroup analyses of the primary efficacy endpoint showed consistent reduction of calculated LDL-C across a range of demographic and baseline characteristics (FIGS. 11A-11C). The percentage reduction in LDL-C(alirocumab vs placebo) was 60.1% in males and 50.6% in females (pooled data from FH I and FH II), with a P-value for interaction of 0.0267. In the individual studies, LDL-C reductions (vs placebo) were 62.6% for males and 51.9% for females in FH I, and 53.5% for males and 49.2% for females in FH II.

A summary of interim safety data pooled from the FH I and FH II studies is set forth in Table 25A. All data was collected up to last patient visit at week 52. The percentage of patients who experienced TEAEs, serious AEs, and TEAEs leading to treatment discontinuation were comparable between treatment groups in the individual studies (Table 25B). A higher proportion of patients experienced injection site reactions in the alirocumab groups vs placebo in FH I (12.4% vs 11.0%) and FH II (11.4% vs 7.4%). Most of the injection site reactions were classified as mild in intensity. No injection site reaction led to study drug discontinuation. None of the reported neurological or allergic events (Table 3) were serious. Pruritus was reported in two (0.6%) and three (1.8%) alirocumab-treated patients in FH I and II, respectively, and one placebo-treated patient in each study (0.6% and 1.2%, respectively). Few neurocognitive events were reported with alirocumab (2 [0.6%] in FH I, none in FH II) or placebo (2 [1.2%] in FH I, 1 [1.2%] in FH II; Table 3). In FH I and FH II, respectively, 85.8% and 91.6% of alirocumab-treated patients (87.7% and 90.1% of placebo) received study treatment for ≥76 weeks.

TABLE 25A

Interim Safety Analysis (Pooled Data from FH I and FH II Studies)

| % (N) of patients<br>All pts on background of max<br>tolerated statin ± other lipid-<br>lowering therapy | Alirocumab<br>(N = 489) | Placebo<br>(N = 244) |
|---|---|---|
| TEAEs | 74.8% (366) | 75.4% (184) |
| Treatment-emergent SAEs | 10.0% (49) | 9.0% (22) |
| TEAEs leading to death | 0.8% (4) | 0 |
| TEAEs leading to discontinuation | 3.1% (15) | 3.7% (9) |
| Adverse Events of Interest | | |
| Adjudicated CV events | 1.6% (8) | 1.2% (3) |
| Injection-site reactions | 11.5% (56) | 9.0% (22) |
| Neurocognitive disorders | 0.2% (1) | 1.2% (3) |
| ALT >3 x ULN | 2.1% (10/488) | 1.2% (3/244) |
| Creatine kinase >3 x ULN | 3.5% (17/483) | 6.2% (15/243) |
| Other Adverse Events | | |
| Nasopharyngitis | 10.2% (50) | 11.1% (27) |
| Influenza | 8.8% (43) | 6.1% (15) |
| Headache | 5.5% (27) | 6.6% (16) |
| Back pain | 4.9% | 3.7% |
| Upper respiratory tract infection | 4.3% | 4.9% |
| arthralgia | 3.9% | 4.9% |
| urinary tract infection | 3.9% | 2.5% |
| Diarrhoea | 3.7% | 2.5% |
| Myalgia | 3.5% | 4.9% |
| gastroenteritis | 3.3% | 3.3% |
| sinusitis | 3.3% | 2.9% |
| muscle spasms | 3.1% | 0.4% |
| dizziness | 2.9% | 3.7% |
| nausea | 2.5% | 3.7% |
| pain in extremities | 1.8% | 3.3% |
| fatigue | 3.1% | 2.5% |
| influenza like illness | 2.9% | 2.0% |
| bronchitis | 2.7% | 2.5% |
| abdominal pain | 2.5% | 1.6% |
| blood creatinine phosphokinase | 2.5% | 2.9% |
| cough | 1.6% | 2.5% |
| hypertension | 1.6% | 2.5% |
| cystitis | 1.2% | 1.6% |
| neck pain | 0.4% | 2.0% |

TABLE 25B

Final Safety Analysis (Pooled Data from FHI and FHII Studies)

| n (%) | FH I | | FH II | |
|---|---|---|---|---|
| | Alirocumab<br>(n = 322) | Placebo<br>(n = 163) | Alirocumab<br>(n = 167) | Placebo<br>(n = 81) |
| TEAEs | 263 (81.7) | 129 (79.1) | 125 (74.9) | 66 (81.5) |
| Treatment-emergent SAEs | 44 (13.7) | 22 (13.5) | 15 (9.0) | 8 (9.9) |
| TEAEs leading to death[a] | 6 (1.9) | 0 | 0 | 0 |
| TEAEs leading to treatment discontinuation | 11 (3.4) | 10 (6.1) | 6 (3.6) | 1 (1.2) |
| TEAEs occurring in ≥5% patients (in any group) | | | | |
| Injection site reaction | 40 (12.4) | 18 (11.0) | 19 (11.4) | 6 (7.4) |
| Exact Fisher test p-value[b] | 0.77 | | 0.38 | |
| Nasopharyngitis | 36 (11.2) | 12 (7.4) | 21 (12.6) | 18 (22.2) |
| Upper respiratory tract infection | 22 (6.8) | 14 (8.6) | 5 (3.0) | 1 (1.2) |
| Arthralgia | 20 (6.2) | 9 (5.5) | 8 (4.8) | 7 (8.6) |
| Influenza | 20 (6.2) | 10 (6.1) | 24 (14.4) | 7 (8.6) |
| Back pain | 18 (5.6) | 7 (4.3) | 12 (7.2) | 6 (7.4) |
| Sinusitis | 17 (5.3) | 7 (4.3) | 1 (0.6) | 2 (2.5) |
| Headache | 15 (4.7) | 9 (5.5) | 16 (9.6) | 7 (8.6) |
| Diarrhoea | 10 (3.1) | 5 (3.1) | 11 (6.6) | 1 (1.2) |
| Bronchitis | 10 (3.1) | 9 (5.5) | 4 (2.4) | 1 (1.2) |

TABLE 25B-continued

Final Safety Analysis (Pooled Data from FHI and FHII Studies)

|  | FH I | | FH II | |
| --- | --- | --- | --- | --- |
| n (%) | Alirocumab (n = 322) | Placebo (n = 163) | Alirocumab (n = 167) | Placebo (n = 81) |
| Dizziness | 7 (2.2) | 6 (3.7) | 8 (4.8) | 5 (6.2) |
| Myalgia | 6 (1.9) | 11 (6.7) | 10 (6.0) | 5 (6.2) |
| Influenza like illness | 6 (1.9) | 1 (0.6) | 9 (5.4) | 5 (6.2) |
| Safety events of interest | | | | |
| Positively adjudicated CV events | 8 (2.5) | 3 (1.8) | 2 (1.2) | 1 (1.2) |
| General allergic TEAEs$^c$ | 28 (8.7) | 16 (9.8) | 19 (11.4) | 5 (6.2) |
| Neurological TEAEs$^c$ | 12 (3.7) | 7 (4.3) | 7 (4.2) | 2 (2.5) |
| Neurocognitive disorders$^c$ | 2 (0.6) | 2 (1.2) | 0 | 1 (1.2) |
| Development/worsening of diabetes$^b$ | 6 (1.9) | 4 (2.5) | 4 (2.4) | 2 (2.5) |
| Ophthalmologic disorders$^c$ | 3 (0.9) | 4 (2.5) | 3 (1.8) | 1 (1.2) |
| Alanine aminotransferase > 3 x ULN | 5/322 (1.6) | 2/163 (1.2) | 6/166 (3.6) | 1/81 (1.2) |
| Creatine kinase > 3 x ULN | 13/318 (4.1) | 10/163 (6.1) | 8/165 (4.8) | 6/80 (7.5) |

Example 4: A Randomized, Double-Blind, Placebo-Controlled, Parallel Group Study to Evaluate the Efficacy and Safety of Alirocumab in Patients with Heterozygous Familial Hypercholesterolemia and LDL-C Higher or Equal to 160 mg/dL with their Lipid-Modifying Therapy Introduction This study included patients with heterozygous familial hypercholesterolemia (heFH) with or without a history of documented MI or ischemic stroke.

The objective of the present study was to assess the efficacy and safety of Alirocumab in patients with heFH whose LDL-C level was higher than or equal to 160 mg/dL (4.14 mmol/L) on maximally tolerated statin therapy with or without additional LMT.

Figure 6:
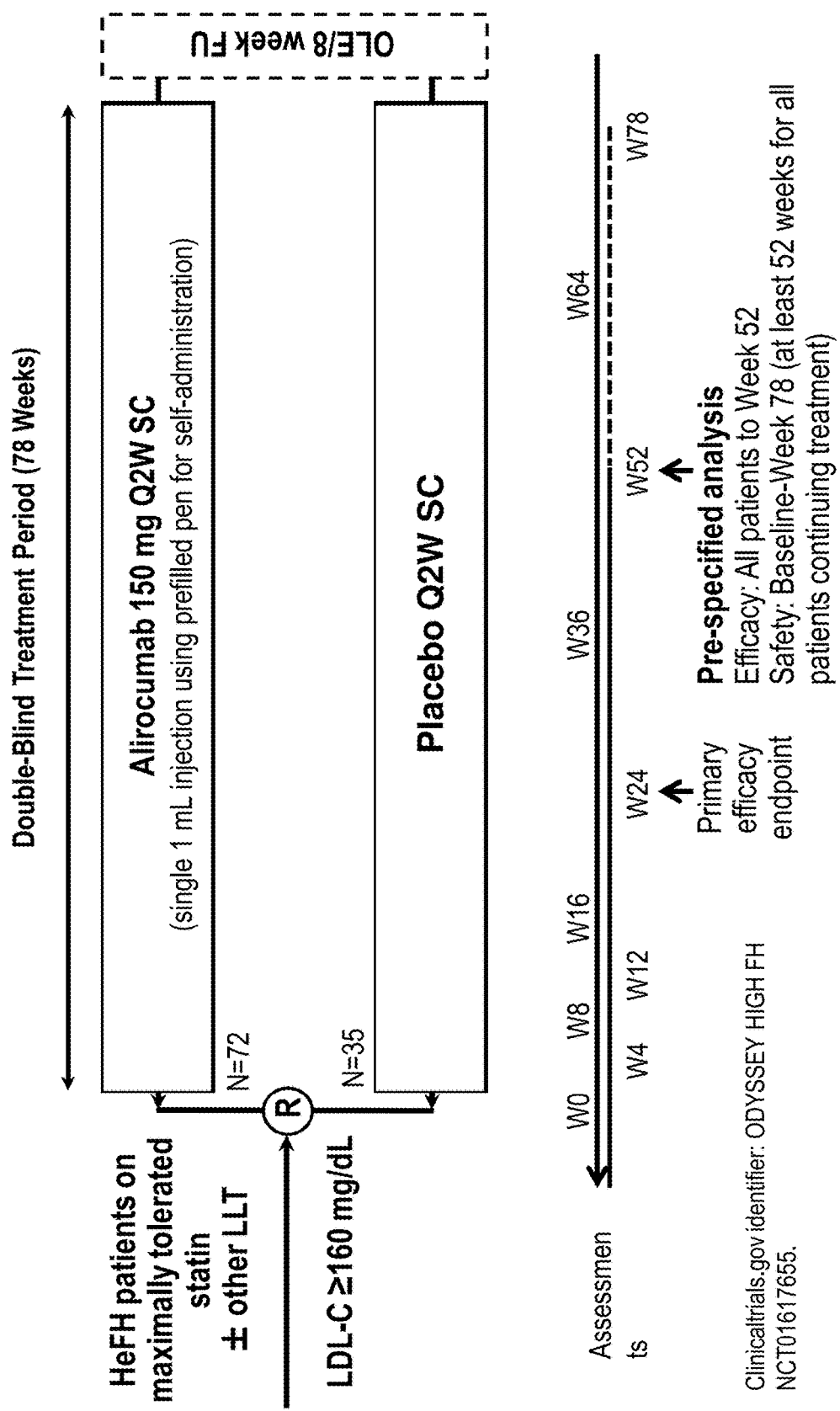
FIG. 6 is a graphic representation of the study design for ODYSSEY HIGH FH (Example 4). Labels in the study design are defined as follows: FU: follow up; HeFH, heterozygous familial hypercholesterolemia; LLT, lipid-lowering therapy; OLE, open-label extension.

This specific study (FIG. 6) was undertaken to demonstrate in heFH patients, with LDL-C higher or equal to 160 mg/dL, that Alirocumab 150 mg Q2W as add-on therapy to statin+/−other LMT causes a statistically significant and clinically meaningful reduction in LDL-C. This population with such a high LDL-C level despite an optimized LMT represents a highest risk group with a well-identified unmet medical need that may be addressed by adding Alirocumab to their LDL-C lowering therapies.

Study Objectives

The primary objective of the study was to demonstrate the reduction of LDL-C by Alirocumab as add-on therapy to stable maximally tolerated daily statin therapy with or without other LMT in comparison with placebo after 24 weeks of treatment in patients with heterozygous familial hypercholesterolemia (heFH) and LDL-C higher than or equal to 160 mg/dL (4.14 mmol/L).

The secondary objectives were: 1) to evaluate the effect of Alirocumab in comparison with placebo on LDL-C after 12 weeks of treatment; 2) to evaluate the effect of Alirocumab on other lipid parameters (i.e., Apo B, non-HDL-C, total-C, Lp (a), HDL-C, TG, and Apo A-1 levels); 3) to evaluate the long-term effect of Alirocumab on LDL-C; 4) to evaluate the safety and tolerability of Alirocumab; 5) to evaluate the development of anti-Alirocumab antibodies.

Study Design

This was a randomized, double-blind, placebo-controlled, parallel-group, unbalanced (2:1, Alirocumab: placebo), multi-center, multi-national study to assess the efficacy and the safety of Alirocumab in patients with heterozygous familial hypercholesterolemia (heFH) and LDL-C higher or equal to 160 mg/dL with or without their LMT (i.e., stable maximally tolerated daily statin therapy+/−other LMT). Randomization was stratified according to prior history of myocardial infarction (MI) or ischemic stroke [Yes/No], and statin treatment (atorvastatin 40 to 80 mg daily or rosuvastatin 20 to 40 mg daily vs. simvastatin whatever the daily dose, atorvastatin below 40 mg daily or rosuvastatin below 20 mg daily). After randomization, patients received double-blind study treatment (either Alirocumab or placebo) every 2 weeks over a period of 78 weeks on top of stable maximally tolerated daily statin therapy+/−other LMT.

After completion of the 18-month double-blind treatment period, all patients who successfully completed the ODYSSEY High FH study had the opportunity to participate in an open-label extension study. Consequently all patients will receive Alirocumab at entry in the open-label extension study regardless the study treatment they received during the 18-month double-blind treatment period.

The study consisted of 3 periods: screening, double-blind treatment, and follow up.

The screening period was up to 3 weeks in duration including an intermediate visit during which the patient (or another designated person such as spouse, relative, etc.) was trained to self-inject/inject with placebo for Alirocumab. Eligibility assessments were performed to permit the randomization of the patients into the study.

The double-blind treatment period was a randomized, double-blind study treatment period of 18 months. The first injection during the double-blind period was done at the site on the day of randomization (Week 0 [D1]-V3) and as soon as possible after the call to IVRS/IWRS for randomization into the study. The subsequent injections were done by the patient (self-injection) or another designated person (such as spouse, relative, etc.) at a patient-preferred location (home . . . ). Patients randomized to Alirocumab received a dose of 150 mg of the IMP from randomization (V3) up to Week 76 (i.e., Weeks 0, 2, 4, 6, 8 . . . to 76).

The follow-up period (if applicable) was a period of 8 weeks after the end of the DBTP for patients not consenting to participate in the open-label extension study or if prematurely discontinuing study treatment.

The laboratory measurement of lipid parameters were performed by a central laboratory (central lab) during the study.

Patients who achieved 2 consecutive calculated LDL-C levels <25 mg/dL (0.65 mmol/L) during the study were monitored and managed.

Statin and other LMT (if applicable) should have been stable (including dose) during the first 24 weeks of the DBTP barring exceptional circumstances whereby overriding concerns (including but not limited to TG alert posted by the central lab) warrant such changes, as per the Investigator's judgment. From Week 24 onwards, background LMT was modified only under certain conditions as described below.

Patients should have been on a stable diet (NCEP-ATPIII TLC diet or equivalent) throughout the entire study duration from screening, as described above in Example 2 (see Table 1). The dietician or site staff with appropriate training reviewed the patient's diet at the screening visit and periodically throughout the study.

The study duration included a screening period of up to 3 weeks, a 78-week DBTP for efficacy and safety assessment, and an 8-week post-treatment follow-up period after the last visit of the DBTP for patients not consenting to participate in the open-label extension study or if prematurely discontinuing study treatment. Thus, the maximum study duration per patient was about 89 weeks (i.e., 20 months) (up to 3 weeks screening+78 weeks double-blind treatment+8 weeks follow-up). The end of the study per patient was the last protocol planned visit or the resolution/stabilization of all SAEs, and AESI, whichever came last.

Selection of Patients

The inclusion criteria were: 1) patients with heterozygous familial hypercholesterolemia (heFH)* who were not adequately controlled with a maximally tolerated daily dose of statin,** with or without other lipid-modifying therapy (LMT) at stable dose prior to the screening visit (Week-3).

*Diagnosis of heFH must have been made either by genotyping or by clinical criteria. For those patients not genotyped, the clinical diagnosis may have been based on either the Simon Broome criteria with a criteria for definite FH or the WHO/Dutch Lipid Network criteria with a score >8 points. See criteria described above in Example 2.

Definition of maximally tolerated dose: any of the following were acceptable): 1) rosuvastatin 20 mg or 40 mg daily; 2) atorvastatin 40 mg or 80 mg daily; 3) simvastatin 80 mg daily (if already on this dose for >1 year—see exclusion criterion E 06); or 4) patients not able to be on any of the above statin doses, should have been treated with the dose of daily atorvastatin, rosuvastain or simvastatin that was considered appropriate for the patient as per the investigator's judgment or concerns. Some examples of acceptable reasons for a patient taking a lower statin dose included, but were not limited to: adverse effects on higher doses, advanced age, low body mass index, regional practices, local prescribing information, concomitant meds, co-morbid conditions such as impaired glucose tolerance/impaired fasting glucose.

Patients who met all the above inclusion criteria were screened for the following exclusion criteria, which are sorted and numbered in the following 3 subsections: exclusion criteria related to study methodology, exclusion criteria related to the background therapies, and exclusion criteria related to Alirocumab.

Exclusion criteria related to study methodology were: 1) patient without diagnosis of heFH made either by genotyping or by clinical criteria; 2) LDL-C<160 mg/dL (<4.14 mmol/L) at the screening visit (Week-3); 3) not on a stable dose of LMT (including statin) for at least 4 weeks and/or fenofibrate for at least 6 weeks as applicable, prior to the screening visit (Week-3) or from screening to randomization; 4) currently taking a statin other than simvastatin, atorvastatin, or rosuvastatin; 5) simvastatin, atorvastatin, or rosuvastatin is not taken daily or not taken at a registered dose; 6) daily doses above atorvastatin 80 mg, rosuvastatin 40 mg or simvastatin 40 mg, (except for patients on simvastatin 80 mg for more than one year, who are eligible); 7) use of fibrates, other than fenofibrate within 6 weeks of the screening visit (Week-3) or between screening and randomization visits; 8) use of nutraceutical products or over-the-counter therapies that may affect lipids which have not been at a stable dose/amount for at least 4 weeks prior to the screening visit (Week-3) or between screening and randomization visits; 9) use of red yeast rice products within 4 weeks of the screening visit (Week-3) or between screening and randomization visits; 10) patient who has received plasmapheresis treatment within 2 months prior to the screening visit (Week-3), or has plans to receive it during the study; 11) recent (within 3 months prior to the screening visit [Week-3] or between screening and randomization visits) MI, unstable angina leading to hospitalization, percutaneous coronary intervention (PCI), coronary artery bypass graft surgery (CABG), uncontrolled cardiac arrhythmia, stroke, transient ischemic attack (TIA), carotid revascularization, endovascular procedure or surgical intervention for peripheral vascular disease; 12) planned to undergo scheduled PCI, CABG, carotid, or peripheral revascularization during the study; 13) systolic blood pressure >160 mmHg or diastolic blood pressure >100 mmHg at screening visit or randomization visit; 14) history of New York Heart Association (NYHA) Class III or IV heart failure within the past 12 months; 15) known history of a hemorrhagic stroke; 16) age <18 years or legal age of majority at the screening visit (Week-3), whichever is greater; 17) patients not previously instructed on a cholesterol-lowering diet prior to the screening visit (Week-3); 18) newly diagnosed (within 3 calendar months prior to randomization visit [Week 0]) or poorly controlled (HbA1c>9% at the screening visit [Week-3]) diabetes; 19) presence of any clinically significant uncontrolled endocrine disease known to influence serum lipids or lipoproteins. Note: patients on thyroid replacement therapy can be included if the dosage has been stable for at least 12 weeks prior to screening and between screening and randomization visits, and TSH level is within the normal range of the Central Laboratory at the screening visit; 20) history of bariatric surgery within 12 months prior to the screening visit (Week-3); 21) unstable weight defined by a variation >5 kg within 2 months prior to the screening visit (Week-3); 22) known history of homozygous FH; 23) known history of loss of function of PCSK9 (i.e., genetic mutation or sequence variation); 24) use of systemic corticosteroids, unless used as replacement therapy for pituitary/adrenal disease with a stable regimen for at least 6 weeks prior to randomization visit (Week 0). Note: topical, intra-articular, nasal, inhaled and ophthalmic steroid therapies are not considered as "systemic" and are allowed; 25) use of continuous estrogen or testosterone hormone replacement therapy unless the regimen has been stable in the past 6 weeks prior to the Screening visit (Week-2) and no plans to change the regimen during the study; 26) history of cancer within the past 5 years, except for adequately treated basal cell skin cancer, squamous cell skin cancer or in situ cervical cancer; 27) known history of positive HIV test; 28) patient who has taken any investigational drugs other than the Alirocumab training placebo kits within 1 month or 5 half lives, whichever is longer; 29) patient who has been previously treated with at least one dose of Alirocumab or any other anti-PCSK9 monoclonal antibody in other clinical trials; 30) patient who withdraws consent during the screening period (patient who is not willing to continue or fails to return); 31) conditions/situations such as any clinically significant abnormality identified at the time of screening that, in the judgment of the Investigator or any sub-Investigator, would preclude safe completion of the study or constrain endpoints assessment; eg, major systemic diseases, patients with short life expectancy considered by the Investigator or any sub-Investigator as inappropriate for this study for any reason, e.g.,: a) deemed unable to meet specific protocol requirements, such as scheduled visits; b) deemed unable to administer or tolerate long-term injections as per the patient or the Investigator; c) investigator or any sub-Investigator, pharmacist, study coordinator, other study staff or relative thereof directly involved in the conduct of the protocol, etc.; d) presence of any other conditions (e.g., geographic or social . . . ) actual or anticipated, that the Investigator feels would restrict or limit the patient's participation for the duration of the study; 32) laboratory findings during screening period (not including randomization Week 0 labs): a) positive test for Hepatitis B surface antigen or Hepatitis C antibody; b) positive serum beta-hCG or urine pregnancy (including Week 0) in women of childbearing potential; c) triglycerides >400 mg/dL (>4.52 mmol/L) (1 repeat lab is allowed); d) eGFR<30 mL/min/1.73 m2 according to 4-variable MDRD Study equation (calculated by central lab); e) ALT or AST>3×ULN (1 repeat lab is allowed); f) CPK>3×ULN (1 repeat lab is allowed); g) TSH<lower limit of normal (LLN) or >upper limit of normal (ULN) (1 repeat lab is allowed).

Exclusion criteria related to the background therapies were: 1) all contraindications to the background therapies or warnings/precautions of use (when appropriate) as displayed in the respective National Product Labeling.

Exclusion criteria related to Alirocumab were: 1) known hypersensitivity to monoclonal antibody or any component of the drug product; 2) pregnant or breast-feeding women; and 3) women of childbearing potential not protected by highly-effective method(s) of birth control (as defined in the informed consent form and/or in a local protocol addendum) and/or who are unwilling or unable to be tested for pregnancy. Note: Women of childbearing potential must have had a confirmed negative pregnancy test at screening and randomization visits. They must have used an effective contraceptive method throughout the entire duration of the study treatment, and for 10 weeks after the last intake of IMP, and agreed to repeat urine pregnancy test at designated visits. The applied methods of contraception had to meet the criteria for a highly effective method of birth control according to the "Note for guidance on non-clinical safety studies for the conduct of human clinical trials and marketing authorization for pharmaceuticals (CPMP/ICH/286/95)". Postmenopausal women must have been amenorrheic for at least 12 months.

Study Treatments

Sterile Alirocumab drug product was supplied at a concentration of 150 mg/mL in histidine, pH 6.0, polysorbate 20, and sucrose. Drug product was supplied as 1 mL volume in an auto-injector.

Sterile placebo for Alirocumab was prepared in the same formulation as Alirocumab without the addition of protein as 1 mL volume in an auto-injector.

During the double-blind treatment period, Alirocumab or placebo was administered subcutaneously every 2 weeks, starting at Week 0 continuing up to the last injection (Week 76) 2 weeks before the end of the double blind treatment period. If the injection was scheduled to take place on the same date as the site visit, then the IMP should have been administered after the blood sampling had been completed.

IMP should ideally have been administered every 2 weeks subcutaneously at approximately the same time of the day; however it was acceptable to have a window period of ±3 days. The time of the day was based on patient's preference.

The following classes of drugs were identified as non-investigational medicinal products (NIMP) because the medication was either a background therapy or a potential rescue medication: statins (rosuvastatin, atorvastatin, simvastatin); cholesterol absorption inhibitors (ezetimibe); bile acid-binding sequestrants (such as cholestyramine, colestipol, colesevelam); nicotinic acid; fenofibrate; omega-3 fatty acids (≥1000 mg daily).

Patients who achieved 2 consecutive calculated LDL-C<25 mg/dL (0.65 mmol/L) were monitored.

Patients who had titers at or above 240 for anti-Alirocumab antibodies at follow-up visit had additional antibody sample(s) at 6 to 12 months after the last dose, and thereafter about every 3 to 6 months until titer returned below 240.

Patients were randomized to receive either placebo or Alirocumab during the double-blind study treatment period using a ratio 1:2, with permuted-block randomization. Randomization was stratified according to prior history of myocardial infarction (MI) or ischemic stroke [Yes/No], and statin treatment (atorvastatin 40 to 80 mg daily or rosuvastatin 20 to 40 mg daily vs. simvastatin whatever the daily dose, atorvastatin below 40 mg daily or rosuvastatin below 20 mg daily).

A concomitant medication was any treatment received by the patient concomitantly to the study (until follow-up visit). Concomitant medications were to be kept to a minimum during the study. However, if these were considered necessary for the patient's welfare and were unlikely to interfere with the IMP, they could be given at the discretion of the Investigator, with a stable dose (when possible). Besides the specific information related to concomitant medications provided in this section, any other concomitant medication (s) will be allowed. If the patient had an LDL-C>or equal 160 mg/dL (4.14 mmol/L) at the screening visit (Week-3) and was treated with a statin only, i.e. without additional LMT, the investigator was to report the reason for the patient not being on a second LMT. For background LMT, including statins, sites must have followed the national product label for the safety monitoring and management of patients.

Nutraceutical products or over-the-counter therapies that may affect lipids were allowed only if they had been used at a stable dose for at least 4 weeks prior to screening visit, during the screening period and maintained during the first 24 weeks of the double-blind treatment period. After the Week 24 visit, modification to these nutraceutical products or over-the-counter therapies was allowed but in general should have been avoided. Examples of such nutraceutical products or over-the-counter therapies included omega-3 fatty acids at doses <1000 mg, plant stanols such as found in Benecol, flax seed oil, and *psyllium*.

Patients must have been on stable maximally tolerated daily registered doses of statins with other LMT for at least 4 weeks (6 weeks for fenofibrate) before screening visit. During the study, the patients should have stayed on these stable maximally tolerated registered daily doses of statins with other LMT. Lipid profile values from samples obtained after randomization were blinded. Nevertheless, sites were made aware of triglyceride alert, as well as rescue threshold of LDL-C value in order to make decisions on the patient's background LMT. From the screening visit (Week-3) until Week 24 of the double-blind treatment period, the background LMT should not have been changed. No dose adjustment, discontinuation or initiation of other statins or other LMT should have taken place during this time, barring exceptional circumstances whereby overriding concerns (including but not limited to triglyceride alert posted by the central lab) warranted such changes, as per the investigator's judgment.

For a triglyceride alert (TG≥500 mg/dL (5.65 mmol/L)) that was confirmed by repeat testing, the investigator was to perform investigations, manage the patient, and modify the background LMT as per his/her medical judgment.

For a rescue notification of LDL-C at the Week 24 visit and later, i.e., LDL-C increase >25% as compared to randomization visit LDL-C on two consecutive occasions, the investigator should have ensured that no reasonable explanation existed for insufficient LDL-C control (such as an alternative medical cause like corticosteroid use, etc.) and in particular that: compliance with diet was appropriate, compliance with background LMT was appropriate, and study treatment was given as planned. If any of the above could have reasonably explained the insufficient LDL-C control, the investigator should have undertaken appropriate action, i.e. stressed the absolute need to be compliant with treatment, if needed organized a specific interview with a qualified nutrition professional and stressed the absolute need to be compliant with diet, and performed a blinded LDL-C assessment within 1 to 2 months. If none of the above mentioned reasons could be found, or if appropriate action failed to decrease LDL-C under the alert value, rescue medication may have been introduced. The effectiveness of any such changes were made based on the absence of rescue notification of LDL-C sent on the blinded lipid testing at the next scheduled lab draw.

If no reason for LDL-C above the threshold value could be found, or if appropriate action failed to decrease LDL-C below the threshold value, rescue medication may have been introduced. The effectiveness of any such changes would be made based on lack of rescue threshold from blinded lipid testing at the next routinely scheduled lab draw. Patients per protocol already received a maximum tolerated dose of statin, so statin up-titration or switch was not an option. For further LDL-C lowering, the investigator may have considered: a cholesterol absorption inhibitor (ezetimibe), or a bile acid-binding sequestrant (the resins cholestyramine and colestipol, or colesevelam, a nonabsorbable polymer). The following lipid modifying agents may have also been considered: fibrate (Note: Caution should be exercised when combining fibrates with other cholesterol-lowering medications such as statins because of the risk of myopathy. When a fibrate is combined with a statin, fenofibrate is the fibrate of choice because it does not affect statin glucuronidation.); the only fibrate allowed per protocol was fenofibrate; nicotinic acid (niacin) (Note: Niacin raises blood glucose but has been shown to be effective in modifying lipid disorders in people with diabetes if glucose control is maintained).

In summary, background LMT should not have been modified from screening to the follow up visit. However, up to Week 24, if a confirmed TG alert was reached or if there was an overwhelming clinical concern (at the discretion of the Investigator) then modification of the background LMT was allowed. From Week 24 onwards, if a confirmed TG alert was reached, or if a rescue threshold for LDL-C was attained (and no other reasonable explanation exists), or if there was an overwhelming clinical concern (at the discretion of the Investigator) then modification of the background LMT was allowed.

Women of childbearing potential were required to take an effective contraceptive method throughout the study treatment and for 10 weeks after the last IMP injection (i.e., Follow-up visit).

Forbidden concomitant medications from the initial screening visit until the follow-up visit included the following: statins other than simvastatin, atorvastatin and rosuvastatin; fibrates, other than fenofibrate; and red yeast rice products.

Study Endpoints

The primary efficacy endpoint was the percent change in calculated LDL-C from baseline to Week 24, which was defined as: 100× (calculated LDL-C value at Week 24−calculated LDL-C value at baseline)/calculated LDL-C value at baseline. The baseline calculated LDL-C value was the last LDL-C level obtained before the first double-blind IMP injection. The calculated LDL-C at Week 24 was the LDL-C level obtained within the Week 24 analysis window and during the main efficacy period. The main efficacy period was defined as the time from the first double-blind IMP injection up to 21 days after the last double-blind IMP injection or up to the upper limit of the Week 24 analysis window, whichever came first. All calculated LDL-C values (scheduled or unscheduled, fasting or not fasting) may be used to provide a value for the primary efficacy endpoint if appropriate according to above definition.

The key secondary efficacy endpoints were: 1) The percent change in calculated LDL-C from baseline to Week 12: similar definition and rules as for primary efficacy endpoint, except that the calculated LDL-C at Week 12 was the LDL-C level obtained within the Week 12 analysis window and during the 12-week efficacy period. The 12-week efficacy period was defined as the time from the first double-blind IMP injection up to the Visit 6 re-supply IVRS contact or up to 21 days after the last double-blind IMP injection, whichever came first. Blood sampling collected the day of the Visit 6 re-supply IVRS contact was considered as before titration; 2) the percent change in Apo B from baseline to Week 24. Same definition and rules as for the primary endpoint; 3) the percent change in non-HDL-C from baseline to Week 24. Same definition and rules as for the primary endpoint; 4) the percent change in total-C from baseline to Week 24. Same definition and rules as for the primary endpoint; 5) the percent change in Apo B from baseline to Week 12. Same definition and rules as for the percent change in calculated LDL-C from baseline to Week 12; 6) the percent change in non-HDL-C from baseline to Week 12. Same definition and rules as for the percent change in calculated LDL-C from baseline to Week 12; 7) the percent change in total-C from baseline to Week 12. Same definition and rules as for the percent change in calculated LDL-C from baseline to Week 12; 8) the percent change in calculated LDL-C from baseline to Week 52. Definitions and rules were similar to the ones used for the primary endpoint replacing Week 24 by Week 52. The 52-week efficacy period was defined as the time from the first double-blind IMP up to 21 days after the last double-blind IMP injection, or up to the upper limit of the Week 52 analysis window whichever came first; 9) the proportion of patients reaching LDL-C goal at Week 24, i.e. LDL-C<70 mg/dL (1.81 mmol/L) in case of prior CVD or <100 mg/dL (2.59 mmol/L) for patients without CVD, defined as: (number of patients whose calculated LDL-C value at Week 24 reach LDL-C goal/number of patients in the mITT population)*100, using definition and rules used for the primary endpoint; 10) the percent change in Lp(a) from baseline to Week 24. Same definition and rules as for the primary endpoint; 11) the percent change in HDL-C from baseline to Week 24. Same definition and rules as for the primary endpoint; 12) the percent change in HDL-C from baseline to Week 12. Same definition and rules as for the percent change in calculated LDL-C from baseline to Week 12; 13) the percent change in Lp(a) from baseline to Week 12. Same definition and rules as for the percent change in calculated LDL-C from baseline to Week 12; 14) the percent change in fasting TG from baseline to Week 24. Same definition and rules as for the primary endpoint; 15) the percent change in fasting TG from baseline to Week 12. Same definition and rules as for the percent change in calculated LDL-C from baseline to Week 12; 16) the percent change in Apo A-1 from baseline to Week 24. Same definition and rules as for the primary endpoint; 17) the percent change in Apo A-1 from baseline to Week 12. Same definition and rules as for the percent change in calculated LDL-C from baseline to Week 12.

Other secondary efficacy endpoints were: 1) the percent change in calculated LDL-C from baseline to Week 78: Definitions and rules were similar to the ones used for the primary endpoint replacing Week 24 by Week 78; 2) the proportion of patients reaching LDL-C goal at Weeks 12, 52 and 78, i.e., LDL-C<70 mg/dL (1.81 mmol/L) in case of prior CVD or <100 mg/dL (2.59 mmol/L) for patients without prior CVD; 3) the proportion of patients reaching LDL C<100 mg/dL (2.59 mmol/L) at Week 24; 4) the proportion of patients reaching LDL-C<100 mg/dL (2.59 mmol/L) at Week 12; 5) the proportion of patients reaching LDL-C<70 mg/dL (1.81 mmol/L) at Week 24; 6) the proportion of patients reaching LDL-C<70 mg/dL (1.81 mmol/L) at Week 12; 7) the absolute change in calculated LDL-C(mg/dL and mmol/L) from baseline to Weeks 12, 24, 52 and 78; 8) the percent change in Apo B, non-HDL-C, total-C, Lp (a), HDL-C, fasting TG, and Apo A-1 from baseline to Week 52 and 78; 9) the change in ratio Apo B/Apo A-1 from baseline to Weeks 12, 24, 52 and 78; 10) the proportion of patients with Apo B<80 mg/dL (0.8 g/L) at Weeks 12, 24, 52 and 78; 11) the proportion of patients with non-HDL-C<100 mg/dL at Weeks 12, 24, 52 and 78; 12) the proportion of patients with calculated LDL-C<70 mg/dL (1.81 mmol/L) and/or ≥50% reduction in calculated LDL-C(if calculated LDL-C>70 mg/dL [1.81 mmol/L]) at Weeks 12, 24, 52 and 78.

Total-C, HDL-C, TG, Apo B, Apo A-1, and Lp (a) were directly measured by the Central Laboratory. LDL-C was calculated using the Friedewald formula at all visits (except Week −1 and Follow Up visit). If TG values exceeded 400 mg/dL (4.52 mmol/L) then the central lab reflexively measured (via the beta quantification method) the LDL-C rather than calculating it. Non-HDL-C was calculated by subtracting HDL-C from the total-C. Ratio Apo B/Apo A-1 was calculated.

The clinical laboratory data consisted of urinalysis, hematology (red blood cell count, hemoglobin, red blood cell distribution width (RDW), reticulocyte count, hematocrit, platelets, white blood cell count with differential blood count), standard chemistry (glucose, sodium, potassium, chloride, bicarbonate, calcium, phosphorous, urea nitrogen, creatinine, uric acid, total protein, LDH, albumin, γ Glutamyl Transferase [γGT]), Hepatitis C antibody, liver panel (ALT, AST, ALP, and total bilirubin), and CPK.

Vital signs included: heart rate, systolic and diastolic blood pressure in sitting position.

Other endpoints included: anti-Alirocumab antibody assessments, hs-CRP, $HbA_{1c}$, EQ-5D Questionnaire, and pharmacogenetic samples.

Anti-Alirocumab antibodies included the antibody status (positive/negative) and antibody titers. Serum samples for anti-Alirocumab antibody determination were drawn periodically throughout the study. The first scheduled sample at randomization visit was obtained before IMP injection (predose). Patients who had titers at or above 240 for anti-Alirocumab antibodies at the follow-up visit had additional antibody sample(s) at 6 to 12 months after the last dose, and thereafter about every 3 to 6 months until titer returned below 240. Anti-Alirocumab antibody samples were analyzed using a validated non-quantitative, titer-based bridging immunoassay. It involved an initial screen, a confirmation assay based on drug specificity, and a measurement of the titer of anti-Alirocumab antibodies in the sample. The lower limit of detection was approximately 1.5 ng/mL. Samples that were positive in the ADA assay were assessed for neutralizing antibodies using a validated, non-quantitative, competitive ligand binding assay. The lower limit of detection based on a monoclonal positive control neutralizing antibody was 390 ng/mL.

The percent change in hs-CRP from baseline to Week 24, 52 and 78.

The absolute change in HbA1c (%) from baseline to Week 24, 52 and 78.

EQ-5D is a standardized measure of health status developed by the EuroQol Group in order to provide a simple, generic measure of health for clinical and economic appraisal. The EQ-5D as a measure of health-related quality of life defines health in terms of 5 dimensions: mobility, self-care, usual activities, pain/discomfort, anxiety/depression. Each dimension can take one of three responses (3 ordinal levels of severity): 'no problem' (1), "some problems" (2), "severe problems" (3). Overall health state was defined as a 5-digit number. Health states defined by the 5-dimensional classification can be converted into corresponding index scores that quantify health status, where 0 represents 'death' and 1 represents "perfect health".

Study Procedures

For all visits after Day 1/Week 0 (randomization visit), a timeframe of a certain number of days was allowed. The window period for visits at Weeks 12 and 24 was ±3 days, at Week 52 and 78 was ±5 days, and for all other site visits it was ±7 days during the double-blind treatment period, and follow-up period. A window period of +3 days was allowed for the randomization visit (Day1/Week 0) and ±7 days for the injection training visit at screening (Week-1).

The blood sampling for determination of lipid parameters (i.e. total-C, LDL-C, HDL-C, TG, non-HDL-C, Apo B, Apo A-1, ratio Apo B/Apo A-1, Lp [a]) was to be performed in the morning, in fasting condition (i.e. overnight, at least 10-12 hours fast and refrain from smoking) for all site visits throughout the study. Alcohol consumption within 48 hours and intense physical exercise within 24 hours preceding the blood sampling were discouraged. Note: if the patient was not in fasting conditions, the blood sample was not be collected and a new appointment was given the day after (or as close as possible to this date) to the patient with instruction to be fasted (see above conditions).

Only patients who met the inclusion criteria were screened. The screening period took place up to 3 weeks or 21 days (and as short as possible, upon receipt of laboratory eligibility criteria) prior to randomization/Day 1 visit. The first screening visit (Week-3) took place from 21 to 8 days before the randomization visit. If it was planned to have another designated person administer the injections to the patient during the study, then this person should have been present at the injection training visit (Week −1).

The following visits were scheduled: Screening Visit (Visit1/Week −3/Day −21 up to −8); Screening (Visit2/Week −1/Day −7±7); Randomization visit (Visit 3/Week 0/Day 1+3); Visit 4/Week 4/Day 29±7); Visit 5/Week 8/Day 57±7); Visit 6/Week 12/Day 85±3; Visit 7/Week 16/Day 113±7): Visit 8/Week 24/Day 169±3; Visit 9/Week 36/Day 253±7; Visit 10/Week 52/Month 12/Day 365±5; Visit 11/Week 64/Day 449±7; Visit 12/Week 78/Month 18/Day 547±5 (end of treatment visit); and Visit 13/Week 86/Day 603±7 (follow up visit).

Safety

Monitored safety events were the occurrence of treatment emergent adverse events (TEAEs) reported by the patient or noted by the investigator, serious adverse events (SAEs), TEAEs leading to treatment discontinuation, AEs of special interest (local Injection site reactions, allergic events, selected neurological events and cardiovascular events with adjudication result), occurrence of PCSA (potentially clinically significant abnormalities) in laboratory parameters, specific analysis for diabetes or impaired glucose control and patients with 2 consecutives LDL-C<25 mg/dL.

Statistical Methods

Sample Size Determination:

A total sample size of 45 patients (30 in alirocumab and 15 in placebo) had 95% power to detect a difference in mean percent change in LDL-C of 30% with a 0.05 two-sided significance level and assuming a common standard deviation of 25%, and all these 45 patients having an evaluable primary endpoint. A final total sample size of 105 patients with a randomization ratio 2:1 (alirocumab 70: placebo 35) has been selected in order to provide at least 50 patients exposed to alirocumab for 12 months at the first step analysis and assuming a drop-out rate of 10% over the first 3-month period and a drop-out rate of 20% over the 3-12-month period.

Timing of Analyses:

The first step analysis included efficacy endpoints up to Week 52 (final efficacy analysis) and interim safety analysis, which was performed on all safety data up to the common study cut-off date (last patient Week 52 visit). Analysis of lipid data beyond Week 52 was descriptive. Results of the first step analysis are presented herein.

Second step (final) analysis will be conducted at the end of the study and will consist in the final analysis of efficacy endpoints up to Week 78 and final safety analysis.

Analysis Populations:

The primary efficacy analysis population was the intent-to-treat (ITT) population, defined as all randomized patients who had an evaluable primary efficacy endpoint, that is, those with an available baseline calculated LDL-C value, and at least one available calculated LDL-C value within one of the analysis windows up to Week 24 (including all calculated LDL-C on-treatment and off-treatment).

The secondary efficacy analysis population was the modified intent-to-treat (mITT) population, defined as all randomized patients who took at least one dose or part of a dose of the double-blind investigational medicinal product (IMP) and who had an available calculated LDL-C value at baseline and at least one within one of the analysis windows up to Week 24 during the efficacy treatment period. The efficacy treatment period was defined as the time from the first double-blind IMP administration up to 21 days after the last double-blind injection.

The safety population included all randomized patients who received at least one dose or part of a dose of the double-blind IMP.

Efficacy Analyses:

Primary analyses of efficacy endpoints were conducted using an ITT approach (based on the ITT population defined above), including all lipid data, regardless of whether the patient was continuing therapy or not. This corresponds to ITT estimands, defined for primary and key secondary endpoints. In addition, analyses were also conducted using an on-treatment approach (based on the mITT population defined above), including lipid data collected during the efficacy treatment period. This corresponds to on-treatment estimands of key secondary endpoints.

The ITT approach analyzed all patients, irrespective of their adherence to the treatment; it assessed the benefit of the treatment strategy and reflected as much as possible the effect in a population of patients. The on-treatment approach analyzed the effect of treatment, restricted to the period during which patients actually received the treatment. It assessed the benefit that a treatment would achieve in patients adherent to treatment up to the considered time point.

Efficacy analyses were performed according to treatment as-randomized.

All measurements, scheduled or unscheduled, fasting or not fasting, were assigned to analysis windows in order to provide an assessment for Week 4 to Week 78 time points.

With regards to the primary efficacy analysis (ITT approach), the percent change in calculated LDL-C from baseline to Week 24 was analyzed using a mixed-effect model with repeated measures (MMRM) approach. All post-baseline data available from Week 4 to Week 52 analysis windows were used and missing data were accounted for by the MMRM. The model included the fixed categorical effects of treatment group (placebo versus alirocumab), randomization strata (as per IVRS), time point (Week 4 to Week 52), treatment-by-time point interaction and strata-by-time point interaction, as well as, the continuous fixed covariates of baseline LDL-C value and baseline value-by-time-point interaction. This model provided baseline adjusted least-squares means (LSmeans) estimates at Week 24 for both treatment groups with their corresponding 95% confidence interval. To compare the alirocumab to the placebo group, an appropriate statement was used to test the differences of these estimates at the 5% alpha level.

A hierarchical procedure has been defined to test key secondary endpoints while controlling for multiplicity (using above order of key secondary endpoints). The first key secondary endpoint was the percent change in calculated LDL-C from baseline to Week 24 using an on-treatment approach.

Continuous secondary variables anticipated to have a normal distribution (i.e., lipids other than TG and Lp(a)) were analyzed using the same MMRM model as for the primary endpoint. Continuous endpoints anticipated to have a non-normal distribution (i.e., TG and Lp(a)) were analyzed using multiple imputation approach for handling of missing values followed by robust regression model with endpoint of interest as response variable using M-estimation (using SAS ROBUSTREG procedure) with treatment group, randomization strata (as per IVRS) and corresponding baseline value(s) as effects to compare treatment effects. Combined estimate for mean in both treatment groups, as well as the differences of these estimates, with their corresponding SEs, 95% CIs and p-value were provided (through SAS MIANALYZE procedure).

Binary secondary efficacy endpoints were analyzed using multiple imputation approach for handling of missing values followed by stratified logistic regression with treatment group as main effect and corresponding baseline value(s) as covariate, stratified by randomization factors (as per IVRS). Combined estimates of odds ratio versus placebo, 95% CI, and p-value were provided (through SAS MIANALYZE procedure).

Safety Analyses:

Safety analyses were descriptive, performed on the safety population according to treatment actually received. The safety analysis focused on the TEAE period defined as the time from the first dose of double-blind up to 70 days after the last double-blind injection. TEAE which developed, worsened or became serious or PCSA occurring after the patient inclusion in the open-label extension study (LTS13643) were not considered in the TEAE period. TEAE period was truncated at the common study cut-off date.

Results

Study Patients

Patient Accountability

Of the 107 randomized patients (72 and 35 patients in the alirocumab and the placebo groups, respectively), one patient in the alirocumab group did not have any baseline calculated LDL-C value and was therefore not included in the ITT and mITT populations.

TABLE 26

Analysis populations

|  | Placebo | Alirocumab 150 Q2W | All |
|---|---|---|---|
| Randomized population | 35 (100%) | 72 (100%) | 107 (100%) |
| Efficacy populations |  |  |  |
| Intent-to-Treat (ITT) | 35 (100%) | 71 (98.6%) | 106 (99.1%) |
| Modified Intent-to-Treat (mITT) | 35 (100%) | 71 (98.6%) | 106 (99.1%) |
| Safety population | 35 | 72 | 107 |

Note:
The safety population patients are tabulated according to treatment actually received (as treated).
For the other populations, patients are tabulated according to their randomized treatment.

Study Disposition

Study disposition, exposure, efficacy and safety analyses were assessed using all data up to the common cut-off date of the study (defined as the date of last patient's Week 52 visit). Therefore, this first step analysis includes efficacy data up to Week 52 and safety data beyond Week 52 and up to Week 78 or Follow-up visit for some patients. Patient disposition is shown in FIG. 12.

In this study, one site with 7 patients randomized and a second site with 6 patients randomized were identified with serious GCP non-compliance, and the sites were closed. For the first closed site, one of the key findings was related to IMP injections reported as having been received by some patients whereas corresponding kits were discovered in the fridge. The reporting of these injections was corrected in the database but other issues on injections could not be excluded. For the second site, persistent concerns with the conduct of the study and associated documentation related to the study were observed during routine monitoring.

Among these 13 patients, one was still ongoing at the cut-off date, one discontinued for adverse event, one patient moved, 3 patients discontinued for poor compliance to protocol and 7 patients discontinued due to decision of site closure.

There were in total 10 (9.3%) randomized patients who completed the 78 weeks double-blind study treatment period and 76 (71.0%) randomized patients with treatment ongoing at the time of the first-step analysis cut-off date. The double-blind IMP was prematurely discontinued before Week 78 for 6 (17.1%) patients in the placebo group and 15 (20.8%) patients in the alirocumab group. All these patients actually prematurely discontinued before Week 52. The main reasons for study treatment discontinuation were "other reasons", poor compliance and adverse events. These "other reasons" included the 7 patients who discontinued due to the decision of site closure as mentioned above, 1 patient withdrawal not otherwise specified, 1 patient withdrew due to cholesterol results obtained independently and 1 patient moved.

In this first step analysis, final results are available for primary efficacy endpoint at Week 24 and key secondary efficacy endpoints assessed at Week 12, Week 24 and Week 52. The following table provides the availability of LDL-C over time. At Week 24, the primary efficacy endpoint was available for 33 (94.3%) in the placebo and 63 (88.7%) in the alirocumab group.

TABLE 27

Calculated LDL-C availability over time - ITT population

| Calculated LDL-C | Placebo (N = 35) | | | Alirocumab 150 Q2W (N = 71) | | |
|---|---|---|---|---|---|---|
|  | On-treatment value | Post-treatment value | Missing value | On-treatment value | Post-treatment value | Missing value |
| Week 4 | 31 (88.6%) | 0 | 4 (11.4%) | 67 (94.4%) | 0 | 4 (5.6%) |
| Week 8 | 34 (97.1%) | 0 | 1 (2.9%) | 66 (93.0%) | 0 | 5 (7.0%) |
| Week 12 | 33 (94.3%) | 0 | 2 (5.7%) | 68 (95.8%) | 0 | 3 (4.2%) |
| Week 16 | 28 (80.0%) | 0 | 7 (20.0%) | 66 (93.0%) | 0 | 5 (7.0%) |
| Week 24 | 33 (94.3%) | 0 | 2 (5.7%) | 62 (87.3%) | 1 (1.4%) | 8 (11.3%) |
| Week 36 | 30 (85.7%) | 1 (2.9%) | 4 (11.4%) | 60 (84.5%) | 3 (4.2%) | 8 (11.3%) |
| Week 52 | 27 (77.1%) | 0 | 8 (22.9%) | 52 (73.2%) | 2 (2.8%) | 17 (23.9%) |

The primary endpoint was missing for 10 patients at Week 24 (2 and 8 patients in placebo and alirocumab groups, respectively). At the Week 24 visit (as per CRF monitoring), the reasons for missingness were as follows: 3 samples not done due to earlier study discontinuation; 3 samples done outside analysis time window; 2 samples not done due to Week 24 visit not done; and 2 samples available but measurement could not be done (lipemia, insufficient quantity, TGs>400 mg/dL[>4.52 mmol/L], sample lost, etc.).

The higher number of missing data at Week 52 is mainly due to the decision to close the two sites due to serious GCP non-compliance.

The LDL-C endpoint at Week 52 was missing for 25 out of 106 patients. The reasons for missing results were as follows: 17 samples not done due to earlier study discontinuation including 11 patients from the two closed sites; 3 samples done outside analysis time window; 1 sample not done due to Week 52 not done; 1 missing sample while visit Week 52 was done; and 3 samples available but measurement could not be done (TGs>400 mg/dL[>4.52 mmol/L] and hemolysis).

Demographics and Baseline Characteristics

Summary Population Characteristics:

107 HeFH patients diagnosed by genotyping (17.8%) and WHO/Dutch Lipid Network criteria (score of >8 points) or Simon Broome criteria for definite FH (82.2%) were randomized 2:1 to alirocumab (150 mg Q2W) or placebo.

Demographics characteristics, disease characteristics and lipid parameters at baseline were generally similar in the alirocumab group as compared to the placebo group: diagnosis of HeFH through genotyping in the alirocumab (19.4%) vs the placebo group (14.3%); diagnosis of HeFH through clinical criteria in the alirocumab (80.6%) vs the placebo group (85.7%); a mean age (SD) in the alirocumab group of 49.8 years (14.2) vs a mean age of the placebo group of 52.1 years (11.2); percentage of white race in the alirocumab (88.9%) vs the placebo (85.7%) group; and a mean BMI (SD) in the alirocumab group of 28.8 kg/m² (5.2) vs a mean BMI in the placebo group of 28.9 kg/m² (4.2). Some imbalances were noted due to the small sample size of the study: a higher proportion of female patients in the alirocumab group (51.4%) vs the placebo group (37.1%); more recent hypercholesterolemia diagnosis in the alirocumab group (median of 9.8 years) vs the placebo group (median of 17.4 years); a lower proportion of patients considered as very high CV risk in the alirocumab group (52.8%) than in the placebo group (65.7%) mainly driven by a medical history of coronary revascularization procedure; and a lower proportion of patients received ezetimibe at randomization in the alirocumab group (19.4%) than in the placebo group (34.3%). The cardiovascular history and risk factors of patients in both the alirocumab and placebo groups are shown in Table 28.

TABLE 28

Cardiovascular history and risk factors

| All patients on background of maximally tolerated statin ± other LLT | Placebo (N = 35) | Alirocumab 150 Q2W (N = 72) | All (N = 107) |
|---|---|---|---|
| CHD history, % (n) | 43.1% (31) | 62.9% (22) | 49.5% (53) |
| Acute MI, % (n) | 22.1% (16) | 22.9% (8) | 22.4% (24) |
| Silent MI, % (n) | 1.4% (1) | 0 | 0.9% (1) |
| Unstable angina, % (n) | 9.7% (7) | 17.1% (6) | 12.1% (13) |
| Coronary revascularization procedures, % (n) | 15.3% (11) | 40.0% (14) | 23.4% (25) |
| Other clinically significant CHD, % (n) | 27.8% (20) | 28.6% (10) | 28.0% (30) |
| Current smoker, % (n) | 16.7% (12) | 25.7% (9) | 19.6% (21) |
| Hypertension, % (n) | 55.6% (40) | 60.0% (21) | 57.0% (61) |
| Type 2 diabetes, % (n) | 12.5% (9) | 17.1% (6) | 14.0% (15) |

At randomization, all patients were treated with a statin, 72.9% receiving high intensity statin (atorvastatin 40 to 80 mg daily or rosuvastatin 20 to 40 mg daily) and 6.5% receiving simvastatin 80 mg. In addition to the statin, 19.4% and 34.3% of patients were receiving ezetimibe in the alirocumab and placebo groups respectively. Table 30 shows the background lipid modifying therapies (LMTs) of the alirocumab and placebo treated populations at randomization as well as those of the total randomized population.

Table 31 shows the lipid efficacy parameters at baseline of the alirocumab and placebo treated populations as well as the total randomized population. Mean (SD) calculated LDL-C at baseline was 197.8 (53.4) mg/dL (5.123 (1.38) mmol/L). Mean (SD) non-HDL-C at baseline was 226.4 (55.3) mg/dL. Mean (SD) Total-C at baseline was 274.4 (54.0) mg/dL. Mean (SD) HDL-C at baseline was 48.1 (13.3) mg/dL. The mean (SD) Total-C/HDL-C ratio at baseline was 6.135 (2.119). Mean (SD) fasting triglycerides (TGs) at baseline was 149.8 (86.6) mg/dL. Mean (SD) Lipoprotein-(a) at baseline was 41.2 (46.6) mg/dL. Mean (SD) Apo-B at baseline was 140.9 (31.0) mg/dL. Mean (SD) Apo-A1 at baseline was 137.5 (23.3) mg/dL. The mean (SD) Apo-B/Apo-A1 ratio at baseline was 1.061 (0.323) mg/dL.

Exposure to injections was similar across treatment groups with a mean exposure of 60.7 weeks in placebo group and 58.3 weeks in alirocumab group.

TABLE 29

Disease characteristics and other relevant baseline data - Randomized population

|  | Placebo (N = 35) | Alirocumab 150 Q2W (N = 72) | All (N = 107) |
|---|---|---|---|
| Type of hypercholesterolemia |  |  |  |
| Heterozygous Familial Hypercholesterolemia (heFH) | 35 (100%) | 72 (100%) | 107 (100%) |
| Non-Familial Hypercholesterolemia (non-FH) | 0 | 0 | 0 |
| Time from hypercholesterolemia diagnosis (years) |  |  |  |
| Number | 35 | 72 | 107 |
| Mean (SD) | 16.41 (12.62) | 11.48 (10.48) | 13.09 (11.41) |
| Median | 17.42 | 9.76 | 11.70 |
| Min:Max | 0.0:42.8 | 0.0:39.9 | 0.0:42.8 |
| Confirmation of diagnosis |  |  |  |
| By genotyping | 5 (14.3%) | 14 (19.4%) | 19 (17.8%) |
| By WHO/Simon Broome[a] | 30 (85.7%) | 58 (80.6%) | 88 (82.2%) |

[a]for heFH diagnosis not confirmed by genotyping.

TABLE 30

Background LMT at randomization - Randomized population

| | Placebo (N = 35) | Alirocumab 150 Q2W (N = 72) | All (N = 107) |
|---|---|---|---|
| Any statin | 35 (100%) | 72 (100%) | 107 (100%) |
| Taking high dose statin | 28 (80.0%) | 57 (79.2%) | 85 (79.4%) |
| Taking high intensity statin | 25 (71.4%) | 53 (73.6%) | 78 (72.9%) |
| Atorvastatin daily dose (mg) | 10 (28.6%) | 22 (30.6%) | 32 (29.9%) |
| 10 | 0 | 0 | 0 |
| 20 | 0 | 0 | 0 |
| 40 | 3 (8.6%) | 10 (13.9%) | 13 (12.1%) |
| 80 | 7 (20.0%) | 11 (15.3%) | 18 (16.8%) |
| Other doses | 0 | 1 (1.4%) | 1 (0.9%) |
| Rosuvastatin daily dose (mg) | 16 (45.7%) | 33 (45.8%) | 49 (45.8%) |
| 5 | 1 (2.9%) | 2 (2.8%) | 3 (2.8%) |
| 10 | 0 | 0 | 0 |
| 20 | 3 (8.6%) | 8 (11.1%) | 11 (10.3%) |
| 40 | 12 (34.3%) | 23 (31.9%) | 35 (32.7%) |
| Other doses | 0 | 0 | 0 |
| Simvastatin daily dose (mg) | 10 (28.6%) | 19 (26.4%) | 29 (27.1%) |
| 10 | 1 (2.9%) | 4 (5.6%) | 5 (4.7%) |
| 20 | 1 (2.9%) | 2 (2.8%) | 3 (2.8%) |
| 40 | 5 (14.3%) | 9 (12.5%) | 14 (13.1%) |
| 80 | 3 (8.6%) | 4 (5.6%) | 7 (6.5%) |
| Other doses | 0 | 0 | 0 |
| Any LMT other than statins[a] | 13 (37.1%) | 16 (22.2%) | 29 (27.1%) |
| Any LMT other than nutraceuticals | 12 (34.3%) | 16 (22.2%) | 28 (26.2%) |
| Ezetimibe | 12 (34.3%) | 14 (19.4%) | 26 (24.3%) |
| Nutraceuticals | 1 (2.9%) | 0 | 1 (0.9%) |

[a]in combination with statins or not.
High intensity statin corresponds to atorvastatin 40 to 80 mg daily or rosuvastatin 20 to 40 mg daily.
High dose statin corresponds to atorvastatin 40 to 80 mg daily, rosuvastatin 20 to 40 mg daily, or simvastatin 80 mg daily.

TABLE 31

Lipid efficacy parameters at baseline - Quantitative summary in conventional units - Randomized population

| | Placebo (N = 35) | Alirocumab 150 Q2W (N = 72) | All (N = 107) |
|---|---|---|---|
| Calculated LDL-C (mg/dL) | | | |
| Number | 35 | 71 | 106 |
| Mean (SD) | 201.0 (43.4) | 196.3 (57.9) | 197.8 (53.4) |
| Median | 201.0 | 180.0 | 181.0 |
| Q1:Q3 | 166.0:240.0 | 165.0:224.0 | 165.0:224.0 |
| Min:Max | 137:279 | 89:402 | 89:402 |
| Non-HDL-C (mg/dL) | | | |
| Number | 35 | 72 | 107 |
| Mean (SD) | 231.5 (47.6) | 223.9 (58.8) | 226.4 (55.3) |
| Median | 226.0 | 204.0 | 209.0 |
| Q1:Q3 | 194.0:274.0 | 189.5:251.0 | 191.0:260.0 |
| Min:Max | 153:326 | 117:419 | 117:419 |
| Total-C (mg/dL) | | | |
| Number | 35 | 72 | 107 |
| Mean (SD) | 276.4 (46.8) | 273.5 (57.5) | 274.4 (54.0) |
| Median | 272.0 | 256.0 | 259.0 |
| Q1:Q3 | 237.0:313.0 | 242.5:300.5 | 241.0:310.0 |
| Min:Max | 202:364 | 171:458 | 171:458 |
| HDL-C (mg/dL) | | | |
| Number | 35 | 72 | 107 |
| Mean (SD) | 44.9 (11.3) | 49.6 (14.0) | 48.1 (13.3) |
| Median | 42.0 | 45.5 | 45.0 |
| Q1:Q3 | 39.0:51.0 | 39.5:57.5 | 39.0:55.0 |
| Min:Max | 24:72 | 28:84 | 24:84 |
| Fasting TGs (mg/dL) | | | |
| Number | 35 | 72 | 107 |
| Mean (SD) | 156.3 (89.3) | 146.6 (85.6) | 149.8 (86.6) |
| Median | 122.0 | 131.5 | 129.0 |
| Q1:Q3 | 95.0:193.0 | 87.5:160.5 | 94.0:171.0 |
| Min:Max | 62:455 | 40:512 | 40:512 |
| Lipoprotein-(a) (mg/dL) | | | |
| Number | 34 | 71 | 105 |
| Mean (SD) | 46.2 (50.3) | 38.8 (44.9) | 41.2 (46.6) |
| Median | 30.0 | 22.0 | 26.0 |
| Q1:Q3 | 11.0:42.0 | 8.0:50.0 | 10.0:48.0 |
| Min:Max | 2:201 | 2:189 | 2:201 |
| Apo-B (mg/dL) | | | |
| Number | 34 | 71 | 105 |
| Mean (SD) | 146.6 (28.3) | 138.2 (32.0) | 140.9 (31.0) |
| Median | 143.0 | 130.0 | 134.0 |
| Q1:Q3 | 121.0:173.0 | 118.0:154.0 | 119.0:158.0 |
| Min:Max | 99:208 | 81:255 | 81:255 |
| Apo-A1 (mg/dL) | | | |
| Number | 34 | 71 | 105 |
| Mean (SD) | 131.5 (19.2) | 140.3 (24.6) | 137.5 (23.3) |
| Median | 127.5 | 137.0 | 134.0 |
| Q1:Q3 | 120.0:142.0 | 122.0:155.0 | 122.0:151.0 |
| Min:Max | 97:181 | 97:211 | 97:211 |
| Apo-B/Apo-A1 (ratio) | | | |
| Number | 34 | 71 | 105 |
| Mean (SD) | 1.141 (0.287) | 1.023 (0.334) | 1.061 (0.323) |
| Median | 1.170 | 0.950 | 1.020 |
| Q1:Q3 | 0.900:1.300 | 0.800:1.170 | 0.850:1.230 |
| Min:Max | 0.58:1.86 | 0.49:2.32 | 0.49:2.32 |
| Total-C/HDL-C (ratio) | | | |
| Number | 35 | 72 | 107 |
| Mean (SD) | 6.540 (1.986) | 5.938 (2.167) | 6.135 (2.119) |
| Median | 6.417 | 5.647 | 5.863 |
| Q1:Q3 | 4.936:7.600 | 4.399:6.878 | 4.545:7.370 |
| Min:Max | 3.29:11.19 | 2.92:13.48 | 2.92:13.48 |

Dosage and Duration

Exposure to injections was similar across treatment groups with a mean exposure of 60.7 weeks in the placebo group and 58.3 weeks in the alirocumab group. Duration of exposure for injection could not be calculated for 1 patient in alirocumab group due to unknown last injection date.

Efficacy

Primary Efficacy Endpoint

The ITT analysis includes all calculated LDL-C values collected on-treatment and off-treatment up to Week 52. The primary endpoint (percent change in calculated LDL-C from baseline to Week 24) analysis is provided based on a MMRM model on the ITT population, using LS means estimates at Week 24. Nine (11.3%) patients in the alirocumab group and 2 (5.7%) patients in the placebo group did not have a calculated LDL-C value at Week 24. These missing values were accounted for by the MMRM model.

Results of the primary endpoint analysis are presented in Table 32, in mmol/L and mg/dL.

Primary Efficacy Analysis

A statistically significant decrease in percent change in LDL-C from baseline to Week 24 was observed in the alirocumab group (LS mean versus baseline −45.7%) compared to the placebo group (LS mean versus baseline −6.6%) (LS mean difference vs. placebo (SE) of −39.1% (6.0%), p<0.0001) (see Table 31). This represents an absolute reduction (SD) of −90.8 (6.7) mg/dL in the alirocumab group and −15.5 (9.5) mg/dL in the placebo group (see Table 33). Percent change from baseline to Week 24 in LDL-C by individual patients are set forth in FIG. 13. All patients were on a background statin (at the maximum tolerated level). A subset of patients also received a further lipid lowering therapy.

Figure 7:
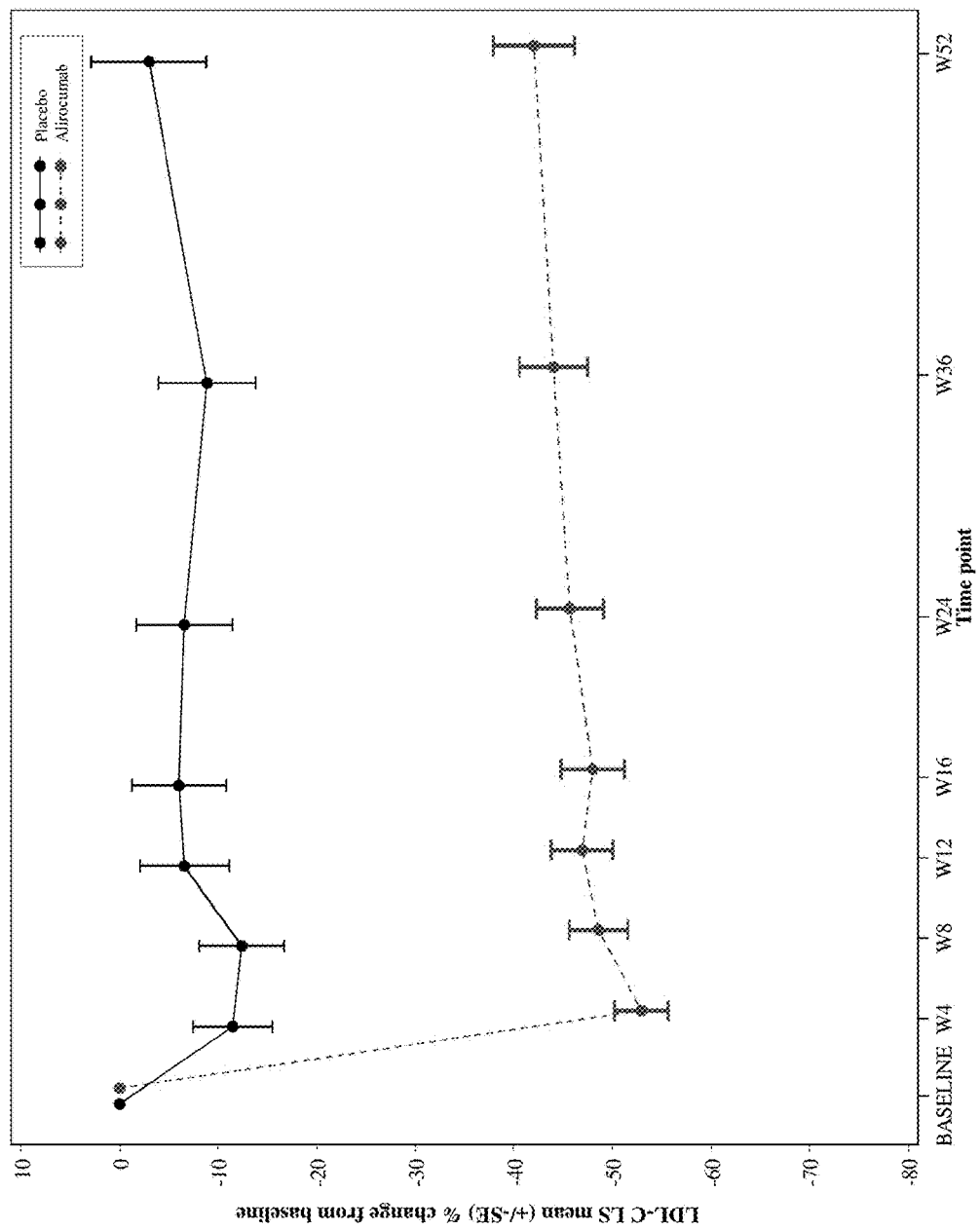
FIG. 7 is a graph showing the calculated LDL-C LS mean percent change from baseline over time for treatment with alirocumab or placebo in the ITT population in the ODYSSEY HIGH FH study (Example 4). The least-squares (LS) means and standard errors (SE) are taken from MMRM (mixed-effect model with repeated measures) analysis.

In the alirocumab group, LDL-C reduction from baseline was observed from Week 4 to Week 52 (see FIG. 7, FIGS. 14A-14B and Table 33). A slight decrease in LDL-C reduction over time was observed in the alirocumab group (LS mean versus baseline at Week 52 of −42.1 versus −45.7 at Week 24), although the overall amount of the decrease stayed the same (75 mg/dL; see FIGS. 14A-14B). Furthermore, significant numbers of patients on alirocumab achieved LDL-C levels of <100 mg/dL (57% vs 11% of placebo patients) and <70 mg/dL (<1.81 mmol/L; 32% vs 3% of placebo patients) at Week 24 despite baseline LDL-C levels of >190 mg/dL (mean (SD) baseline calculated LDL-C 196.3 (57.9) mg/dL for alirocumab group; 201 (43.4) mg/dL for placebo group). At week 12, 31.0% of alirocumab group patients (vs. 0.0% of placebo group; ITT analysis) reached calculated LDL-C levels of <70 mg/dL (<1.81 mmol/L). Similarly, at Week 52, 31.0% of alirocumab group patients (vs 5.7% of placebo group; ITT analysis) reached calculated LDL-C levels of <70 mg/dL (<1.81 mmol/L).

A sensitivity analysis of the primary efficacy endpoint was performed excluding 13 patients from 2 sites with serious GCP non compliance. The decrease in percent change in LDL-C from baseline to Week 24 was still statistically significant in the alirocumab group (LS mean versus baseline −50.3%) compared to the placebo group (LS mean versus baseline −2.3%) (LS mean difference vs. placebo (SE) of −48.0% (5.8%), p<0.0001) (see Table 34).

TABLE 32

Percent change from baseline in calculated LDL-C at Week 24: MMRM - ITT analysis - ITT population

| Calculated LDL Cholesterol | Placebo (N = 35) | Alirocumab 150 Q2W (N = 71) |
|---|---|---|
| Baseline (mmol/L) | | |
| Number | 35 | 71 |
| Mean (SD) | 5.205 (1.125) | 5.083 (1.499) |
| Median | 5.206 | 4.662 |
| Min:Max | 3.55:7.23 | 2.31:10.41 |
| Baseline (mg/dL) | | |
| Number | 35 | 71 |
| Mean (SD) | 201.0 (43.4) | 196.3 (57.9) |
| Median | 201.0 | 180.0 |
| Min:Max | 137:279 | 89:402 |
| Week 24 percent change from baseline (%) | | |
| LS Mean (SE) | −6.6 (4.9) | −45.7 (3.5) |
| LS mean difference (SE) vs placebo | | −39.1 (6.0) |
| 95% CI | | (−51.1 to −27.1) |
| p-value vs placebo | | <0.0001* |

Note:
Least-squares (LS) means, standard errors (SE) and p-value taken from MMRM (mixed-effect model with repeated measures) analysis. The model includes the fixed categorical effects of treatment group, randomization strata as per IVRS, time point, treatment-by-time point and strata-by-time point interaction, as well as the continuous fixed covariates of baseline calculated LDL-C value and baseline calculated LDL-C value-by-time point interaction
MMRM model and baseline description run on patients with a baseline value and a post-baseline value in at least one of the analysis windows used in the model.
The p-value is followed by a '*' if statistically significant according to the fixed hierarchical approach used to ensure a strong control of the overall type-I error rate at the 0.05 level

TABLE 33

Calculated LDL-C over time - ITT analysis - ITT population

| | Placebo (N = 35) | | | Alirocumab 150 Q2W (N = 71) | | |
|---|---|---|---|---|---|---|
| Calculated LDL-C | Value | Change from baseline | Percent change from baseline | Value | Change from baseline | Percent change from baseline |
| LS Mean (SE) (mmol/L) | | | | | | |
| Baseline[a] | 5.205 (0.190) | NA | NA | 5.083 (0.178) | NA | NA |
| Week 4 | 4.537 (0.221) | −0.586 (0.221) | −11.5 (4.1) | 2.522 (0.154) | −2.601 (0.154) | −52.9 (2.8) |
| Week 8 | 4.435 (0.229) | −0.688 (0.229) | −12.4 (4.3) | 2.647 (0.161) | −2.477 (0.161) | −48.6 (3.1) |
| Week 12 | 4.702 (0.234) | −0.422 (0.234) | −6.6 (4.6) | 2.692 (0.164) | −2.432 (0.164) | −46.9 (3.2) |
| Week 16 | 4.779 (0.235) | −0.344 (0.235) | −6.1 (4.8) | 2.633 (0.161) | −2.490 (0.161) | −48.0 (3.3) |
| Week 24 | 4.722 (0.246) | −0.401 (0.246) | −6.6 (4.9) | 2.771 (0.174) | −2.352 (0.174) | −45.7 (3.5) |
| Week 36 | 4.666 (0.251) | −0.457 (0.251) | −8.9 (5.0) | 2.832 (0.176) | −2.292 (0.176) | −44.0 (3.5) |
| Week 52 | 4.862 (0.275) | −0.262 (0.275) | −3.0 (5.9) | 2.921 (0.197) | −2.202 (0.197) | −42.1 (4.2) |

TABLE 33-continued

Calculated LDL-C over time - ITT analysis - ITT population

| Calculated LDL-C | Placebo (N = 35) | | | Alirocumab 150 Q2W (N = 71) | | |
|---|---|---|---|---|---|---|
| | Value | Change from baseline | Percent change from baseline | Value | Change from baseline | Percent change from baseline |
| Week 78 LS Mean (SE) (mg/dL) | | 1.2 (6.4) | | | −37.9 (4.5) | |
| Baseline[a] | 201.0 (7.3) | NA | NA | 196.3 (6.9) | NA | NA |
| Week 4 | 175.2 (8.5) | −22.6 (8.5) | −11.5 (4.1) | 97.4 (5.9) | −100.4 (5.9) | −52.9 (2.8) |
| Week 8 | 171.2 (8.8) | −26.6 (8.8) | −12.4 (4.3) | 102.2 (6.2) | −95.6 (6.2) | −48.6 (3.1) |
| Week 12 | 181.5 (9.0) | −16.3 (9.0) | −6.6 (4.6) | 103.9 (6.3) | −93.9 (6.3) | −46.9 (3.2) |
| Week 16 | 184.5 (9.1) | −13.3 (9.1) | −6.1 (4.8) | 101.7 (6.2) | −96.1 (6.2) | −48.0 (3.3) |
| Week 24 | 182.3 (9.5) | −15.5 (9.5) | −6.6 (4.9) | 107.0 (6.7) | −90.8 (6.7) | −45.7 (3.5) |
| Week 36 | 180.2 (9.7) | −17.7 (9.7) | −8.9 (5.0) | 109.3 (6.8) | −88.5 (6.8) | −44.0 (3.5) |
| Week 52 | 187.7 (10.6) | −10.1 (10.6) | −3.0 (5.9) | 112.8 (7.6) | −85.0 (7.6) | −42.1 (4.2) |

[a]Baseline is described using means and standard errors.

Note:
Least-squares (LS) means, standard errors (SE) and p-value taken from MMRM (mixed-effect model with repeated measures) analysis. The model includes the fixed categorical effects of treatment group, randomization strata as per IVRS, time point, treatment-by-time point interaction, strata-by-time point interaction, as well as the continuous fixed covariates of baseline LDL-C value and baseline LDL-C value-by-time point interaction
MMRM model and baseline description run on patients with a baseline value and a post-baseline value in at least one of the analysis windows used in the model.

Sensitivity Analysis of Primary Endpoint

TABLE 34

Percent change from baseline in calculated LDL-C at Week 24: MMRM - ITT analysis - ITT population excluding sites with serious GCP non compliance

| Calculated LDL Cholesterol | Placebo (N = 31) | Alirocumab 150 Q2W (N = 62) |
|---|---|---|
| Baseline (mmol/L) | | |
| Number | 31 | 62 |
| Mean (SD) | 5.310 (1.146) | 5.101 (1.460) |
| Median | 5.258 | 4.675 |
| Min:Max | 3.55:7.23 | 2.31:10.41 |
| Baseline (mg/dL) | | |
| Number | 31 | 62 |
| Mean (SD) | 205.0 (44.2) | 197.0 (56.4) |
| Median | 203.0 | 180.5 |
| Min:Max | 137:279 | 89:402 |
| Week 24 percent change from baseline (%) | | |
| LS Mean (SE) | −2.3 (4.7) | −50.3 (3.3) |
| LS mean difference (SE) vs placebo | | −48.0 (5.8) |
| 95% CI | | (−59.4 to −36.6) |
| p-value vs placebo | | <0.0001 |

Note:
Least-squares (LS) means, standard errors (SE) and p-value taken from MMRM (mixed-effect model with repeated measures) analysis. The model includes the fixed categorical effects of treatment group, randomization strata as per IVRS, time point, treatment-by-time point and strata-by-time point interaction, as well as the continuous fixed covariates of baseline calculated LDL-C value and baseline calculated LDL-C value-by-time point interaction
MMRM model and baseline description run on patients with a baseline value and a post-baseline value in at least one of the analysis windows used in the model.
The p-value is not adjusted for multiplicity and provided for descriptive purpose only
Note:
Sites No. 643-710 and No. 840-743 were excluded from analysis

Key Secondary Efficacy Endpoints

The following table summarizes analysis results on key secondary endpoints in the hierarchical order. All key secondary endpoints are statistically significant according to the hierarchical testing procedure up to Lp(a) endpoint at Week 24 (ITT estimand) included.

Statistically significance was not reached for HDL-C at Week 24 (ITT estimand) and therefore the testing procedure was stopped, p-values are provided from this endpoint for descriptive purpose only.

TABLE 35

| Endpoint | Analysis | Results | P-value |
|---|---|---|---|
| Calculated LDL-C - Percent change from baseline to Week 24 | On-treatment | LS mean difference vs. placebo of −38.9% | <0.0001 |
| Calculated LDL-C - Percent change from baseline to Week 12 | ITT | LS mean difference vs. placebo of −40.3% | <0.0001 |
| Calculated LDL-C - Percent change from baseline to Week 12 | On-treatment | LS mean difference vs. placebo of −40.3% | <0.0001 |

TABLE 35-continued

| Endpoint | Analysis | Results | P-value |
|---|---|---|---|
| Apo-B - Percent change from baseline to Week 24 | ITT | LS mean difference vs. placebo of −30.3% | <0.0001 |
| Apo-B - Percent change from baseline to Week 24 | On-treatment | LS mean difference vs. placebo of −30.2% | <0.0001 |
| Non-HDL-C - Percent change from baseline to Week 24 | ITT | LS mean difference vs. placebo of −35.8% | <0.0001 |
| Non-HDL-C - Percent change from baseline to Week 24 | On-treatment | LS mean difference vs. placebo of −35.5% | <0.0001 |
| Total-C - Percent change from baseline to Week 24 | ITT | LS mean difference vs. placebo of −28.4% | <0.0001 |
| Apo-B - Percent change from baseline to Week 12 | ITT | LS mean difference vs. placebo of −30.2% | <0.0001 |
| Non-HDL-C - Percent change from baseline to Week 12 | ITT | LS mean difference vs. placebo of −34.5% | <0.0001 |
| Total-C - Percent change from baseline to Week 12 | ITT | LS mean difference vs. placebo of −27.8% | <0.0001 |
| Calculated LDL-C - Percent change from baseline to Week 52 | ITT | LS mean difference vs. placebo of −39.1% | <0.0001 |
| Proportion of very high CV risk patients reaching calculated LDL-C < 70 mg/dL (1.81 mmol/L) or high CV risk patients reaching calculated LDL-C < 100 mg/dL (2.59 mmol/L) at Week 24 | ITT | combined estimate for odds-ratio vs. placebo of 11.7 | 0.0016 |
| Proportion of very high CV risk patients reaching calculated LDL-C < 70 mg/dL (1.81 mmol/L) or high CV risk patients reaching calculated LDL-C < 100 mg/dL (2.59 mmol/L) at Week 24 | On-treatment | combined estimate for odds-ratio vs. placebo of 11.9 | 0.0014 |
| Lp(a) - Percent change from baseline to Week 24 | ITT | combined estimate for adjusted mean difference vs. placebo of −14.8% | 0.0164 |
| HDL-C - Percent change from baseline to Week 24 | ITT | LS mean difference vs. placebo of 3.7% | 0.2745 |
| Fasting TGs - Percent change from baseline to Week 24 | ITT | combined estimate for adjusted mean difference vs. placebo of −8.7% | 0.1386 |

The on-treatment analysis of the LDL-C percent change from baseline to Week 24 shows very consistent results with the ITT analysis (LS mean difference vs. placebo of −38.9% in the on-treatment analysis versus −39.1% in the ITT analysis). Indeed, only 3 patients (2 in placebo and 1 in alirocumab) had LDL-C values collected post-treatment (ie more than 21 days after last injection) at Week 24.

The key secondary endpoints including Apo B, non-HDL-C, Total-C, Lp(a) at various time points as well as the proportion of patients reaching their LDL-C goals at Week 24 were statistically significant according to the hierarchical testing procedure. Significant reductions were seen in non-HDL-C, Apo B, and Lp(a) levels at Week 24. The alirocumab vs placebo LS mean percent change from baseline to week 24 was −41.9 vs −6.2 for non-HDL-C(p value <0.0001), −39.0 vs −8.7 for Apo B (p value <0.0001), and −23.5 vs −8.7 for Lp(a) (p value=0.0164).

The proportion of very high cardiovascular (CV) risk patients reaching calculated LDL-C<70 mg/dL (1.81 mmol/L) or high CV risk patients reaching calculated LDL-C<100 mg/dL (2.59 mmol/L) at Week 24 was significantly higher in the alirocumab than in the placebo group (combined estimate for proportion of 41.0% in the alirocumab group vs 5.7% in the placebo group, p=0.0016).

Analyses performed with on-treatment approach were consistent with these analyses.

The differences in percent change in HDL-C and fasting TGs from baseline to Week 24 in the ITT analysis were non-statistically significant: HDL-C at Week 24: LS mean versus baseline was +7.5% in the alirocumab group and +3.9% in the placebo group (LS mean difference vs. placebo of +3.7%, p=0.2745); and Fasting TGs at Week 24: LS mean versus baseline was −10.5% in the alirocumab group and −1.1% in the placebo group (LS mean difference vs. placebo of −9.4%, p=0.1299).

Four (5.6%) patients experienced two consecutive calculated LDL-C values <25 mg/dL. No particular safety concern has been observed in these patients.

Summary Safety Results:

The proportion of patients who experienced a treatment emergent adverse event (TEAE) was lower in the alirocumab group (61.1%) compared to placebo group (71.4%) in the present study. The proportion of patients who experienced a serious TEAE was similar between treatment groups. A similar proportion of patients experienced TEAEs leading to treatment discontinuation (1 patient (2.9%) and 3 patients (4.2%) in the placebo and alirocumab groups, respectively). These results are consistent with the proportion of patients who have experienced TEAEs in previous alirocumab Phase 2/3 placebo-controlled studies (results from 2476 and 1276 patients in the alirocumab and placebo groups, respectively). Specifically, in this study TEAEs were 75.8% vs 76.4%, treatment-emergent SAEs were 13.7% vs 14.3%, TEAEs leading to death were 0.5% vs 0.9%, and TEAEs leading to discontinuation were 5.3% vs 5.1%, for alirocumab vs. placebo groups, respectively.

The most frequently reported SOC (and PT) in both treatment groups of the present study were: "infections and infestations": 40.3% in the alirocumab group vs 34.3% in the placebo group (with influenza reported in 11.1% vs 2.9% and urinary tract infection in 6.9% vs 0 in alirocumab vs placebo group respectively); "cardiac disorders": 12.5% in the alirocumab group vs no case in the placebo group. Among the events sent to adjudication, events were confirmed for 6 patients presenting: 4 MI, 1 heart failure requiring hospitalization and 5 ischemia driven coronary revascularization procedures; "nervous system disorders": 11.1% in the alirocumab group vs 8.6% in the placebo group (with headache reported in 5.6% vs 0 and dizziness 4.2% vs 0 in alirocumab vs placebo group respectively); and "musculoskeletal and connective tissue disorders": 16.7% in the alirocumab group vs 28.6% in the placebo group. No death was reported during the study in either group.

SAEs were reported by 11.1% patients in the alirocumab group and 11.4% in the placebo group. There is no particular clinical pattern among SAEs preferred terms which were individually reported. The most frequently reported SOC (system organ class) for SAEs is "cardiac disorders".

Seven patients, 6 (8.3%) in the alirocumab group and 1 (2.9%) in the placebo group experienced a treatment-emergent local injection site reaction. These events were of mild intensity except one of moderate intensity. Two patients, one (1.4%) in the alirocumab group and one (2.9%) in the placebo group experienced neurocognitive disorders. Four patients, three (4.2%) in the alirocumab group and one (2.9%) in the placebo group experienced ALT>3×ULN. Two patients out of 71 analysed (2.8%, in comparison to 0 patients in the placebo group) experienced a creatine kinase level >3×ULN. None of the events were serious or led to treatment discontinuation. TEAEs occurring in alirocumab and placebo patient groups were collected until the last patient visit at Week 52 and are categorized in Table 36.

TABLE 36

TEAE safety analysis through week 52.

| | Placebo (N = 35) | Alirocumab 150 Q2W (N = 72) |
|---|---|---|
| % (n) of patientsAll patients on background of maximally tolerated statin ± other LLT | | |
| Nasopharyngitis | 11.4% (4) | 11.1% (8) |
| Influenza | 2.9% (1) | 11.1% (8) |
| Injection-site reaction | 2.9% (1) | 8.3% (6) |
| Urinary tract infection | 0 | 6.9% (5) |
| Diarrhea | 8.6% (3) | 5.6% (4) |
| Sinusitis | 5.7% (2) | 5.6% (4) |
| Bronchitis | 2.9% (1) | 5.6% (4) |
| Headache | 0 | 5.6% (4) |
| Fatigue | 0 | 5.6% (4) |
| Myalgia | 8.6% (3) | 4.2% (3) |
| Nausea | 5.7% (2) | 1.4% (1) |
| Vertigo | 5.7% (2) | 1.4% (1) |
| Dyspepsia | 5.7% (2) | 0 |
| Increased Blood Uric Acid | 5.7% (2) | 0 |
| Rheumatoid arthritis | 5.7% (2) | 0 |

Among the events of interest no particular signal was detected for TEAE related to neurological events, general allergic events and diabetes.

No relevant abnormality for PCSA was observed.

The present invention is not limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Conclusion:

The following conclusions regarding patients with HeFH and high baseline levels of LDL-C despite maximally tolerated statin with or without another LLT can be drawn from the ODYSSEY HIGH FH study: 1) self-administered alirocumab produced significantly greater LDL-C reductions vs. placebo after 24 weeks, with absolute mean decreasing from baseline in LDL-C was −90.8 mg/dL at Week 24 with alirocumab versus −15.5 mg/dL with placebo, and resultant LDL-C levels of 107 mg/dL with alirocumab at Week 24 versus 182 mg/dL with placebo; 2) 32% of alirocumab patients reached LDL-C<70 mg/dL despite baseline LDL-C>190 mg/dL; 3) 57% of alirocumab patients achieved LDL-C<100 mg/dL at Week 24; 4) alirocumab was generally well tolerated and TEAEs occurred in a similar frequency in the alirocumab and placebo arms.

Example 5: Efficacy and Safety of the PCSK9 Monoclonal Antibody Alirocumab Vs Placebo in 1254 Patients with Heterozygous Familial Hypercholesterolemia (HeFH): Analyses Up to 78 Weeks from Four ODYSSEY Trials Background:

Previous studies have shown that only ~20% of heterozygous familial hypercholesterolemia (HeFH) patients treated with lipid-lowering therapies (LLTs) achieved pre-defined LDL-C target levels of ≤2.5 mmol/L [97 mg/dL]. The efficacy and safety of alirocumab vs placebo was studied in 1254 HeFH pts on maximally-tolerated statin±other LLT from four, 18-month, placebo-controlled ODYSSEY trials (FHI, FHII, HIGH FH, LONG TERM). This represents the single largest collection of patients with HeFH studied in a Phase 3 clinical trials program. A description of the LONG TERM study is set forth in Robinson et al., (2015) NEJM 372:16 pg 1489-99, which is incorporated by reference herein in its entirety.

Methods:

Data were pooled by initial alirocumab dose. In FH I/II, patients with LDL-C levels ≥1.81/2.59 mmol/L [70/100 mg/dL], depending on CV risk, received placebo (N=244) or alirocumab 75 mg Q2W (N=488); the alirocumab dose was increased to 150 mg Q2W at week 12 if LDL-C at week 8≥1.81 mmol/L [70 mg/dL] (41.8% of patients). Separately, data was pooled from HIGH FH (LDL-C≥4.14 mmol/L [160 mg/dL]) and the subset of patients with HeFH from LONG TERM (LDL-C≥1.81 mmol/L [70 mg/dL]), where patients received placebo (N=180) or alirocumab 150 mg Q2W (N=342). All doses were 1-mL subcutaneous (SC) injections. Data for change in LDL-C from baseline was pooled through week 52.

Results:

Baseline LDL-C levels and changes from baseline with treatment are shown in Table 37. Compared to placebo, alirocumab reduced LDL-C by 49% and 61% (p<0.0001) at week 12 for the 75 and 150 mg Q2W doses, respectively. At week 24, LDL-C reductions with alirocumab vs placebo were 56% (alirocumab 75 mg Q2W with a possible week 12 dose increase) and 59% (alirocumab 150 mg Q2W), respectively (p<0.0001). For both dose regimens, despite high baseline LDL-C levels, LS mean LDL-C levels of ~2 mmol/L [77 mg/dL] were achieved by week 12 (Table 37), with reductions maintained through Week 52. Additional beneficial effects were observed in other parameters including non-HDL-C and Apo B.

In the individual studies to date, generally similar rates of treatment-emergent adverse events (TEAEs) were observed in alirocumab and placebo-treated patients. Across placebo-controlled studies in the ODYSSEY Program (patients both with and without HeFH), TEAEs (preferred terms) reported in ≥5% of alirocumab or placebo patients include nasopharyngitis (11.3% and 11.1% of alirocumab and placebo-treated patients, respectively), upper respiratory tract infection (URI) (6.1% vs 7.0%), injection site reaction (6.7% vs 4.8%), influenza (5.7% vs 4.6%), headache (4.8% vs 5.2%) and arthralgia (4.0% vs 5.5%).

TABLE 37

Least-squares (LS) mean (SE) calculated LDL-C at week 12 (W12), week 24 (W24) and week 52 (W52) (intent-to-treat analyses)

| | Placebo (N = 244) | | | Alirocumab 75/150 mg Q2W (N = 488) | | | |
| --- | --- | --- | --- | --- | --- | --- | --- |
| Pool of FHI and FHII studies† | Calculated LDL-C, mmol/L | Change from baseline, mmol/L | % change from baseline | Calculated LDL-C, mmol/L | Change from baseline, mmol/L | % change from baseline | % difference versus placebo |
| Baseline, mean (SE) | 3.65 (0.08) | — | — | 3.66 (0.06) | — | — | — |
| W12 | 3.80 (0.06) | 0.14 (0.06) | 5.4 (1.6) | 2.04 (0.04) | −1.62 (0.04) | −43.6 (1.1)* | −49.0 (1.9)* |
| W24 | 3.86 (0.07) | 0.21 (0.07) | 7.1 (1.7) | 1.82 (0.05) | −1.84 (0.05) | −48.8 (1.2)* | −55.8 (2.1)* |
| W52 | 3.90 (0.07) | 0.25 (0.07) | 8.8 (2.0) | 1.85 (0.05) | −1.81 (0.05) | −48.2 (1.5)* | −57.0 (2.5)* |
| Pool of LONG TERM (HeFH patients only) and HIGH FH‡ | Placebo (N = 180) | | | Alirocumab 150 mg Q2W (N = 342) | | | |
| Baseline, mean (SE) | 3.99 (0.11) | — | — | 4.16 (0.09) | — | — | — |
| W12 | 4.03 (0.08) | −0.07 (0.08) | 1.9 (1.7) | 1.75 (0.06) | −2.35 (0.06) | −58.8 (1.3)* | −60.7 (2.1)* |
| W24 | 4.03 (0.08) | −0.07 (0.08) | 2.6 (1.9) | 1.86 (0.06) | −2.24 (0.06) | −56.3 (1.4)* | −58.9 (2.4)* |
| W52 | 4.19 (0.10) | 0.09 (0.10) | 6.2 (2.5) | 1.94 (0.07) | −2.16 (0.07) | −53.4 (1.8)* | −59.6 (3.1)* |

†alirocumab dose 75 mg Q2W, increasing to 150 mg Q2W at W12 if LDL-C at W8 ≥ 1.81 mmol/L;
‡alirocumab dose 150 mg Q2W;
*p < 0.0001 vs placebo Conclusions:

In this large cohort of 1254 pts with HeFH, alirocumab reduced mean LDL-C levels to <2 mmol/L [77 mg/dL] at week 24-52 of treatment, levels hitherto unobtainable with current LLTs.

What is claimed is:

1. A method for treating hypercholesterolemia, the method comprising:
   (a) selecting a patient with heterozygous familial hypercholesterolemia (heFH) not adequately controlled by a maximally tolerated statin therapy; and
   (b) administering to the patient one or more doses of a therapeutically effective amount of an antibody or antigen-binding fragment thereof that specifically binds human proprotein convertase subtilisin/kexin type 9 (PCSK9), wherein the antibody or antigen-binding fragment thereof comprises heavy and light chain CDR amino acid sequences having SEQ ID NOs:2, 3, 4, 7, 8 and 10, thereby treating hypercholesterolemia in the patient.

2. The method of claim 1, wherein the patient has a low-density lipoprotein cholesterol (LDL-C) level higher than or equal to 160 mg/dL.

3. The method of claim 1, wherein the diagnosis of heFH is made either by genotyping or clinical criteria.

4. The method of claim 3, wherein the clinical criteria is either the Simon Broome Register Diagnostic Criteria for Heterozygous Familial Hypercholesterolemia, or the WHO/Dutch Lipid Network criteria with a score >8.

5. The method of claim 1, wherein the patient has type 2 diabetes mellitus.

6. The method of claim 1, wherein the antibody or antigen-binding fragment thereof comprises the heavy chain variable region (HCVR) amino acid sequence set forth in SEQ ID NO:1 and the light chain variable region (LCVR) amino acid sequence set forth in SEQ ID NO:6.

7. The method of claim 1, wherein the antibody or antigen-binding fragment thereof that specifically binds PCSK9 is administered to the patient at a dose of about 75 mg at a frequency of once every two weeks.

8. The method of claim 1, wherein administering one or more doses of the antibody or antigen-binding fragment thereof to the patient comprises:
   (i) administering to the patient two or more initial doses of 75 mg of the antibody or antigen-binding fragment thereof about every two weeks; and
   (ii) administering to the subject one or more further doses of 75 mg of the antibody or antigen-binding fragment thereof about every two weeks if the LDL-C level in the patient after step (i) is lower than a threshold level, or administering to the subject one or more doses of 150 mg of the antibody or antigen-binding fragment thereof about every two weeks if the LDL-C level in the patient after step (i) is greater than or equal to the threshold level.

9. The method of claim 8, wherein the threshold level is 70 mg/dL.

10. The method of claim 1, wherein the antibody or antigen-binding fragment thereof that specifically binds PCSK9 is administered to the patient at a dose of about 150 mg at a frequency of once every two weeks.

11. The method of claim 1, wherein the antibody or antigen-binding fragment thereof is administered to the patient in combination with the maximally tolerated statin therapy.

12. The method of claim 11, wherein the antibody or antigen-binding fragment thereof is administered to the patient in further combination with at least one other lipid lowering therapy.

13. The method of claim 1, wherein the maximally tolerated statin therapy comprises a daily dose of about 40 mg to about 80 mg of atorvastatin.

14. The method of claim 1, wherein the maximally tolerated statin therapy comprises a daily dose of about 20 mg to about 40 mg of rosuvastatin.

15. The method of claim 1, wherein the maximally tolerated statin therapy comprises a daily dose of about 80 mg of simvastatin.

16. The method of claim 1, wherein the method improves at least one hypercholesterolemia-associated parameter selected from the group consisting of:
   (a) reduction of the patient's low density lipoprotein cholesterol (LDL-C) by at least 40%;
   (b) reduction of the patient's apolipoprotein B (ApoB) by at least 30%;
   (c) reduction of the patient's non-high density lipoprotein cholesterol (non-HDL-C) by at least 35%;
   (d) reduction of the patient's total cholesterol by at least 20%;
   (e) increase of the patient's high density lipoprotein cholesterol (HDL-C) by at least 3%;
   (f) reduction of the patient's triglycerides by at least 5%;
   (g) reduction of the patient's lipoprotein a (Lp(a)) by at least 10%; and
   (h) increase of the patient's apolipoprotein A-1 by at least 1%.

* * * * *

SEQUENCE LISTING

<160> NUMBER OF SEQ ID NOS: 198

<210> SEQ ID NO 1
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Asn Tyr

```
            20                  25                  30
Ala Met Asn Trp Val Arg Gln Ala Pro Gly Lys Gly Leu Asp Trp Val
            35                  40                  45

Ser Thr Ile Ser Gly Ser Gly Gly Thr Thr Asn Tyr Ala Asp Ser Val
        50                  55                  60

Lys Gly Arg Phe Ile Ile Ser Arg Asp Ser Lys His Thr Leu Tyr
 65                  70                  75                  80

Leu Gln Met Asn Ser Leu Arg Ala Glu Asp Thr Ala Val Tyr Tyr Cys
                 85                  90                  95

Ala Lys Asp Ser Asn Trp Gly Asn Phe Asp Leu Trp Gly Arg Gly Thr
            100                 105                 110

Leu Val Thr Val Ser Ser
        115

<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Phe Thr Phe Asn Asn Tyr Ala
1               5

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ile Ser Gly Ser Gly Gly Thr Thr
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Ala Lys Asp Ser Asn Trp Gly Asn Phe Asp Leu
1               5                   10

<210> SEQ ID NO 5
<211> LENGTH: 447
<212> TYPE: PRT
<213> ORGANISM: Artificial Sequence
<220> FEATURE:
<223> OTHER INFORMATION: Description of Artificial Sequence: Synthetic
      REGN727 heavy chain polypeptide

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ser Gly Phe Thr Phe Asn Asn Tyr
            20                  25                  30
```

```
Ala Met Asn Trp Val Arg Gln Ala Pro Gly Lys Gly Leu Asp Trp Val
         35                  40                  45
Ser Thr Ile Ser Gly Ser Gly Gly Thr Thr Asn Tyr Ala Asp Ser Val
 50                  55                  60
Lys Gly Arg Phe Ile Ile Ser Arg Asp Ser Ser Lys His Thr Leu Tyr
 65                  70                  75                  80
Leu Gln Met Asn Ser Leu Arg Ala Glu Asp Thr Ala Val Tyr Tyr Cys
                 85                  90                  95
Ala Lys Asp Ser Asn Trp Gly Asn Phe Asp Leu Trp Gly Arg Gly Thr
            100                 105                 110
Leu Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
    210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly
        435                 440                 445
```

```
<210> SEQ ID NO 6
<211> LENGTH: 113
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 6

Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Leu Tyr Arg
            20                  25                  30
Ser Asn Asn Arg Asn Phe Leu Gly Trp Tyr Gln Gln Lys Pro Gly Gln
        35                  40                  45
Pro Pro Asn Leu Leu Ile Tyr Trp Ala Ser Thr Arg Glu Ser Gly Val
    50                  55                  60
Pro Asp Arg Phe Ser Gly Ser Gly Ser Gly Thr Asp Phe Thr Leu Thr
65                  70                  75                  80
Ile Ser Ser Leu Gln Ala Glu Asp Val Ala Val Tyr Tyr Cys Gln Gln
                85                  90                  95
Tyr Tyr Thr Thr Pro Tyr Thr Phe Gly Gln Gly Thr Lys Leu Glu Ile
            100                 105                 110
Lys

<210> SEQ ID NO 7
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gln Ser Val Leu Tyr Arg Ser Asn Asn Arg Asn Phe
1               5                   10

<210> SEQ ID NO 8
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Trp Ala Ser
1

<210> SEQ ID NO 9
<211> LENGTH: 220
<212> TYPE: PRT
<213> ORGANISM: Artificial Sequence
<220> FEATURE:
<223> OTHER INFORMATION: Description of Artificial Sequence: Synthetic
      REGN727 light chain polypeptide

<400> SEQUENCE: 9

Asp Ile Val Met Thr Gln Ser Pro Asp Ser Leu Ala Val Ser Leu Gly
1               5                   10                  15
Glu Arg Ala Thr Ile Asn Cys Lys Ser Ser Gln Ser Val Leu Tyr Arg
            20                  25                  30
Ser Asn Asn Arg Asn Phe Leu Gly Trp Tyr Gln Gln Lys Pro Gly Gln
```

```
                35                  40                  45
Pro Pro Asn Leu Leu Ile Tyr Trp Ala Ser Thr Arg Glu Ser Gly Val
 50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Tyr Tyr Thr Thr Pro Tyr Thr Phe Gly Gln Gly Thr Lys Leu Glu Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
                180                 185                 190

Glu Lys His Lys Val Tyr Ala Cys Glu Val Thr His Gln Gly Leu Ser
                195                 200                 205

Ser Pro Val Thr Lys Ser Phe Asn Arg Gly Glu Cys
                210                 215                 220

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Gln Gln Tyr Tyr Thr Thr Pro Tyr Thr
1               5

<210> SEQ ID NO 11
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Glu Met Gln Leu Val Glu Ser Gly Gly Gly Leu Val Gln Pro Gly Gly
1               5                  10                  15

Ser Leu Arg Leu Ser Cys Ala Ala Ser Gly Phe Thr Phe Ser Ser His
                 20                  25                  30

Trp Met Lys Trp Val Arg Gln Ala Pro Gly Lys Gly Leu Glu Trp Val
                 35                  40                  45

Ala Asn Ile Asn Gln Asp Gly Ser Glu Lys Tyr Tyr Val Asp Ser Val
 50                  55                  60

Lys Gly Arg Phe Thr Ile Ser Arg Asp Asn Lys Asn Ser Leu Phe
 65                  70                  75                  80

Leu Gln Met Asn Ser Leu Arg Ala Glu Asp Thr Ala Val Tyr Tyr Cys
                 85                  90                  95

Ala Arg Asp Ile Val Leu Met Val Tyr Asp Met Asp Tyr Tyr Tyr Tyr
```

```
                    100                 105                 110
Gly Met Asp Val Trp Gly Gln Gly Thr Thr Val Thr Val Ser Ser
            115                 120                 125

<210> SEQ ID NO 12
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Gly Phe Thr Phe Ser Ser His Trp
1               5

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Ile Asn Gln Asp Gly Ser Glu Lys
1               5

<210> SEQ ID NO 14
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ala Arg Asp Ile Val Leu Met Val Tyr Asp Met Asp Tyr Tyr Tyr
1               5                   10                  15

Gly Met Asp Val
            20

<210> SEQ ID NO 15
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asp Trp Tyr Leu Gln Lys Pro Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Met Gln Thr
                85                  90                  95
```

```
Leu Gln Thr Pro Leu Thr Phe Gly Gly Gly Thr Lys Val Glu Ile Lys
            100                 105                 110
```

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Gln Ser Leu Leu His Ser Asn Gly Asn Asn Tyr
1               5                   10
```

<210> SEQ ID NO 17
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Leu Gly Ser
1
```

<210> SEQ ID NO 18
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

```
Met Gln Thr Leu Gln Thr Pro Leu Thr
1               5
```

<210> SEQ ID NO 19
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

```
Gly Phe Thr Phe Ser Ser His Trp
1               5
```

<210> SEQ ID NO 20
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

```
Ile Asn Gln Asp Gly Ser Glu Lys
1               5
```

<210> SEQ ID NO 21
<211> LENGTH: 20
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 21

Ala Arg Asp Ile Val Leu Met Val Tyr Asp Met Asp Tyr Tyr Tyr
1               5                   10                  15
Gly Met Asp Val
            20

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gln Ser Leu His His Ser Asn Gly Asn Asn Tyr
1               5                   10

<210> SEQ ID NO 23
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 23

Leu Gly Ser
1

<210> SEQ ID NO 24
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Met Gln Thr Leu Gln Thr Pro Leu Thr
1               5

<210> SEQ ID NO 25
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Phe Thr Phe Ser Ser His Trp
1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ile Asn Gln Asp Gly Ser Glu Lys

```
<210> SEQ ID NO 27
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Ala Arg Asp Ile Val Leu Met Val Tyr His Met Asp Tyr Tyr Tyr Tyr
1               5                   10                  15

Gly Met Asp Val
            20

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Ser Leu Leu His Ser Asn Gly Asn Asn Tyr
1               5                   10

<210> SEQ ID NO 29
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Leu Gly Ser
1

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Met Gln Thr Leu Gln Thr Pro Leu Thr
1               5

<210> SEQ ID NO 31
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Phe Thr Phe Ser Ser His Trp
1               5

<210> SEQ ID NO 32
<211> LENGTH: 8
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 32

Ile Asn Gln Asp Gly Ser Glu Lys
1               5

<210> SEQ ID NO 33
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Ala Arg Asp Ile Val Leu Met Val Tyr His Met Asp Tyr Tyr Tyr Tyr
1               5                   10                  15

Gly Met Asp Val
            20

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Gln Ser Leu His His Ser Asn Gly Asn Asn Tyr
1               5                   10

<210> SEQ ID NO 35
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Leu Gly Ser
1

<210> SEQ ID NO 36
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Met Gln Thr Leu Gln Thr Pro Leu Thr
1               5

<210> SEQ ID NO 37
<211> LENGTH: 131
<212> TYPE: PRT
<213> ORGANISM: Artificial Sequence
<220> FEATURE:
<223> OTHER INFORMATION: Description of Artificial Sequence: Synthetic
      VH; m2CX1D05 polypeptide

<400> SEQUENCE: 37
```

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Asn Ser His
                20                  25                  30

Ala Ile Ser Trp Val Arg Gln Ala Pro Gly Gln Gly Leu Glu Trp Met
            35                  40                  45

Gly Gly Ile Asn Pro Ile Leu Gly Ile Ala Asn Tyr Ala Gln Lys Phe
        50                  55                  60

Gln Gly Arg Val Thr Ile Thr Ala Asp Glu Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg His Tyr Glu Ile Gln Ile Gly Arg Tyr Gly Met Asn Val Tyr
                100                 105                 110

Tyr Leu Met Tyr Arg Phe Ala Ser Trp Gly Gln Gly Thr Leu Val Thr
            115                 120                 125

Val Ser Ser
    130

<210> SEQ ID NO 38
<211> LENGTH: 10
<212> TYPE: PRT
<213> ORGANISM: Artificial Sequence
<220> FEATURE:
<223> OTHER INFORMATION: Description of Artificial Sequence: Synthetic
      VH CDR1; m2CX1D05 peptide

<400> SEQUENCE: 38

Gly Gly Thr Phe Asn Ser His Ala Ile Ser
1               5                   10

<210> SEQ ID NO 39
<211> LENGTH: 20
<212> TYPE: PRT
<213> ORGANISM: Artificial Sequence
<220> FEATURE:
<223> OTHER INFORMATION: Description of Artificial Sequence: Synthetic
      VH CDR2; m2CX1D05 peptide

<400> SEQUENCE: 39

Trp Met Gly Gly Ile Asn Pro Ile Leu Gly Ile Ala Asn Tyr Ala Gln
1               5                   10                  15

Lys Phe Gln Gly
            20

<210> SEQ ID NO 40
<211> LENGTH: 22
<212> TYPE: PRT
<213> ORGANISM: Artificial Sequence
<220> FEATURE:
<223> OTHER INFORMATION: Description of Artificial Sequence: Synthetic
      VH CDR3; m2CX1D05 peptide

<400> SEQUENCE: 40

His Tyr Glu Ile Gln Ile Gly Arg Tyr Gly Met Asn Val Tyr Tyr Leu
1               5                   10                  15

Met Tyr Arg Phe Ala Ser
            20

<210> SEQ ID NO 41
<211> LENGTH: 213
```

```
<212> TYPE: PRT
<213> ORGANISM: Artificial Sequence
<220> FEATURE:
<223> OTHER INFORMATION: Description of Artificial Sequence: Synthetic
      LC; m2CX1D05 polypeptide

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Ser Ala
            20                  25                  30

Leu Asn Trp Tyr Gln Gln Lys Pro Gly Lys Ala Pro Lys Leu Leu Ile
        35                  40                  45

Tyr Asn Gly Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Val Tyr Tyr Cys Gln Gln Phe Asp Gly Asp Pro Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Ala
    210

<210> SEQ ID NO 42
<211> LENGTH: 11
<212> TYPE: PRT
<213> ORGANISM: Artificial Sequence
<220> FEATURE:
<223> OTHER INFORMATION: Description of Artificial Sequence: Synthetic
      VL CDR 1; m2CX1D05 peptide

<400> SEQUENCE: 42

Arg Ala Ser Gln Gly Ile Arg Ser Ala Leu Asn
1               5                   10

<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      VL CDR2; m2CX1D05 peptide

<400> SEQUENCE: 43

Leu Leu Ile Tyr Asn Gly Ser Thr Leu Gln Ser
1               5                   10
```

```
<210> SEQ ID NO 44
<211> LENGTH: 7
<212> TYPE: PRT
<213> ORGANISM: Artificial Sequence
<220> FEATURE:
<223> OTHER INFORMATION: Description of Artificial Sequence: Synthetic
      VL CDR3; m2CX1D05 peptide

<400> SEQUENCE: 44

Gln Gln Phe Asp Gly Asp Pro
1               5

<210> SEQ ID NO 45
<211> LENGTH: 119
<212> TYPE: PRT
<213> ORGANISM: Artificial Sequence
<220> FEATURE:
<223> OTHER INFORMATION: Description of Artificial Sequence: Synthetic
      VH; 1B20 polypeptide

<400> SEQUENCE: 45

Gln Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Asn Tyr
            20                  25                  30

Trp Ile Ser Trp Val Arg Gln Met Pro Gly Lys Gly Leu Glu Trp Met
        35                  40                  45

Gly Ile Ile Tyr Pro Gly Asp Ser Tyr Thr Asn Tyr Ser Pro Ser Phe
    50                  55                  60

Gln Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Asp Tyr Trp Tyr Lys Pro Leu Phe Asp Ile Trp Gly Gln Gly
            100                 105                 110

Thr Leu Val Thr Val Ser Ser
        115

<210> SEQ ID NO 46
<211> LENGTH: 10
<212> TYPE: PRT
<213> ORGANISM: Artificial Sequence
<220> FEATURE:
<223> OTHER INFORMATION: Description of Artificial Sequence: Synthetic
      VH CDR1; 1B20 peptide

<400> SEQUENCE: 46

Gly Tyr Ser Phe Thr Asn Tyr Trp Ile Ser
1               5                   10

<210> SEQ ID NO 47
<211> LENGTH: 20
<212> TYPE: PRT
<213> ORGANISM: Artificial Sequence
<220> FEATURE:
<223> OTHER INFORMATION: Description of Artificial Sequence: Synthetic
      VH CDR2; 1B20 peptide

<400> SEQUENCE: 47

Trp Met Gly Ile Ile Tyr Pro Gly Asp Ser Tyr Thr Asn Tyr Ser Pro
1               5                   10                  15

Ser Phe Gln Gly
            20
```

```
<210> SEQ ID NO 48
<211> LENGTH: 10
<212> TYPE: PRT
<213> ORGANISM: Artificial Sequence
<220> FEATURE:
<223> OTHER INFORMATION: Description of Artificial Sequence: Synthetic
      VH CDR3; 1B20 peptide

<400> SEQUENCE: 48

Asp Tyr Trp Tyr Lys Pro Leu Phe Asp Ile
1               5                   10

<210> SEQ ID NO 49
<211> LENGTH: 220
<212> TYPE: PRT
<213> ORGANISM: Artificial Sequence
<220> FEATURE:
<223> OTHER INFORMATION: Description of Artificial Sequence: Synthetic
      LC; 1B20 polypeptide

<400> SEQUENCE: 49

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
            20                  25                  30

Ser Asn Asn Lys Asn Tyr Leu Ala Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Ser Ser Phe Pro Ile Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Ala
    210                 215                 220

<210> SEQ ID NO 50
<211> LENGTH: 17
<212> TYPE: PRT
<213> ORGANISM: Artificial Sequence
<220> FEATURE:
<223> OTHER INFORMATION: Description of Artificial Sequence: Synthetic
      VL CDR1; 1B20 peptide

<400> SEQUENCE: 50

Arg Ser Ser Gln Ser Val Leu Tyr Ser Ser Asn Asn Lys Asn Tyr Leu
```

Ala

<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      VL CDR2; 1B20 peptide

<400> SEQUENCE: 51

Leu Leu Ile Tyr Trp Ala Ser Thr Arg Glu Ser
1               5                   10

<210> SEQ ID NO 52
<211> LENGTH: 8
<212> TYPE: PRT
<213> ORGANISM: Artificial Sequence
<220> FEATURE:
<223> OTHER INFORMATION: Description of Artificial Sequence: Synthetic
      VL CDR3; 1B20 peptide

<400> SEQUENCE: 52

Gln Gln Tyr Ser Ser Phe Pro Ile
1               5

<210> SEQ ID NO 53
<211> LENGTH: 120
<212> TYPE: PRT
<213> ORGANISM: Artificial Sequence
<220> FEATURE:
<223> OTHER INFORMATION: Description of Artificial Sequence: Synthetic
      variable heavy antibody region polypeptide

<400> SEQUENCE: 53

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Gly Met Tyr Trp Val Arg Gln Ala Pro Gly Lys Gly Leu Glu Trp Ile
        35                  40                  45

Gly Trp Ile Asp Pro Gly Ser Gly Thr Lys Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Tyr Gly Tyr Tyr Phe Asp Tyr Trp Gly Gln Gly Thr
            100                 105                 110

Leu Val Thr Val Ser Ser Ala Ser
        115                 120

<210> SEQ ID NO 54
<211> LENGTH: 16
<212> TYPE: PRT
<213> ORGANISM: Artificial Sequence
<220> FEATURE:
<223> OTHER INFORMATION: Description of Artificial Sequence: Synthetic
      AX132 heavy chain CDR1 antibody region peptide

<400> SEQUENCE: 54

Lys Ala Ser Gly Tyr Thr Phe Ser Ser Tyr Gly Met Tyr Trp Val Arg

<210> SEQ ID NO 55
<211> LENGTH: 23
<212> TYPE: PRT
<213> ORGANISM: Artificial Sequence
<220> FEATURE:
<223> OTHER INFORMATION: Description of Artificial Sequence: Synthetic
      AX132 heavy chain CDR2 antibody region peptide

<400> SEQUENCE: 55

Trp Ile Gly Trp Ile Asp Pro Gly Ser Gly Gly Thr Lys Tyr Asn Glu
1               5                   10                  15

Lys Phe Lys Gly Lys Ala Thr
            20

<210> SEQ ID NO 56
<211> LENGTH: 15
<212> TYPE: PRT
<213> ORGANISM: Artificial Sequence
<220> FEATURE:
<223> OTHER INFORMATION: Description of Artificial Sequence: Synthetic
      AX132 heavy chain CDR3 antibody region peptide

<400> SEQUENCE: 56

Cys Ala Arg Glu Arg Tyr Gly Tyr Tyr Phe Asp Tyr Trp Gly Gln
1               5                   10                  15

<210> SEQ ID NO 57
<211> LENGTH: 108
<212> TYPE: PRT
<213> ORGANISM: Artificial Sequence
<220> FEATURE:
<223> OTHER INFORMATION: Description of Artificial Sequence: Synthetic
      variable light antibody region polypeptide

<400> SEQUENCE: 57

Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Tyr Val Gly Ser Tyr
            20                  25                  30

Leu Asn Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Asp Ser Ser Pro Pro
                85                  90                  95

Val Val Phe Gly Gly Gly Thr Lys Val Glu Ile Lys
            100                 105

<210> SEQ ID NO 58
<211> LENGTH: 17
<212> TYPE: PRT
<213> ORGANISM: Artificial Sequence
<220> FEATURE:
<223> OTHER INFORMATION: Description of Artificial Sequence: Synthetic
      AX213 and AX132 light chain CDR1 antibody region peptide

<400> SEQUENCE: 58

Ile Thr Cys Arg Ala Ser Gln Tyr Val Gly Ser Tyr Leu Asn Trp Tyr
1               5                   10                  15

Gln

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequence: Synthetic
      AX213 and AX132 light chain CDR2 antibody region peptide

<400> SEQUENCE: 59

Leu Ile Tyr Asp Ala Ser Asn Arg Ala Thr Gly Ile Pro
1               5                   10

<210> SEQ ID NO 60
<211> LENGTH: 16
<212> TYPE: PRT
<213> ORGANISM: Artificial Sequence
<220> FEATURE:
<223> OTHER INFORMATION: Description of Artificial Sequence: Synthetic
      AX132 & AX213 light chain CDR3 antibody region peptide

<400> SEQUENCE: 60

Tyr Tyr Cys Gln Val Trp Asp Ser Ser Pro Val Val Phe Gly Gly
1               5                   10                  15

<210> SEQ ID NO 61
<211> LENGTH: 120
<212> TYPE: PRT
<213> ORGANISM: Artificial Sequence
<220> FEATURE:
<223> OTHER INFORMATION: Description of Artificial Sequence: Synthetic
      variable heavy antibody region polypeptide

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Arg Tyr
            20                  25                  30

Gly Ile Asn Trp Val Arg Gln Ala Pro Gly Lys Gly Leu Glu Trp Ile
        35                  40                  45

Gly Arg Ile Asp Pro Gly Asn Gly Gly Thr Arg Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Asn Asp Gly Tyr Ser Phe Asp Tyr Trp Gly Gln Gly Thr
            100                 105                 110

Leu Val Thr Val Ser Ser Ala Ser
        115                 120

<210> SEQ ID NO 62
<211> LENGTH: 16
<212> TYPE: PRT
<213> ORGANISM: Artificial Sequence
<220> FEATURE:
<223> OTHER INFORMATION: Description of Artificial Sequence: Synthetic
      AX213 heavy chain CDR1 antibody region peptide

<400> SEQUENCE: 62

Lys Ala Ser Gly Tyr Thr Phe Ser Arg Tyr Gly Ile Asn Trp Val Arg
1               5                   10                  15

<210> SEQ ID NO 63
<211> LENGTH: 23
<212> TYPE: PRT
<213> ORGANISM: Artificial Sequence
<220> FEATURE:
<223> OTHER INFORMATION: Description of Artificial Sequence: Synthetic
      AX213 heavy chain CDR2 antibody region peptide

<400> SEQUENCE: 63

Trp Ile Gly Arg Ile Asp Pro Gly Asn Gly Gly Thr Arg Tyr Asn Glu
1               5                   10                  15

Lys Phe Lys Gly Lys Ala Thr
            20

<210> SEQ ID NO 64
<211> LENGTH: 15
<212> TYPE: PRT
<213> ORGANISM: Artificial Sequence
<220> FEATURE:
<223> OTHER INFORMATION: Description of Artificial Sequence: Synthetic
      AX213 heavy chain CDR3 antibody region peptide

<400> SEQUENCE: 64

Cys Ala Arg Ala Asn Asp Gly Tyr Ser Phe Asp Tyr Trp Gly Gln
1               5                   10                  15

<210> SEQ ID NO 65
<211> LENGTH: 108
<212> TYPE: PRT
<213> ORGANISM: Artificial Sequence
<220> FEATURE:
<223> OTHER INFORMATION: Description of Artificial Sequence: Synthetic
      variable light antibody region polypeptide

<400> SEQUENCE: 65

Glu Ile Val Leu Thr Gln Ser Pro Ala Thr Leu Ser Leu Ser Pro Gly
1               5                   10                  15

Glu Arg Ala Thr Ile Thr Cys Arg Ala Ser Gln Tyr Val Gly Ser Tyr
            20                  25                  30

Leu Asn Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Val Trp Asp Ser Ser Pro Pro
                85                  90                  95

Val Val Phe Gly Gly Gly Thr Lys Val Glu Ile Lys
            100                 105

<210> SEQ ID NO 66
<211> LENGTH: 17
<212> TYPE: PRT
<213> ORGANISM: Artificial Sequence
<220> FEATURE:
<223> OTHER INFORMATION: Description of Artificial Sequence: Synthetic
      AX213 and AX132 light chain CDR1 antibody region peptide

<400> SEQUENCE: 66

Ile Thr Cys Arg Ala Ser Gln Tyr Val Gly Ser Tyr Leu Asn Trp Tyr
1               5                   10                  15

Gln

<210> SEQ ID NO 67
<211> LENGTH: 13
<212> TYPE: PRT
<213> ORGANISM: Artificial Sequence
<220> FEATURE:
<223> OTHER INFORMATION: Description of Artificial Sequence: Synthetic
    AX213 and AX132 light chain CDR2 antibody region peptide

<400> SEQUENCE: 67

Leu Ile Tyr Asp Ala Ser Asn Arg Ala Thr Gly Ile Pro
1               5                   10

<210> SEQ ID NO 68
<211> LENGTH: 16
<212> TYPE: PRT
<213> ORGANISM: Artificial Sequence
<220> FEATURE:
<223> OTHER INFORMATION: Description of Artificial Sequence: Synthetic
    AX132 & AX213 light chain CDR3 antibody region peptide

<400> SEQUENCE: 68

Tyr Tyr Cys Gln Val Trp Asp Ser Ser Pro Pro Val Val Phe Gly Gly
1               5                   10                  15

<210> SEQ ID NO 69
<211> LENGTH: 119
<212> TYPE: PRT
<213> ORGANISM: Artificial Sequence
<220> FEATURE:
<223> OTHER INFORMATION: Description of Artificial Sequence: Synthetic
    AX1 VH antibody sequence polypeptide

<400> SEQUENCE: 69

Glu Val Gln Leu Leu Glu Ser Gly Gly Gly Leu Val Gln Pro Gly Gly
1               5                   10                  15

Ser Leu Arg Leu Ser Cys Lys Ala Ser Gly Phe Thr Phe Thr Ser Tyr
            20                  25                  30

Tyr Met His Trp Val Arg Gln Ala Pro Gly Lys Gly Leu Glu Trp Ile
        35                  40                  45

Gly Arg Ile Asn Pro Asp Ser Gly Ser Thr Lys Tyr Asn Glu Lys Phe
    50                  55                  60

Lys Gly Arg Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Arg Leu Ser Trp Asp Phe Asp Val Trp Gly Gln Gly
            100                 105                 110

Thr Leu Val Thr Val Ser Ser
        115

<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence: Synthetic
    AX1 VH CDR1 antibody sequence peptide

<400> SEQUENCE: 70

Lys Ala Ser Gly Phe Thr Phe Thr Ser Tyr Tyr Met His Trp Val Arg
1               5                   10                  15

<210> SEQ ID NO 71

-continued

```
<211> LENGTH: 23
<212> TYPE: PRT
<213> ORGANISM: Artificial Sequence
<220> FEATURE:
<223> OTHER INFORMATION: Description of Artificial Sequence: Synthetic
      AX1 VH CDR2 antibody sequence peptide

<400> SEQUENCE: 71

Trp Ile Gly Arg Ile Asn Pro Asp Ser Gly Ser Thr Lys Tyr Asn Glu
1               5                   10                  15

Lys Phe Lys Gly Arg Ala Thr
            20

<210> SEQ ID NO 72
<211> LENGTH: 16
<212> TYPE: PRT
<213> ORGANISM: Artificial Sequence
<220> FEATURE:
<223> OTHER INFORMATION: Description of Artificial Sequence: Synthetic
      AX1 VH CDR3 antibody sequence peptide

<400> SEQUENCE: 72

Cys Ala Arg Gly Gly Arg Leu Ser Trp Asp Phe Asp Val Trp Gly Gln
1               5                   10                  15

<210> SEQ ID NO 73
<211> LENGTH: 109
<212> TYPE: PRT
<213> ORGANISM: Artificial Sequence
<220> FEATURE:
<223> OTHER INFORMATION: Description of Artificial Sequence: Synthetic
      AX1 VL antibody sequence polypeptide

<400> SEQUENCE: 73

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Arg Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Ala Ala Tyr Asp Tyr Ser Leu Gly
                85                  90                  95

Gly Tyr Val Phe Gly Asp Gly Thr Lys Val Glu Ile Lys
            100                 105

<210> SEQ ID NO 74
<211> LENGTH: 11
<212> TYPE: PRT
<213> ORGANISM: Artificial Sequence
<220> FEATURE:
<223> OTHER INFORMATION: Description of Artificial Sequence: Synthetic
      AX1 VL CDR1 antibody sequence peptide

<400> SEQUENCE: 74

Arg Ala Ser Gln Asp Ile Ser Arg Tyr Leu Ala
1               5                   10

<210> SEQ ID NO 75
<211> LENGTH: 7
<212> TYPE: PRT
```

```
<213> ORGANISM: Artificial Sequence
<220> FEATURE:
<223> OTHER INFORMATION: Description of Artificial Sequence: Synthetic
      AX1 AX9 AX189 VL CDR2 antibody sequence peptide

<400> SEQUENCE: 75

Ala Ala Ser Ser Leu Gln Ser
1               5

<210> SEQ ID NO 76
<211> LENGTH: 11
<212> TYPE: PRT
<213> ORGANISM: Artificial Sequence
<220> FEATURE:
<223> OTHER INFORMATION: Description of Artificial Sequence: Synthetic
      AX1 VL CDR3 antibody sequence peptide

<400> SEQUENCE: 76

Ala Ala Tyr Asp Tyr Ser Leu Gly Gly Tyr Val
1               5                   10

<210> SEQ ID NO 77
<211> LENGTH: 121
<212> TYPE: PRT
<213> ORGANISM: Artificial Sequence
<220> FEATURE:
<223> OTHER INFORMATION: Description of Artificial Sequence: Synthetic
      AX9 AX189 VH antibody sequence polypeptide

<400> SEQUENCE: 77

Glu Val Gln Leu Leu Glu Ser Gly Gly Gly Leu Val Gln Pro Gly Gly
1               5                   10                  15

Ser Leu Arg Leu Ser Cys Lys Ala Ser Gly Tyr Thr Phe Ser Ser Tyr
            20                  25                  30

Trp Met His Trp Val Arg Gln Ala Pro Gly Lys Gly Leu Glu Trp Ile
        35                  40                  45

Gly Arg Ile Asp Pro Tyr Asn Gly Gly Thr Lys Tyr Asn Glu Lys Phe
    50                  55                  60

Lys Gly Lys Ala Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Gly Tyr Tyr Leu Ser Tyr Ala Met Asp Tyr Trp Gly
            100                 105                 110

Gln Gly Thr Leu Val Thr Val Ser Ser
        115                 120

<210> SEQ ID NO 78
<211> LENGTH: 16
<212> TYPE: PRT
<213> ORGANISM: Artificial Sequence
<220> FEATURE:
<223> OTHER INFORMATION: Description of Artificial Sequence: Synthetic
      AX9 AX189 VH CDR1 antibody sequence peptide

<400> SEQUENCE: 78

Lys Ala Ser Gly Tyr Thr Phe Ser Ser Tyr Trp Met His Trp Val Arg
1               5                   10                  15

<210> SEQ ID NO 79
<211> LENGTH: 23
<212> TYPE: PRT
<213> ORGANISM: Artificial Sequence
<220> FEATURE:
```

<223> OTHER INFORMATION: Description of Artificial Sequence: Synthetic
AX9 AX189 VH CDR2 antibody sequence peptide

<400> SEQUENCE: 79

Trp Ile Gly Arg Ile Asp Pro Tyr Asn Gly Gly Thr Lys Tyr Asn Glu
1               5                   10                  15

Lys Phe Lys Gly Lys Ala Thr
            20

<210> SEQ ID NO 80
<211> LENGTH: 18
<212> TYPE: PRT
<213> ORGANISM: Artificial Sequence
<220> FEATURE:
<223> OTHER INFORMATION: Description of Artificial Sequence: Synthetic
AX9 AX189 VH CDR3 antibody sequence peptide

<400> SEQUENCE: 80

Cys Ala Arg Tyr Gly Tyr Tyr Leu Gly Ser Tyr Ala Met Asp Tyr Trp
1               5                   10                  15

Gly Gln

<210> SEQ ID NO 81
<211> LENGTH: 109
<212> TYPE: PRT
<213> ORGANISM: Artificial Sequence
<220> FEATURE:
<223> OTHER INFORMATION: Description of Artificial Sequence: Synthetic
AX189 VL antibody sequence polypeptide

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Arg Tyr
            20                  25                  30

Leu Thr Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Tyr Asp Tyr Ser Leu Ser
                85                  90                  95

Gly Tyr Val Phe Gly Gly Gly Thr Lys Val Glu Ile Lys
            100                 105

<210> SEQ ID NO 82
<211> LENGTH: 11
<212> TYPE: PRT
<213> ORGANISM: Artificial Sequence
<220> FEATURE:
<223> OTHER INFORMATION: Description of Artificial Sequence: Synthetic
AX189 VL CDR1 antibody sequence peptide

<400> SEQUENCE: 82

Arg Ala Ser Gln Asp Val Ser Arg Tyr Leu Thr
1               5                   10

<210> SEQ ID NO 83
<211> LENGTH: 7
<212> TYPE: PRT
<213> ORGANISM: Artificial Sequence
<220> FEATURE:

<223> OTHER INFORMATION: Description of Artificial Sequence: Synthetic
      AX1 AX9 AX189 VL CDR2 antibody sequence peptide

<400> SEQUENCE: 83

Ala Ala Ser Ser Leu Gln Ser
1               5

<210> SEQ ID NO 84
<211> LENGTH: 11
<212> TYPE: PRT
<213> ORGANISM: Artificial Sequence
<220> FEATURE:
<223> OTHER INFORMATION: Description of Artificial Sequence: Synthetic
      AX189 VL CDR3 antibody sequence peptide

<400> SEQUENCE: 84

Gln Ala Tyr Asp Tyr Ser Leu Ser Gly Tyr Val
1               5                   10

<210> SEQ ID NO 85
<211> LENGTH: 115
<212> TYPE: PRT
<213> ORGANISM: Homo sapiens

<400> SEQUENCE: 85

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Leu Thr Ser Tyr
                20                  25                  30

Gly Ile Ser Trp Val Arg Gln Ala Pro Gly Gln Gly Leu Glu Trp Met
            35                  40                  45

Gly Trp Val Ser Phe Tyr Asn Gly Asn Thr Asn Tyr Ala Gln Lys Leu
    50                  55                  60

Gln Gly Arg Gly Thr Met Thr Thr Asp Pro Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Tyr Gly Met Asp Val Trp Gly Gln Gly Thr Thr Val Thr
                100                 105                 110

Val Ser Ser
        115

<210> SEQ ID NO 86
<211> LENGTH: 5
<212> TYPE: PRT
<213> ORGANISM: Homo sapiens

<400> SEQUENCE: 86

Ser Tyr Gly Ile Ser
1               5

<210> SEQ ID NO 87
<211> LENGTH: 17
<212> TYPE: PRT
<213> ORGANISM: Homo sapiens

<400> SEQUENCE: 87

Trp Val Ser Phe Tyr Asn Gly Asn Thr Asn Tyr Ala Gln Lys Leu Gln
1               5                   10                  15

Gly

<210> SEQ ID NO 88
<211> LENGTH: 6
<212> TYPE: PRT
<213> ORGANISM: Homo sapiens

<400> SEQUENCE: 88

Gly Tyr Gly Met Asp Val
1               5

<210> SEQ ID NO 89
<211> LENGTH: 109
<212> TYPE: PRT
<213> ORGANISM: Homo sapiens

<400> SEQUENCE: 89

Gln Ser Ala Leu Thr Gln Pro Ala Ser Val Ser Gly Ser Pro Gly Gln
1               5                   10                  15

Ser Ile Thr Ile Ser Cys Thr Gly Thr Ser Ser Asp Val Gly Gly Tyr
            20                  25                  30

Asn Ser Val Ser Trp Tyr Gln Gln His Pro Gly Lys Ala Pro Lys Leu
        35                  40                  45

Met Ile Tyr Glu Val Ser Asn Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Asn Ser Tyr Thr Ser Thr
                85                  90                  95

Ser Met Val Phe Gly Gly Gly Thr Lys Leu Thr Val Leu
            100                 105

<210> SEQ ID NO 90
<211> LENGTH: 14
<212> TYPE: PRT
<213> ORGANISM: Homo sapiens

<400> SEQUENCE: 90

Thr Gly Thr Ser Ser Asp Val Gly Gly Tyr Asn Ser Val Ser
1               5                   10

<210> SEQ ID NO 91
<211> LENGTH: 7
<212> TYPE: PRT
<213> ORGANISM: Homo sapiens

<400> SEQUENCE: 91

Glu Val Ser Asn Arg Pro Ser
1               5

<210> SEQ ID NO 92
<211> LENGTH: 9
<212> TYPE: PRT
<213> ORGANISM: Homo sapiens

<400> SEQUENCE: 92

Asn Ser Tyr Thr Ser Thr Ser Met Val
1               5

<210> SEQ ID NO 93
<211> LENGTH: 123
<212> TYPE: PRT
<213> ORGANISM: Homo sapiens

<400> SEQUENCE: 93

```
Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Ser Ile Ser Ser Ser Ser Tyr Ile Ser Tyr Ala Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Phe Cys
            85                  90                  95

Ala Arg Asp Tyr Asp Phe Trp Ser Ala Tyr Tyr Asp Ala Phe Asp Val
        100                 105                 110

Trp Gly Gln Gly Thr Met Val Thr Val Ser Ser
        115                 120
```

<210> SEQ ID NO 94
<211> LENGTH: 10
<212> TYPE: PRT
<213> ORGANISM: Homo sapiens

<400> SEQUENCE: 94

```
Gly Phe Thr Phe Ser Ser Tyr Ser Met Asn
1               5                   10
```

<210> SEQ ID NO 95
<211> LENGTH: 17
<212> TYPE: PRT
<213> ORGANISM: Homo sapiens

<400> SEQUENCE: 95

```
Ser Ile Ser Ser Ser Ser Tyr Ile Ser Tyr Ala Asp Ser Val Lys
1               5                   10                  15

Gly
```

<210> SEQ ID NO 96
<211> LENGTH: 14
<212> TYPE: PRT
<213> ORGANISM: Homo sapiens

<400> SEQUENCE: 96

```
Asp Tyr Asp Phe Trp Ser Ala Tyr Tyr Asp Ala Phe Asp Val
1               5                   10
```

<210> SEQ ID NO 97
<211> LENGTH: 111
<212> TYPE: PRT
<213> ORGANISM: Homo sapiens

<400> SEQUENCE: 97

```
Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Asp Val His Trp Tyr Gln Gln Leu Pro Gly Thr Ala Pro Lys Leu
        35                  40                  45

Leu Ile Ser Gly Asn Ser Asn Arg Pro Ser Gly Val Pro Asp Arg Phe
50                  55                  60
```

```
Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Tyr Asp Ser Ser
                 85                  90                  95

Leu Ser Gly Ser Val Phe Gly Gly Gly Thr Lys Leu Thr Val Leu
            100                 105                 110
```

<210> SEQ ID NO 98
<211> LENGTH: 14
<212> TYPE: PRT
<213> ORGANISM: Homo sapiens

<400> SEQUENCE: 98

```
Thr Gly Ser Ser Ser Asn Ile Gly Ala Gly Tyr Asp Val His
 1               5                  10
```

<210> SEQ ID NO 99
<211> LENGTH: 7
<212> TYPE: PRT
<213> ORGANISM: Homo sapiens

<400> SEQUENCE: 99

```
Gly Asn Ser Asn Arg Pro Ser
 1               5
```

<210> SEQ ID NO 100
<211> LENGTH: 11
<212> TYPE: PRT
<213> ORGANISM: Homo sapiens

<400> SEQUENCE: 100

```
Gln Ser Tyr Asp Ser Ser Leu Ser Gly Ser Val
 1               5                  10
```

<210> SEQ ID NO 101
<211> LENGTH: 114
<212> TYPE: PRT
<213> ORGANISM: Homo sapiens

<400> SEQUENCE: 101

```
Gln Val Gln Leu Val Glu Ser Gly Gly Val Ala Gln Pro Gly Arg
 1               5                  10                  15

Ser Leu Arg Leu Ser Cys Ala Ala Ser Gly Phe Thr Phe Ser Ser Tyr
                 20                  25                  30

Gly Met His Trp Val Arg Gln Ala Pro Gly Lys Gly Leu Glu Trp Val
             35                  40                  45

Ala Val Ile Tyr Tyr Asp Gly Ile Asn Lys His Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Gly Leu Asp Trp Gly Gln Gly Thr Leu Val Thr Val
            100                 105                 110

Ser Ser
```

<210> SEQ ID NO 102
<211> LENGTH: 10
<212> TYPE: PRT
<213> ORGANISM: Homo sapiens

<400> SEQUENCE: 102

Gly Phe Thr Phe Ser Ser Tyr Gly Met His
1               5                   10

<210> SEQ ID NO 103
<211> LENGTH: 17
<212> TYPE: PRT
<213> ORGANISM: Homo sapiens

<400> SEQUENCE: 103

Val Ile Tyr Tyr Asp Gly Ile Asn Lys His Tyr Ala Asp Ser Val Lys
1               5                   10                  15

Gly

<210> SEQ ID NO 104
<211> LENGTH: 5
<212> TYPE: PRT
<213> ORGANISM: Homo sapiens

<400> SEQUENCE: 104

Asp Arg Gly Leu Asp
1               5

<210> SEQ ID NO 105
<211> LENGTH: 113
<212> TYPE: PRT
<213> ORGANISM: Homo sapiens

<400> SEQUENCE: 105

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Ser Lys Asn Tyr Leu Val Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Trp Thr Phe Gly Gln Gly Thr Lys Val Glu Ile
            100                 105                 110

Lys

<210> SEQ ID NO 106
<211> LENGTH: 17
<212> TYPE: PRT
<213> ORGANISM: Homo sapiens

<400> SEQUENCE: 106

Lys Ser Ser Gln Ser Val Leu Tyr Ser Ser Asn Ser Lys Asn Tyr Leu
1               5                   10                  15

Val

<210> SEQ ID NO 107
<211> LENGTH: 7
<212> TYPE: PRT
<213> ORGANISM: Homo sapiens

```
<400> SEQUENCE: 107

Trp Ala Ser Thr Arg Glu Ser
1               5

<210> SEQ ID NO 108
<211> LENGTH: 9
<212> TYPE: PRT
<213> ORGANISM: Homo sapiens

<400> SEQUENCE: 108

Gln Gln Tyr Tyr Ser Thr Pro Trp Thr
1               5

<210> SEQ ID NO 109
<211> LENGTH: 118
<212> TYPE: PRT
<213> ORGANISM: Artificial Sequence
<220> FEATURE:
<223> OTHER INFORMATION: Description of Artificial Sequence: Synthetic
      anti-PCSK9 monoclonal antibody pJG04 (clones LGT-209 and
      LGT-210) Vh heavy chain variable region (FR1-FR4)
      polypeptide

<400> SEQUENCE: 109

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Thr Met
            20                  25                  30

Tyr Met Ser Trp Val Arg Gln Ala Pro Gly Gln Gly Leu Glu Trp Met
        35                  40                  45

Gly Arg Ile Asp Pro Ala Asn Glu His Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Thr Ser Asp Asp Thr Ala Val Tyr Tyr Cys
                85                  90                  95

Ala Arg Ser Tyr Tyr Tyr Tyr Asn Met Asp Tyr Trp Gly Gln Gly Thr
            100                 105                 110

Leu Val Thr Val Ser Ser
        115

<210> SEQ ID NO 110
<211> LENGTH: 5
<212> TYPE: PRT
<213> ORGANISM: Artificial Sequence
<220> FEATURE:
<223> OTHER INFORMATION: Description of Artificial Sequence: Synthetic
      anti-PCSK9 monoclonal antibody clones LGT-209,
      LGT-210 and LGT-211 heavy chain CDR1 peptide

<400> SEQUENCE: 110

Thr Met Tyr Met Ser
1               5

<210> SEQ ID NO 111
<211> LENGTH: 17
<212> TYPE: PRT
<213> ORGANISM: Artificial Sequence
<220> FEATURE:
<223> OTHER INFORMATION: Description of Artificial Sequence: Synthetic
      anti-PCSK9 monoclonal antibody clones LGT-209,
      LGT-210 and LGT-211 heavy chain CDR2 peptide
```

```
<400> SEQUENCE: 111

Arg Ile Asp Pro Ala Asn Glu His Thr Asn Tyr Ala Gln Lys Phe Gln
1               5                   10                  15

Gly

<210> SEQ ID NO 112
<211> LENGTH: 9
<212> TYPE: PRT
<213> ORGANISM: Artificial Sequence
<220> FEATURE:
<223> OTHER INFORMATION: Description of Artificial Sequence: Synthetic
      anti-PCSK9 monoclonal antibody pJG04(clones
      LGT-209 and LGT-210) Vh heavy chain complementarity
      determining region 3 (CDR3) peptide

<400> SEQUENCE: 112

Ser Tyr Tyr Tyr Tyr Asn Met Asp Tyr
1               5

<210> SEQ ID NO 113
<211> LENGTH: 106
<212> TYPE: PRT
<213> ORGANISM: Artificial Sequence
<220> FEATURE:
<223> OTHER INFORMATION: Description of Artificial Sequence: Synthetic
      anti-PCSK9 monoclonal antibody pJG10(clones
      LGT-209 and LGT-211) Vk light chain variable
      region (FR1-FR4) polypeptide

<400> SEQUENCE: 113

Gln Ile Val Leu Thr Gln Ser Pro Ala Thr Leu Ser Val Ser Pro Gly
1               5                   10                  15

Glu Arg Ala Thr Leu Ser Cys Arg Ala Ser Gln Ser Val Ser Tyr Met
                20                  25                  30

His Trp Tyr Gln Gln Lys Pro Gly Gln Ala Pro Arg Leu Leu Ile Tyr
            35                  40                  45

Gly Val Phe Arg Arg Ala Thr Gly Ile Pro Asp Arg Phe Ser Gly Ser
     50                  55                  60

Gly Ser Gly Thr Asp Phe Thr Leu Thr Ile Gly Arg Leu Glu Pro Glu
65                  70                  75                  80

Asp Phe Ala Val Tyr Tyr Cys Leu Gln Trp Ser Ser Asp Pro Pro Thr
                85                  90                  95

Phe Gly Gln Gly Thr Lys Leu Glu Ile Lys
            100                 105

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      anti-PCSK9 monoclonal antibody clones LGT-209,
      LGT-210 and LGT-211 light chain CDR1 peptide

<400> SEQUENCE: 114

Arg Ala Ser Gln Ser Val Ser Tyr Met His
1               5                   10

<210> SEQ ID NO 115
<211> LENGTH: 7
<212> TYPE: PRT
<213> ORGANISM: Artificial Sequence
<220> FEATURE:
<223> OTHER INFORMATION: Description of Artificial Sequence: Synthetic
``` anti-PCSK9 monoclonal antibody clones LGT-209,
LGT-210 and LGT-211 light chain CDR1 peptide

<400> SEQUENCE: 115

Gly Val Phe Arg Arg Ala Thr
1               5

<210> SEQ ID NO 116
<211> LENGTH: 9
<212> TYPE: PRT
<213> ORGANISM: Artificial Sequence
<220> FEATURE:
<223> OTHER INFORMATION: Description of Artificial Sequence: Synthetic
      mouse anti-PCSK9 monoclonal antibody LFU720 and
      anti-PCSK9 monoclonal antibody clones LGT-209,
      LGT-210 and LGT-211 light chain CDR3 peptide

<400> SEQUENCE: 116

Leu Gln Trp Ser Ser Asp Pro Pro Thr
1               5

<210> SEQ ID NO 117
<211> LENGTH: 118
<212> TYPE: PRT
<213> ORGANISM: Homo sapiens

<400> SEQUENCE: 117

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Glu Ile Ser Pro Phe Gly Arg Thr Asn Tyr Asn Glu Lys Phe
        50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Leu Tyr Ala Ser Asp Leu Trp Gly Gln Gly Thr
                100                 105                 110

Thr Val Thr Val Ser Ser
            115

<210> SEQ ID NO 118
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Gly Tyr Thr Phe Thr Ser Tyr
1               5

<210> SEQ ID NO 119
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 119

Ser Pro Phe Gly Gly Arg
1               5

<210> SEQ ID NO 120
<211> LENGTH: 9
<212> TYPE: PRT
<213> ORGANISM: Artificial Sequence
<220> FEATURE:
<223> OTHER INFORMATION: Description of Artificial Sequence: Synthetic
      variable heavy chain CDR peptide

<400> SEQUENCE: 120

Glu Arg Pro Leu Tyr Ala Ser Asp Leu
1               5

<210> SEQ ID NO 121
<211> LENGTH: 107
<212> TYPE: PRT
<213> ORGANISM: Homo sapiens

<400> SEQUENCE: 121

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Ala
            20                  25                  30

Leu Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Arg Tyr Ser Leu Trp Arg
                85                  90                  95

Thr Phe Gly Gln Gly Thr Lys Leu Glu Ile Lys
            100                 105

<210> SEQ ID NO 122
<211> LENGTH: 11
<212> TYPE: PRT
<213> ORGANISM: Artificial Sequence
<220> FEATURE:
<223> OTHER INFORMATION: Description of Artificial Sequence: Synthetic
      variable light chain CDR peptide

<400> SEQUENCE: 122

Arg Ala Ser Gln Gly Ile Ser Ser Ala Leu Ala
1               5                   10

<210> SEQ ID NO 123
<211> LENGTH: 7
<212> TYPE: PRT
<213> ORGANISM: Artificial Sequence
<220> FEATURE:
<223> OTHER INFORMATION: Description of Artificial Sequence: Synthetic
      variable light chain CDR peptide

<400> SEQUENCE: 123

Ser Ala Ser Tyr Arg Tyr Thr
1               5

<210> SEQ ID NO 124
<211> LENGTH: 9
```

```
<212> TYPE: PRT
<213> ORGANISM: Artificial Sequence
<220> FEATURE:
<223> OTHER INFORMATION: Description of Artificial Sequence: Synthetic
      variable light chain CDR peptide

<400> SEQUENCE: 124

Gln Gln Arg Tyr Ser Leu Trp Arg Thr
1               5

<210> SEQ ID NO 125
<211> LENGTH: 118
<212> TYPE: PRT
<213> ORGANISM: Homo sapiens

<400> SEQUENCE: 125

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Glu Ile His Pro Ser Gly Gly Arg Thr Asn Tyr Asn Glu Lys Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Glu Arg Pro Leu Tyr Ala Met Asp Tyr Trp Gly Gln Gly Thr
            100                 105                 110

Thr Val Thr Val Ser Ser
        115

<210> SEQ ID NO 126
<211> LENGTH: 10
<212> TYPE: PRT
<213> ORGANISM: Homo sapiens

<400> SEQUENCE: 126

Gly Tyr Thr Phe Thr Ser Tyr Tyr Met His
1               5                   10

<210> SEQ ID NO 127
<211> LENGTH: 17
<212> TYPE: PRT
<213> ORGANISM: Homo sapiens

<400> SEQUENCE: 127

Glu Ile His Pro Ser Gly Gly Arg Thr Asn Tyr Asn Glu Lys Phe Lys
1               5                   10                  15

Ser

<210> SEQ ID NO 128
<211> LENGTH: 9
<212> TYPE: PRT
<213> ORGANISM: Homo sapiens

<400> SEQUENCE: 128

Glu Arg Pro Leu Tyr Ala Met Asp Tyr
1               5
```

```
<210> SEQ ID NO 129
<211> LENGTH: 107
<212> TYPE: PRT
<213> ORGANISM: Homo sapiens

<400> SEQUENCE: 129

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val His Thr Ala
            20                  25                  30

Val Ala Trp Tyr Gln Gln Lys Pro Gly Lys Ala Pro Lys Leu Leu Ile
        35                  40                  45

Tyr His Ala Ser Tyr Arg Tyr Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Arg Tyr Ser Leu Trp Arg
                85                  90                  95

Thr Phe Gly Gln Gly Thr Lys Leu Glu Ile Lys
            100                 105

<210> SEQ ID NO 130
<211> LENGTH: 11
<212> TYPE: PRT
<213> ORGANISM: Homo sapiens

<400> SEQUENCE: 130

Lys Ala Ser Gln Asp Val His Thr Ala Val Ala
1               5                   10

<210> SEQ ID NO 131
<211> LENGTH: 7
<212> TYPE: PRT
<213> ORGANISM: Homo sapiens

<400> SEQUENCE: 131

His Ala Ser Tyr Arg Tyr Thr
1               5

<210> SEQ ID NO 132
<211> LENGTH: 9
<212> TYPE: PRT
<213> ORGANISM: Homo sapiens

<400> SEQUENCE: 132

Gln Gln Arg Tyr Ser Leu Trp Arg Thr
1               5

<210> SEQ ID NO 133
<211> LENGTH: 118
<212> TYPE: PRT
<213> ORGANISM: Homo sapiens

<400> SEQUENCE: 133

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Glu Ile His Pro Ser Gly Gly Arg Thr Asn Tyr Asn Glu Lys Phe
```

```
                 50                  55                  60
Lys Ser Arg Val Thr Met Thr Arg Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Glu Arg Pro Leu Tyr Ala Ser Asp Leu Trp Gly Gln Gly Thr
                100                 105                 110

Thr Val Thr Val Ser Ser
            115

<210> SEQ ID NO 134
<211> LENGTH: 10
<212> TYPE: PRT
<213> ORGANISM: Homo sapiens

<400> SEQUENCE: 134

Gly Tyr Thr Phe Thr Ser Tyr Tyr Met His
 1               5                  10

<210> SEQ ID NO 135
<211> LENGTH: 17
<212> TYPE: PRT
<213> ORGANISM: Homo sapiens

<400> SEQUENCE: 135

Glu Ile His Pro Ser Gly Gly Arg Thr Asn Tyr Asn Glu Lys Phe Lys
 1               5                  10                  15

Ser

<210> SEQ ID NO 136
<211> LENGTH: 9
<212> TYPE: PRT
<213> ORGANISM: Homo sapiens

<400> SEQUENCE: 136

Glu Arg Pro Leu Tyr Ala Ser Asp Leu
 1               5

<210> SEQ ID NO 137
<211> LENGTH: 107
<212> TYPE: PRT
<213> ORGANISM: Homo sapiens

<400> SEQUENCE: 137

Asp Ile Gln Met Thr Gln Ser Pro Ser Ser Leu Ser Ala Ser Val Gly
 1               5                  10                  15

Asp Arg Val Thr Ile Thr Cys Lys Ala Ser Gln Asp Val His Thr Ala
                20                  25                  30

Val Ala Trp Tyr Gln Gln Lys Pro Gly Lys Ala Pro Lys Leu Leu Ile
            35                  40                  45

Tyr His Ala Ser Tyr Arg Tyr Thr Gly Val Pro Ser Arg Phe Ser Gly
        50                  55                  60

Ser Gly Ser Gly Thr Asp Phe Thr Phe Thr Ile Ser Ser Leu Gln Pro
 65                  70                  75                  80

Glu Asp Ile Ala Thr Tyr Tyr Cys Gln Gln Arg Tyr Ser Leu Trp Arg
                85                  90                  95

Thr Phe Gly Gln Gly Thr Lys Leu Glu Ile Lys
                100                 105
```

```
<210> SEQ ID NO 138
<211> LENGTH: 11
<212> TYPE: PRT
<213> ORGANISM: Homo sapiens

<400> SEQUENCE: 138

Lys Ala Ser Gln Asp Val His Thr Ala Val Ala
1               5                   10

<210> SEQ ID NO 139
<211> LENGTH: 7
<212> TYPE: PRT
<213> ORGANISM: Homo sapiens

<400> SEQUENCE: 139

His Ala Ser Tyr Arg Tyr Thr
1               5

<210> SEQ ID NO 140
<211> LENGTH: 9
<212> TYPE: PRT
<213> ORGANISM: Homo sapiens

<400> SEQUENCE: 140

Gln Gln Arg Tyr Ser Leu Trp Arg Thr
1               5

<210> SEQ ID NO 141
<211> LENGTH: 118
<212> TYPE: PRT
<213> ORGANISM: Mus musculus

<400> SEQUENCE: 141

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Asn Pro Ser Asn Gly Arg Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Glu Arg Pro Leu Tyr Ala Met Asp Tyr Trp Gly Gln Gly Thr
            100                 105                 110

Ser Val Thr Val Ser Ser
        115

<210> SEQ ID NO 142
<211> LENGTH: 7
<212> TYPE: PRT
<213> ORGANISM: Mus musculus

<400> SEQUENCE: 142

Gly Tyr Thr Phe Thr Ser Tyr
1               5

<210> SEQ ID NO 143
<211> LENGTH: 6
<212> TYPE: PRT
```

<213> ORGANISM: Mus musculus

<400> SEQUENCE: 143

Asn Pro Ser Asn Gly Arg
1               5

<210> SEQ ID NO 144
<211> LENGTH: 9
<212> TYPE: PRT
<213> ORGANISM: Mus musculus

<400> SEQUENCE: 144

Glu Arg Pro Leu Tyr Ala Met Asp Tyr
1               5

<210> SEQ ID NO 145
<211> LENGTH: 108
<212> TYPE: PRT
<213> ORGANISM: Mus musculus

<400> SEQUENCE: 145

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
                20                  25                  30

Val Ala Trp Tyr Gln Gln Lys Pro Gly Gln Ser Pro Lys Leu Leu Ile
            35                  40                  45

Tyr Ser Ala Ser Tyr Arg Tyr Thr Gly Val Pro Asp Arg Phe Thr Gly
        50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln Arg Tyr Ser Thr Pro Arg
                85                  90                  95

Thr Phe Gly Gly Gly Thr Lys Leu Glu Ile Lys Arg
            100                 105

<210> SEQ ID NO 146
<211> LENGTH: 11
<212> TYPE: PRT
<213> ORGANISM: Mus musculus

<400> SEQUENCE: 146

Lys Ala Ser Gln Asp Val Ser Thr Ala Val Ala
1               5                   10

<210> SEQ ID NO 147
<211> LENGTH: 7
<212> TYPE: PRT
<213> ORGANISM: Artificial Sequence
<220> FEATURE:
<223> OTHER INFORMATION: Description of Artificial Sequence: Synthetic
      variable light chain CDR peptide

<400> SEQUENCE: 147

Ser Ala Ser Tyr Arg Tyr Thr
1               5

<210> SEQ ID NO 148
<211> LENGTH: 9
<212> TYPE: PRT
<213> ORGANISM: Mus musculus

<400> SEQUENCE: 148

Gln Gln Arg Tyr Ser Thr Pro Arg Thr
1               5

<210> SEQ ID NO 149
<211> LENGTH: 115
<212> TYPE: PRT
<213> ORGANISM: Mus musculus

<400> SEQUENCE: 149

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Gly Thr Thr Tyr Asn Gln Lys Phe
    50                  55                  60

Lys Gly Lys Ala Thr Leu Thr Val Asp Lys Ser Ser Tyr Thr Ala Tyr
65                  70                  75                  80

Met Glu Leu Arg Ser Leu Thr Ser Glu Asp Ser Ala Val Tyr Tyr Cys
                85                  90                  95

Ala Arg Trp Leu Leu Phe Ala Tyr Trp Gly Gln Gly Thr Leu Val Thr
            100                 105                 110

Val Ser Ala
        115

<210> SEQ ID NO 150
<211> LENGTH: 7
<212> TYPE: PRT
<213> ORGANISM: Mus musculus

<400> SEQUENCE: 150

Gly Tyr Thr Phe Thr Asp Tyr
1               5

<210> SEQ ID NO 151
<211> LENGTH: 6
<212> TYPE: PRT
<213> ORGANISM: Mus musculus

<400> SEQUENCE: 151

Asn Pro Asn Asn Gly Gly
1               5

<210> SEQ ID NO 152
<211> LENGTH: 6
<212> TYPE: PRT
<213> ORGANISM: Mus musculus

<400> SEQUENCE: 152

Trp Leu Leu Phe Ala Tyr
1               5

<210> SEQ ID NO 153
<211> LENGTH: 108
<212> TYPE: PRT
<213> ORGANISM: Mus musculus

<400> SEQUENCE: 153

Asp Ile Val Met Thr Gln Ser Gln Lys Phe Met Ser Thr Ser Val Gly
1               5                   10                  15

```
Asp Arg Val Ser Val Thr Cys Lys Ala Ser Gln Asn Val Gly Thr Asn
            20                  25                  30

Val Ala Trp Tyr Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Leu Ser
65                  70                  75                  80

Glu Asp Leu Ala Glu Tyr Phe Cys Gln Gln Phe Tyr Ser Tyr Pro Tyr
                85                  90                  95

Thr Phe Gly Gly Gly Thr Lys Leu Glu Ile Lys Arg
            100                 105
```

<210> SEQ ID NO 154
<211> LENGTH: 11
<212> TYPE: PRT
<213> ORGANISM: Mus musculus

<400> SEQUENCE: 154

```
Lys Ala Ser Gln Asn Val Gly Thr Asn Val Ala
1               5                   10
```

<210> SEQ ID NO 155
<211> LENGTH: 7
<212> TYPE: PRT
<213> ORGANISM: Mus musculus

<400> SEQUENCE: 155

```
Ser Ala Ser Tyr Arg Tyr Ser
1               5
```

<210> SEQ ID NO 156
<211> LENGTH: 9
<212> TYPE: PRT
<213> ORGANISM: Mus musculus

<400> SEQUENCE: 156

```
Gln Gln Phe Tyr Ser Tyr Pro Tyr Thr
1               5
```

<210> SEQ ID NO 157
<211> LENGTH: 123
<212> TYPE: PRT
<213> ORGANISM: Mus musculus

<400> SEQUENCE: 157

```
Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Gly Thr Ser Tyr Asn Gln Lys Phe
    50                  55                  60

Lys Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Gly Gly Gly Ile Tyr Tyr Arg Tyr Asp Arg Asn Tyr Phe Asp Tyr
```

-continued

```
                100                 105                 110
Trp Gly Gln Gly Thr Thr Leu Thr Val Ser Ser
        115                 120
```

<210> SEQ ID NO 158
<211> LENGTH: 7
<212> TYPE: PRT
<213> ORGANISM: Mus musculus

<400> SEQUENCE: 158

```
Gly Tyr Thr Phe Thr Asp Tyr
1               5
```

<210> SEQ ID NO 159
<211> LENGTH: 6
<212> TYPE: PRT
<213> ORGANISM: Mus musculus

<400> SEQUENCE: 159

```
Asn Pro Asn Asn Gly Gly
1               5
```

<210> SEQ ID NO 160
<211> LENGTH: 14
<212> TYPE: PRT
<213> ORGANISM: Mus musculus

<400> SEQUENCE: 160

```
Gly Gly Ile Tyr Tyr Arg Tyr Asp Arg Asn Tyr Phe Asp Tyr
1               5                   10
```

<210> SEQ ID NO 161
<211> LENGTH: 107
<212> TYPE: PRT
<213> ORGANISM: Mus musculus

<400> SEQUENCE: 161

```
Asp Ile Gln Met Thr Gln Thr Thr Ser Ser Leu Ser Ala Ser Leu Gly
1               5                   10                  15
Asp Arg Val Thr Ile Ser Cys Ser Ala Ser Gln Gly Ile Ser Asn Tyr
            20                  25                  30
Leu Asn Trp Tyr Gln Gln Lys Pro Asp Gly Thr Val Lys Leu Leu Ile
        35                  40                  45
Tyr Tyr Thr Ser Ser Leu His Ser Gly Val Pro Ser Arg Phe Ser Gly
    50                  55                  60
Ser Gly Ser Gly Thr Asp Tyr Ser Leu Thr Ile Ser Asn Leu Glu Pro
65                  70                  75                  80
Glu Asp Ile Ala Thr Tyr Tyr Cys Gln Gln Tyr Ser Lys Leu Pro Phe
                85                  90                  95
Thr Phe Gly Ser Gly Thr Lys Leu Glu Ile Lys
            100                 105
```

<210> SEQ ID NO 162
<211> LENGTH: 11
<212> TYPE: PRT
<213> ORGANISM: Mus musculus

<400> SEQUENCE: 162

```
Ser Ala Ser Gln Gly Ile Ser Asn Tyr Leu Asn
1               5                   10
```

```
<210> SEQ ID NO 163
<211> LENGTH: 7
<212> TYPE: PRT
<213> ORGANISM: Mus musculus

<400> SEQUENCE: 163

Tyr Thr Ser Ser Leu His Ser
1               5

<210> SEQ ID NO 164
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 164

Gln Gln Tyr Ser Lys Leu Pro Phe Thr
1               5

<210> SEQ ID NO 165
<211> LENGTH: 117
<212> TYPE: PRT
<213> ORGANISM: Mus musculus

<400> SEQUENCE: 165

Glu Val Lys Leu Val Glu Ser Glu Gly Gly Leu Val Gln Pro Gly Ser
1               5                   10                  15

Ser Met Lys Leu Ser Cys Thr Ala Ser Gly Phe Thr Phe Ser Asp Tyr
            20                  25                  30

Tyr Met Ala Trp Val Arg Gln Val Pro Glu Lys Gly Leu Glu Trp Val
        35                  40                  45

Ala Asn Ile Asn Tyr Asp Gly Ser Asn Thr Ser Tyr Leu Asp Ser Leu
    50                  55                  60

Lys Ser Arg Phe Ile Ile Ser Arg Asp Asn Ala Lys Asn Ile Leu Tyr
65                  70                  75                  80

Leu Gln Met Ser Ser Leu Lys Ser Glu Asp Thr Ala Thr Tyr Tyr Cys
                85                  90                  95

Ala Arg Glu Lys Phe Ala Ala Met Asp Tyr Trp Gly Gln Gly Thr Ser
            100                 105                 110

Val Thr Val Ser Ser
        115

<210> SEQ ID NO 166
<211> LENGTH: 7
<212> TYPE: PRT
<213> ORGANISM: Mus musculus

<400> SEQUENCE: 166

Gly Phe Thr Phe Ser Asp Tyr
1               5

<210> SEQ ID NO 167
<211> LENGTH: 6
<212> TYPE: PRT
<213> ORGANISM: Mus musculus

<400> SEQUENCE: 167

Asn Tyr Asp Gly Ser Asn
1               5
```

```
<210> SEQ ID NO 168
<211> LENGTH: 8
<212> TYPE: PRT
<213> ORGANISM: Mus musculus

<400> SEQUENCE: 168

Glu Lys Phe Ala Ala Met Asp Tyr
1               5

<210> SEQ ID NO 169
<211> LENGTH: 108
<212> TYPE: PRT
<213> ORGANISM: Mus musculus

<400> SEQUENCE: 169

Asp Ile Val Met Thr Gln Ser His Lys Phe Met Ser Thr Ser Phe Gly
1               5                   10                  15

Asp Arg Val Ser Ile Thr Cys Lys Ala Ser Gln Asp Val Ser Asn Ala
            20                  25                  30

Leu Ala Trp Tyr Gln Gln Lys Pro Gly His Ser Pro Lys Leu Leu Ile
        35                  40                  45

Phe Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Trp
                85                  90                  95

Thr Phe Gly Gly Gly Thr Lys Leu Glu Ile Lys Arg
            100                 105

<210> SEQ ID NO 170
<211> LENGTH: 11
<212> TYPE: PRT
<213> ORGANISM: Mus musculus

<400> SEQUENCE: 170

Lys Ala Ser Gln Asp Val Ser Asn Ala Leu Ala
1               5                   10

<210> SEQ ID NO 171
<211> LENGTH: 7
<212> TYPE: PRT
<213> ORGANISM: Artificial Sequence
<220> FEATURE:
<223> OTHER INFORMATION: Description of Artificial Sequence: Synthetic
      variable light chain CDR peptide

<400> SEQUENCE: 171

Ser Ala Ser Tyr Arg Tyr Thr
1               5

<210> SEQ ID NO 172
<211> LENGTH: 9
<212> TYPE: PRT
<213> ORGANISM: Mus musculus

<400> SEQUENCE: 172

Gln Gln His Tyr Ser Thr Pro Trp Thr
1               5

<210> SEQ ID NO 173
<211> LENGTH: 121
<212> TYPE: PRT
```

<213> ORGANISM: Artificial Sequence
<220> FEATURE:
<223> OTHER INFORMATION: Description of Artificial Sequence: Synthetic
      polypeptide

<400> SEQUENCE: 173

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Arg His
            20                  25                  30

Thr Ile His Trp Val Arg Gln Ala Pro Gly Lys Gly Leu Glu Trp Val
        35                  40                  45

Ala Arg Ile Ser Pro Ala Asn Gly Asn Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Ile Gly Ser Arg Glu Leu Tyr Ile Met Asp Tyr Trp Gly
            100                 105                 110

Gln Gly Thr Leu Val Thr Val Ser Ser
        115                 120

<210> SEQ ID NO 174
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 174

Gly Phe Thr Phe Thr Arg His Thr Ile His
1               5                   10

<210> SEQ ID NO 175
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 175

Arg Ile Ser Pro Ala Asn Gly Asn Thr Asn Tyr Ala Asp Ser Val Lys
1               5                   10                  15

Gly

<210> SEQ ID NO 176
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 176

Trp Ile Gly Ser Arg Glu Leu Tyr Ile Met Asp Tyr
1               5                   10

<210> SEQ ID NO 177
<211> LENGTH: 108
<212> TYPE: PRT

<213> ORGANISM: Artificial Sequence
<220> FEATURE:
<223> OTHER INFORMATION: Description of Artificial Sequence: Synthetic polypeptide

<400> SEQUENCE: 177

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Arg Ile Gln Pro
                85                  90                  95

Thr Phe Gly Gln Gly Thr Lys Val Glu Ile Lys Arg
            100                 105
```

<210> SEQ ID NO 178
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 178

```
Arg Ala Ser Gln Asp Val Ser Thr Ala Val Ala
1               5                   10
```

<210> SEQ ID NO 179
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 179

```
Ser Ala Ser Phe Leu Tyr Ser
1               5
```

<210> SEQ ID NO 180
<211> LENGTH: 9
<212> TYPE: PRT
<213> ORGANISM: Artificial Sequence
<220> FEATURE:
<223> OTHER INFORMATION: Description of Artificial Sequence: Synthetic peptide

<400> SEQUENCE: 180

```
Gln Gln Ser Tyr Arg Ile Gln Pro Thr
1               5
```

<210> SEQ ID NO 181
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

```
<400> SEQUENCE: 181

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Thr
            20                  25                  30

Ala Ile His Trp Val Arg Gln Ala Pro Gly Lys Gly Leu Glu Trp Val
        35                  40                  45

Ala Arg Ile Ser Pro Ala Asn Gly Asn Thr Asn Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Trp Ile Gly Ser Arg Glu Leu Tyr Ile Met Asp Tyr Trp Gly
            100                 105                 110

Gln Gly Thr Leu Val Thr Val Ser Ser
        115                 120

<210> SEQ ID NO 182
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 182

Gly Phe Thr Phe Ser Ser Thr Ala Ile His
1               5                   10

<210> SEQ ID NO 183
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 183

Arg Ile Ser Pro Ala Asn Gly Asn Thr Asn Tyr Ala Asp Ser Val Lys
1               5                   10                  15

Gly

<210> SEQ ID NO 184
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 184

Trp Ile Gly Ser Arg Glu Leu Tyr Ile Met Asp Tyr
1               5                   10

<210> SEQ ID NO 185
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 185

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Pro Ala Leu His
                85                  90                  95

Thr Phe Gly Gln Gly Thr Lys Val Glu Ile Lys Arg
            100                 105

<210> SEQ ID NO 186
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 186

Arg Ala Ser Gln Asp Val Ser Thr Ala Val Ala
1               5                   10

<210> SEQ ID NO 187
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 187

Ser Ala Ser Phe Leu Tyr Ser
1               5

<210> SEQ ID NO 188
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 188

Gln Gln Ser Tyr Pro Ala Leu His Thr
1               5

<210> SEQ ID NO 189
<211> LENGTH: 125
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 189

Glu Val Gln Leu Val Glu Ser Gly Gly Gly Leu Val Lys Pro Gly Gly
1               5                   10                  15

```
Ser Leu Arg Leu Ser Cys Ala Ala Ser Gly Phe Pro Phe Ser Lys Leu
            20                  25                  30

Gly Met Val Trp Val Arg Gln Ala Pro Gly Lys Gly Leu Glu Trp Val
        35                  40                  45

Ser Thr Ile Ser Ser Gly Gly Tyr Thr Tyr Tyr Pro Asp Ser Val
    50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                85                  90                  95

Ala Arg Glu Gly Ile Ser Phe Gln Gly Gly Thr Tyr Thr Tyr Val Met
            100                 105                 110

Asp Tyr Trp Gly Gln Gly Thr Leu Val Thr Val Ser Ser
        115                 120                 125

<210> SEQ ID NO 190
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 190

Gly Phe Pro Phe Ser Lys Leu Gly Met Val
1               5                   10

<210> SEQ ID NO 191
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 191

Thr Ile Ser Ser Gly Gly Gly Tyr Thr Tyr Tyr Pro Asp Ser Val Lys
1               5                   10                  15

Gly

<210> SEQ ID NO 192
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 192

Glu Gly Ile Ser Phe Gln Gly Gly Thr Tyr Thr Tyr Val Met Asp Tyr
1               5                   10                  15

<210> SEQ ID NO 193
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 193

Asp Ile Val Met Thr Gln Ser Pro Leu Ser Leu Pro Val Thr Pro Gly
1               5                   10                  15
```

Glu Pro Ala Ser Ile Ser Cys Arg Ser Ser Lys Ser Leu Leu His Arg
            20                  25                  30

Asn Gly Ile Thr Tyr Ser Tyr Trp Tyr Leu Gln Lys Pro Gly Gln Ser
        35                  40                  45

Pro Gln Leu Leu Ile Tyr Gln Leu Ser Asn Leu Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Tyr Gln Asn
                85                  90                  95

Leu Glu Leu Pro Leu Thr Phe Gly Gln Gly Thr Lys Val Glu Ile Lys
            100                 105                 110

<210> SEQ ID NO 194
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 194

Arg Ser Ser Lys Ser Leu Leu His Arg Asn Gly Ile Thr Tyr Ser Tyr
1               5                   10                  15

<210> SEQ ID NO 195
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 195

Gln Leu Ser Asn Leu Ala Ser
1               5

<210> SEQ ID NO 196
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 196

Tyr Gln Asn Leu Glu Leu Pro Leu Thr
1               5

<210> SEQ ID NO 197
<211> LENGTH: 2076
<212> TYPE: DNA
<213> ORGANISM: Homo sapiens

<400> SEQUENCE: 197
atgggcaccg tcagctccag gcggtcctgg tggccgctgc cactgctgct gctgctgctg      60
ctgctcctgg gtcccgcggg cgccgtgcg caggaggacg aggacggcga ctacgaggag     120
ctggtgctag ccttgcgttc cgaggaggac ggcctggccg aagcacccga gcacggaacc     180
acagccacct tccaccgctg cgccaaggat ccgtggaggt tgcctggcac ctacgtggtg    240
gtgctgaagg aggagaccca cctctcgcag tcagagcgca ctgcccgccg cctgcaggcc    300
caggctgccc gcgggata cctcaccaag atcctgcatg tcttccatgg ccttcttcct     360

```
ggcttcctgg tgaagatgag tggcgacctg ctggagctgg ccttgaagtt gccccatgtc      420
gactacatcg aggaggactc ctctgtcttt gcccagagca tcccgtggaa cctggagcgg      480
attacccctc cacggtaccg ggcggatgaa taccagcccc ccgacggagg cagcctggtg      540
gaggtgtatc tcctagacac cagcatacag agtgaccacc gggaaatcga gggcagggtc      600
atggtcaccg acttcgagaa tgtgcccgag gaggacggga cccgcttcca cagacaggcc      660
agcaagtgtg acagtcatgg cacccacctg cagggggtgg tcagcggccg ggatgccggc      720
gtggccaagg gtgccagcat gcgcagcctg cgcgtgctca actgccaagg gaagggcacg      780
gttagcggca ccctcatagg cctggagttt attcggaaaa gccagctggt ccagcctgtg      840
gggccactgg tggtgctgct gcccctggcg ggtgggtaca gccgcgtcct caacgccgcc      900
tgccagcgct ggcgagggc tggggtcgtg ctggtcaccg ctgccggcaa cttccgggac      960
gatgcctgcc tctactcccc agcctcagct cccgaggtca tcacagttgg ggccaccaat     1020
gcccaagacc agccggtgac cctggggact ttggggacca actttggccg ctgtgtggac     1080
ctctttgccc caggggagga catcattggt gcctccagcg actgcagcac ctgctttgtg     1140
tcacagagtg ggacatcaca ggctgctgcc acgtggctg gcattgcagc catgatgctg     1200
tctgccgagc cggagctcac cctggccgag ttgaggcaga gactgatcca cttctctgcc     1260
aaagatgtca tcaatgaggc ctggttccct gaggaccagc gggtactgac ccccaacctg     1320
gtggccgccc tgcccccccag cacccatggg gcaggttggc agctgttttg caggactgta     1380
tggtcagcac actcggggcc tacacggatg ccacagccg tcgcccgctg cgccccagat     1440
gaggagctgc tgagctgctc cagtttctcc aggagtggga gcggcgggg cgagcgcatg     1500 gaggcccaag ggggcaagct ggtctgccgg gcccacaacg ctttggggg tgagggtgtc     1560 tacgccattg ccaggtgctg cctgctaccc caggccaact gcagcgtcca cacagctcca     1620
ccagctgagg ccagcatggg gacccgtgtc cactgccacc aacagggcca cgtcctcaca     1680
ggctgcagct cccactggga ggtggaggac cttggcaccc acaagccgcc tgtgctgagg     1740
ccacgaggtc agcccaacca gtgcgtgggc cacaggagg ccagcatcca cgcttcctgc     1800
tgccatgccc caggtctgga atgcaaagtc aaggagcatg gaatcccggc ccctcaggag     1860
caggtgaccg tggcctgcga ggagggctgg accctgactg gctgcagtgc cctccctggg     1920
acctcccacg tcctggggc ctacgccgta gacaacacgt gtgtagtcag gagccgggac     1980
gtcagcacta caggcagcac cagcgaaggg gccgtgacag ccgttgccat ctgctgccgg     2040
agccggcacc tggcgcaggc ctcccaggag ctccag                               2076
```

<210> SEQ ID NO 198
<211> LENGTH: 692
<212> TYPE: PRT
<213> ORGANISM: Homo sapiens

<400> SEQUENCE: 198

```
Met Gly Thr Val Ser Ser Arg Arg Ser Trp Trp Pro Leu Pro Leu Leu
1               5                   10                  15

Leu Leu Leu Leu Leu Leu Leu Gly Pro Ala Gly Ala Arg Ala Gln Glu
            20                  25                  30

Asp Glu Asp Gly Asp Tyr Glu Glu Leu Val Leu Ala Leu Arg Ser Glu
        35                  40                  45

Glu Asp Gly Leu Ala Glu Ala Pro Glu His Gly Thr Thr Ala Thr Phe
    50                  55                  60
```

```
His Arg Cys Ala Lys Asp Pro Trp Arg Leu Pro Gly Thr Tyr Val Val
 65                  70                  75                  80

Val Leu Lys Glu Glu Thr His Leu Ser Gln Ser Glu Arg Thr Ala Arg
                 85                  90                  95

Arg Leu Gln Ala Gln Ala Ala Arg Arg Gly Tyr Leu Thr Lys Ile Leu
            100                 105                 110

His Val Phe His Gly Leu Leu Pro Gly Phe Leu Val Lys Met Ser Gly
        115                 120                 125

Asp Leu Leu Glu Leu Ala Leu Lys Leu Pro His Val Asp Tyr Ile Glu
    130                 135                 140

Glu Asp Ser Ser Val Phe Ala Gln Ser Ile Pro Trp Asn Leu Glu Arg
145                 150                 155                 160

Ile Thr Pro Pro Arg Tyr Arg Ala Asp Glu Tyr Gln Pro Pro Asp Gly
                165                 170                 175

Gly Ser Leu Val Glu Val Tyr Leu Leu Asp Thr Ser Ile Gln Ser Asp
            180                 185                 190

His Arg Glu Ile Glu Gly Arg Val Met Val Thr Asp Phe Glu Asn Val
        195                 200                 205

Pro Glu Glu Asp Gly Thr Arg Phe His Arg Gln Ala Ser Lys Cys Asp
    210                 215                 220

Ser His Gly Thr His Leu Ala Gly Val Val Ser Gly Arg Asp Ala Gly
225                 230                 235                 240

Val Ala Lys Gly Ala Ser Met Arg Ser Leu Arg Val Leu Asn Cys Gln
                245                 250                 255

Gly Lys Gly Thr Val Ser Gly Thr Leu Ile Gly Leu Glu Phe Ile Arg
            260                 265                 270

Lys Ser Gln Leu Val Gln Pro Val Gly Pro Leu Val Val Leu Leu Pro
        275                 280                 285

Leu Ala Gly Gly Tyr Ser Arg Val Leu Asn Ala Ala Cys Gln Arg Leu
    290                 295                 300

Ala Arg Ala Gly Val Val Leu Val Thr Ala Ala Gly Asn Phe Arg Asp
305                 310                 315                 320

Asp Ala Cys Leu Tyr Ser Pro Ala Ser Ala Pro Glu Val Ile Thr Val
                325                 330                 335

Gly Ala Thr Asn Ala Gln Asp Gln Pro Val Thr Leu Gly Thr Leu Gly
            340                 345                 350

Thr Asn Phe Gly Arg Cys Val Asp Leu Phe Ala Pro Gly Glu Asp Ile
        355                 360                 365

Ile Gly Ala Ser Ser Asp Cys Ser Thr Cys Phe Val Ser Gln Ser Gly
    370                 375                 380

Thr Ser Gln Ala Ala His Val Ala Gly Ile Ala Ala Met Met Leu
385                 390                 395                 400

Ser Ala Glu Pro Glu Leu Thr Leu Ala Glu Leu Arg Gln Arg Leu Ile
                405                 410                 415

His Phe Ser Ala Lys Asp Val Ile Asn Glu Ala Trp Phe Pro Glu Asp
            420                 425                 430

Gln Arg Val Leu Thr Pro Asn Leu Val Ala Ala Leu Pro Pro Ser Thr
        435                 440                 445

His Gly Ala Gly Trp Gln Leu Phe Cys Arg Thr Val Trp Ser Ala His
    450                 455                 460

Ser Gly Pro Thr Arg Met Ala Thr Ala Val Ala Arg Cys Ala Pro Asp
465                 470                 475                 480

Glu Glu Leu Leu Ser Cys Ser Ser Phe Ser Arg Ser Gly Lys Arg Arg
```

-continued

```
                        485                 490                 495
Gly Glu Arg Met Glu Ala Gln Gly Gly Lys Leu Val Cys Arg Ala His
                500                 505                 510

Asn Ala Phe Gly Gly Glu Gly Val Tyr Ala Ile Ala Arg Cys Cys Leu
                515                 520                 525

Leu Pro Gln Ala Asn Cys Ser Val His Thr Ala Pro Pro Ala Glu Ala
                530                 535                 540

Ser Met Gly Thr Arg Val His Cys His Gln Gln Gly His Val Leu Thr
545                 550                 555                 560

Gly Cys Ser Ser His Trp Glu Val Glu Asp Leu Gly Thr His Lys Pro
                565                 570                 575

Pro Val Leu Arg Pro Arg Gly Gln Pro Asn Gln Cys Val Gly His Arg
                580                 585                 590

Glu Ala Ser Ile His Ala Ser Cys Cys His Ala Pro Gly Leu Glu Cys
                595                 600                 605

Lys Val Lys Glu His Gly Ile Pro Ala Pro Gln Glu Gln Val Thr Val
                610                 615                 620

Ala Cys Glu Glu Gly Trp Thr Leu Thr Gly Cys Ser Ala Leu Pro Gly
625                 630                 635                 640

Thr Ser His Val Leu Gly Ala Tyr Ala Val Asp Asn Thr Cys Val Val
                645                 650                 655

Arg Ser Arg Asp Val Ser Thr Thr Gly Ser Thr Ser Glu Gly Ala Val
                660                 665                 670

Thr Ala Val Ala Ile Cys Cys Arg Ser Arg His Leu Ala Gln Ala Ser
                675                 680                 685

Gln Glu Leu Gln
            690
```